US012497665B2

(12) United States Patent
Choudhury et al.

(10) Patent No.: US 12,497,665 B2
(45) Date of Patent: *Dec. 16, 2025

(54) METHOD OF DETECTING AND QUANTIFYING GENOMIC AND GENE EXPRESSION ALTERATIONS USING RNA

(71) Applicant: LUCENCE LIFE SCIENCES PTE. LTD., Singapore (SG)

(72) Inventors: Yukti Choudhury, Singapore (SG); Chae Yin Cher, Singapore (SG); Jia Min Ho, Singapore (SG); Min-Han Tan, Singapore (SG); Kao Chin Ngeow, Singapore (SG); Pannapa Pinweha, Singapore (SG)

(73) Assignee: Lucence Life Sciences Pte. Ltd., Singapore (SG)

( * ) Notice: Subject to any disclaimer, the term of this patent is extended or adjusted under 35 U.S.C. 154(b) by 168 days.

This patent is subject to a terminal disclaimer.

(21) Appl. No.: 18/345,676

(22) Filed: Jun. 30, 2023

(65) Prior Publication Data

US 2023/0416842 A1 Dec. 28, 2023

Related U.S. Application Data

(63) Continuation of application No. 17/825,669, filed on May 26, 2022, now Pat. No. 11,873,533.

(51) Int. Cl.
*C12P 19/34* (2006.01)
*C12N 15/10* (2006.01)
(Continued)

(52) U.S. Cl.
CPC ....... *C12Q 1/6886* (2013.01); *C12N 15/1065* (2013.01); *C12N 15/1096* (2013.01);
(Continued)

(58) Field of Classification Search
CPC .................................................... C12Q 1/6886
See application file for complete search history.

(56) References Cited

U.S. PATENT DOCUMENTS

| | | | |
|---|---|---|---|
| 2013/0210663 | A1 | 8/2013 | Coverley |
| 2014/0066317 | A1 | 3/2014 | Talasaz |

(Continued)

FOREIGN PATENT DOCUMENTS

| | | | |
|---|---|---|---|
| WO | 2020206184 | A1 | 10/2020 |

OTHER PUBLICATIONS

International Search Report mailed Dec. 28, 2022 in reference to co-pending Singapore Application PCT/SG2022/050354 filed May 26, 2022.

(Continued)

*Primary Examiner* — Kenneth R Horlick
(74) *Attorney, Agent, or Firm* — Dinsmore & Shohl LLP

(57) ABSTRACT

Disclosed is a method of detecting and quantifying genomic and gene expression alterations using RNA in a biological sample. The disclosed method may include determining presence or absence of the genomic alteration and/or determining presence or absence of the gene expression and/or quantifying the level of the gene expression, by performing variant calling of the sequence alignment obtained from the disclosed method. Variant calling may comprise the steps of identifying differences between a consensus read and a reference genome based on the sequence alignment from the disclosed method; and determining the read count of sequence alignments comprising genomic alteration. The genomic alteration may be an insertion (such as a duplication), a deletion, a single nucleotide variant, or combinations thereof. Also disclosed is a kit for detecting and quantifying (Continued)

genomic and gene expression alterations using RNA in a biological sample.

23 Claims, 34 Drawing Sheets

Specification includes a Sequence Listing.

(51) Int. Cl.
*C12Q 1/6886* (2018.01)
*C12Q 1/6806* (2018.01)
*C12Q 1/6869* (2018.01)

(52) U.S. Cl.
CPC ......... *C12Q 1/6806* (2013.01); *C12Q 1/6869* (2013.01); *C12Q 2600/158* (2013.01); *C12Q 2600/16* (2013.01)

(56) References Cited

U.S. PATENT DOCUMENTS

| | | | |
|---|---|---|---|
| 2014/0272956 | A1 | 9/2014 | Huang et al. |
| 2015/0044687 | A1 | 2/2015 | Schmitt et al. |
| 2016/0275240 | A1 | 9/2016 | Huelga et al. |
| 2020/0024644 | A1 | 1/2020 | Wang et al. |
| 2020/0048694 | A1 | 2/2020 | Godwin et al. |

OTHER PUBLICATIONS

Written Opinion mailed Dec. 28, 2022 in reference to co-pending Singapore Application PCT/SG2022/050354 filed May 26, 2022.
Hasegawa, et al., Cancer Science 112, 4393-4403 (epub Aug. 18, 2021). (Year: 2021).
Written Opinion pertaining to co-pending application SG11202401460Y mailed Jan. 3, 2025.
Hasegawa. N. et al., Highly sensitive fusion detection using plasma cell-free RNA in non-small-cell lung cancers. Cancer Science. 2021;112:4393-4403.

| Sample | Diagnosis | cfDNA per ml plasma (ng) | cfRNA per ml plasma (ng) |
| --- | --- | --- | --- |
| Ca-1 | Metastatic Prostate Cancer | 145 | 43.7 |
| Ca-2 | Metastatic Lung Cancer | 26.6 | 27.1 |
| Ca-3 | Metastatic Pancreatic Cancer | 25.8 | 61.5 |
| Ca-4 | Metastatic Prostate Cancer | 356.5 | 52.1 |
| Ca-5 | Metastatic Lung Cancer | 2156 | 96.8 |
| Hth-1 | Healthy | 7.92 | 8.2 |
| Hth-2 | Healthy | 4.76 | 5.71 |
| Hth-3 | Healthy | 7.37 | 3.33 |

FIG. 4

| Sample | Type | RNA (ng) |
|---|---|---|
| C_20-146 | Metastatic Lung Cancer | 35 |
| C_20-347 | Metastatic Prostate Cancer | 24 |
| C_20-126.1 | Metastatic Lung Cancer | 33 |
| C_20-126.2 | | 83 |
| C_20-1069.1 | Metastatic Lung Cancer | 10.9 |
| C_20-1069.2 | | 27 |
| C_21-7 | Metastatic Breast Cancer | 25 |
| C_21-93 | Metastatic Lung Cancer | 30.2 |
| H_A_1 | Healthy | 4.1 |
| H_A_2 | Healthy | 3.5 |
| H_B | Healthy | 2.43 |
| H_C | Healthy | 3.7 |

| | cfDNA fusion+ | cfDNA fusion- |
|---|---|---|
| cfRNA fusion+ | 12 | 5 |
| cfRNA fusion- | 1 | 27 |

FIG. 14A

| cfDNA and cfRNA fusion+ | Only cfRNA fusion+ | Only cfDNA fusion- |
|---|---|---|
| EML4-ALK (n = 4) | LMNA-NTRK1 (n = 2) | KIF5B-RET (n = 1) |
| MET exon 14 skipping (n = 3) | CD74-NRG1 (n = 1) | |
| CD74-ROS1 (n = 2) | ETV6-MET (n = 1) | |
| NCOA4-RET (n =1) | ETV6-NTRK3 (n = 1) | |
| CCDC6-RET (n=1) | | |
| FGFR3-TACC3 (n=1) | | |
| Co-occurring fusions detected in cfRNA | | |
| EML4-ALK* and EWSR1-FLI1 | | |
| EML4-ALK*, SQSTM1-MET and CCDC6-RET | | |
| CD74-ROS1* and SND1-BRAF | | |

FIG. 14B

| Sample | Sample Type | Diagnosis | Mutation | Mutation Type | Mutant expression (Mutant read counts) | Wild-type expression (Wild-type read counts) | VAF (Mutant read counts)/(Total read counts) |
|---|---|---|---|---|---|---|---|
| F_22-274 | FFPE Tumor Tissue | Metastatic Pancreatic Cancer | KRAS c.35G>A p.G12D | SNV | 9142 | 13373 | 41% |
| F_22-83 | FFPE Tumor Tissue | Metastatic Endometrial Cancer | KRAS c.35G>T p.G12V | SNV | 424 | 885 | 32% |
| F_22-137 | FFPE Tumor Tissue | Metastatic Lung Cancer | EGFR c.2311_2319dup p.N771_H773dup | Insertion | 40628 | 26099 | 61% |
| F_22-55 | FFPE Tumor Tissue | Localised Lung Cancer | EGFR c.2240_2257del p.L747_P753delinsS | Deletion | 4266 | 369 | 92% |

FIG. 18A

| Sample | Sample Type | Diagnosis | Mutation | Mutation Type | Mutant expression (Mutant read counts) | Wild-type expression (Wild-type read counts) | VAF (Mutant read counts)/(Total read counts) |
|---|---|---|---|---|---|---|---|
| P_19-2372 | Plasma | Metastatic Lung Cancer | KRAS c.34G>T p.G12C | SNV | 67 | 1100 | 6% |
| P_20-953 | Plasma | Metastatic Lung Cancer | EGFR c.2573T>G p.L858R | SNV | 78 | 82 | 49% |
| P_22-265 | Plasma | Metastatic Lung Cancer | EGFR c.2573T>G p.L858R | SNV | 112 | 48 | 70% |

FIG. 18B

METHOD OF DETECTING AND QUANTIFYING GENOMIC AND GENE EXPRESSION ALTERATIONS USING RNA

CROSS REFERENCE TO RELATED APPLICATIONS

This application is a continuation of U.S. application Ser. No. 17/825,669, now U.S. Pat. No. 11,873,533, filed May 26, 2022, which claims priority to Singapore Patent Application No. 10202109756V, filed Sep. 6, 2021, the entire contents of which are incorporated by reference.

FIELD OF INVENTION

The present invention relates to the detection and quantification of nucleic acid. In particular, the present invention relates to the detection and quantification of RNA.

BACKGROUND

Circulating biomarkers are promising tools used for cancer detection, prognostication and prediction of cancer treatment response. These circulating biomarkers typically include DNA samples such as cell-free DNA (cfDNA) and circulating-tumor cells. It is known that various RNA molecules are also potential biomarkers for the diagnosis and prognosis of various diseases such as cancer and are useful for early cancer diagnosis, tumor progression monitor, and prediction of therapy response. It is also known that cancer cells release cell-free RNA (cfRNA) into the body circulation. These cancer-associated cfRNA, also known as circulating-tumor RNA (ctRNA) can be found in the serum and blood plasma of cancer patients. While both cfDNA and cfRNA are promising cancer biomarkers, the measurement of cfDNA is traditionally preferred due to its stability in biological fluids. Despite the discovery of RNA in blood plasma and serum over 20 years ago, there is still a general perception that extracellular RNA in blood is extremely unstable and highly fragmented, given the relative instability of RNA compared to DNA, which in itself is unstable when fragmented in the blood, due to the presence of a high concentration of ribonucleases in the blood circulation. Multiple studies have documented the presence of tumor-specific circulating RNA (ctRNA) in serum and plasma in cancer patients. Current non-oncology clinical applications of cfRNA include the measurement of maternal and fetal cfRNA transcripts to monitor longitudinal phenotypic changes in both the mother and the fetus and to assess fetal gestational age. It is known that in blood circulation, cfRNA occur in free form, bound to proteins or lipids, or as exosomes protected in various types of membrane-derived microvesicles, making them highly stable. It is plausible that plasma cfRNA is a mixture of RNA protected by RNA binding proteins and RNA contained within extracellular vesicles. The wide availability of cfRNA in plasma, serum and many other bodily fluids and their paradoxical stability makes them potential candidates for the development of biomarkers for rapid, sensitive and inexpensive diagnostics. Furthermore, detection of ctRNA provides the same mutational information as ctDNA, but additionally, it can also provide quantitative information about the expression levels of target genes of interest, and can potentially increase the sensitivity of detection of variants with low allelic frequencies due to the overexpression of tumor-specific transcripts. Lastly, the expression of various ctRNA species is dysregulated due to uncontrolled cell proliferation, rendering it a potential valuable tool for cancer detection. At present, the most common technique for detection of cfRNA is using quantitative Real-time Polymerase Chain Reaction (qRT-PCR). However, methods involving qRT-PCR are often limited by their sensitivity when assaying low input samples. NGS may be more well-suited due the ability to detect novel cfRNAs and differentiate RNA isoforms. With hybridization-based library preparation methods, sequence-specific biases due to enzymatic ligation during library construction step leads to biased representation of transcripts, particularly during analysis of small RNA. Targeted NGS assays such as hybridization capture or amplicon sequencing may also allow for sensitive quantification of cfRNAs (as opposed to whole transcriptome analysis with low conversion efficiency).

Many cancer genes exhibit genomic alterations, and these genomic alteration events have been discovered in a wide variety of tumors. Targeted DNA-based next generation sequencing techniques specifically designed to detect rearrangements in kinases can effectively detect oncogenic kinase fusions with high confidence. However, there are technical limitations to the ability of such DNA-based assays to detect certain genomic alterations, such as gene fusions. DNA-based assays can only identify fusions in genes where the genomic rearrangements occur in typically short introns effectively covered in the panel. Some clinically important fusions arise from rearrangements in very long introns, the complete coverage of which would significantly compromise coverage of the remainder of the genes on the panel. Hence, there are gaps in the coverage of certain introns resulting in blind spots in the detection of potential rearrangement breakpoint. Fusion detection using DNA does not provide direct evidence that the rearrangement produces a fusion expressed at the mRNA level, a particular problem for rearrangements that appear non-canonical at the genomic DNA level. In fact, in one study in lung cancer tissue samples, it was shown that by using RNA sequencing, alterations were detected in 14% (36/254) cases which were otherwise negative for clinically actionable mutations by DNA sequencing. For example, gene fusion events involving Neurotrophic Receptor Tyrosine Kinase (NTRK) gene (NTRK1/2/3) and neuregulin-1 (NRG1) gene cannot be effectively covered in a targeted DNA sequencing panel without compromising on the cost of sequencing and the coverage of the remaining genes in the sequencing panel.

Apart from detecting genomic alterations events, the ability to accurately quantify genomic expression of relevant cancer biomarkers non-invasively is important for predicting the response to cancer therapies and making the appropriate treatment decision. For example, the gene expression level of Programmed death-ligand 1 (PD-L1) is a predictive cancer biomarker used to identify cancer patients with a greater likelihood of responding to immunotherapy. PD-L1 is also a potential predictive biomarker to measure the sensitivity of tumors to immune checkpoint blockade drug inhibitors such as anti-PD-1 inhibitors (pembrolizumab and nivolumab), anti-cytotoxic T-lymphocyte-associated protein 4 (CTLA-4) inhibitors, (ipilimumab and tremelimumab) and anti-programmed death protein 1 (PD-1) (atezolizumab, durvalumab and avelumab). Other genetic biomarkers that are useful for predicting the likelihood of responding to immune checkpoint inhibitor therapy include T cell immunoglobulin and mucin domain-containing protein 3 (TIM-3), Lymphocyte Activating 3 (LAG-3) and cytotoxic T-lymphocyte-associated protein 4 (CTLA-4). The ability to quantify the expression of these target biomarkers longitudinally and non-invasively can be very useful for monitoring treatment response and making treatment decisions.

Conventional assays routinely detect for genomic alterations at the DNA level, limiting the scope of detection to DNA genomic alterations such as mutations and quantifying genomic copy number changes.

Thus, there is a need to provide a method for sensitive detection and quantification of genomic alteration events and expression of genes associated with disease (such as cancer) that overcomes, or at least ameliorates, one or more of the disadvantages described above. There is a need to provide a method to simultaneously detect genomic alterations such as structural rearrangements, and gene expression using an alternative sample input such as RNA (such as circulating cell-free RNA (cfRNA)).

SUMMARY

In one aspect, the present disclosure refers to a method of detecting genomic alteration and/or detecting gene expression and/or quantifying a level of gene expression using RNA in a biological sample, comprising:

(a) extracting RNA from the biological sample and converting the RNA to complementary DNA (cDNA);

(b) performing a plurality of multiplexed PCR reactions on the converted cDNA using (I) a plurality of forward and reverse primer pairs specific to a plurality of target genes that are capable of undergoing genomic alteration, wherein each forward primer of the plurality of forward and reverse primer pairs specific to the plurality of target genes that are capable of undergoing genomic alteration is complementary to a sequence located about 50 base pairs upstream of an exonic junction of each target gene that is capable of undergoing genomic alteration, wherein each reverse primer of the plurality of forward and reverse primer pairs specific to the plurality of target genes that are capable of undergoing genomic alteration is complementary to a sequence located about 50 base pairs downstream of an exonic junction of each target gene that is capable of undergoing genomic alteration, wherein each reverse primer of the plurality of forward and reverse primer pairs specific to the plurality of target genes that are capable of undergoing genomic alteration comprises a barcode sequence on its 5' end, wherein the barcode sequence of each reverse primer corresponding to each target gene that is capable of undergoing genomic alteration is different, and/or (II) a plurality of forward and reverse primer pairs specific to a plurality of control housekeeping genes, wherein:

(i) each forward primer of the plurality of forward and reverse primer pairs specific to the plurality of control housekeeping genes is complementary to a sequence spanning an exon-exon junction of each control housekeeping gene, wherein each reverse primer of the plurality of forward and reverse primer pairs specific to the plurality of control housekeeping genes is complementary to a sequence about 100 base pairs downstream of the sequence spanning the exon-exon junction of each control housekeeping gene, wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;

(ii) each reverse primer of the plurality of forward and reverse primer pairs specific to the plurality of control housekeeping genes is complementary to a sequence spanning an exon-exon junction of each control housekeeping gene, wherein each forward primer of the plurality of forward and reverse primer pairs specific to the plurality of control housekeeping genes is complementary to a sequence about 100 base pairs downstream of the sequence spanning the exon-exon junction of each control housekeeping gene, wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;

(iii) each forward and each reverse primer of the plurality of forward and reverse primer pairs specific to the plurality of control housekeeping genes is complementary to consecutive sequences spanning an exon-exon junction of each control housekeeping gene, wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different, and/or (III) a plurality of primer sets specific to a plurality of target genes related to protein expression, wherein each primer set comprises a plurality of forward and reverse primer pairs specific to each target gene related to protein expression, wherein:

(i) each forward primer of the of the plurality of forward and reverse primer pairs specific to each target gene related to protein expression is complementary to a sequence spanning an exon-exon junction of each target gene related to protein expression, wherein each reverse primer of the of the plurality of forward and reverse primer pairs specific to each target gene related to protein expression is complementary to a sequence about 100 base pairs downstream of the sequence spanning the exon-exon junction of each target gene related to protein expression, wherein each reverse primer of the plurality of forward and reverse primer pairs specific to each target gene related to protein expression comprises a barcode sequence on its 5' end, wherein the barcode sequence of each reverse primer corresponding to each target gene related to protein expression is different, (ii) each reverse primer of the plurality of forward and reverse primer pairs specific to the plurality of target genes related to protein expression is complementary to a sequence spanning an exon-exon junction of each target gene related to protein expression, wherein each forward primer of the plurality of forward and reverse primer pairs specific to the plurality of target genes related to protein expression is complementary to a sequence about 100 base pairs downstream of the sequence spanning the exon-exon junction of each target gene related to protein expression, wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different;

(iii) each forward and each reverse primer of the plurality of forward and reverse primer pairs specific to the plurality of target genes related to protein expression is complementary to consecutive sequences spanning an exon-exon junction of each target gene related to protein expression, wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different, thereby generating a plurality of amplicons;

(c) purifying the plurality of amplicons from step (b);

(d) amplifying the purified product from step (c) by using universal indexed adapter primers to generate a sequencing library;

(e) purifying the sequencing library obtained from step (d);

(f) subjecting the purified sequencing library from step (e) to multiplex sequencing on a next-generation sequencing platform to obtain a plurality of sequencing reads;

(g) deriving a consensus read of each sequence from the plurality of sequencing reads obtained from step (f);

(h) performing a sequence alignment of the consensus read obtained from step (g) to a reference genome, (I) if the sequence alignment results in a partial alignment to the reference genome of an exon from a first gene and a partial alignment to the reference genome of an exon from a second gene, then:

(i) determining the sequence alignment as a split read, (ii) counting/enumerating the number of split reads from step (h)(I)(i) that supports a fusion junction, and (iii) if the number of split reads from step (h)(I)(ii) is two or more, then determining the first gene and the second gene as fusion partners, (II) if the sequence alignment results in an alignment to the reference genome of the control housekeeping gene, then:

(i) determining the sequence alignment as a consensus read of the control housekeeping gene, (ii) counting/enumerating consensus read pairs of the control housekeeping gene from step (h)(II)(i), and (iii) determining the level of gene expression of the control housekeeping gene, (III) if the sequence alignment results in an alignment to the reference genome of the target gene related to protein expression, (i) determining the sequence alignment as a consensus read of the target gene related to protein expression, (ii) counting/enumerating consensus read pairs of the target gene related to protein expression from step (h)(III)(i), and (iii) determining the level of gene expression of the target gene related to protein expression;

(i) determining presence or absence of the genomic alteration and/or determining presence or absence of the gene expression and/or quantifying the level of the gene expression based on the sequence alignment from step (h).

In another aspect, the present disclosure refers to a kit for detecting genomic alteration and/or detecting gene expression and/or quantifying a level of gene expression using RNA in a biological sample according to the method disclosed herein, wherein the kit comprises:

a plurality of forward and reverse primer pairs specific to a plurality of target genes that are capable of undergoing genomic alteration as defined in the method disclosed herein, a plurality of forward and reverse primer pairs specific to a plurality of control housekeeping genes as defined in the method disclosed herein, and a plurality of primer sets specific to a plurality of target genes related to protein expression as defined in the method disclosed herein.

BRIEF DESCRIPTION OF THE DRAWINGS

The invention will be better understood with reference to the detailed description when considered in conjunction with the non-limiting examples and the accompanying drawings, in which:

FIGS. 2A-2B illustrate examples of primer design of the disclosed method, wherein FIG. 2A illustrates examples of primer design for capturing control housekeeping genes (left panel) and expression genes (right panel) in cfRNA. At least one primer of a primer pair spans an exon-exon junction, to prevent unintended amplification of cfDNA and the resulting amplicons are approximately 100 base pairs in length. It should be noted that the primer pairs for the housekeeping genes differ from that of the expression genes, and FIG. 2B illustrates an example of a forward primer and a reverse primer designed to bind to two different exons, intervened by an intron >5000 base pairs in length.

FIGS. 3A-3D show the size and concentration analysis of cfRNA from plasma total nucleic acid extracts from cancer patients and healthy individuals, wherein FIG. 3A shows the size and concentration analysis of cfRNA from plasma total nucleic acid extracts from a cancer patient (sample A), FIG. 3B shows the size and concentration analysis of cfRNA from plasma total nucleic acid extracts from another cancer patient (sample B), FIG. 3C shows the size and concentration analysis of cfRNA from plasma total nucleic acid extracts from a healthy individual (sample C), and FIG. 3D shows the size and concentration analysis of cfRNA from plasma total nucleic acid extracts from another healthy individual (sample D). Bioanalyzer RNA 6000 Pico kit or the High Sensitivity RNA Screentape on the 4200 Tapestation were used to quantify and profile the samples. The total concentration of cfRNA (representative of abundance) is generally higher in the representative plasma extracted from cancer patients, relative to those extracted from healthy individuals.

FIG. 4 shows the comparison of yield for cfDNA and cfRNA in total nucleic acid extracts from plasma extracted from cancer patients and healthy individuals.

FIGS. 5A-5C show an example of the fragmentation of extracted H2228 cell line RNA by physical shearing of large size nucleotides (>1500 nucleotides) into smaller size to mimic cfRNA fragment size. Bioanalyzer RNA 6000 Pico kit or the High Sensitivity RNA Screentape on the 4200 Tapestation were used to quantify and profile the samples, wherein FIG. 5A shows the fragmentation profile of extracted H2228 cell line RNA, FIG. 5B shows the resulting fragmentation profile of fragmented H2228 cell line RNA, and FIG. 5C shows the fragmentation profile of plasma cfRNA. The resulting fragmentation profile of H2228 cell line RNA is similar to that of plasma cfRNA, with a dominant RNA peak at 119 nucleotides (represented by arrows).

FIGS. 6A-6B illustrate the detection of EML4-ALK fusion in 1 ng of fragmented H2228 RNA showing the alignment of split reads capturing the fusion break points of exon 6b of EML4 and exon 20 of ALK, wherein FIG. 6A is a visualization of the split read on Integrated Genome Viewer (IGV), and FIG. 6B is a diagrammatic representation showing exonic fusion (from Arriba tool for detection of gene fusions).

FIGS. 8A-8C show detection of TMPRSS2-ERG gene fusion in nucleic acid extracts from a metastatic prostate patient using the cfRNA-based method described herein, compared to a cfDNA-based method, wherein FIG. 8A is an IGV graphic view showing 17 split reads, which supported the presence of intronic breakpoints, detected with the cfDNA-based detection method, FIG. 8B is an IGV graphic report showing 4123 split reads, which supported the presence of corresponding exonic breakpoints, detected with the cfRNA-based method described herein, and FIG. 8C is a diagrammatic representation from Arriba tool showing TMPRS S2-ERG gene fusion.

FIGS. 9A-9C show detection of CCDC6-RET gene fusion in a nucleic acid extract from a metastatic lung cancer patient using the cfRNA-based method described herein, compared to a cfDNA-based method, wherein FIG. 9A is an IGV graphic report showing 12 split reads, which supported the presence of intronic breakpoints, detected with the cfDNA-based detection method, FIG. 9B is an IGV graphic report showing 1474 split reads, which supported the presence of corresponding exonic breakpoints, detected with the cfRNA-based method described herein, and FIG. 9C is a diagrammatic representation from Arriba tool showing CCDC6-RET gene fusion.

FIGS. 10A-10B show the detection of BCR-ABL1 gene fusion in an RNA sample extracted from the peripheral blood cell fraction of an acute lymphoblastic leukaemia clinical sample using the cfRNA-based method described herein, wherein FIG. 10A is an IGV graphic report showing BCR-ABL1 gene fusion, and FIG. 10B is a diagrammatic representation from Arriba tool showing BCR-ABL1 gene fusion.

FIGS. 13A-13C show the identification of actionable driver fusions in untreated lung cancer cases using cfRNA using the method described herein, wherein FIG. 13A shows detection of LMNA-NTRK1 fusion, FIG. 13B shows detection of CD74-NRG1 fusion, and FIG. 13C shows detection of ETV6-NTRK3 fusion in cfRNA in three lung cancer cases, respectively, that were negative for the presence of other driver gene mutations in cfDNA.

FIGS. 14A-14B show fusion detection in 45 lung cancer cases by cfDNA and cfRNA using the method described herein and that additional fusions were identified when cfRNA fraction was used, compared to cfDNA. Clinical samples processed simultaneously using cfRNA and cfDNA were compared for fusion detection, wherein FIG. 14A shows concordance of fusion detection based on cfDNA and cfRNA, showing cfRNA identified additional fusions in 5 cases, and missed 1 fusion detectable by cfDNA. There were 12 cases with concordant fusion detection by both methods, and FIG. 14B lists the range of fusions detected by both cfDNA and cfRNA methods, or by one of the two methods and the detection of multiple co-occurring fusions detected by cfRNA. (*=fusion detected by both cfDNA and cfRNA).

FIGS. 18A-18B show the detection of expressed transcripts containing single nucleotide variation, insertion (e.g. duplication) or deletion mutations using cfRNA-based method described herein, wherein FIG. 18A shows single nucleotide variation, insertion or deletion mutations detected in tissue RNA extracted from FFPE tumor samples, and FIG. 18B shows single nucleotide variation detected in cfRNA extracted from plasma.

DETAILED DESCRIPTION

Figure 1:
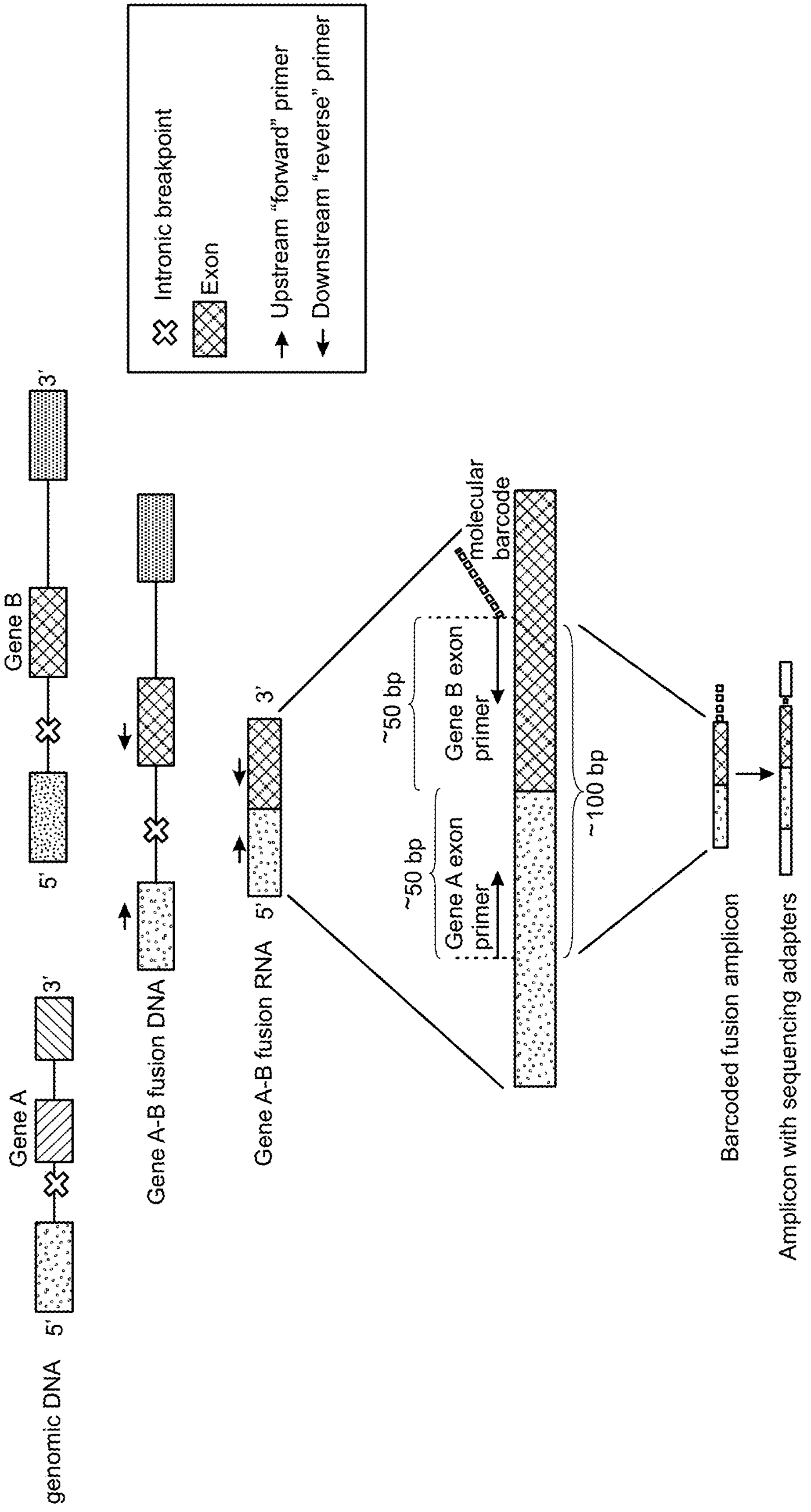
FIG. 1 is a general overview of the cfRNA-based detection method of a gene fusion event resulting from the intronic DNA rearrangement between two genes as described herein. Primers (represented by arrows) are designed to flank exonic junctions of genes known to undergo fusions. Primers (→) are designed such that the if a fusion product is present, the resulting amplicon would be of ~100 base pairs in length to be compatible with the observed cfRNA fragment size in plasma samples.

The disclosed method allows for detection of genomic alteration and gene expression as well as quantifying the level of gene expression of RNA (such as cfRNA) in a biological sample, for the purpose of non-invasive cancer detection, prognostication, and prediction of treatment response. The present disclosure describes a method based on highly multiplexed amplicon-based NGS, that involves the tagging of individual cfRNA molecules using barcode sequences, and the optimized design of amplicons to be compatible with the fragmented nature of cfRNA. The method described herein can be applied to circulating nucleic acid extracts containing both cfDNA and cfRNA, and can detect and quantitate fusion RNA transcript and gene expression simultaneously, in nucleic acid extracts samples. The applicability of cfRNA is extended in the present disclosure with a novel amplicon-based NGS assay combining fusion detection and gene expression monitoring. With hybridization-based library preparation methods sequence-specific biases due to enzymatic ligation during library construction step lead to biased representation of transcripts, particularly during analysis of small amount of input RNA. Targeted NGS assays such as hybridization capture or amplicon sequencing can allow for sensitive quantification of cfRNA. A targeted NGS-based method has a higher conversion efficiency as compared to whole transcriptome analysis, which has disadvantages such as cost and manpower.

In a first aspect, the present disclosure refers to a method of detecting genomic alteration and/or detecting gene expression and/or quantifying a level of gene expression using RNA in a biological sample, comprising:

(a) extracting RNA from the biological sample and converting the RNA to complementary DNA (cDNA);

(b) performing a plurality of multiplexed PCR reaction on the converted cDNA using (I) a plurality of forward and reverse primer pairs specific to a plurality of target genes that are capable of undergoing genomic alteration, wherein each forward primer of the plurality of forward and reverse primer pairs specific to the plurality of target genes that are capable of undergoing genomic alteration is complementary to a sequence located about 50 base pairs upstream of an exonic junction of each target gene that is capable of undergoing genomic alteration, wherein each reverse primer of the plurality of forward and reverse primer pairs specific to the plurality of target genes that are capable of undergoing genomic alteration is complementary to a sequence located about 50 base pairs downstream of an exonic junction of each target gene that is capable of undergoing genomic alteration, wherein each reverse primer of the plurality of forward and reverse primer pairs specific to the plurality of target genes that are capable of undergoing genomic alteration comprises a barcode sequence on its 5' end, wherein the barcode sequence of each reverse primer corresponding to each target gene that is capable of undergoing genomic alteration is different, and/or (II) a plurality of forward and reverse primer pairs specific to a plurality of control housekeeping genes, wherein:

(i) each forward primer of the plurality of forward and reverse primer pairs specific to the plurality of control housekeeping genes is complementary to a sequence spanning an exon-exon junction of each control housekeeping gene, wherein each reverse primer of the plurality of forward and reverse primer pairs specific to the plurality of control housekeeping genes is complementary to a sequence about 100 base pairs downstream of the sequence spanning the exon-exon junction of each control housekeeping gene, wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;

(ii) each reverse primer of the plurality of forward and reverse primer pairs specific to the plurality of control housekeeping genes is complementary to a sequence spanning an exon-exon junction of each control housekeeping gene, wherein each forward primer of the plurality of forward and reverse primer pairs specific to the plurality of control housekeeping genes is complementary to a sequence about 100 base pairs downstream of the sequence spanning the exon-exon junction of each control housekeeping gene, wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;

(iii) each forward and each reverse primer of the plurality of forward and reverse primer pairs specific to the plurality of control housekeeping genes is complementary to consecutive sequences spanning an exon-exon junction of each control housekeeping gene, wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different, and/or (III) a plurality of primer sets specific to a plurality of target genes related to protein expression, wherein each primer set comprises a plurality of forward and reverse primer pairs specific to each target gene related to protein expression, wherein:

(i) each forward primer of the of the plurality of forward and reverse primer pairs specific to each target gene related to protein expression is complementary to a sequence spanning an exon-exon junction of each target gene related to protein expression wherein each reverse primer of the of the plurality of forward and reverse primer pairs specific to each target gene related to protein expression is complementary to a sequence about 100 base pairs downstream of the sequence spanning the exon-exon junction of each target gene related to protein expression, wherein each reverse primer of the plurality of forward and reverse primer pairs specific to each target gene related to protein expression comprises a barcode sequence on its 5' end, wherein the barcode sequence of each reverse primer corresponding to each target gene related to protein expression is different, (ii) each reverse primer of the plurality of forward and reverse primer pairs specific to the plurality of target genes related to protein expression is complementary to a sequence spanning an exon-exon junction of each target gene related to protein expression, wherein each forward primer of the plurality of forward and reverse primer pairs specific to the plurality of target genes related to protein expression is complementary to a sequence about 100 base pairs downstream of the sequence spanning the exon-exon junction of each target gene related to protein expression, wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different;

(iii) each forward and each reverse primer of the plurality of forward and reverse primer pairs specific to the plurality of target genes related to protein expression is complementary to consecutive sequences spanning an exon-exon junction of each target gene related to protein expression, wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different, thereby generating a plurality of amplicons;

(c) purifying the plurality of amplicons from step (b);

(d) amplifying the purified product from step (c) by using universal indexed adapter primers to generate a sequencing library;

(e) purifying the sequencing library obtained from step (d);

(f) subjecting the purified sequencing library from step (e) to multiplex sequencing on a next-generation sequencing platform to obtain a plurality of sequencing reads;

(g) deriving a consensus read of each sequence from the plurality of sequencing reads obtained from step (f);

(h) performing a sequence alignment of the consensus read obtained from step (g) to a reference genome, (I) if the sequence alignment results in a partial alignment to the reference genome of an exon from a first gene and a partial alignment to the reference genome of an exon from a second gene, then:

(i) determining the sequence alignment as a split read, (ii) counting/enumerating the number of split reads from step (h)(I)(i) that supports a fusion junction, and (iii) if the number of split reads from step (h)(I)(ii) is two or more, then determining the first gene and the second gene as fusion partners, (II) if the sequence alignment results in an alignment to the reference genome of the control housekeeping gene, then:

(i) determining the sequence alignment as a consensus read of the control housekeeping gene, (ii) counting/enumerating consensus read pairs of the control housekeeping gene from step (h)(II)(i), and (iii) determining the level of gene expression of the control housekeeping gene, (III) if the sequence alignment results in an alignment to the reference genome of the target gene related to protein expression, (i) determining the sequence alignment as a consensus read of the target gene related to protein expression, (ii) counting/enumerating consensus read pairs of the target gene related to protein expression from step (h)(III)(i), and (iii) determining the level of gene expression of the target gene related to protein expression, (i) determining presence or absence of the genomic alteration and/or determining presence or absence of the gene expression and/or quantifying the level of the gene expression based on the sequence alignment from step (h).

In one example, the disclosed method is used to detect genomic alteration of RNA in a biological sample. For example, the method may be used to detect known and unknown fusions and their quantification, relative to the quantity of control housekeeping genes expression in a given sample. In another example, the disclosed method is used to detect gene expression of RNA in a biological sample. In yet another example, the disclosed method is used to quantify the level of gene expression of RNA in a biological sample. In a further example, the disclosed method is used to simultaneously detect genomic alteration of RNA and detect gene expression of RNA in a biological sample. In a further example, the disclosed method is used to simultaneously detect genomic alteration of RNA and quantify gene expression of RNA in a biological sample. In a further example, the disclosed method is used to simultaneously detect genomic alteration of RNA, detect gene expression of RNA, and quantify gene expression of RNA in a biological sample.

In one example, the disclosed method is used to detect genomic alteration of cfRNA in a biological sample. For example, the method may be used to detect known and unknown fusions and their quantification, relative to the quantity of control housekeeping genes expression in a given sample. In another example, the disclosed method is used to detect gene expression of cfRNA in a biological sample. In yet another example, the disclosed method is used to quantify the level of gene expression of cfRNA in a biological sample. In a further example, the disclosed method is used to simultaneously detect genomic alteration of cfRNA and detect gene expression of cfRNA in a biological sample. In a further example, the disclosed method is used to simultaneously detect genomic alteration of cfRNA and quantify gene expression of cfRNA in a biological sample. In a further example, the disclosed method is used to simultaneously detect genomic alteration of cfRNA, detect gene expression of cfRNA, and quantify gene expression of cfRNA in a biological sample.

In one example, the design of the primers to capture fusion transcripts has two main features—1) the presence of a random barcode sequence in the downstream primers (downstream relative to the target gene (e.g. fusion) transcript) to individually tag each copy of the RNA transcript if present, and 2) the location of each primer approximately 50 base pairs from each exonic junction in the panel, such that the expected total amplicon length would be close to 90-110 base pairs. This was done in order to meet the sample cfRNA size distribution observed which peaked at 110-120 nucleotides.

In one example, the plurality of forward and reverse primer pairs specific to a plurality of target genes that are capable of undergoing genomic alteration as disclosed in step (b)(I) is designed as shown in FIG. 1:

wherein each forward primer of the plurality of forward and reverse primer pairs specific to the plurality of target genes that are capable of undergoing genomic alteration is complementary to a sequence located about 50 base pairs upstream of an exonic junction of each target gene that is capable of undergoing genomic alteration, wherein each reverse primer of the plurality of forward and reverse primer pairs specific to the plurality of target genes that are capable of undergoing genomic alteration is complementary to a sequence located about 50 base pairs downstream of an exonic junction of each target gene that is capable of undergoing genomic alteration, wherein each reverse primer of the plurality of forward and reverse primer pairs specific to the plurality of target genes that are capable of undergoing genomic alteration comprises a barcode sequence on its 5' end, wherein the barcode sequence of each reverse primer corresponding to each target gene that is capable of undergoing genomic alteration is different.

Figure 2A:
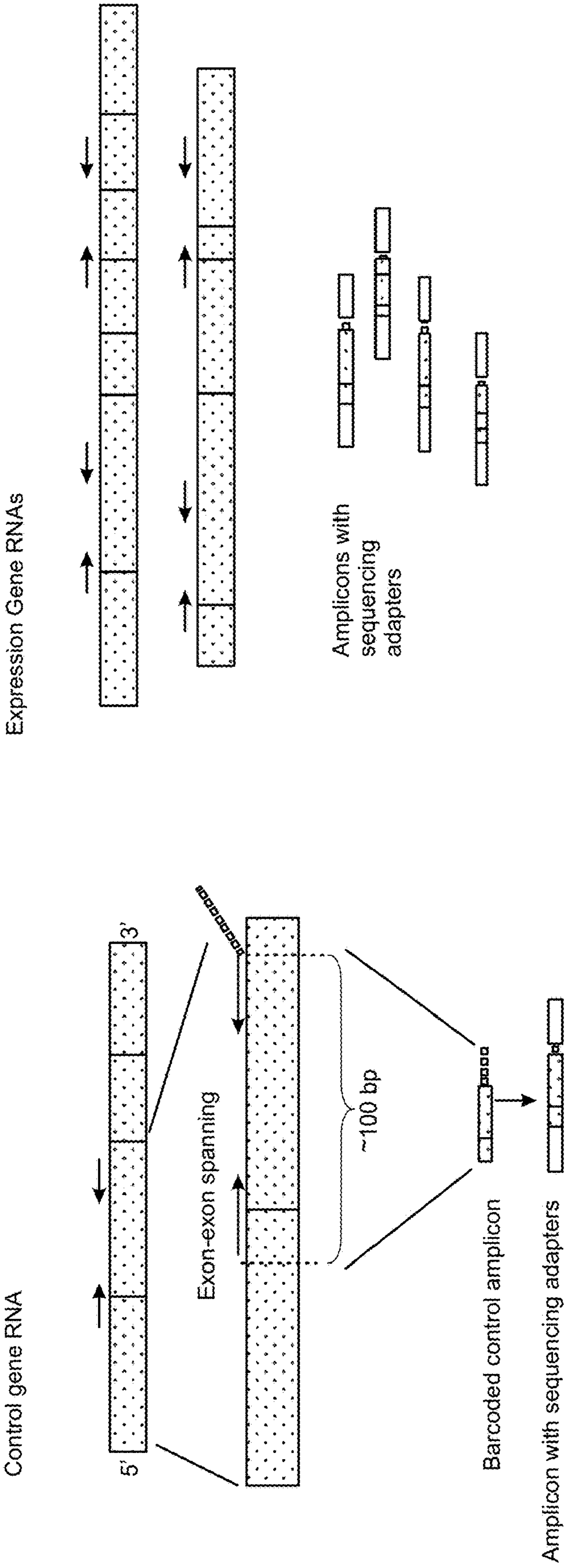

In one example, the plurality of forward and reverse primer pairs specific to a plurality of control housekeeping genes as disclosed in step (b)(II) is designed, wherein:

(i) each forward primer of the plurality of forward and reverse primer pairs specific to the plurality of control housekeeping genes is complementary to a sequence spanning an exon-exon junction of each control housekeeping gene, wherein each reverse primer of the plurality of forward and reverse primer pairs specific to the plurality of control housekeeping genes is complementary to a sequence about 100 base pairs downstream of the sequence spanning the exon-exon junction of each control housekeeping gene, wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different, as shown in FIG. 2A (left);

(ii) each reverse primer of the plurality of forward and reverse primer pairs specific to the plurality of control housekeeping genes is complementary to a sequence spanning an exon-exon junction of each control housekeeping gene, wherein each forward primer of the plurality of forward and reverse primer pairs specific to the plurality of control housekeeping genes is complementary to a sequence about 100 base pairs downstream of the sequence spanning the exon-exon junction of each control housekeeping gene, wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different;

(iii) each forward and each reverse primer of the plurality of forward and reverse primer pairs specific to the plurality of control housekeeping genes is complementary to consecutive sequences spanning an exon-exon junction of each control housekeeping gene, wherein each reverse primer of the plurality of forward and reverse primer pairs specific to the plurality of control housekeeping genes comprises a barcode sequence on its 5' end, wherein the barcode sequence of each reverse primer corresponding to each control housekeeping gene is different.

In one example, the plurality primer sets specific to a plurality of target genes related to protein expression as disclosed in step (b)(III) is designed, wherein each primer set comprises a plurality of forward and reverse primer pairs specific to each target gene related to protein expression, wherein:

(i) each forward primer of the of the plurality of forward and reverse primer pairs specific to each target gene related to protein expression is complementary to a sequence spanning an exon-exon junction of each target gene related to protein expression, wherein each reverse primer of the of the plurality of forward and reverse primer pairs specific to each target gene related to protein expression is complementary to a sequence about 100 base pairs downstream of the sequence spanning the exon-exon junction of each target gene related to protein expression, wherein each reverse primer of the plurality of forward and reverse primer pairs specific to each target gene related to protein expression comprises a barcode sequence on its 5' end, wherein the barcode sequence of each reverse primer corresponding to each target gene related to protein expression is different, as shown in FIG. 2A (right);

(ii) each reverse primer of the plurality of forward and reverse primer pairs specific to the plurality of target genes related to protein expression is complementary to a sequence spanning an exon-exon junction of each target gene related to protein expression, wherein each forward primer of the plurality of forward and reverse primer pairs specific to the plurality of target genes related to protein expression is complementary to a sequence about 100 base pairs downstream of the sequence spanning the exon-exon junction of each target gene related to protein expression, wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different;

(iii) each forward and each reverse primer of the plurality of forward and reverse primer pairs specific to the plurality of target genes related to protein expression is complementary to consecutive sequences spanning an exon-exon junction of each target gene related to protein expression, wherein each reverse primer of the plurality of forward and reverse primer pairs specific to the plurality of target genes related to protein expression comprises a barcode sequence on its 5' end, wherein the barcode sequence of each reverse primer corresponding to each target gene related to protein expression is different.

Figure 2B:
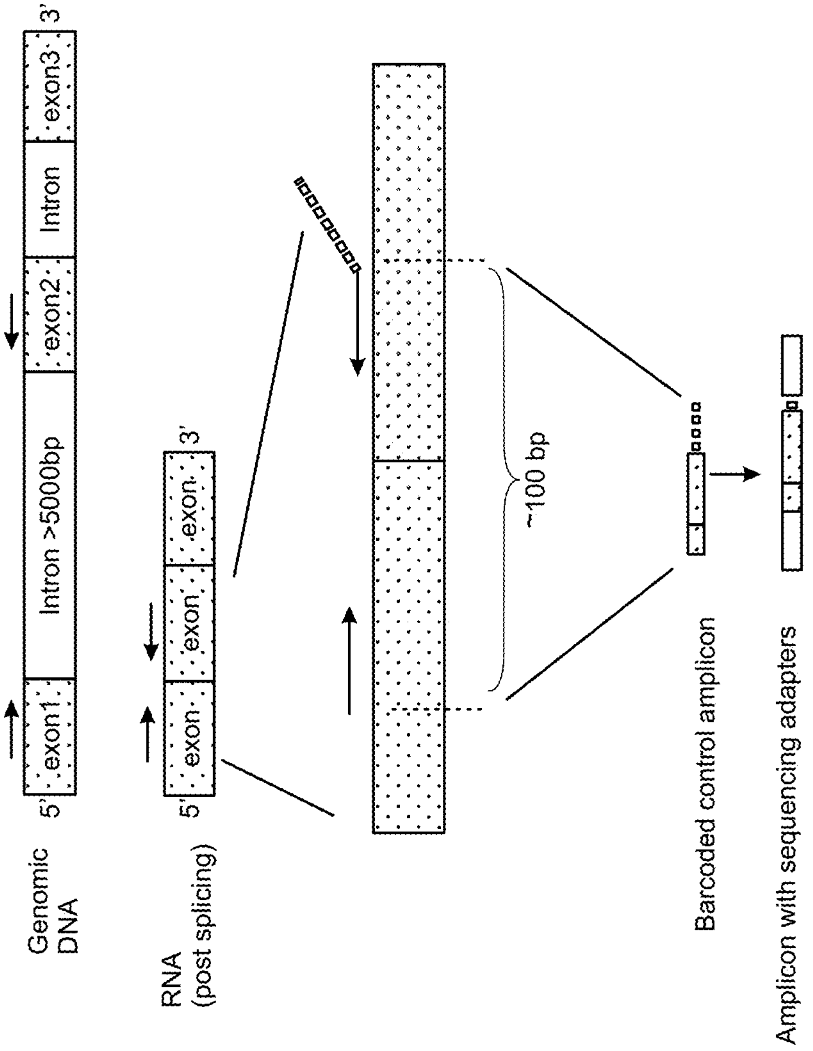

In one example, the forward primer of the plurality of forward and reverse primer pairs specific to a plurality of control housekeeping genes as disclosed in step (b)(II) is complementary to a sequence in a first exon and the reverse primer of the plurality of forward and reverse primer pairs specific to a plurality of control housekeeping genes as disclosed in step (b)(II) is complementary to a sequence in a second exon as shown in FIG. 2B, wherein the first exon and the second exon is intervened by an intron of >5000 base pairs in length, thereby avoiding unintended amplification of any genomic DNA during the plurality of multiplexed PCR reactions.

In one example, at least one of the primers of each forward and reverse primer pair of the plurality of forward and reverse primer pairs specific to a plurality of control housekeeping genes as disclosed in step (b)(II) span an exon-exon junction. In one example, at least one of the primers of each forward and reverse primer pair of the plurality of forward and reverse primer pairs specific to a plurality of target genes related to protein expression as disclosed in step (b)(III) span an exon-exon junction. In one example, at least one of the primers of each forward and reverse primer pair of the plurality of forward and reverse primer pairs specific to a plurality of control housekeeping genes as disclosed in step (b)(II), and/or at least one of the primers of each forward and reverse primer pair of the plurality of forward and reverse primer pairs specific to a plurality of target genes related to protein expression as disclosed in step (b)(III) span an exon-exon junction. In one example, a forward primer or a reverse primer of the plurality of forward and reverse primer pairs specific to a plurality of control housekeeping genes as disclosed in step (b)(II), and/or a forward primer or a reverse primer of the plurality of forward and reverse primer pairs specific to a plurality of target genes related to protein expression as disclosed in step (b)(III) span an exon-exon junction. In another example, both the forward primer and the reverse primer of the plurality of forward and reverse primer pairs specific to a plurality of control housekeeping genes as disclosed in step (b)(II), and/or both the forward primer and the reverse primer of the plurality of forward and reverse primer pairs specific to a plurality of target genes related to protein expression as disclosed in step (b)(III) span an exon-exon junction, wherein the exon length is about 100 base pairs.

In one example, each reverse primer of the plurality of forward and reverse primer pairs specific to a plurality of target genes that are capable of undergoing genetic alteration as disclosed in step (b)(I), each reverse primer of the plurality of forward and reverse primer pairs specific to a plurality of control housekeeping genes as disclosed in step (b)(II), and each reverse primer of the plurality of forward and reverse primer pairs specific to a plurality of target genes related to protein expression as disclosed in step (b)(III) comprise a barcode sequence on its 5' end, wherein each barcode sequence is different. As used herein, the term “barcode sequence” refers to an encoded molecule or barcode that includes variable amount of information within the nucleic acid sequence. For example, the barcode sequence is a tag that can be read out using any of a variety of sequence identification techniques, for example, nucleic acid sequencing, probe hybridization-based assay, and the like. In some examples, the barcode sequence is used in the method as described herein to tag different converted cDNA sequences of target regions of a sample, such that when the barcode sequence tags to the converted DNA sequences of target regions, each different converted cDNA sequence of target region would then have a unique barcode sequence that is attached to it and read out with the converted cDNA sequence of target region from the sample.

The barcode sequence allows the pooled analysis of multiple unique target sequences, where the resulting sequence information from the pool can be later attributed back to each starting target sequence. That is, after the process of amplification, the barcode sequence is used to group amplicons to form a family of amplicons having the same barcode sequence. In some examples, the barcode sequence is an overhang that does not complement any sequence within the target region. As each reverse primer carries on its 5' end a randomly assigned barcode sequence as disclosed herein, the barcode sequence allows individual cDNA molecules to be tagged uniquely in the step of sequencing library formation.

In one example, the barcode sequence is an oligonucleotide comprising 10 to 16 random nucleotides, or 10 to 15 random nucleotides, or 10 to 13 random nucleotides, or 10 random nucleotides, or 11 random nucleotides, or 12 random nucleotides, or 13 random nucleotides, or 14 random nucleotides, or 15 random nucleotides, or 16 random nucleotides. In one example, the barcode sequence is an oligonucleotide comprising 10 to 16 random nucleotides. In one example, the barcode sequence is an oligonucleotide comprising 10 random nucleotides. In one specific example, the barcode sequence is an oligonucleotide comprising 10 random nucleotides which can be represented as NNNNNNNNNN (SEQ ID NO: 615).

In one example, the typical length of each forward primer of the plurality of forward and reverse primers pairs as disclosed in step (b), excluding the barcode sequence and partial adapter sequence, is about 20 base pairs. In one example, the typical length of each reverse primer of the plurality of forward and reverse primers pairs as disclosed in step (b), excluding the barcode sequence and partial adapter sequence, is about 20 base pairs. In one example, the typical length of each forward primer of the plurality of forward and reverse primer pairs as disclosed in step (b), including the barcode sequence and partial adapter sequence, is about 45 base pairs, wherein the length of the barcode sequence is about 10 base pairs, wherein the length of the partial adapter sequence is about 20 base pairs. In one example, the typical length of each reverse primer of the plurality of forward and reverse primer pairs as disclosed in step (b), including the barcode sequence and partial adapter sequence, is about 45 base pairs, wherein the length of the barcode sequence is about 10 base pairs, wherein the length of the partial adapter sequence is about 20 base pairs.

In one example, the biological sample contains RNA. In one example, the RNA is cfRNA. In one example, the cfRNA is present freely in the biological sample and can be converted to cDNA directly as disclosed in step (a) of the disclosed method.

In one example, the cfRNA is extracted from the biological sample prior to step (a) of the disclosed method. In a further example, the RNA may be those that are originally encapsulated within cells and needs to be extracted prior to step (a) of the disclosed method. In one example, the cell may be any type of cell in the body. In one example, the cell is from bone, epithelial, cartilage, adipose tissue, nerves, muscle, connective tissue, esophagus, stomach, liver, gallbladder, pancreas, adrenal glands, bladder, gallbladder, large intestine, small intestine, kidneys, liver, pancreas, colon, stomach, thymus, spleen, brain, spinal cord, heart, lungs, eyes, corneal, skin, or islet tissue or organs. In one example, the cell may be a cancer cell, a stem cell, an endothelial cell, or a fat cell. In one example, the cell is a blood cell. The blood cell may be a white blood cell, or a platelet. In one example, the cell is selected from cancer cells known to harbour genomic alterations. In one example, the cell is selected from cancer cell lines known to harbour fusion genes. In one example, the cancer cell lines harbouring fusion genes may include, but are not limited to, CRL-9591, H-2228, CRL-2724, VCaP, CRL-5813, etc. Various methods for RNA extraction are known in the art and may be used for the purpose of the disclosed method. Various methods for RNA extraction are known in the art and may be used for the purpose of the disclosed method. In one example, the cfRNA is extracted from the biological sample before step (a) using a kit such as, but not limited to Zymo Quick-cfRNA Serum & Plasma Kit (Zymo Research), NextPrep™ Magnazol™ cfRNA Isolation Kit (PerkinElmer), Isopure Plasma cfDNA/RNA Isolation Kit (Aline Biosciences), QIAmp Circulating Nucleic Acid Kit (Qiagen), QlAamp ccfDNA/RNA Kit (Qiagen), MagMAX™ Cell-Free Total Nucleic Acid Isolation Kit (Applied Biosystems), etc.

In one example, the RNA extracted from cells are subjected to ultrasonification to thereby resemble the size of cfRNA more closely. In another example, the ultrasonification is achieved using Covaris, Qsonica, Diagenode Bioruptor, etc. In another example, the RNA extracted from the cells are subjected to heat and divalent cation-based fragmentation. In yet another example, the fragmentation is achieved using NEBNext® Magnesium RNA Fragmentation Module.

In one example, the biological sample contains both cfRNA and cfDNA. As used herein, cfDNA refers to non-encapsulated DNA which is present freely in a liquid sample disclosed herein and not contained within cells. The presence of long intervening introns which have undergone rearrangements prevents rearranged cfDNA from forming sequenceable products.

In the disclosed method, cfRNA present freely in the biological sample or those extracted from the biological sample, is first converted to cDNA as disclosed in step (a) of the method of the first aspect. In one example, cfRNA is converted to cDNA by reverse transcription. The term "reverse transcription" and its grammatical variants as used herein refers to the enzyme-mediated synthesis of a DNA molecule from an RNA template. The resulting DNA, known as complementary DNA (cDNA), can be used as a template for PCR amplification. Methods of reverse transcription, which typically involve the use of non-target specific primers (random primers), are well known in the art. In one example, cfRNA is converted to cDNA using a reverse transcription kit, wherein the reverse transcription kit comprises a reverse transcriptase enzyme and a plurality of random primers. In one example, the random primers are 6-mer primers, 7-mer primers, 8-mer primers, 9-mer primers or combinations thereof. In one example, the random primers are 6-mer (hexamer/hexanucleotide) primers. In one example, the reverse transcription kit is selected from, but is not limited to, High-Capacity cDNA Reverse Transcription Kit (Thermo Fisher Scientific), SuperScript IV One-Step RT-PCR System (Invitrogen), etc.

In one example, the biological sample containing the RNA is a liquid sample, a tissue sample, or a cell sample. In yet another example, the tissue sample is a frozen tissue sample or a fixed tissue sample. In another example, the fixed tissue sample is a Formalin-Fixed Paraffin-Embedded (FFPE) tissue sample. In another example, the liquid sample is a bodily fluid. In one example, the bodily fluid is selected from the group consisting of blood, bone marrow, cerebral spinal fluid, peritoneal fluid, pleural fluid, lymph fluid, ascites, serous fluid, sputum, lacrimal fluid, stool, urine, saliva, ductal fluid from breast, gastric juice, and pancreatic juice. In one example, the bodily fluid is blood. In one example, the blood is plasma.

In another example, the biological sample is obtained from a subject having and/or suspected of having a disease. In another example, the disease is cancer. In yet another example, the cancer is selected from the group consisting of leukemia, lung cancer, colorectal cancer, breast cancer, pancreatic cancer, prostate cancer, nasopharyngeal cancer, liver cancer, cholangiocarcinoma, esophageal cancer, urothelial cancer, and gastrointestinal cancer. In one example, the cancer is an early-stage cancer. In another example, the cancer is a late-stage or metastatic cancer. In one example, the cancer is selected from the group consisting of metastatic prostate cancer, metastatic lung cancer, metastatic breast cancer and leukemia.

In one example, the genomic alteration(s) detected using the disclosed method comprise(s) structural rearrangement(s). In one example, the term "rearrangement" refers to—rearrangement in the order of sections of the DNA. In one example, the structural rearrangement is a fusion, such as a gene fusion. In one example, the term "fusion" refers to structural variations produced through structural rearrangements, such as interchromosomal or intrachromosomal rearrangements. In one example, the structural rearrangement may include, but are not limited to, deletion, insertion (such as duplication), inversion, transversion, translocation, alternative splicing, and the like. In one example, the structural rearrangement results in formation of a fusion gene, such as one that is detectable using the methods disclosed herein. In one example, the "deletion" is a sequence change where at least one nucleotide is removed. In one example, the "deletion" is a sequence change where more than 10 nucleotides are removed. In one example, the "deletion" is a sequence change where more than 20 nucleotides are removed. In one example, the "deletion" is a sequence change where more than 30 nucleotides are removed. In one example, the "deletion" is a sequence change where more than 40 nucleotides are removed. In one example, the "deletion" is a sequence change where more than 50 nucleotides are removed. In one example, the "deletion" may be a "small deletion" where less than 50 nucleotides are removed. In one example, the "insertion" is a sequence change where at least one nucleotide is inserted between two nucleotides. In one example, the "insertion" is a sequence change where more than 10 nucleotides are inserted between two nucleotides. In one example, the "insertion" is a sequence change where more than 20 nucleotides are inserted between two nucleotides. In one example, the "insertion" is a sequence change where more than 30 nucleotides are inserted between two nucleotides. In one example, the "insertion" is a sequence change where more than 40 nucleotides are inserted between two nucleotides. In one example, the "insertion" is a sequence change where more than 50 nucleotides are inserted between two nucleotides. In one example, the "insertion" may be a "small insertion" where less than 50 nucleotides are inserted between two nucleotides. In one example, the "insertion" is a "duplication". In one example, the "duplication" is a sequence change where a copy of one or more nucleotides are inserted directly 3'-flanking of the original copy. In one example, the term "inversion" refers to a sequence change where more than one nucleotide replacing the original sequence are the reverse complement of the original sequence. In one example, the term "translocation" refers to rearrangement of parts between non-homologous chromosomes, which can result in "fusion". In one example, "altered splicing" refers to aberrant splicing of a single gene transcript that may cause one or more exons in sequence to be spliced out of the RNA, bringing usually more distant exons of the same gene in juxtaposition. Altered splicing involves the same gene, compared to fusion which is a definition reserved for two genes. In one example, altered splicing included MET exon 14 skipping where exon 14 of MET gene is spliced out bringing exon 13 and exon 15 in proximity, which is detectable using the method described herein (FIGS. 14A-14B). In one example, the genomic alteration(s) detected using the disclosed method comprise(s) single nucleotide variations. In one example, "single nucleotide variations" refer to variation in a single nucleotide that occurs at a specific position in the genome, differing from the nucleotide defining the position in the reference genome.

In one example, "housekeeping genes" refer to highly conserved genes which are essential for maintaining cellular function. In one example, the control housekeeping gene comprises Glucose-6-phosphate isomerase (GPI), FERM domain containing 8 (FRMD8), Small nuclear ribonucleoprotein D3 (SNRPD3), Proteasome subunit, beta type, 2 (PSMB2), TATA box binding protein (TBP), REL proto-oncogene, NF-kB subunit (REL), synaptosome associated protein 29 (SNAP29), Tubulin gamma complex associated protein 2 (TUBGCP2), Receptor accessory protein 5 (REEPS), Solute carrier family 4 member 1 adaptor protein (SLC4A1AP), Integrin subunit beta 7 (ITGB7), Protein-O-mannose kinase (POMK), ER membrane protein complex subunit 7 (EMC7), Nuclear autoantigenic sperm protein (NASP), Checkpoint with forkhead and ring finger domains (CHFR), Ribosomal RNA processing 1 (RRP1), Cytosolic iron-sulfur assembly component 1 (CIAO1), Pumilio RNA binding family member 1 (PUM1), Retention in endoplasmic reticulum sorting receptor 1 (RER1), Serine and arginine rich splicing factor 4 (SRSF4) (see FIG. 12B). The expression of housekeeping genes is assumed to be relatively constant across samples. For example, for samples containing the same amount of RNA, the number and expression of housekeeping genes will be similar. For example, for samples containing a smaller amount of RNA, the number and expression of housekeeping genes will be fewer than samples containing a larger amount of RNA, or vice versa. Therefore, the enumeration of RNA molecules of housekeeping genes on average can be used for the normalisation of RNA molecules of gene alteration targets and target genes related to protein expression.

In one example, the amount of cfRNA used in the method disclosed herein is at least 6 ng. In another example, the amount of cfRNA used in the method disclosed herein is about 6 ng to about 100 ng, or about 10 ng, or about 20 ng, or about 30 ng, or about 40 ng, or about 50 ng, or about 60 ng, or about 70 ng, or about 80 ng, or about 90 ng, or about 100 ng. In one example, the amount of cfRNA used in the method disclosed herein is 20 ng to 50 ng.

A multiplexed PCR reaction is then performed on the converted cDNA as disclosed in step (b) of the first aspect, using a plurality of forward and reverse primers pairs specific to a plurality of target genes that are capable of undergoing genomic alteration as disclosed in (b)(I), and/or a plurality of forward and reverse primer pairs specific to a plurality of control housekeeping genes as disclosed in (b)(II), and/or a plurality of forward and reverse primer pairs specific to a plurality of target genes related to protein expression as disclosed in (b)(III), wherein the plurality of forward and reverse primer pairs specific to a plurality of target genes that are capable of undergoing genomic alteration differ from that of a plurality of control housekeeping genes, and differ from that of a plurality of target genes related to protein expression.

In one example, the plurality of multiplexed PCR reaction on the converted cDNA in step (b) is performed using a plurality of forward and reverse primer pairs specific to a plurality of target genes that are capable of undergoing genomic alteration as disclosed in step (b)(I), a plurality of forward and reverse primer pairs specific to a plurality of control housekeeping genes as disclosed in step (b)(II), and a plurality of primer sets specific to a plurality of target genes related to protein expression as disclosed in step (b)(III). In one example, the plurality of multiplexed PCR reactions on the converted cDNA in step (b) is performed using a plurality of forward and reverse primer pairs specific to a plurality of target genes that are capable of undergoing genomic alteration disclosed in step (b)(I) and a plurality of forward and reverse primer pairs specific to a plurality of control housekeeping genes as disclosed in step (b)(II). In another example, the plurality of multiplexed PCR reactions on the converted cDNA in step (b) is performed using a plurality of forward and reverse primers specific to a plurality of control housekeeping genes as disclosed in step (b)(II) and a plurality of primer sets specific to a plurality of target genes related to protein expression as disclosed in step (b)(III). In one example, the plurality of multiplexed PCR reactions on the converted cDNA in step (b) is performed using a plurality of forward and reverse primer pairs specific to a plurality of target genes that are capable of undergoing genomic alteration as disclosed in step (b)(I) and a plurality of forward and reverse primer pairs specific to a plurality of target genes related to protein expression as disclosed in step (b)(III).

In one example, the multiplexed PCR reaction is performed on the converted cDNA using Platinum SuperFi II DNA Polymerase (Invitrogen), KAPA HiFi DNA Polymerase (Roche), Platinum Taq DNA Polymerase or Platinum SuperFi DNA Polymerase (Invitrogen) and Q5 High-Fidelity DNA Polymerase (NEB), etc.

In one example, the plurality of multiplexed PCR reactions performed on the converted cDNA comprises 3 to 15 PCR cycles. In one example, the PCR amplification comprises 3 PCR cycles. In one example, the PCR amplification comprises 4 PCR cycles. In one example, the PCR amplification comprises 5 PCR cycles. In one example, the PCR amplification comprises 6 PCR cycles. In one example, the PCR amplification comprises 7 PCR cycles. In one example, the PCR amplification comprises 8 PCR cycles. In one example, the PCR amplification comprises 9 PCR cycles. In one example, the PCR amplification comprises 10 PCR cycles. In one example, the PCR amplification comprises 11 PCR cycles. In one example, the PCR amplification comprises 12 PCR cycles. In one example, the PCR amplification comprises 13 PCR cycles.

In one example, the number of the forward and reverse primer pairs specific to the plurality of target genes that are capable of undergoing genomic alteration as disclosed in step (b)(I) is at least 100. In another example, the number of the plurality of forward and reverse primer pairs specific to the plurality of target genes that are capable of undergoing genomic alteration as disclosed in step (b)(I) is from 100 to 2000. In one example, the number of the forward and reverse primer pairs specific to the plurality of target genes that are capable of undergoing genomic alteration as disclosed in step (b)(I) is from 200 to 1900, or from 300 to 1800, or from 400 to 1700, or from 500 to 1600, or from 600 to 1500, or from 700 to 1400, or from 800 to 1300, or from 900 to 1200, or from 1000 to 1100. In one example, the number of the plurality of forward and reverse primer pairs specific to the plurality of target genes that are capable of undergoing genomic alteration as disclosed in step (b)(I) is about 100, about 200, about 300, or about 400, or about 500, or about 600, or about 700, or about 800, or about 900, or about 1000, or about 1100, or about 1200, or about 1300, or about 1400, or about 1500, or about 1600, or about 1700, or about 1800, or about 1900, or about 2000. In one example, there is no upper limit on the number of the plurality of forward and reverse primer pairs specific to the plurality of target genes that are capable of undergoing genomic alteration as disclosed in step (b)(I).

In one example, the number of the plurality of forward and reverse primer pairs specific to the plurality of control housekeeping genes as disclosed in step (b)(II) is at least 20. In one example, the number of the plurality of forward and reverse primer pairs specific to the plurality of control housekeeping genes as disclosed in step (b)(II) is from 20 to 300. In one example, the number of the plurality of forward and reverse primer pairs specific to the plurality of control housekeeping genes as disclosed in step (b)(II) is from 30 to 290, or from 40 to 280, or from 50 to 260, or from 60 to 250, or from 70 to 240, or from 80 to 230, or from 90 to 220, or from 100 to 210, or from 110 to 200, or from 120 to 190, or from 130 to 180, or from 140 to 170. In one example, the number of the plurality of forward and reverse primer pairs specific to the plurality of control housekeeping genes as disclosed in step (b)(II) is about 20, or about or about 40, or about 50, or about 60, or about 70, or about 80, or about 90, or about 100, or about 110, or about 120, or about 130, or about 140, or about 150, or about 160, or about 170, or about 180, or about 190, or about 200, or about 210, or about 220, or about 230, or about 240, or about 250, or about 260, or about 270, or about 280, or about 290, or about 300. In one example, there is no upper limit on the number of the plurality of forward and reverse primer pairs specific to the plurality of control housekeeping genes as disclosed in step (b)(II).

In one example, the number of the plurality of forward and reverse primer pairs specific to the plurality of target genes related to protein expression as disclosed in step (b)(III) is at least 10. In one example, the number of the plurality of forward and reverse primer pairs specific to the plurality of target genes related to protein expression as disclosed in step (b)(III) is from 10 to 1700. In one example, the number of the plurality of forward and reverse primer pairs specific to the plurality of target genes related to protein expression as disclosed in step (b)(III) is from 10 to 1700, or from 100 to 1600, or from 200 to 1500, or from 300 to 1400, or from 400 to 1300, or from 500 to 1200, or from 600 to 1100, or from 700 to 1000. In one example, the number of the plurality of forward and reverse primer pairs specific to the plurality of target genes related to protein expression as disclosed in step (b)(III) is about 10, or about 100, or about 200, or about 300, or about 400, or about 500, or about 600, or about 700, or about 800, or about 900, or about 1000, or about 1100, or about 1200, or about 1300, or about 1400, or about 1500, or about 1600, or about 1700. In one example, there is no upper limit on the number of the plurality of forward and reverse primer pairs specific to the plurality of target genes related to protein expression as disclosed in step (b)(III).

In another example, the maximum total number of plurality of forward and reverse primer pairs in the multiplexed PCR reaction is about 4000, wherein the number of plurality of forward and reverse primer pairs specific to a plurality of target genes that are capable of undergoing genomic alteration as disclosed in step (b)(I) is about 2000, wherein the number of plurality of forward and reverse primer pairs specific to a plurality of control housekeeping genes as disclosed in step (b)(II) is about 300, and wherein the number of plurality of forward and reverse primer pairs specific to a plurality of target genes related to protein expression as disclosed in step (b)(III) is about 1700.

In one example, the plurality of target genes that are capable of undergoing genomic alterations comprise an exon from a gene known to undergo fusion fused to an exon from a partner gene of the gene known to undergo fusion. In one example, the gene known to undergo fusion is selected from the group consisting ALK receptor tyrosine kinase, RET proto-oncogene, ROS proto-oncogene 1, fibroblast growth factor receptor 1 (FGFR1), fibroblast growth factor receptor 2 (FGFR2), fibroblast growth factor receptor 3 (FGFR3), neurotrophic receptor tyrosine kinase 1 (NTRK1), neurotrophic receptor tyrosine kinase 2 (NTRK2), neurotrophic receptor tyrosine kinase 3 (NTRK3), neuregulin 1 (NRG1), B-Raf proto-oncogene, serine/threonine kinase (BRAF), transmembrane serine protease 2 (TMPRSS2), MET proto-oncogene, receptor tyrosine kinase (MET), epidermal growth factor receptor (EGFR), estrogen receptor 1 (ESR1), platelet derived growth factor receptor alpha (PDGFRA), androgen receptor (AR), BCR activator of RhoGEF and GTPase (BCR), core-binding factor subunit beta (CBFB), lysine methyltransferase 2A (KMT2A), nucleophosmin 1 (NPM1), PML nuclear body scaffold (PML), and RUNX family transcription factor 1 (RUNX1). In one example, the partner gene of the gene known to undergo fusion is selected from the group consisting of EMAP like 4 (EML4), kinesin family member 5B (KIFSB), coiled-coil domain containing 6 (CCDC6), CD74 molecule (CD74), transforming acidic coiled-coil containing protein 3 (TACC3), ezrin (EZR), ETS transcription factor ERG (ERG), ArfGAP with GTPase domain, ankyrin repeat and PH domain 3 (AGAP3), A-kinase anchoring protein 9 (AKAP9), KIAA1549, tropomyosin 3 (TMP3), translocated promoter region, nuclear basket protein (TPR), trafficking from ER to golgi regulator (TFG), lamin A/C (LMNA), BicC family RNA binding protein 1 (BICC1), RAD51 recombinase (RAD51), CD47 molecule (CD47), Yes 1 associated transcriptional regulator (YAP1), ETS variant transcription factor 1 (ETV1), ETS variant transcription factor 4 (ETV4), ETS variant transcription factor 5 (ETV5), ETS variant transcription factor 6 (ETV6), factor interacting with PAPOLA and CPSF1 (FIP1L1), centriolin (CNTRL), ABL proto-oncogene 1, non-receptor tyrosine kinase (ABL1), AF4/FMR2 family member 1 (AFF1), MDS1 and EVI1 complex locus (MECOM), MLLT3 super elongation complex subunit (MLLT3), myosin heavy chain 11 (MYH11), PBX homeobox 1 (PBX1), retinoic acid receptor alpha (RARA), and RUNX1 partner transcriptional co-repressor 1 (RUNX1T1).

The method of the present disclosure is optimized for generating amplicons having certain sizes. The chosen length of 90-110 base pairs was considered optimal because products of shorter amplicons (<80 base pairs) would be less effectively retained through the multi-step library preparation method for amplicon sequencing. In one example, the length of the plurality of amplicons derived from cDNA in step (b) is 90 to 110 base pairs. In one example, the length of the plurality of amplicons derived from cDNA in step (b) is about 90 base pairs, or about 100 base pairs, or about 110 base pairs.

The plurality of amplicons derived from the cDNA in step (b) are then purified, as disclosed in step (c) of the first aspect.

The method of the present disclosure is designed to involve size-based separation (magnetic bead based) of smaller primer dimer artefacts to be removed and desired products to be retained, and excess primers to be enzymatically digested (e.g. using endonucleases and exonucleases). In one example, the purification of DNA is performed using an agent such as paramagnetic beads. In one example, the paramagnetic beads are selected from the group consisting of AMPure XP beads, SPRI beads, and Dynabeads. In one example, the paramagnetic beads are AMPure XP beads.

Next, the purified plurality of amplicons is amplified using universal indexed adapter primers to generate a plurality of sequencing library, as disclosed in step (d) of the first aspect.

In one example, the amplification is performed by using KAPA Hifi HotStart ReadyMix, Phusion U Hot Start DNA Polymerase (Thermo Scientific), ZymoTaq DNA Polymerase (Zymo Research) and Q5U Hot Start High-Fidelity DNA Polymerase (NEB), etc.

In one example, each universal indexed adapter primer as disclosed in step (d) comprises an adapter sequence. In one example, the term "adapter sequence" refers to any nucleotide sequence which can be added to an oligonucleotide of interest to prepare said oligonucleotide of interest for various purposes. The adapter sequences are complementary to the plurality of oligonucleotides present on the surface of the flow cells of the sequencing tools thereby allowing the DNA fragment to attach to the sequencing tool. In some examples, an adapter sequence allows for the sequencing of the oligonucleotide of interest. Sequencing platform specific adapter sequences are known in the art, and include, for example, the Illumina P5/P7 adapter sequences.

In one example, the universal indexed adapter primers as disclosed in step (d) of the method of the first aspect comprise:

a forward primer comprising the sequence of (SEQ ID NO: 616)
AATGATACGGCGACCACCGAGATCTACAC<u>CTAGCGCT</u>ACACTCTTTCCCT

ACACGACGCTCTTCCGATC*T;

and a reverse primer comprising the sequence of (SEQ ID NO: 617)
CAAGCAGAAGACGGCATACGAGAT<u>AACCGCGG</u>GTGACTGGAGTTCAGACG

TGTGCTCTTCCGATC*T,, wherein "*" represents a phosphorothioate bond, and wherein the underlined sequences are the barcode sequences. The plurality of sequencing library formed is then purified, as disclosed in step (e) of the first aspect.

In one example, the purification of the plurality of sequencing library is performed using an agent such as paramagnetic beads. In one example, the paramagnetic beads are selected from the group consisting of AMPure XP beads, SPRI beads, and Dynabeads. In one example, the paramagnetic beads are AMPure XP beads.

The purified plurality of sequencing library is then subjected to multiplex sequencing on a next-generation sequencing platform, as disclosed in step (f) of the first aspect, to obtain a plurality of sequencing reads.

In one example, the plurality of sequencing library is sequenced on NextSeq 550, NovaSeq 6000, or BGI MGISEQ-2000, DNBSEQ-G400, DNBSEQ-T7.

Figure 15:
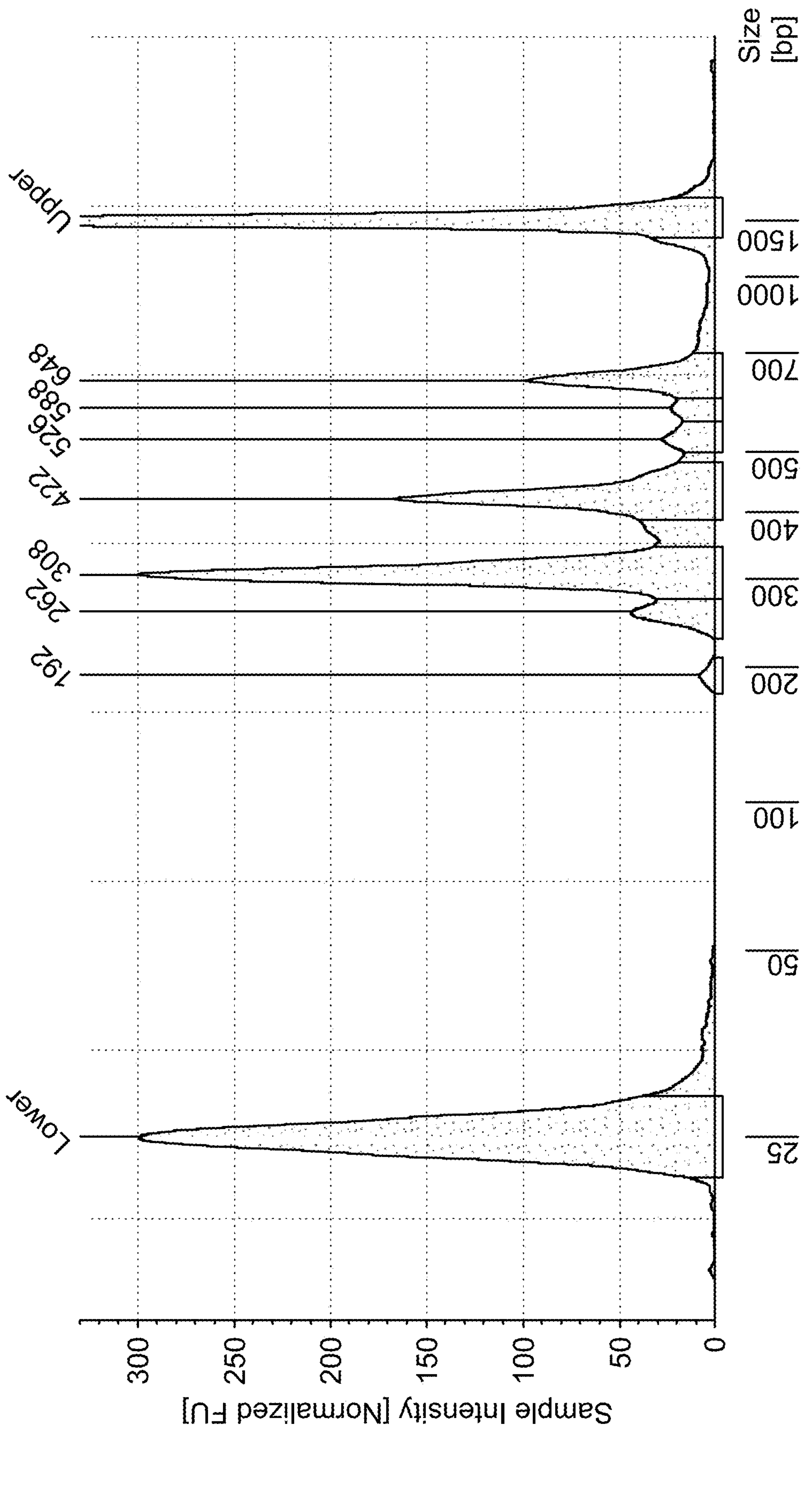
FIG. 15 illustrates a typical library profile for a cfRNA sample converted to a sequencing library as seen on the High Sensitivity DNA Screentape. The multiple peaks >200 base pairs correspond to the multiple products encompassing potential fusion products, control gene products and other gene expression products for which the multiplicity of forward and reverse primers are included. Qualified libraries will have prominent peaks of size >200 base pairs.

In one example, the plurality of sequencing library is qualified using the Agilent High Sensitivity DNA Screentape and quantified using KAPA Library Quantification Kit. In one example, the plurality of sequencing library is qualified by determining the size profile of the sequencing library which if successful will have a typical size profile of multiple prominent peaks greater than 200 base pairs (for example, as shown in FIG. 15).

Subsequently, a plurality of consensus reads is derived from each sequence of the plurality of sequencing reads obtained from step (f), as disclosed in step (g) of the first aspect. In one example, step (g) of the first aspect further comprises:

(g)(I) detecting the presence of the barcode sequence from each sequencing read, (g)(II) performing cluster reassignment for the plurality of sequencing reads having the same barcode sequence to generate a plurality of barcode clusters, wherein each barcode cluster contains reads from the same amplicon and with the same barcode sequence, and (g)(III) performing consensus calling for each barcode cluster to obtain the consensus read of each sequence.

The derived consensus sequence is aligned to the reference genome, as disclosed in step (h) of the first aspect. In one example, the term "reference genome" refers to DNA sequences known in the art that may be obtainable from public databases. In one example, the term "consensus read" refers to a nucleotide sequence obtained from consensus calling. In one example, consensus calling is performed by identifying the nucleotide at each position for each sequencing result within the subgroup, comparing the identity for the nucleotide at each position across the plurality of sequencing results, and determining a majority nucleotide at each position. If the majority nucleotide count is above a threshold set for determining majority for a specific position, the assignment for said position is the majority nucleotide. If the majority nucleotide count is below this threshold, no assignment is made for said position. The threshold is variable for every position and is a function of the total number of sequencing results corresponding to a specific position.

In one example, step (h) of the disclosed method further comprises, if the sequence alignment results in a partial alignment to the reference genome of an exon from a first gene and a partial alignment to the reference genome of an exon from a second gene as disclosed in step (h)(I), then the result is used to (i) determine the sequence alignment as a split read, (ii) count/enumerate the number of split reads from step (h)(I)(i) that supports a fusion junction, and (iii) if the number of split reads from step (h)(I)(ii) is two or more, determine the first gene and the second gene as fusion partners. In one example, step (h) of the disclosed method further comprises, if the sequence alignment results in an alignment to the reference genome of the control housekeeping gene as disclosed in step (h)(II), then the result is used to (i) determine the sequence alignment as a consensus read of the control housekeeping gene and (ii) count/enumerate consensus read pairs of the control housekeeping gene from step (h)(II)(i) to determine the level of gene expression of the control housekeeping gene. In one example, step (h) of the disclosed method further comprises, if the sequence alignment results in an alignment to the reference genome of the target gene related to protein expression as disclosed in step (h)(III), then the result is used to (i) determine the sequence alignment as a consensus read of the target gene related to protein expression and (ii) count/enumerate consensus read pairs of the target gene related to protein expression from step (h)(III)(i) to determine the level of gene expression of the target gene related to protein expression.

In one example, "consensus read pairs" refers to the consensus sequence called after collapsing all sequencing reads containing the same barcode sequence and primer pair. Each consensus read pair, for example, is presumed to belong to an original RNA molecule converted to cDNA. In one example, counting/enumerating as disclosed in step (h) is achieved based on the barcode sequence-based consensus counting, wherein each RNA molecule comprising the same barcode sequence and primer pair combination represents a unique RNA molecule. In one example, all reverse primers of the plurality of forward and reverse primer pairs as disclosed in step (b) of the first aspect comprise a barcode sequence. Therefore, all RNA molecules captured by a given barcode sequence and primer pair combination can be detected and counted/enumerated.

In one example, the alignment of the derived plurality of consensus sequence to the reference genome is performed using a sequence alignment tool. In one example, the alignment tool is STAR, HISAT2, bwa, CLC, RSEM, kallisto, salmon, etc.

The results of sequence alignment from step (h) is used to determine presence or absence of the genomic alteration and/or determine presence or absence of gene expression and/or quantify the level of gene expression as disclosed in step (i) of the first aspect.

In one example, the disclosed method further comprises visualisation and fusion calling of the sequence alignment from step (h)(I). In one example, the visualisation is performed using Integrated Genome Viewer, or Savant Genome Browser, etc. In one example, the fusion calling is performed using Arriba and Fusion Catcher, etc.

In one example, the step of determining presence or absence of the genomic alteration and/or determining presence or absence of the gene expression and/or quantifying the level of the gene expression, further comprises performing variant calling of the sequence alignment from step (h). In one example, the step of determining presence or absence of the genomic alteration and/or determining presence or absence of the gene expression and/or quantifying the level of the gene expression, further comprises performing variant calling of the sequence alignment from step (h)(II). In one example, the step of determining presence or absence of the genomic alteration and/or determining presence or absence of the gene expression and/or quantifying the level of the gene expression, further comprises performing variant calling of the sequence alignment from step (h)(III). In one example, the step of variant calling comprises: (i) identifying differences between a consensus read and a reference genome based on the sequence alignment from step (h); and ii) determining the read count of sequence alignments comprising genomic alteration. In one example, the step of variant calling comprises: (i) identifying differences between a consensus read and a reference genome based on the sequence alignment from step (h)(II); and ii) determining the read count of sequence alignments comprising genomic alteration. In one example, the step of variant calling comprises: (i) identifying differences between a consensus read and a reference genome based on the sequence alignment from step (h)(III); and ii) determining the read count of sequence alignments comprising genomic alteration. In one example, the genomic alteration is selected from the group comprising of insertions (e.g., duplications), deletions, and single nucleotide variants. In one example, the variant calling is performed using Mutect2 and a custom variant caller.

In one example, wherein the disclosed method of the first aspect is used to simultaneously detect gene expression, structural rearrangements and quantify gene expression in cfRNA from a biological sample, the expression level of genes that are known to be overexpressed in cancer cells is quantified. In one example, wherein the disclosed method of the first aspect is used to simultaneously detect genomic alteration in cfRNA and quantify gene expression in cfRNA from a biological sample, the expression level of target genes that have undergone genomic alterations is quantified. In one example, wherein the disclosed method of the first aspect is used to simultaneously detect gene expression and quantify gene expression of cfRNA, the expression level of target genes related to protein expression is quantified.

In one example, the statistical modelling technique used to visualise the level of expression of genes related to protein expression is heatmap visualisation, principal component analysis, hierarchical clustering, etc.

In a second aspect, the present disclosure refers to a kit for detecting genomic alteration and/or detecting gene expression and/or quantifying the level of gene expression using RNA in a biological sample according to the method of the first aspect, wherein the kit comprises:

(a) a plurality of forward and reverse primer pairs specific to a plurality of target genes that are capable of undergoing genomic alteration as defined in step (b)(I) of the method of the first aspect;
(b) a plurality of forward and reverse primer pairs specific to a plurality of control housekeeping genes as defined in step (b)(II) of the method of the first aspect; and
(c) a plurality of primer sets specific to a plurality of genes related to protein expression as defined in step (b)(III) of the method of the first aspect.

In one example, a person skilled in the art would be able to design the plurality of primer pairs and primer sets in (a), (b) and (c) of the kit of the second aspect based on the disclosure herein, for example, as described in steps (b)(I), (b)(II) and (b)(III) of the method of the first aspect. In one example, the plurality of primer sets specific to a plurality of genes related to protein expression as defined in step (b)(III) of the method of the first aspect provided in the kit as described herein may be used for determining presence or absence of the genomic alteration. In one example, the plurality of primer sets specific to a plurality of genes related to protein expression as defined in step (b)(III) of the method of the first aspect provided in the kit as described herein may be used for determining presence or absence of the genomic alteration such as deletions, insertions (e.g., duplications) and single nucleotide variations. In one example, the plurality of primer sets specific to a plurality of genes related to protein expression as defined in step (b)(III) of the method of the first aspect provided in the kit as described herein may be used for determining presence or absence of the genomic alteration by further performing the step of variant calling as described herein. In one example, the genomic alteration may be single nucleotide variation, insertion (e.g., duplications) or deletion. In one example, the kit for detecting genomic alteration and/or detecting gene expression and/or quantifying the level of gene expression of cfRNA in a biological sample according to the method of the first aspect further comprises a buffer for performing a plurality of multiplexed PCR reactions, a reverse transcriptase, a DNA polymerase, and a plurality of deoxynucleotide triphosphates (dNTPs). In some examples, the reagents provided in the kit as described herein may be provided in separate containers comprising the components independently distributed in one or more containers. As the method as described herein relates to sequencing (such as high-throughput sequencing), further components required in sequencing process could be easily determined by the person skilled in the art.

As used in this application, the singular form “a,” “an,” and “the” include plural references unless the context clearly dictates otherwise. For example, the term “a primer” includes a plurality of primers, including mixtures and combinations thereof.

As used herein, the terms “increase” and “decrease” refer to the relative alteration of a chosen trait or characteristic in a subset of a population in comparison to the same trait or characteristic as present in the whole population. An increase thus indicates a change on a positive scale, whereas a decrease indicates a change on a negative scale. The term “change”, as used herein, also refers to the difference between a chosen trait or characteristic of an isolated population subset in comparison to the same trait or characteristic in the population as a whole. However, this term is without valuation of the difference seen.

As used herein, the term “about” in the context of concentration of a substance, size of a substance, length of time, or other stated values means +/−5% of the stated value, or +/−4% of the stated value, or +/−3% of the stated value, or +/−2% of the stated value, or +/−1% of the stated value, or +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The present disclosure illustratively described herein may suitably be practiced in the absence of any element or elements, limitation or limitations, not specifically disclosed herein. Thus, for example, the terms “comprising”, “including”, “containing”, etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the present disclosure embodied therein herein disclosed may be resorted to by those skilled in the art, and that such modifications and variations are considered to be within the scope of this present disclosure.

The invention has been described broadly and generically herein. Each of the narrower species and subgeneric groupings falling within the generic disclosure also form part of the present disclosure. This includes the generic description of the present disclosure with a proviso or negative limitation removing any subject matter from the genus, regardless of whether or not the excised material is specifically recited herein.

Other embodiments are within the following claims and non-limiting examples.

EXAMPLES

Methods

Sample collection and Processing

Blood collected into Streck Cell-free DNA BCT® was shipped at ambient temperature before plasma separation. Briefly, blood plasma was prepared using a 2-step centrifugation process: first centrifugation was done at 1500×g for 10 min at 4° C. to separate plasma. The plasma layer was transferred to a separate tube and centrifuged at 15,000×g for 10 min at 4° C. to further remove cellular contaminants, and immediately processed for nucleic acid extraction or stored at −80° C. until used for extraction. If frozen, the plasma was fully thawed at room temperature before extraction.

Plasma cell-free total nucleic acids were extracted using the QlAamp Circulating Nucleic Acids kit (Qiagen). The nucleic acid extract contains co-eluted cfDNA and cfRNA fractions. The cfDNA was quantified using the Qubit Fluorometer (Thermo Fisher Scientific), and sized using the Genomic DNA ScreenTape on the 4200 TapeStation (Agilent). cfRNA was quantified and profiled using the Bioanalyzer RNA 6000 Pico kit or the High Sensitivity RNA Screentape on the 4200 Tapestation.

Design of Primers for Fusions and Expression in a Sequencing Library

A highly multiplex amplicon-based NGS assay was designed to capture potential fusions in cfRNA sample. Depending on the expected orientation of a partner exon in a fusion gene, a primer upstream of the exonic fusion junction (“forward” primer) or downstream of the fusion junction (“reverse” primer) was designed for the target gene’s exon. Broadly, multiple exon-flanking primers were designed for target genes that are known to participate in fusion events in cancer. For all downstream primers, a random 10-base pairs barcode sequence was incorporated upstream of the gene-specific sequence for consensus calling and unique molecule enumeration. A pool of >300 “forward” primers and >300 “reverse” primers was prepared. A multiplicity of “upstream” and “downstream” primers were included in the multiplex PCR to optimally capture potential fusions known to occur between genes. The design of primers included exons of well-characterized genes known to undergo fusions and the addition of barcode sequence primers allowed for accurate enumeration of copies of RNA transcript as per method of enumeration (FIG. 1).

For the capture of transcripts corresponding to control genes and other genes for which expression was to be quantified, primers were designed such that at least one primer of a pair landed on an exon-exon junction, or the primer pairs were within two exons intervened by an intron >5000 base pairs in length. These primers were also included in the final primer pools. The specificity of cfRNA amplification was verified by performing the whole cfRNA sequencing workflow, but with leaving out the reverse transcriptase enzyme during the complementary DNA preparation. Any sequencing for intended regions, particularly control and expression genes, when no reverse transcription was performed, could then be attributed to the primers amplifying cfDNA. Any such primers were redesigned to improve specificity for RNA by reducing the 3' exon span of the exon-exon spanning primer. The design of primers for target genes related to expression were similar to the control gene targets, and at least one primer of primer pair spanned an exon-exon junction, and two or more primer pairs were designed per target gene covering both 5' and 3' end exons, to more reliably capture expression of target genes for expression, by allowing one or more amplicons to represent a given target gene. A highly multiplexed primer pool was employed with a plurality of upstream and downstream primers, some of which are expected to generate sequenceable targets in most samples depending on expression variability, and some primers which are expected to generate a product only when a sample is positive for structural rearrangement, generating a fusion gene that is productively expressed. The primers additionally carried the appropriate extensions necessary for generating sequenceable libraries with sequencing adapters for Illumina sequencing (FIGS. 2A and 2B).

Preparation of cfRNA Sequencing library

Between 20-50 ng of cfRNA was converted to complementary DNA (cDNA) using the High-Capacity cDNA Reverse Transcription Kit (Thermo Fisher Scientific) in a total volume of 20 ul using random primers. The converted cDNA was used as a template in a highly multiplexed PCR reaction for target capture using the Platinum™ SuperFi II DNA Polymerase (Thermo Fisher Scientific). Briefly, cDNA was combined with primers and DNA Polymerase in a single reaction, and subjected to 3 to 15 cycles of PCR with the following conditions: 98° C., 1 min; 60° C., 1 min; 72° C., 1 min, followed by a final extension for 5 min at 72° C. The amplification product was subjected to one round of enzymatic digestion (using exonucleases, Exof and ExoT) and two rounds of clean-up using 1.8× volume of AMPure XP beads and eluted in Buffer EB or nuclease-free water. The purified PCR products were then amplified with universal indexed adapter primers, compatible for sequencing with Illumina platform, with primers using KAPA HiFi HotStart ReadyMix. The final amplified library was purified with two rounds of 0.8× volume AMPure XP beads to remove excess adapters and size-select the final sequencing library. Library was quantified using the High Sensitivity DNA Screentape and quantified using KAPA Library Quantification Kit. Each library was sequenced on a Nextseq 550 to a depth of 3 million paired-end reads per sample.

Data Analysis

FASTQ files were processed using a custom pipeline. First, sequenced amplicons were identified and labelled in the FASTQ files based on the presence of any potential primer sequences in the right directionality, upstream or downstream (from a predetermined list of primer sequences based on panel design) in Read 1 and paired Read 2. Barcode sequence sequences in read 1 were identified upstream of primer in Read 1 and trimmed using cutadapt. The extracted molecular tag sequences were used to derive the consensus read sequence for all duplicate reads of a sequence identifiable by a given primer pair and unique barcode sequence. The consensus reads were then written to a new FASTQ file and aligned to human genome reference hg19 using STAR aligner. Fusion reads in which non-contiguous regions of the genome are captured within a read were identified as split reads and fusion partners were identified based on the sequence alignment. The presence of split read sequences mapping to two reciprocal partner genes were additionally confirmed to have been captured by primers specific to identified genes. Number of split reads (read pairs) supporting a fusion junction were enumerated. Visualization and fusion calling were also performed using Arriba and FusionCatcher. At least 2 supporting split reads were required for calling fusion and exon skipping variants (transcript variants). With molecular barcoding, the sequencing is error-free and increases confidence fusion calls due to the high quality of sequencing data.

Expression-level analysis was done by enumerating consensus read pairs which supported a given amplicon predefined by primer pairs for expression. Read pair counts were enumerated and tabulated for downstream analysis as control genes or target genes. Variant calling was performed on consensus BAM files using Mutect2 and a custom variant caller to identify single nucleotide variations, insertion and deletion mutations relative to the reference sequence. Expression of mutant transcripts comprising single nucleotide variations, insertion and deletion was quantified based on the number of reads containing the particular single nucleotide variation, insertion or deletion mutation and mapping to the intended target region. Expression of wild-type transcripts was quantified based on the number of reads matching the reference sequence and mapping to the intended target region. The relative expression of each mutation was also determined based on the proportion of mutant read counts relative to total read counts.

Results

The present disclosure describes a method for the simultaneous detection and quantification of clinically relevant genomic and gene expression alteration using cfRNA, with high sensitivity, specificity, and minimal invasive procedures.

Figure 3A:
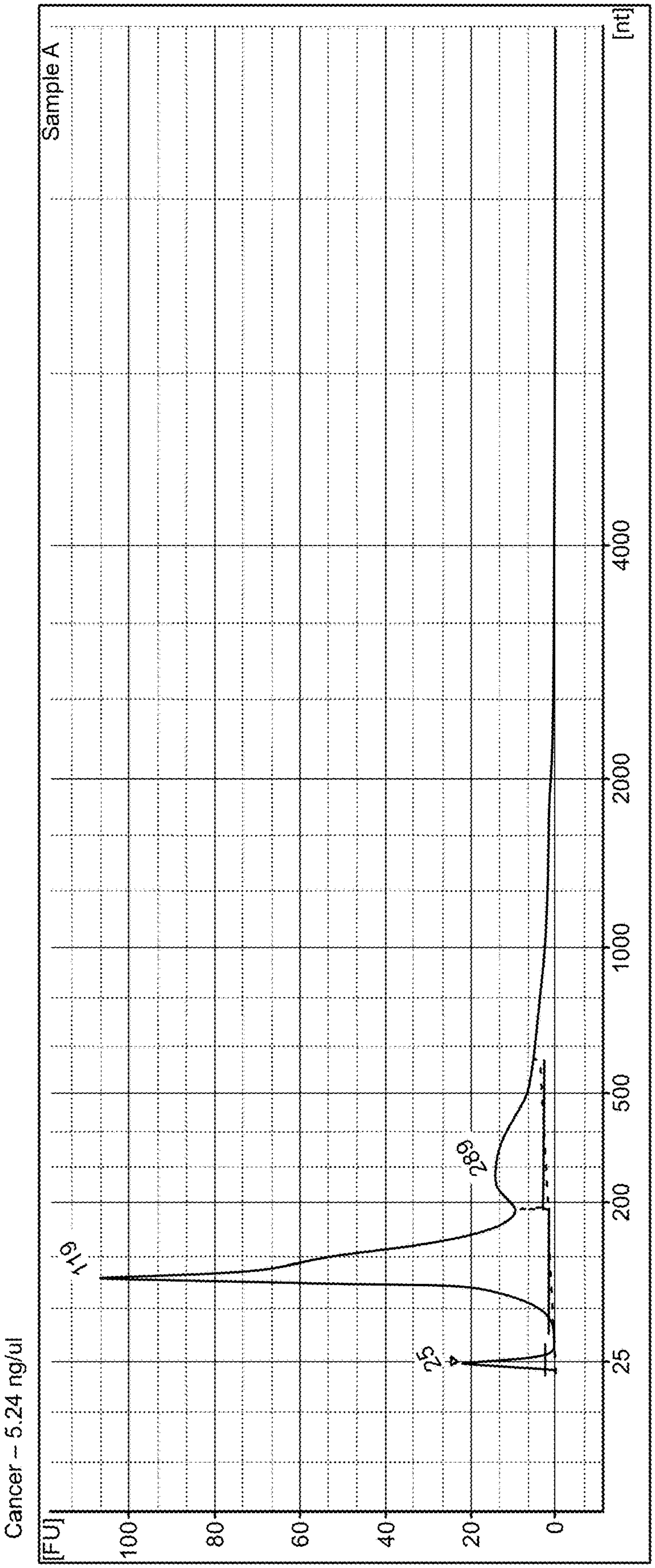
Figure 3B:
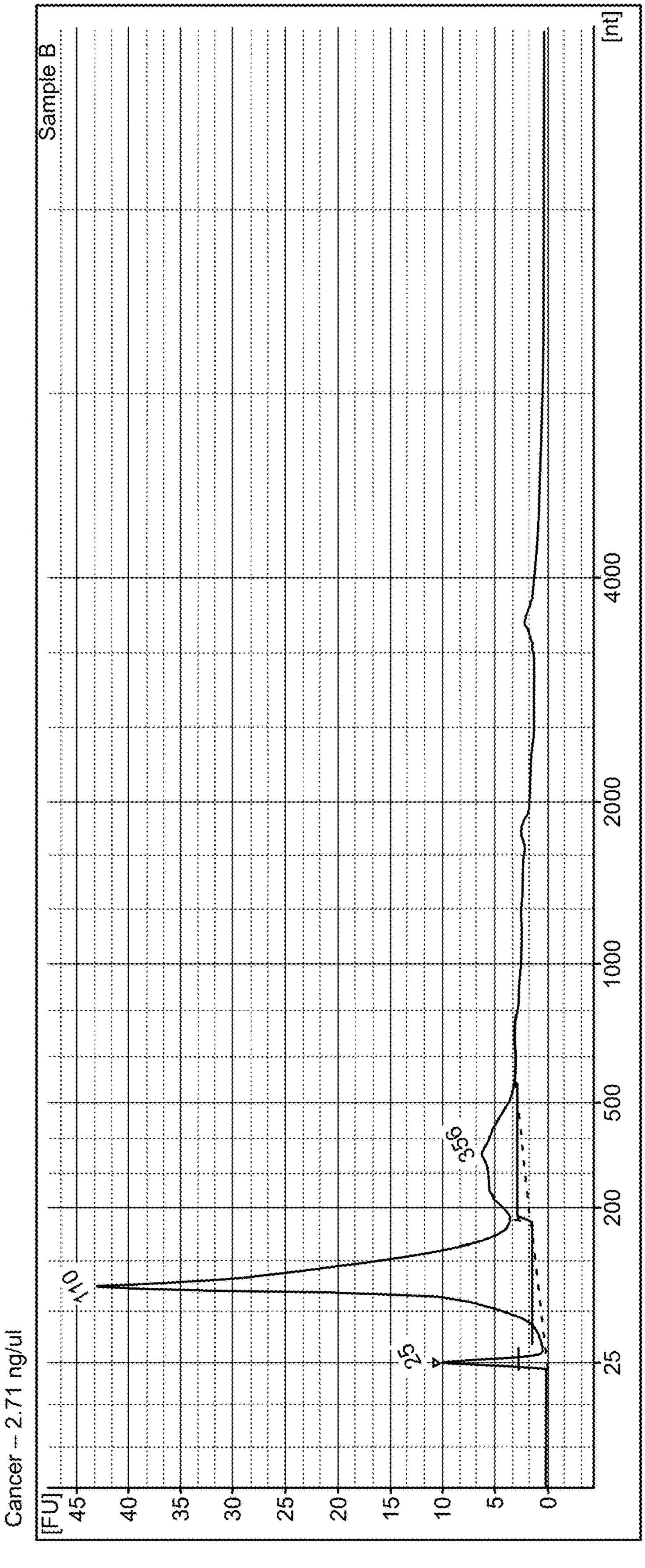
Figure 3C:
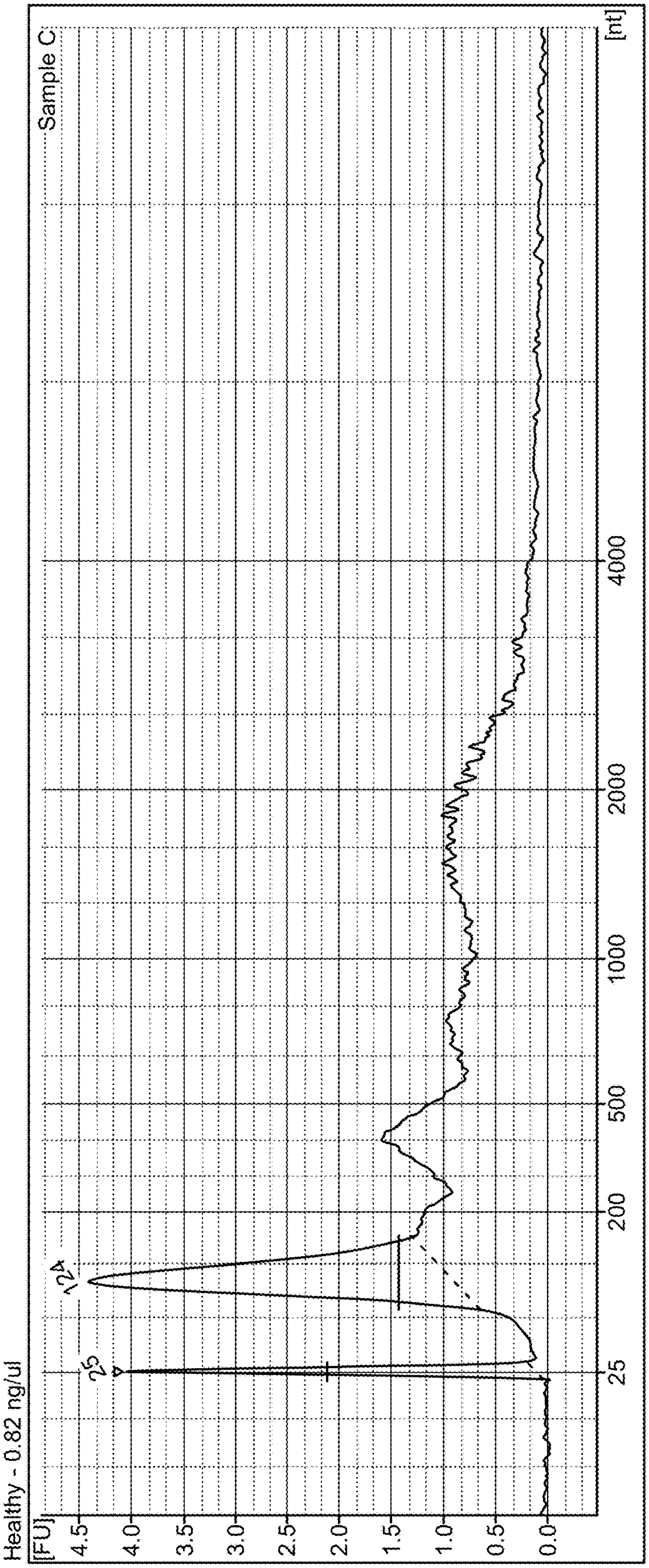
Figure 3D:
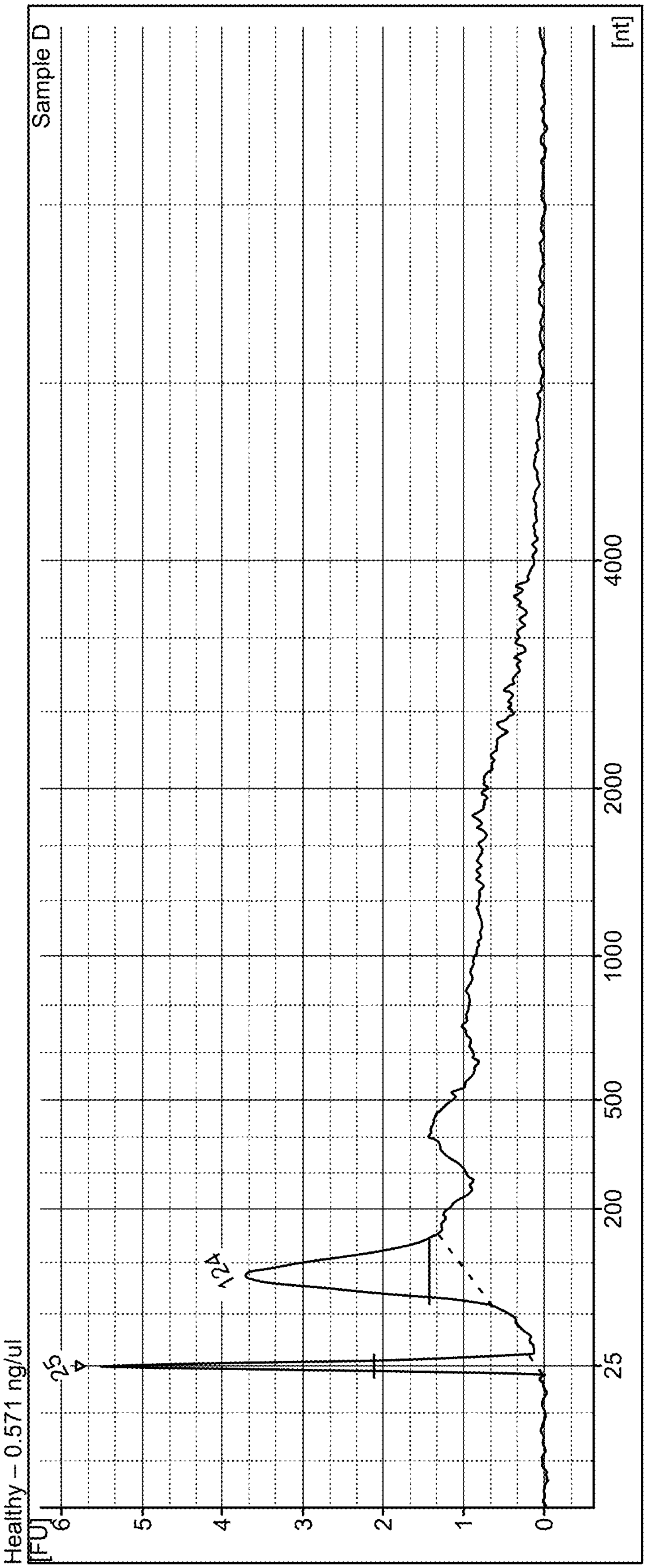

Validation of cfRNA-Based Detection Assay: Relative Abundance of Cell-Free Nucleic Acid in Plasma Total cfRNA concentration from plasma of healthy individuals and cancer patients were characterized for presence of cfRNA and analyzed for fragment size distribution using Bioanalyzer RNA 6000 Pico assay. cfRNA was present in all cancer samples and showed a predominant peak at 110 to 120 nucleotides in size and a second population of RNA in the 200 to 300 nucleotides range (FIGS. 3A and 3B). In terms of relative abundance, the shorter fragments (110 to 120 nucleotides) were about 5 to 10 times more abundant than the larger size RNA fragments (200 to 300 nucleotides). cfRNA from healthy individuals also showed the same pattern of size distribution, but at significantly lower cfRNA concentrations (FIGS. 3C and 3D).

Total nucleic acid extracts comprising cfDNA and cfRNA from plasma of healthy and cancer individuals were analyzed. Relative to each extract's cfDNA concentration, cfRNA concentrations were generally lower, and differed most significantly when the concentration of cfDNA exceeded 10 ng/ml plasma (FIG. 4).

Figure 5A:
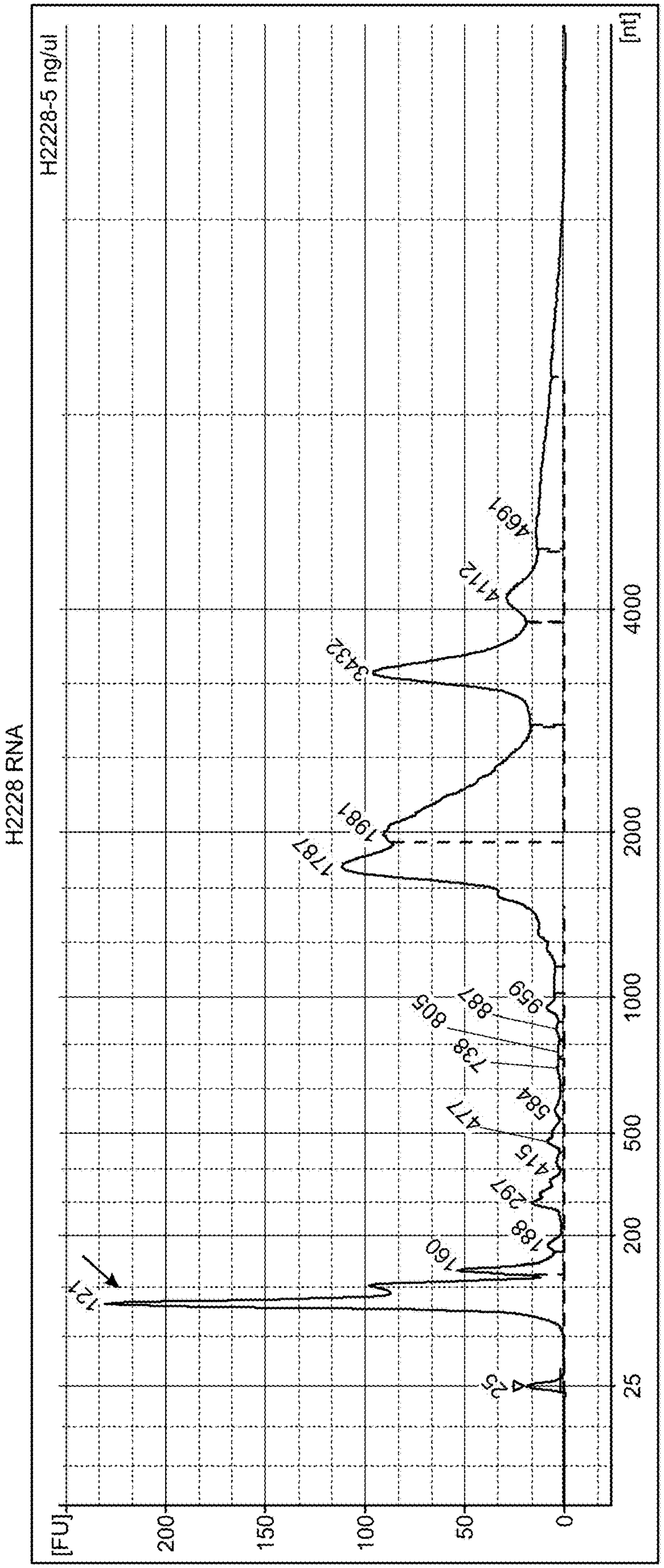
Figure 5B:
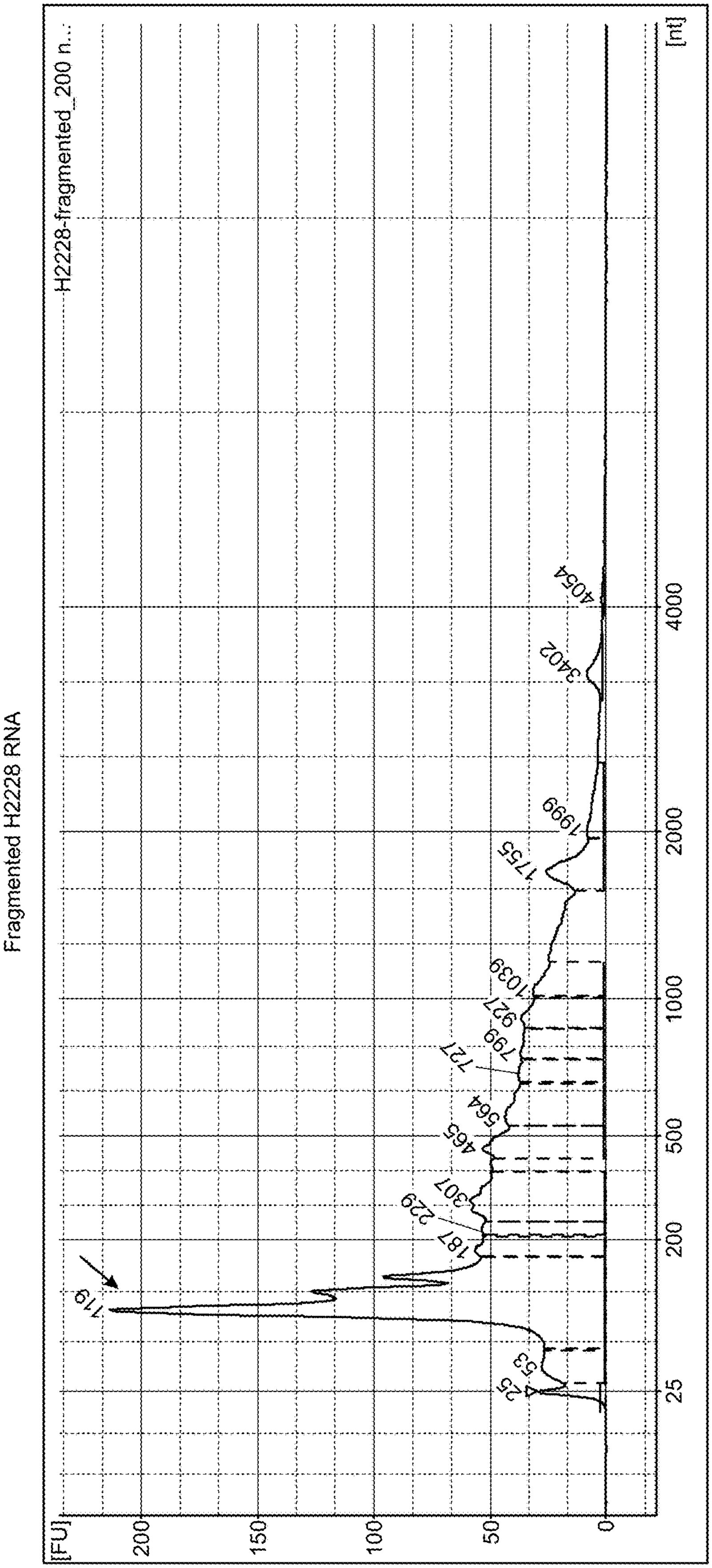
Figure 5C:
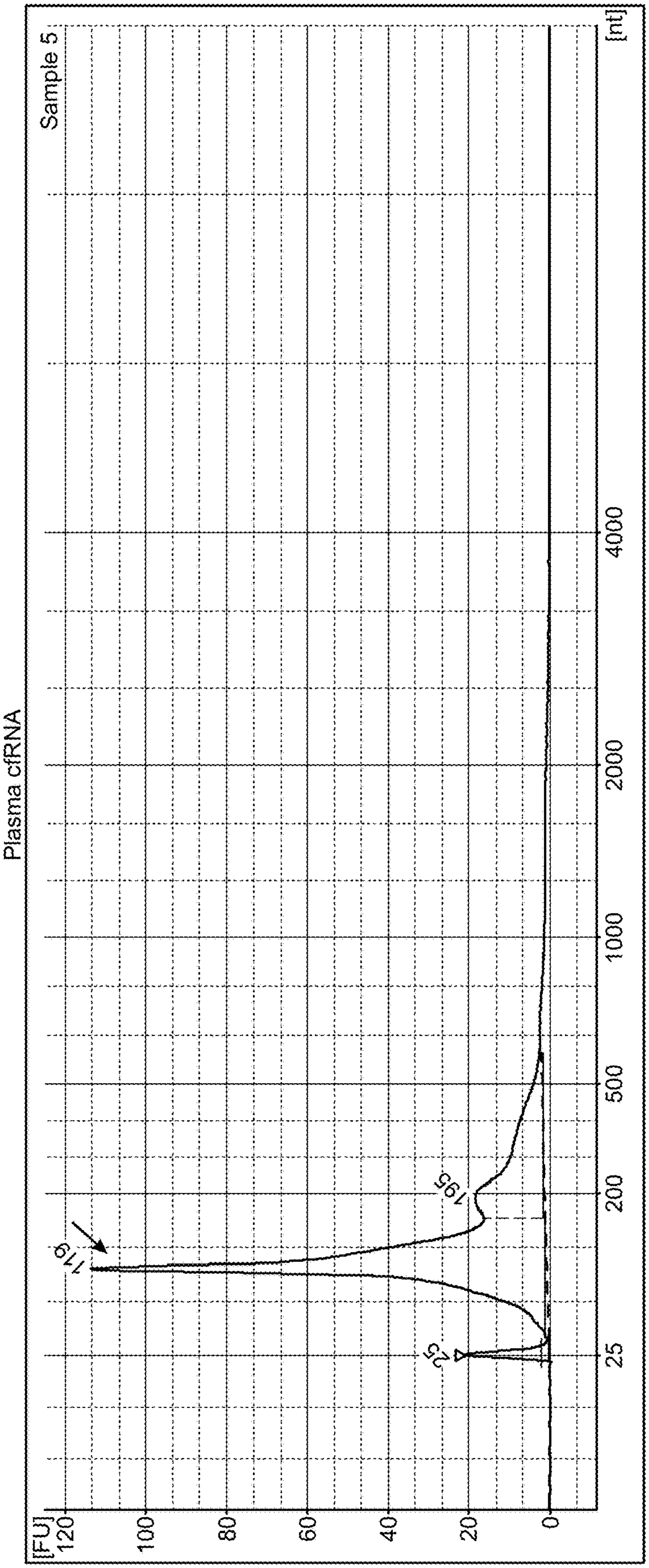
Figure 7:
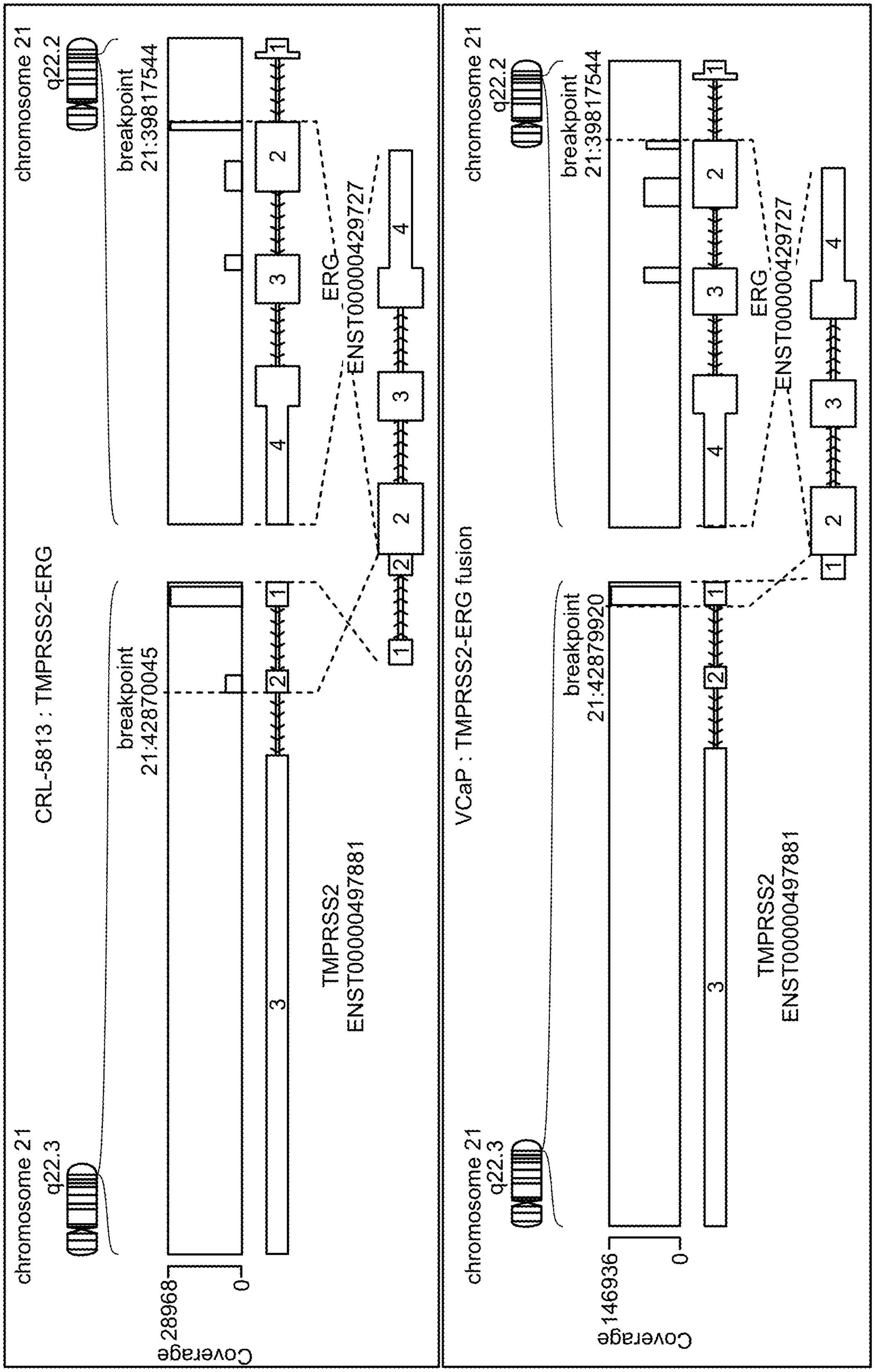
FIG. 7 is a diagrammatic representation from Arriba tool showing the detection of various exonic fusion in cancer cell lines: NCI-H660 cell line (CRL-5813, ATCC), VCaP cell line (CRL-2876, ATCC), MV-4-11 cell line (CRL-9591, ATCC) and Kasumi-1 cell line (CRL-2724, ATCC), using the multiplex amplicon sequencing method as described herein for fragmented RNA samples.
Figure 7:
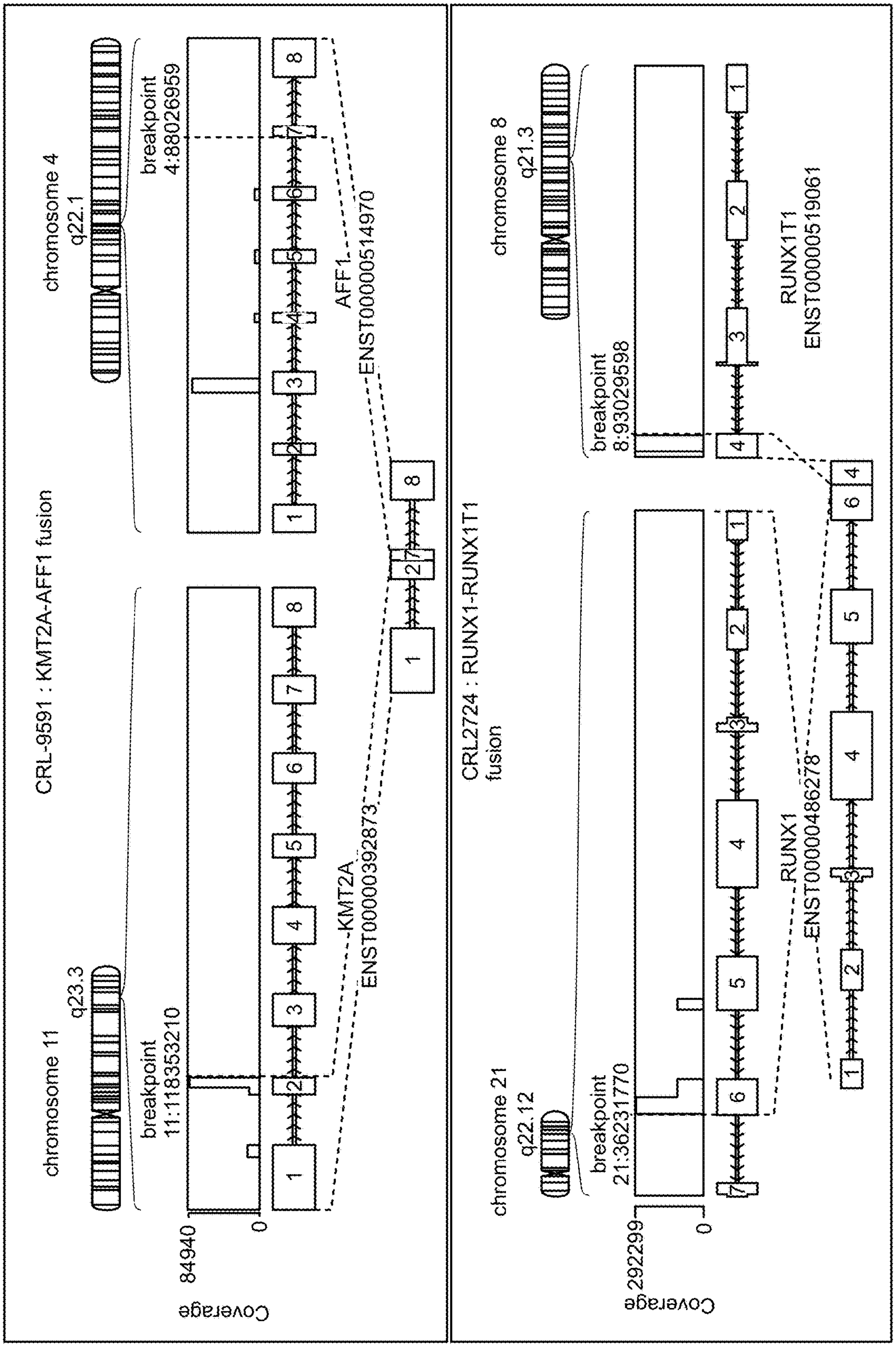

Technical Validation of cfRNA-Based Multiplex Amplicon Sequencing Detection with RNA Extracted from Cancerous Cell Lines The method described herein showed the ability to detect fusions using RNA extracted from cultured cancer cell lines known to harbor fusion genes, such as CRL-9591 (KMT2A-AFF 1), H2228 (EML4-ALK), CRL-2724 (RUNX1-RUNX1T1), VCaP (TMPRS S2-ERG) and CRL-5813 (TMPRSS2-ERG). As RNA from cultured cells is relatively intact compared for plasma cfDNA, the cell line RNA was subjected to ultrasonication (using Covaris) in order to more closely resemble the size of cfRNA. The resulting fraction as used to mimic cfRNA to demonstrate the performance of the multiplex amplicon sequencing for the detection of a variety of known fusions (FIGS. 5A, 5B and 5C), This was used to provide adequate material to mimic cfRNA to demonstrate the performance of the multiplex amplicon sequencing for the detection of a variety of known fusions. RNA-based detection of fusions in all five cancer cell lines was successful (FIG. 7). The plurality of sequencing library obtained can be qualified using the Agilent High Sensitivity DNA Screentape as shown in FIG. 15, which illustrates a typical library profile for a cfRNA sample converted to a sequencing library as seen on the High Sensitivity DNA Screentape. The multiple peaks >200 base pairs correspond to the multiple products encompassing potential fusion products, control gene products and other gene expression products for which the multiplicity of forward and reverse primers are included. Qualified libraries will have prominent peaks of size >200 base pairs.

Figure 6A:
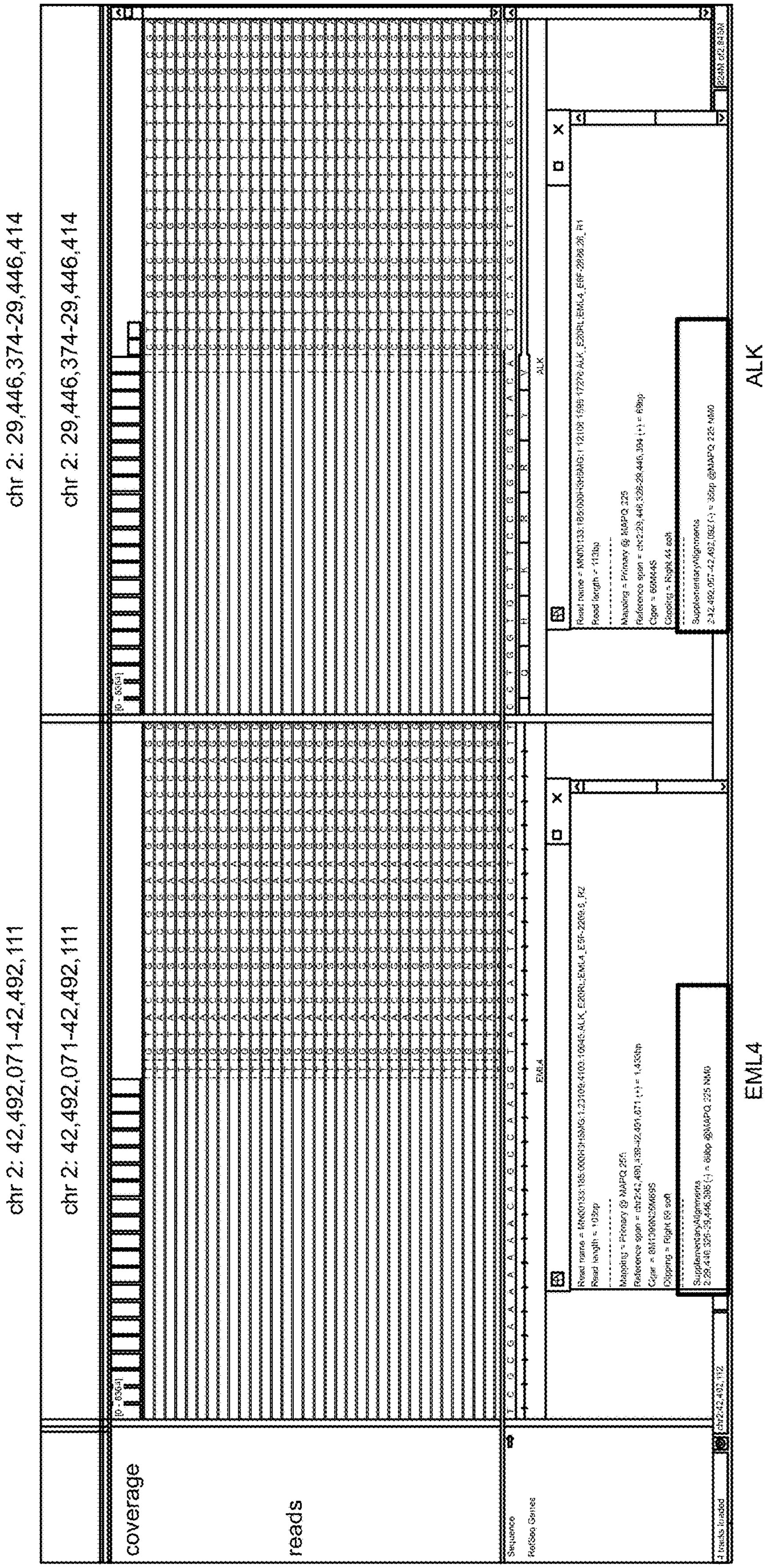
Figure 6B:
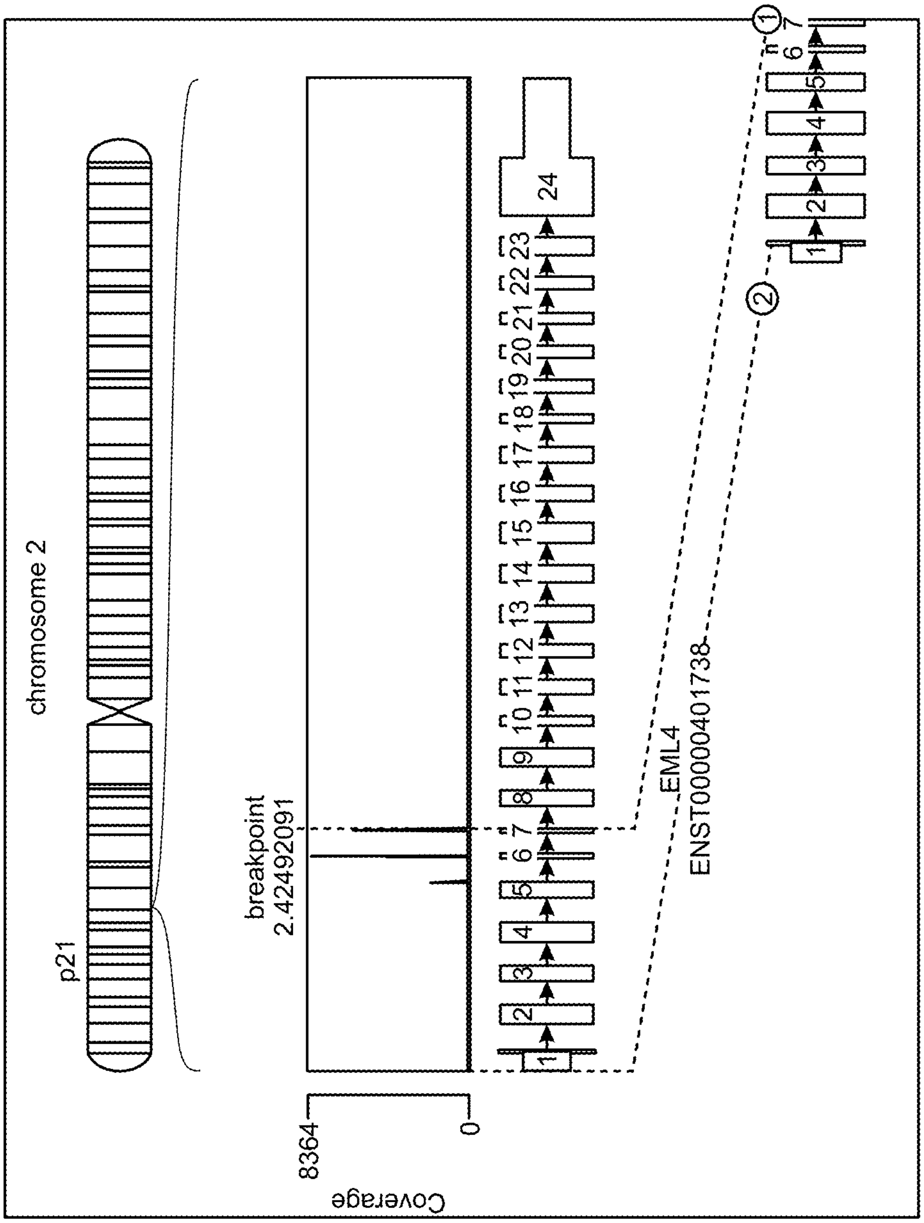
Figure 6B:
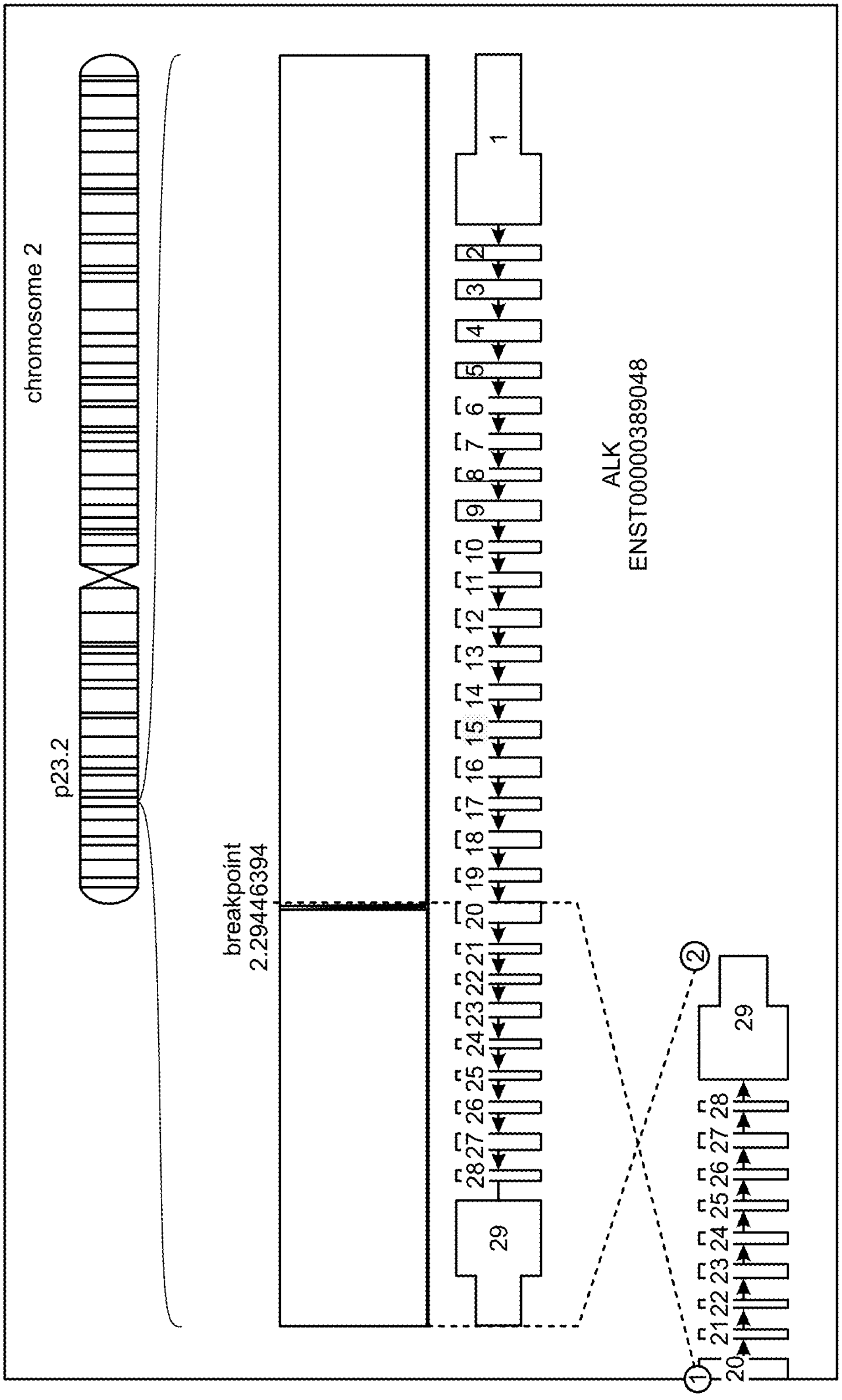

Sequence alignments to the reference genome showed the capture of sequencing reads with partial alignment to the target exon, and partial alignment to another part of the genome sequence of which corresponds to the partner gene exon, known as a split read, and confirmed the detection of the EML4-ALK fusion transcript in H2228 cell line with as little as 1 ng of fragmented RNA with 8364 reads supporting the split configuration. (FIGS. 6A and 6B). The alignment of split reads showed that fusions in cancer cell lines: NCI-H660 cell line (CRL-5813, ATCC), VCaP cell line (CRL-2876, ATCC), Human MV-4-11 cell line (CRL-9591, ATCC) and Kasumi-1 (CRL-2724, ATCC), were accurately detected as visualized by Arriba tool for detection of fusions in RNA sequencing data using the multiplex amplicon sequencing method in fragmented RNA. (FIG. 7).

Data Comparison Between cfDNA and cfRNA-Based Detection Assay

Figure 8A:
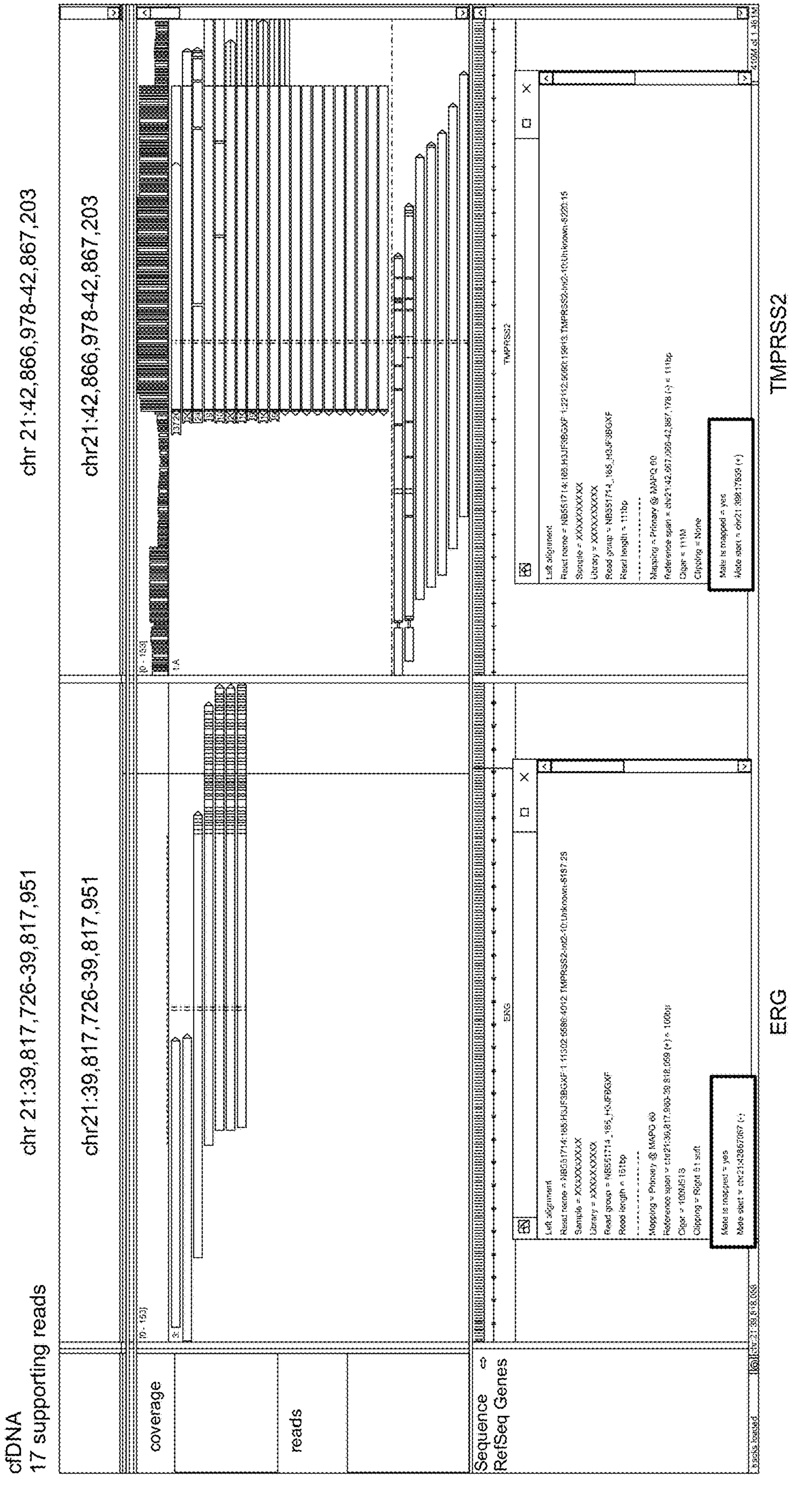
Figure 8B:
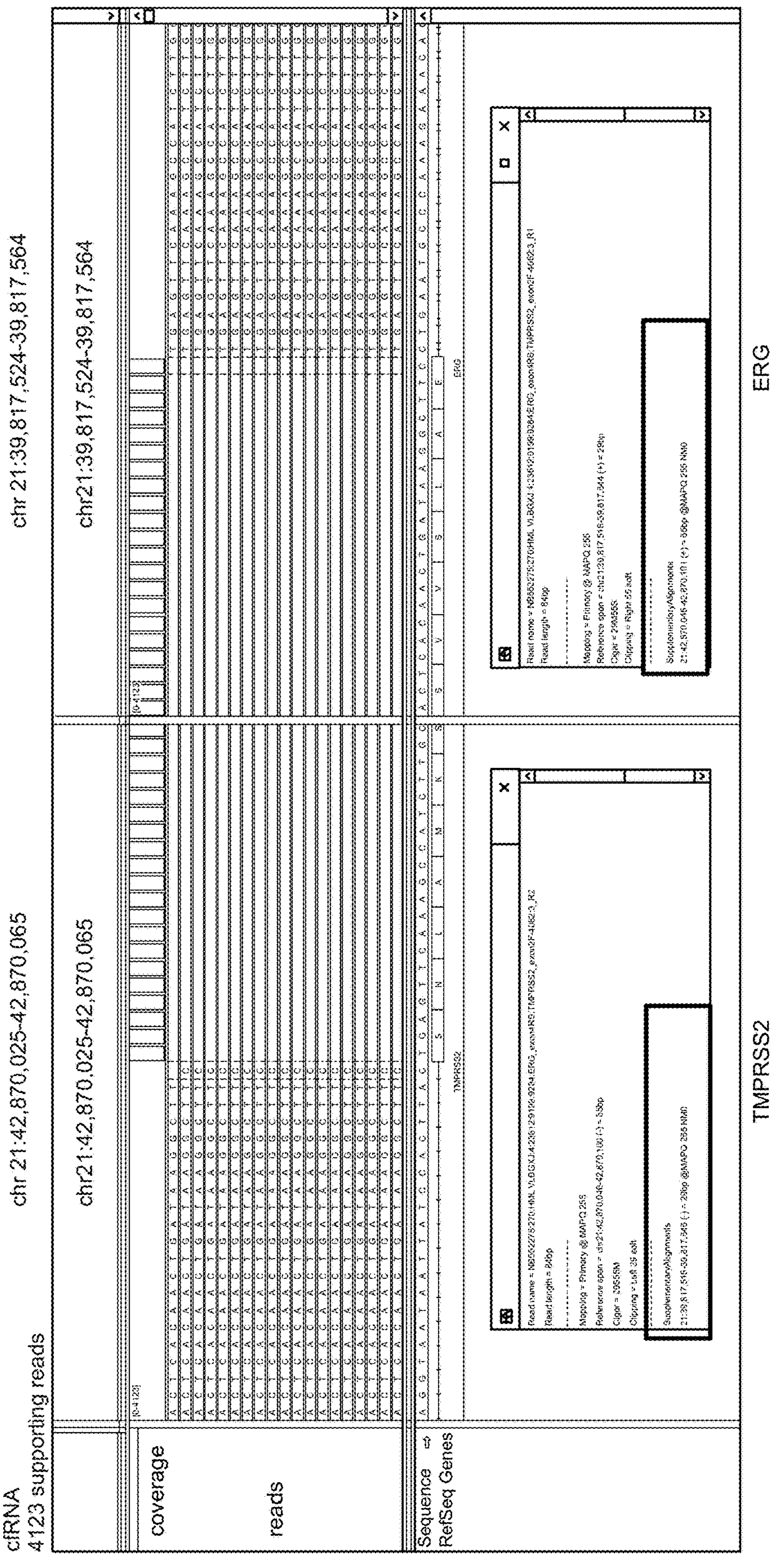
Figure 8C:
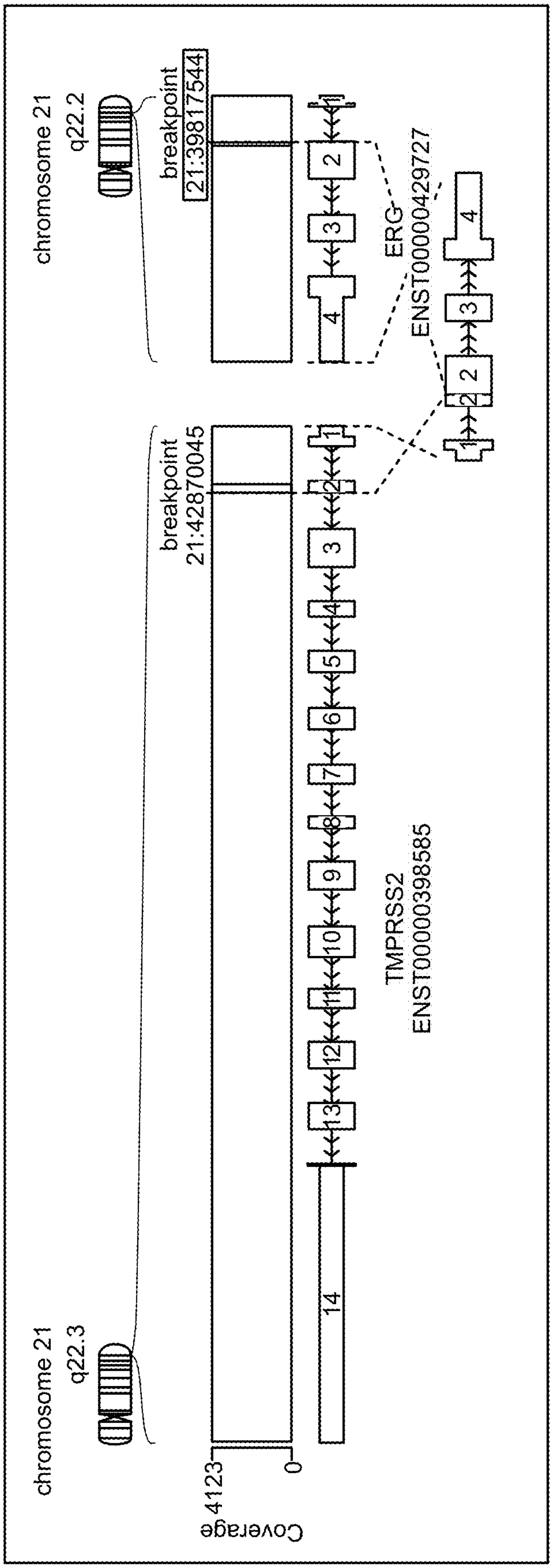

Nucleic acid extracts from plasma of two cancer patients previously characterized to be positive for fusions using a DNA-based method (Liquid Hallmark) were tested. In the first case of a metastatic prostate cancer, TMPRSS2-ERG fusion was detected in cfDNA (using 70 ng of cfDNA) supported by 17 split reads mapping to intronic position chr21:42867069 within TMPRSS2 (intron 2 of TMPRSS2-NM_005656.4) and intronic position chr21:39818058 within ERG (intron 3 of ERG-NM_001291391.1) (FIG. 8A). Using the same circulating nucleic acid extract, fusion in the cfRNA (equivalent of just 24 ng cfRNA) was detected with 4123 supporting split reads, fusing exon 2 of TMPRSS2 (chr21: 21:42870045) with exon 4 of NM_001291391.1 (or exon 2 of ERG NM_182918.4) (chr 21:39817544) (FIG. 8B).

Figure 9A:
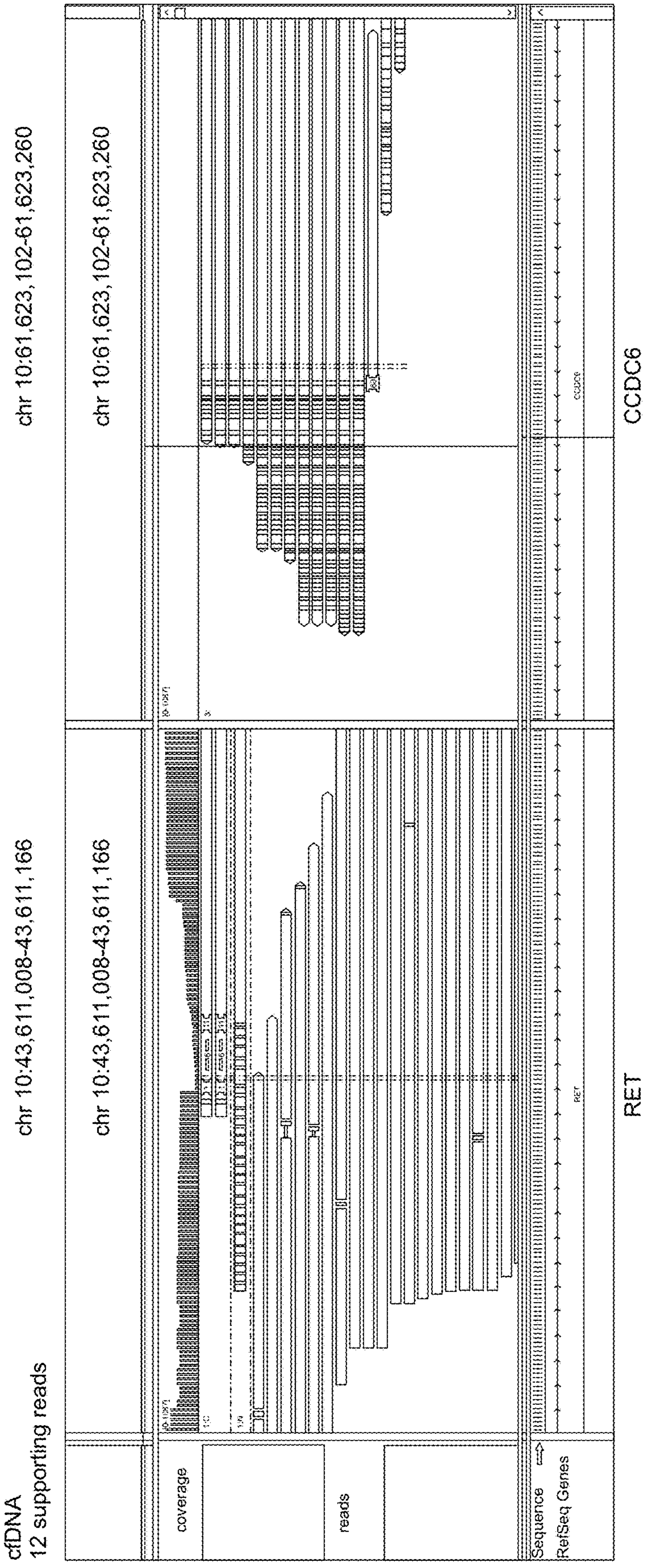
Figure 9B:
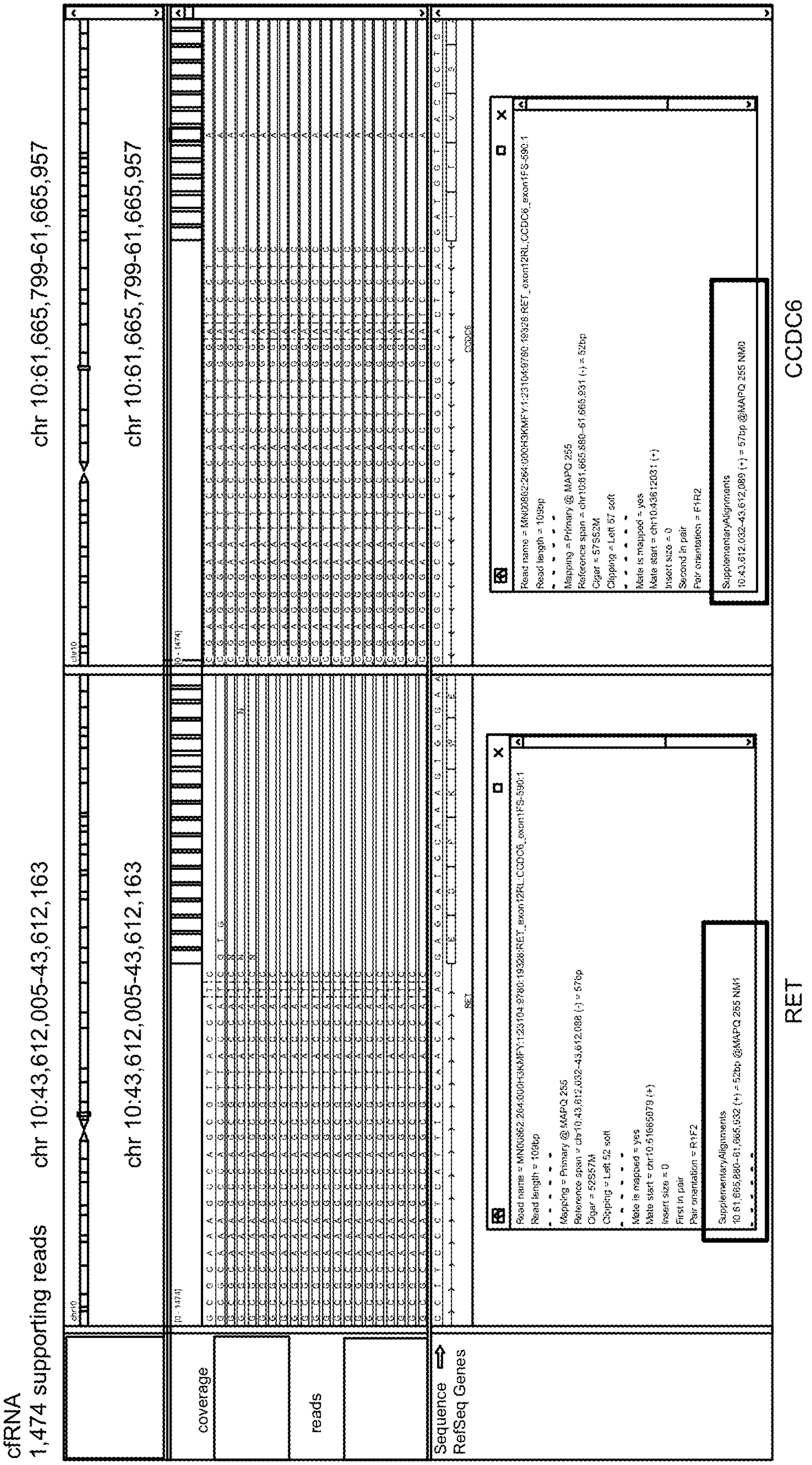
Figure 9C:
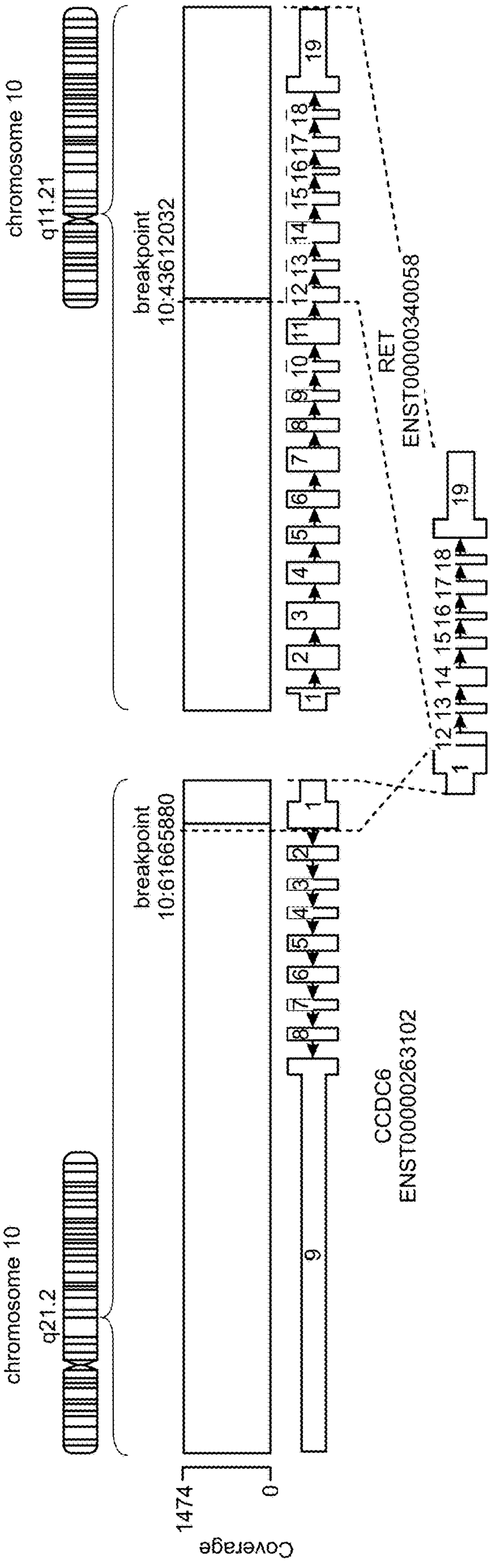

In a second case of metastatic lung cancer, a CCDC6-RET fusion detected using cfDNA (breakpoints CCDC6 Intron 1 (chr10:61623181) and RET intron 11 (chr10:43611035) and cfRNA CCDC6 exon 1 (10:61665879) and RET exon 12 (10:43612031). cfDNA was detected with 12 supporting reads, while fusion in cfRNA was supported by 13 split reads (FIGS. 9A and 9B).

Figure 10A:
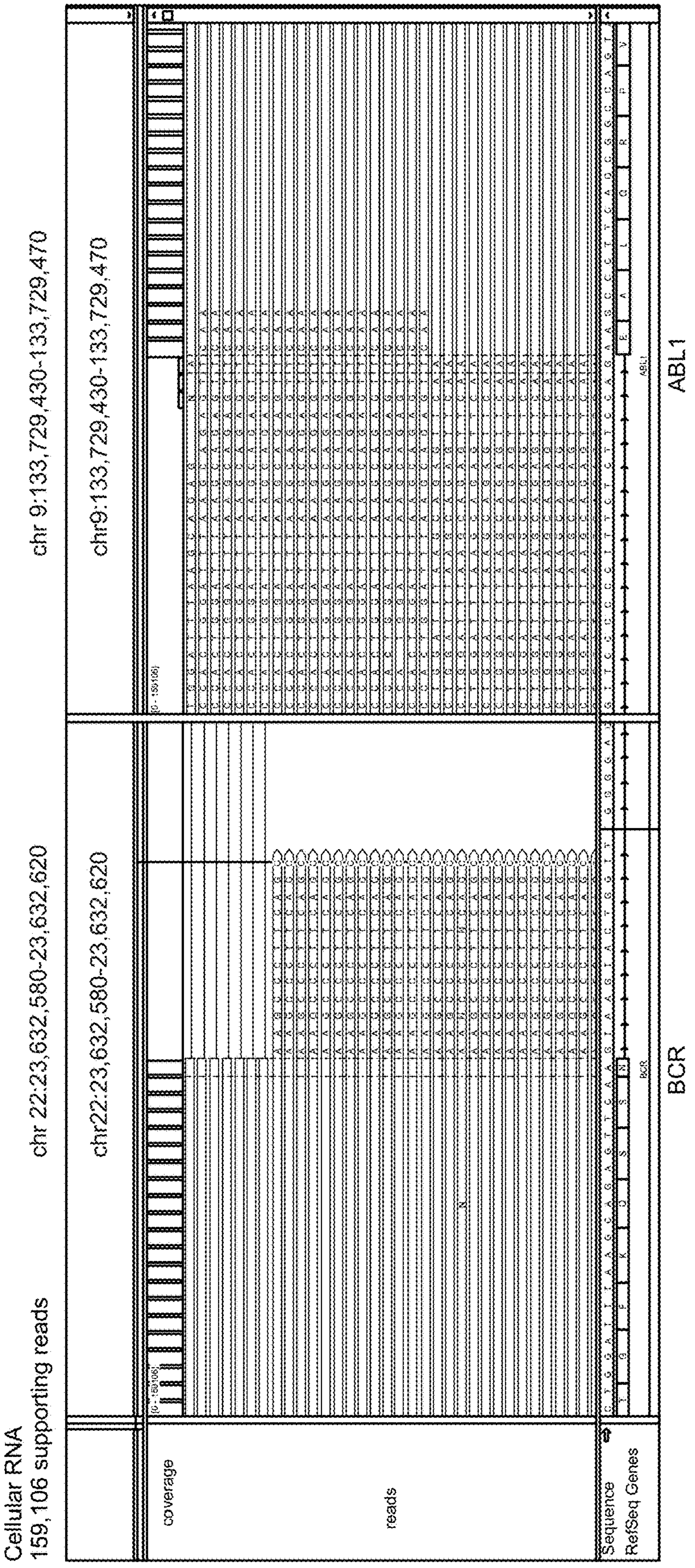
Figure 10B:
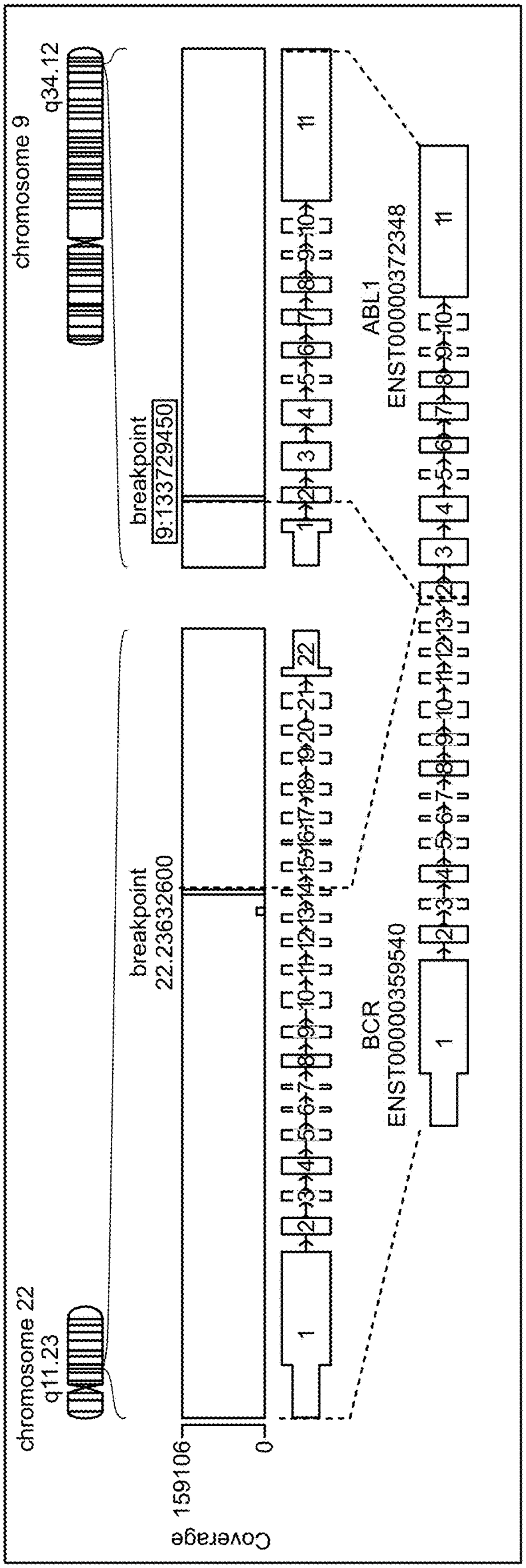

In a third clinical sample from a hematological malignancy (acute lymphoblastic leukemia) with BCR-ABL1 rearrangement confirmed in DNA from the peripheral blood cells, RNA was extracted from another fraction of archived buffy coat and tested with the multiplex amplicon sequencing method described here. The fusion between exon 14 of BCR, and exon 2 of ABL1 was readily detectable in the RNA fraction with an abundant 159,106 supporting reads. The large number of supporting reads is indicative of the enrichment of transcripts with BCR-ABL1 fusion, due to increased expression and secondary enrichment of cancer cells positive for the fusion in sample tested (buffy coat RNA) (FIG. 10A and FIG. 10B).

Figure 13A:
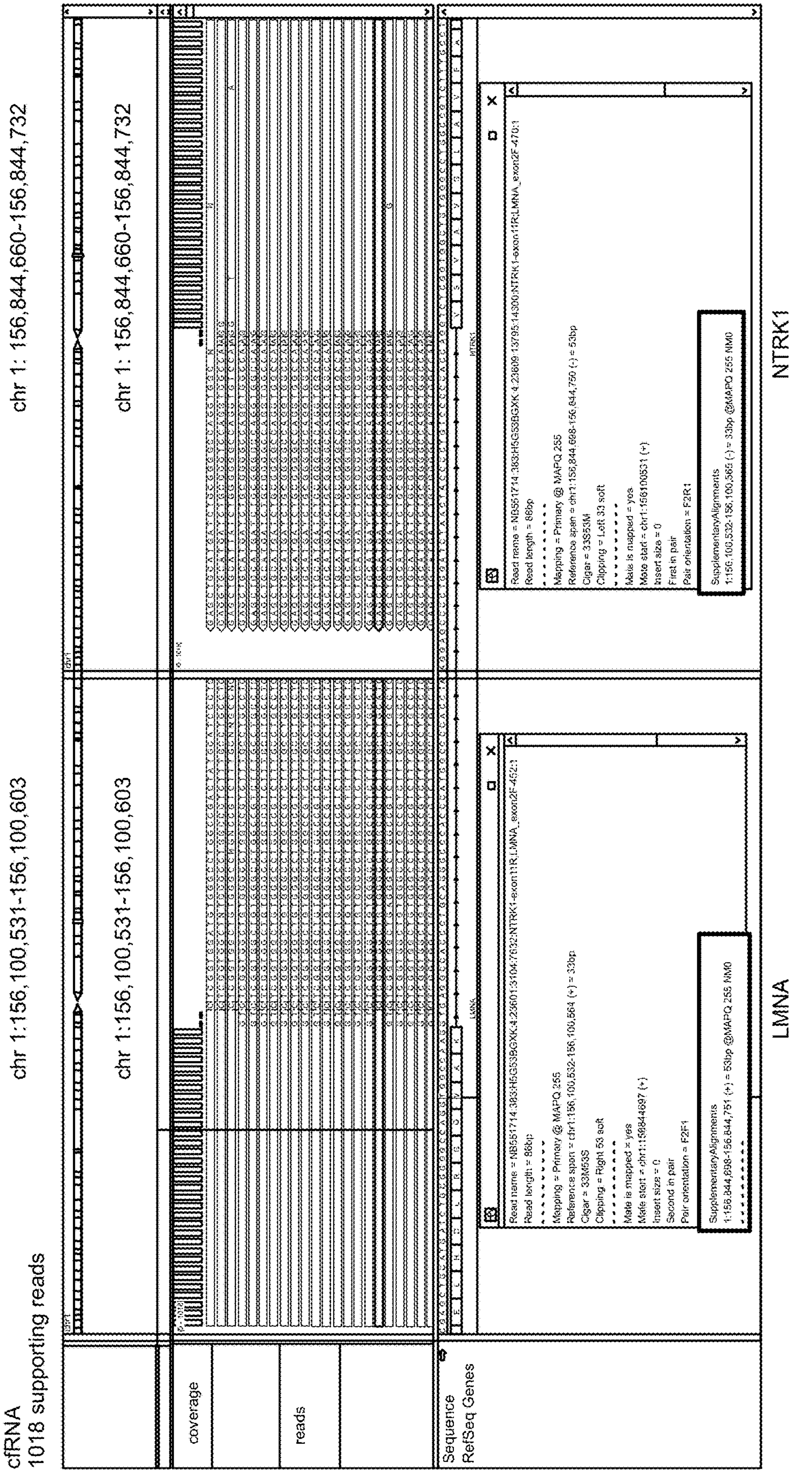
Figure 13B:
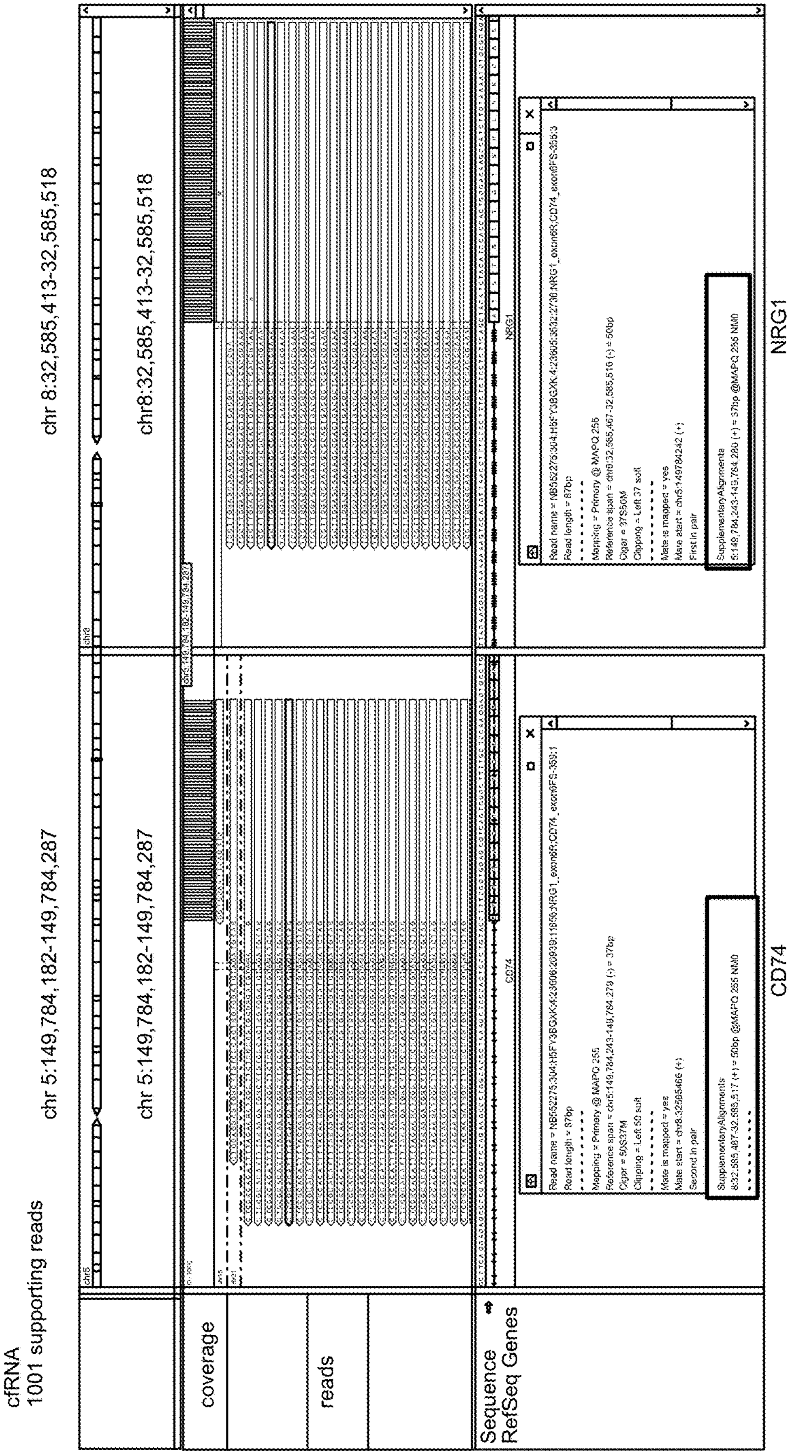
Figure 13C:
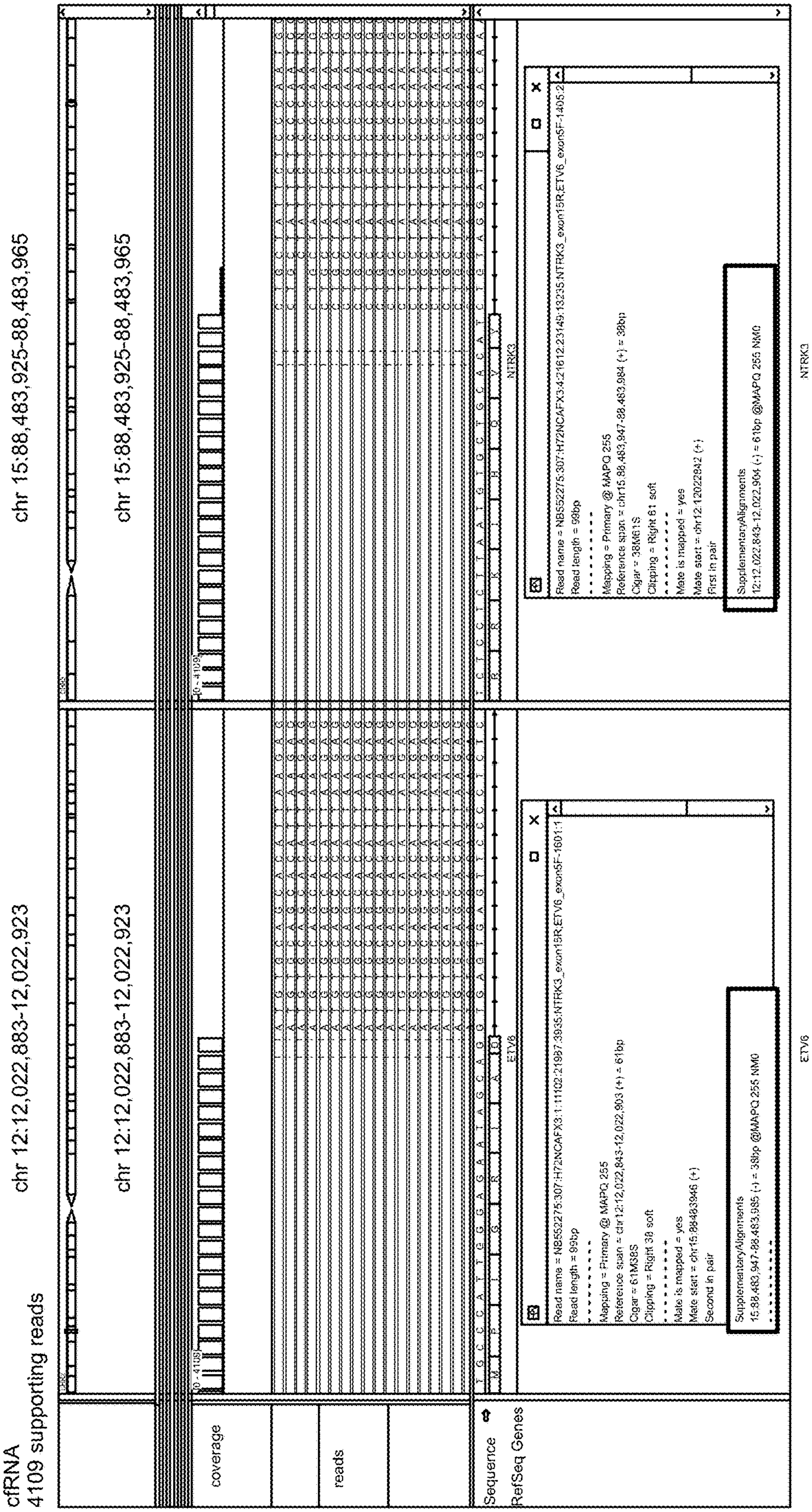

Additional fusion events are shown in FIGS. 13A-13C illustrating the identification of actionable driver fusions in untreated lung cancer cases using cfRNA using the method described herein. FIG. 13A, FIG. 13B and FIG. 13C show the detection of various gene fusion events namely LMNA-NTRK1 fusion, CD74-NRG1 and ETV6-NTRK3 fusion in cfRNA samples in three lung cancer cases, respectively. These mutations were otherwise undetectable using a DNA-based assay and appear as negative for the presence of other driver gene mutations in cfDNA. In addition, when the method described used cfDNA and cfRNA for fusion detection in 45 lung cancer cases, additional fusions were identified when cfRNA fraction was used compared to cfDNA (FIGS. 14A-14B). When testing for fusion was performed with DNA and RNA as sample input orthogonally, there were 12 cases with concordant fusion detection based on cfDNA and cfRNA as sample input. There were additional fusions detected in 5 cases and 1 fusion that was missed and not detected when cfRNA was used as sample input instead of cfDNA. The list of range of fusions detected by both cfDNA and cfRNA methods or by one of the two methods shown in FIG. 14B.

Limit of Detection

Figure 11:
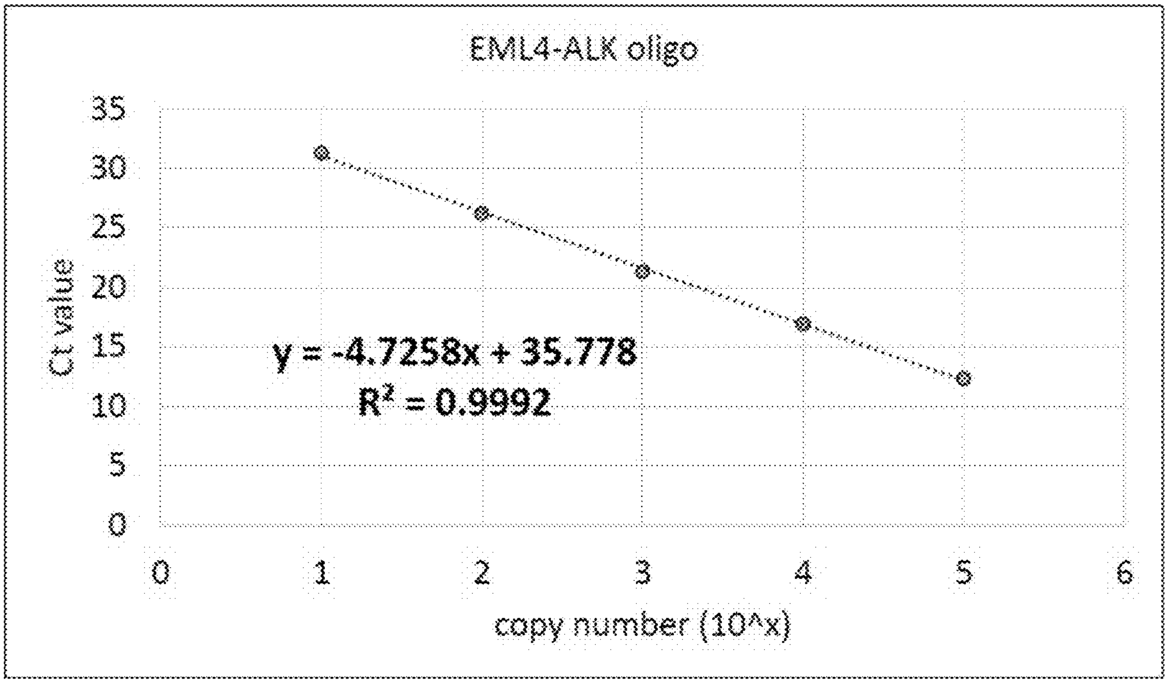
FIG. 11 shows the result from quantitating the number of EML4-ALK fusion transcript copies per nanogram RNA from H2228 cell line, for determining the sensitivity limits of detection of the cfRNA-based method described herein.

The limit of detection is defined as the lowest RNA concentration at which fusion events can be readily detectable. Initial determination of limit of detection of RNA-based fusion was done by quantitating the number of EML4-ALK fusion transcripts present in 1 ng of H2228 cell line RNA, from which EML4-ALK fusion was readily detectable using the method described herein (FIGS. 6A-6B and FIG. 7). The number of EML4-ALK fusion RNA transcripts was determined to be ~13.7 copies per 5 ng of RNA using a qRT-PCR assay designed specifically for the EML4-ALK transcript present in H2228 cells (FIG. 11). Therefore, the method described herein is shown to be able to detect down to 2.72 copies of EML4-ALK fusion (in 1 ng of H2228 RNA), suggesting a very sensitive detection for RNA-based fusions.

Figure 12:
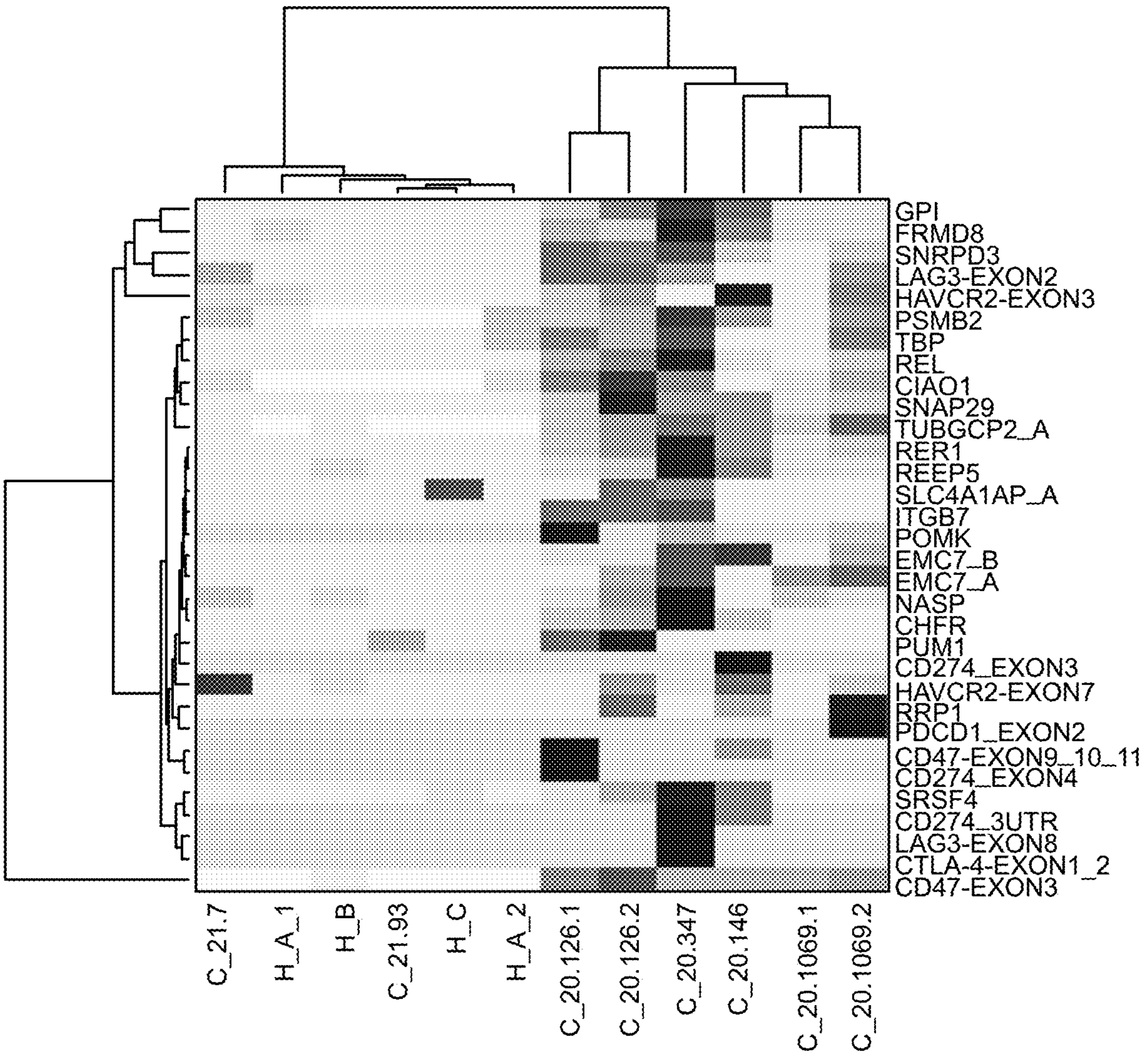
FIG. 12 shows the detection and quantification of expression of control genes and other target genes in cfRNA from both cancer and healthy samples, using the method described herein. The table (top panel) describes the amount of cfRNA input for each sample tested, including repeats of two samples with differing input cfRNA amounts. The expression heatmap (bottom panel) demonstrates the distribution of the expression read counts, as derived from the method described herein, for each sample. Fusion detection in the same sample is feasible and shown for C_20-347, and C_20-146, which were simultaneously positive for CCDC6-RET and TMPRSS2-ERG fusion, respectively, as depicted in FIG. 8 and FIG. 9.

Simultaneous Detection and Quantification of Expression cfRNA-Based Fusion Events Besides the detection of fusions in cfRNA, simultaneous detection of targets genes intended for non-invasive expression monitoring was also done for cfRNA from cancer and healthy samples. In the same multiplex reaction, primers for 22 control genes and 13 amplicons for 6 genes related to immunotherapy response (CD274, PDCD1, CTLA4, LAG3, HAVCR2 and CD47) were included, and the combined target capture was performed. Based on read counts mapping to the intended target regions, the determination of expression level of each target was done. The range of expression levels were visualized in an expression heatmap (FIG. 12).

As healthy samples typically had very low yields of both cfRNA and cfDNA, the expression was low for control genes and immunotherapy response genes across along healthy samples as expected. However, among cancer samples, a range of expression patterns was observed, with some samples showing limited expression of nearly all targets, despite an equivalent amount of cfRNA material used in the method. The reliability of detection and the quantitative ability of the method was demonstrated by the performing repeats of the same sample with differing amounts of cfRNA, which showed an increase in the expression read count, but similarity in pattern among the sample repeats (FIG. 12). The repeats are represented by C_20.126.1 and C_20.126.2 (sample 20.126 repeated) and C_20.1069.1 and C_20.1069.2 (sample 20.1069 repeated). In the heatmap, the two repeats are closest to each other indicating greater similarity between two repeats of same sample, compared to other samples.

Detection of Expressed Transcripts Comprising Deletion Mutation in RNA Sample

Figure 16:
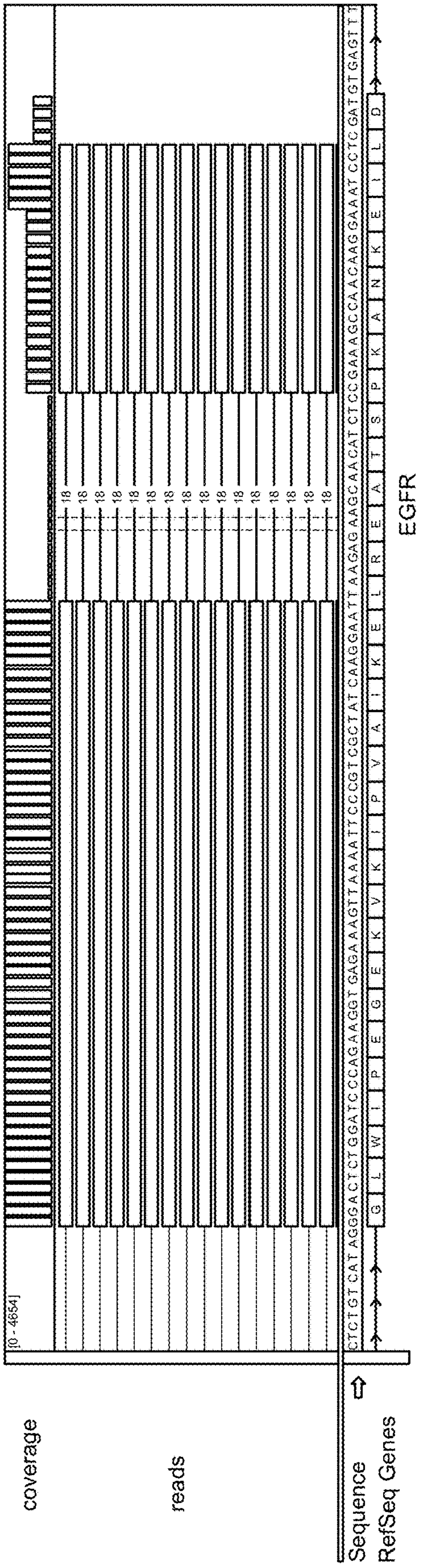
FIG. 16 is an IGV graphic report showing the detection of an 18-bp deletion in RNA extracted from FFPE lung tumor tissue using cfRNA-based method described herein. The expression of EGFR c.2240_2257del p.L747_P753delinsS mutant transcript (comprising the deletion) was supported by 4266 reads.

The method described herein showed the ability to detect an 18-nucleotide deletion in an RNA sample extracted from FFPE lung tumor tissue. The expression of EGFR c.2240_2257del p.L747_P753delinsS mutant transcript (comprising the deletion) was detected with 4266 supporting reads (FIG. 16).

Figure 17:
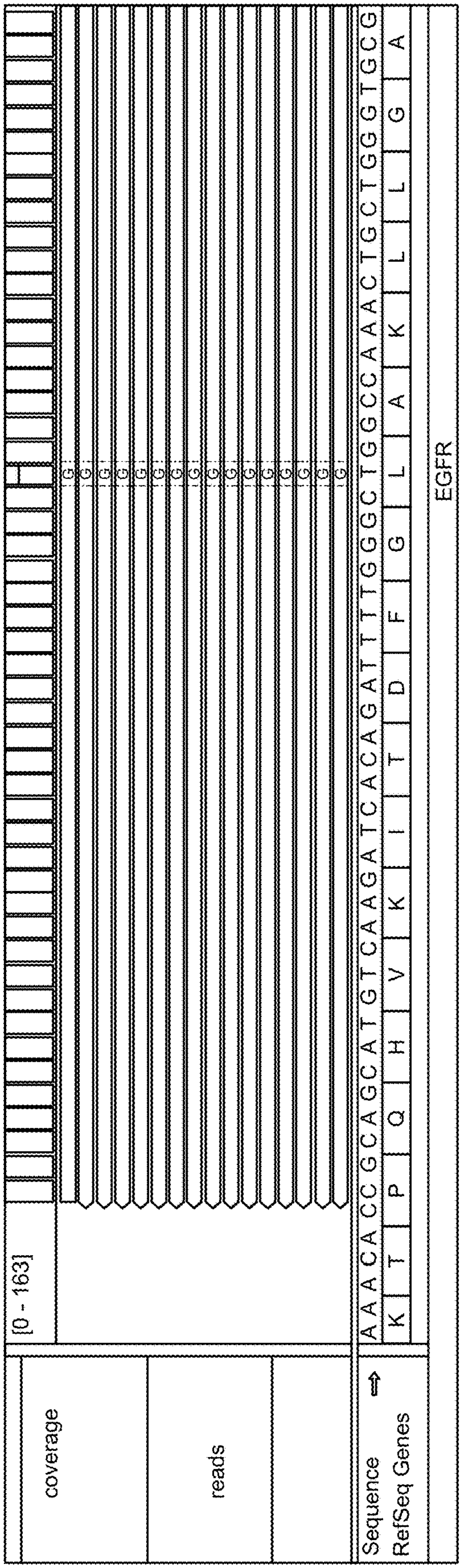
FIG. 17 is an IGV graphic report showing the detection of a single nucleotide variation in cfRNA extracted from the plasma of a metastatic lung cancer patient using cfRNA-based method described herein. Expression of EGFR c.2573T>G p.L858R mutant transcript (comprising the single nucleotide variation) was supported by 112 reads.

Detection of Expressed Transcripts Comprising Single Nucleotide Variations in RNA Sample The method described herein showed the ability to detect single nucleotide variation in a cfRNA sample extracted from the plasma of a metastatic lung cancer patient. The expression of EGFR c.2573T>G p.L858R mutant transcript (comprising the single nucleotide variation) was supported by 112 reads. (FIG. 17)

Detection of Expressed Transcripts Comprising Single Nucleotide Variations, Insertion and Deletion Mutation in RNA Sample The method described herein showed the ability to detect single nucleotide variations, insertion and deletion mutations in tissue RNA extracted from FFPE tumor samples (FIG. 18A) and cfRNA extracted from plasma (FIG. 18B). Simultaneous detection of target genes intended for detection of expressed transcripts containing single nucleotide variations, insertion (e.g., duplications) and deletion mutations was performed for tumor tissue RNA from 4 cancer samples and plasma cfRNA from 3 cancer samples. In the same multiplex PCR reaction, primers for desired targets were included, and combined target capture was performed. The variant allele frequency (VAF) was determined based on the proportion of mutant read counts relative to total read counts detected from the method described herein. The validity of the RNA-based method described herein is shown by the VAF percentage depicted in FIGS. 18A and 18B.

Discussion

In the present disclosure, a method to simultaneously detect genomic alterations such as structural rearrangements, and gene expression using circulating cell-free RNA (cfRNA) is described. Such detection and quantification non-invasively is envisioned to allow the detection of cancer, determination of prognosis and prediction of therapy response. The method is based on highly multiplexed amplicon-based NGS, and involves the tagging of individual cfRNA molecules using barcode sequences, and the optimized design of amplicons to be compatible with the fragmented nature of cfRNA. The inventors have shown that the method can be applied to circulating nucleic acid extracts containing both cfDNA and cfRNA, and can detect and quantitate fusion RNA transcript and gene expression simultaneously, in such samples.

In order to detect structural rearrangements, such as gene fusions—that result in the juxtaposition of exons from different genes, resulting in a fusion transcript—from cfRNA analyte, a targeted multiplex amplicon panel for detection of fusions by next-generation sequencing (NGS) was designed. The juxtaposition of gene exons was exploited to amplify fusion transcripts, by a pair of primers flanking the exonic junctions involved in the fusion. Primers specific for exons of fusion and partner genes known to undergo fusions were designed just flanking the exonic junction sites. Such juxtaposition of exons from different genes can only happen when processed mRNA is generated (by splicing) bringing fused exons together, and so equivalent DNA sequences are unlikely to contribute to productive amplification with the same primers, because of the intervening fused relatively long introns separating the exons in the DNA.

The design of the primers to capture fusion transcripts had two main features—1) the presence of a random barcode sequence in the downstream primers (downstream relative to the fusion transcript) to individually tag each copy of the RNA fusion transcript if present, and 2) the location of each primer approximately 50 base pairs from each exonic junction in the panel, such that the expected total amplicon length would be close to 90-110 base pairs. This was done in order to meet the sample cfRNA size distribution observed which peaked at 110-120 nucleotides. The chosen length of 90-110 base pairs was considered optimal because products of shorter amplicons (<80 base pairs) would be less effectively retained through the multi-step library preparation method for amplicon sequencing, involving size-based separation (magnetic bead based) of smaller primer dimer artefacts to be removed and desired products to be retained. A multiplicity of "upstream" and "downstream" primers were included in the multiplex PCR to optimally capture potential fusions known to occur between genes. The design of primers includes exons of well-characterized genes known to undergo fusions, such as ALK, RET, ROS1, FGFR2, FGFR3 and exons of their partner genes, such as EML4, KIF5B, CCDC6, CD74, TACC3, among others. Potential fusions between any upstream and any downstream exon (not limited to gene pairs for which design was intended) can theoretically be detected if present in a sample, if the capture reaction simultaneously includes the multiplicity of primers. Broadly, primers to capture all exonic junctions known to undergo fusions (and intervening exons which may not have been previously reported to be involved in fusions) in target and partner genes were designed. The barcode sequence primers allow for accurate enumeration of copies of RNA transcript as per method of enumeration.

The first step in the process of preparing a cfRNA NGS library based on this method is the conversion of cfRNA (naturally fragmented) into complementary DNA (cDNA) using reverse transcriptase enzyme with random primers. The result of the reverse transcription reaction is a total complement of the cfRNA molecules present in the sample. In addition to the exon flanking primers for fusion detection, and in order to provide a quantitative measure of amount of cfRNA included in a reaction, primers were also included for several (>20) control housekeeping genes in the multiplex reaction. The purpose of capturing transcripts of genes expressed at some baseline line across all sample types, was to estimate an average abundance of cellular material going into the multiplex PCR reaction, and to serve as a control for the whole process of preparation of cfRNA sequencing libraries, including the sample extraction, reverse transcription, and PCR steps. The design of primers intended for control target genes differed from that of fusion targets, in that at least one primer of a control gene primer pair was designed to span an exon-exon junction, in order to prevent unintended amplification of DNA of the control target gene, and the resulting amplicon was ~100 base pairs in length (FIG. 1). The design of primers for target genes related to expression were similar to the control gene targets, and at least one primer of primer pair spanned an exon-exon junction, and two or more primer pairs were designed per target gene covering both 5' and 3' end exons, to more reliably capture expression of target genes for expression, by allowing one or more amplicons to represent a given target gene. A highly multiplexed primer pool was employed with a plurality of upstream and downstream primers, some of which are expected to generate sequenceable targets in most samples depending on expression variability, and some primers which are expected to generate a product only when a sample is positive for structural rearrangement, generating a fusion gene that is productively expressed. The primers additionally carried the appropriate extensions necessary for generating sequenceable libraries with sequencing adapters for Illumina sequencing.

In this disclosure, the use of cfRNA analyte for the enhanced detection of structural rearrangements and gene expression simultaneously, was demonstrated. This was achieved by the design of multiplex amplicon NGS assay encompassing the exons of genes involved in fusion and the design of amplicons for the expression of target genes, with use of barcode sequences and optimal size selection of amplicons for cfRNA applications. Overall presence of abundance was quantified by read density of accumulated read numbers. In this disclosure, issues related to whole-transcriptome sequencing including cost and manpower were partially overcome with the application of targeted sequencing for plasma cfRNA.

In the present disclosure, clinically relevant altered splicing events such as MET proto-oncogene, receptor tyrosine kinase (MET) exon 14 skipping, Androgen receptor (AR) transcript variants are approached as intra-gene fusions events and are designed to be captured if present using a combination of primers which would capture the aberrant splicing as the juxtaposition of exons of the same gene not normally observed, but that which can occur in cancers. The ability to quantify expression of relevant genes, non-invasively, for the prediction of response to various treatments is valuable, as it allows the longitudinal monitoring of response, and informs clinical decision. However, this has not been routinely implemented in clinical practice, and is largely limited to the detection of DNA level alterations such as mutations and genomic copy number changes. Using sequencing technology such as NGS, mutations are identified by comparing sequencing reads to reference sequences (genomes). Genomic copy number changes are quantified by counting the number of reads corresponding to a gene, and quantifying the deviation from normal copy number count expected from cells or samples having two copies of DNA per gene. In one example, DNA level alterations include single nucleotide variants leading to missense mutations, frameshift mutations, insertion-deletions, splice site mutations. The non-invasive monitoring of expression changes by accessing the cfRNA analyte can exploit the overexpression of tumor-specific transcripts, lead to amplification of tumor-derived RNA signals in blood, thereby increasing sensitivity of detection. For the non-invasive characterization of structural rearrangements, for example, gene fusions in plasma, typically targeted cfDNA-based next-generation sequencing (NGS)-based methods are utilized.

To overcome the issues of stability, appropriate RNA isolation procedures, removing DNA contamination and the use of endogenous housekeeping control genes, has been applied in this disclosure. Combined together, cfRNA can be used to provide precise information related to cancer diagnosis, prognosis and prediction of therapy response. The novel features of the present disclosure and the reason why they are technologically significant are as follows:

1. The specific design of primers to allow amplification of consistently short amplicons to be able to amplify targets from cfRNA which is usually about 100 nucleotides in length when isolated from plasma.
2. The inclusion of barcode sequences in the primer design for accurate enumeration of specific targets, whether containing fusions or not.
3. The combination of designs for the simultaneous capture of fusions (if any) and target gene expression.
4. The ability to detect novel fusions with any potential primer combination included in the multiplex panel.
5. The design of data analysis workflows which allow the parallel analysis of RNA-based fusions and expression.

The method of the present disclosure has the following advantages:

1. The method of the present disclosure uses cfRNA (which lacks introns) for sample input, thereby allowing the identification of genetic fusions involving long introns which are typically excluded from conventional DNA-based assays.
2. The method of the present disclosure allows for identification of both fully characterised genomic alteration targets and novel genomic alteration targets (i.e. genomic alteration targets which are not previously characterised). Novel genomic alteration targets can be detected with any potential primer combination included in the multiplexed panel. The design of data analysis workflows which allow the parallel analysis of RNA-based fusions and expression.
3. The method of the present disclosure allows for simultaneous detection of structural rearrangement and determination of expression level of cfRNA. For cancer-related genes that are expressed, ctRNA provides the same mutational information as ctDNA; additionally, it can provide quantitative information about the expression levels of target genes of interest, and can potentially increase the sensitivity of detection of variants with low allelic frequencies due to the overexpression of tumor-specific transcripts. The ability to quantitate the expression of these targets non-invasively can be very useful for the monitoring treatment response and making treatment decisions.
4. The method of the present disclosure may be used on a blood-based test (for example, to detect fusion targets in cfRNA in the blood) that is fast and non-invasive (only one draw of blood is needed). In addition, the method is scalable for the detection of multiple cancers in a single test and is suitable for cancer screening in an asymptomatic population.
5. The method of the present disclosure is highly sensitive compared to conventional methods of genomic structural alteration detection. Smaller starting material (cfRNA) is required for equivalent or better detection capabilities. For example, only 24 ng of cfRNA is required for detection of TMPRSS2-ERG fusion in a metastatic prostate cancer sample, as compared to using 70 ng of cfDNA to generate similar sequencing reads.

6. The technological significance lies in the generalizable use of primers for target capture, which allows working with smaller, limiting amounts of input of nucleic acid sample. In addition, the unique combination of targets is selected for the sensitivity and specific detection of multiple cancers.
7. The method of the present disclosure is scalable and allows the capture of multiple genomic regions for the identification of several cancer types in a single assay. The target gene coverage can be expanded by the addition of forward and reverse primer pairs.
8. The method of the present disclosure may be used in the following applications:
   - Detection, identification and quantification of well-characterised genomic alterations (such as gene fusions) that are clinically relevant, for example those associated with to cancers.
   - Identification of novel genomic alterations specific to cancers.
   - Cancer screening in healthy individuals and individuals at high risk for the tested cancers.
   - Disease monitoring in cancer patients, including monitoring response to treatment, such as immunotherapy.
9. Shorter fragments are more challenging as starting material for sequencing-based assays, due to restrictions on primer design and the sequence information that can be optimally captured. The method of the present disclosure uses cfRNA, which is shorter (about 100 nucleotides) in length compared to cfDNA (about 160 base pairs) in length. The primers described herein have been optimally designed to capture fragmented cfRNA of about 100 nucleotides in length to maximize sensitivity of detection of fusions and expression changes.
10. The method of the present disclosure uses RNA and not DNA as the sample input for detection of genomic alteration events. This allows for detection of genomic alteration events that would have been excluded in a typical DNA-based detection assay. Examples of such genomic alterations include:
   - Copy number gains in DNA leading to overexpression of RNA;
   - Structural rearrangements involving very long introns of two or more genes; and
   - Changes in gene expression patterns corresponding to drug response or resistance.

SEQUENCE LISTING

Table of forward primers specific to genes that are capable of undergoing genomic alteration.

| SEQ ID NO | Primer name | Sequence |
|---|---|---|
| 1 | AGAP3_exon9F | AGAAGAAGGCTGCCGAGTG |
| 2 | AGK_exon2F | GCTCTGCCTGCTGACCTG |
| 3 | AGTRAP_exon5F | CAGAGCACAGCATTAAAGTTTGG |
| 4 | AKAP9_exon21F | AGGCATCTGTAAAGTCATGTGTC |
| 5 | AKAP9_exon8F | GAGCAACTCAACCAAGTGAAAATG |
| 6 | ARMC10_exon4F | GCACTAAATAACCTGAGTGTGAATG |
| 7 | ATIC_exon7F | GTACACACTGCAGCCCAAG |
| 8 | BCR_E1_F | GCAGATCTGGCCCAACGAT |
| 9 | BCR_E13_F | CTGACCAACTCGTGTGTGAAACTCC |
| 10 | BCR_E14_F | CGGGGCTCTATGGGTTTCTG |
| 11 | BCR_E18_F | GTCTTCGGAGTCAAGATTGCTG |
| 12 | BCR_E19_F | ATCTACCGCGTGTCCGGT |
| 13 | BCR_E2_F_rdsgn | ACATTGATGACTCGCCCTCC |
| 14 | BCR_E6_F | AAGATGCCAAGGATCCAACGAC |
| 15 | BCR_E8_F | CAATGAGGAGATCACACCCCG |
| 16 | BRAF_exon1F | TCTTCGGCTGCGGACCCT |
| 17 | BRAF_exon2F | GAACATATAGAGGCCCTATTGGAC |
| 18 | BRAF_exon3F | GAGCAACCCCAAGTCACCA |
| 19 | BRAF_exon4F | TGAGAGGTCTAATCCCAGAGT |
| 20 | BTF3L4_exon3F | CAGAGTTCTCTAAAAAAACTGGCTG |

-continued

| Table of forward primers specific to genes that are capable of undergoing genomic alteration. | | |
|---|---|---|
| SEQ ID NO | Primer name | Sequence |
| 21 | CARS_exon17F | GAGAAGGAGTGCGGAAGATTG |
| 22 | CBFB_E4_F | TGGTATGGGCTGTCTGGAGT |
| 23 | CBFB_E5_F | CGGAGAAGGACACGCGAAT |
| 24 | CCDC6_exon1FS | CAAGGCACTGCAGGAGGAGAAC |
| 25 | CCDC6_exon2F | GAATTCCTCACTAATGAGCTCTCCAG |
| 26 | CCDC6_exon8F | CTTCACGTGCAGCACATGG |
| 27 | CCDC91_exon11F | GGCAGTGAAAAGAACAAGAGATG |
| 28 | CD74_exon6FS | TCCTTGGAGCAAAAGCCCACTG |
| 29 | CDC27_exon16F | TTGATCCCAAGAACCCTCTATG |
| 30 | CLTC_exon30F | CATGCCCTATTTCATCCAGGT |
| 31 | CLTC_exon31F | GAAGAAGAACAAGCTACAGAGACAC |
| 32 | CUX1_exon10F_new | GCCAATCACTCCCTCCAG |
| 33 | DCTN1_exon16F | ATGACTGCGTTCTGGTGCTG |
| 34 | DCTN1_exon26F | CATTGCTACTCTGGTCTCTGG |
| 35 | EML4_exon13F | CTACTGTAGAGCCCACACCTG |
| 36 | EML4_exon14F | ATTAACTGGAGGAGGGAAAGACAG |
| 37 | EML4_exon15F | CGAGGAACATTTAATGATGGCTTC |
| 38 | EML4_exon16F | TGCTCTTGACATGTGCTCAGGACAG |
| 39 | EML4_exon17F | CTGTGCAGATTTTCATCCAAGTGGC |
| 40 | EML4_exon18F | TCTATCCACACAGACGGGAATGAAC |
| 41 | EML4_exon20FS | ATAATGTCTAACTCGGGAGACTATG |
| 42 | EML4_exon2F | GCAATCTCTGAAGATCATGTGG |
| 43 | EML4_exon5F | GCAGACAAGCATAAAGATGTCATCATC |
| 44 | EPS15_exon22F | AATCATTTGGAGGTGGATTTGCTG |
| 45 | ERC1_exon12F | GAGGTGGAAAATGAGAAGAATGAC |
| 46 | EWSR1_exon7F | CTACAGCCAAGCTCCAAGTC |
| 47 | EWSR1_exon9_10F | GCTTCAATAAGCCTGGTGGA |
| 48 | EZR_exon10F | GGCTGCAGGACTATGAGG |
| 49 | FAM131B_exon2F | CATGGACAGCACCAGCTCA |
| 50 | FCHSD1_exon13F | GATGAGGTGGAGCAGGAG |
| 51 | FGFR1OP_exon12FS | GTGGAAATAGATGACATCAATACCAGTG |
| 52 | GHR_exon1F | CGAACCCGCGCTCTCTGA |
| 53 | GOLGA5_exon7F | GGCCAGATACATCAGCTCAG |
| 54 | GOPC_exon4F | TGTTCTCCAGGCTGAAGTATATG |
| 55 | GOPC_exon8F | CAAGTGGGGAAATCAAAGTATTACAAG |
| 56 | GTF2I_exon4F | CAGTTGAGGACTATTTCTGCTTTTG |
| 57 | HIP1_exon21F | ACCACCTGCCTCAGAGCC |

-continued

| Table of forward primers specific to genes that are capable of undergoing genomic alteration. | | |
|---|---|---|
| SEQ ID NO | Primer name | Sequence |
| 58 | HIP1_exon28F | CTCAACCATTTCCGGCAAATCAC |
| 59 | HIP1_exon30F | CTTGCTGGTGTTGCTGAGG |
| 60 | IRF2BP2_E1a_F | GAGCAAGTTTAAGAAGGAGCCG |
| 61 | IRF2BP2_E1b_F | GCAGGTTGTTGGGTTTCGAG |
| 62 | IRF2BP2_E2_F | GGAGAGGTCTATTGTCCCAGTG |
| 63 | KIAA1468_exon10FS | CTGCCTGCCACACATTGTTC |
| 64 | KIAA1549_exon12F | ACGCAGGAGATAAGACGCC |
| 65 | KIAA1549_exon13F | CTTATCGCCATGCAGCCGA |
| 66 | KIAA1549_exon14F | ACAAGATCCTGGACCCCAC |
| 67 | KIAA1549_exon15F | AGCGATGGCACCTACAGGA |
| 68 | KIAA1549_exon16F | AAGAGAGGCGAGCCACCC |
| 69 | KIAA1549_exon18F | GGAGGAGATGCCGTCGGT |
| 70 | KIAA1549_exon19F | AAGCAGAGGCAGCCAGTAT |
| 71 | KIF5B_exon15F | CTTGCAGAAATAGGAATTGCTGTGG |
| 72 | KIF5B_exon16FS | TGAAAAGGAGTTAGCAGCATGTCAG |
| 73 | KIF5B_exon17F | ATGCCCTCAGTGAAGAACTAGTCC |
| 74 | KIF5B_exon22F | GAACTTCAGACTTTACACAACCTGCG |
| 75 | KIF5B_exon23FS | ATCTTGAACAGCTCACTAAAGTGC |
| 76 | KIF5B_exon24F_new | GAAGCAGTCAGGTCAAAGAATATGG |
| 77 | KLC1_exon9F | TGCACATGAAAGGGAGTTTGGTTC |
| 78 | KMT2A_E10_F | CCA GGG TGG TTT GCT TTC TCT |
| 79 | KMT2A_E11_F | TCT GTC ACG TTT GTG GAA GG |
| 80 | KMT2A_E5_F | AAG CCC AAG TTT GGT GGT CG |
| 81 | KMT2A_E6_F | CAATGGATGCCTTCCAAAGCC |
| 82 | KMT2A_E7_F | AAACCACTCCTAGTGAGCCC |
| 83 | KMT2A_E8_F | GCT CCC CGC CCA AGT ATC |
| 84 | KMT2A_E9_F | GCAGATGGAGTCCACAGGAT |
| 85 | KTN1_exon29F | CATGCTAAAAGAGAGGGAGAGTG |
| 86 | LRIG3_exon16F | TTCTTACCACAACATGACAGTAGTG |
| 87 | MKRN1_exon4F | ATCCAATGGATGCTGCCCAGA |
| 88 | MSN_exon11F | GACAGAAGAAGGAGAGTGAGG |
| 89 | NCOA4_exon6FS | TTGAAGCTGACACAATTACTCTGC |
| 90 | NCOA4_exon7F | CCTGGAGAAGAGAGGCTGTATC |
| 91 | NCOA4_exon8F_new | AGGACTGGCTTACCCAAAAGCAG |
| 92 | NPM1_E4_F | AAGTGTGGTTCAGGGCCAGT |
| 93 | NPM1_E5_F | TATCTGGAAAGCGGTCTGCC |
| 94 | NUP214_exon21F | AAGACCCCACCAGTGAGAT |

-continued

| Table of forward primers specific to genes that are capable of undergoing genomic alteration. | | |
|---|---|---|
| SEQ ID NO | Primer name | Sequence |
| 95 | PAPSSI_exon5F | CTCCTGTGATGTAAATGACTGTG |
| 96 | PML_E3_F | AGTTCAAGGTGCGCCTGC |
| 97 | PML_E6a_F | CTTCCTGCCCAACAGCAAC |
| 98 | PML_E6b_F | TGCCCCAGGAAGGTCATCAAG |
| 99 | PPFIBP1_exon12F | ATGCAAGACACGGTGGTACTG |
| 100 | PPFIBP1_exon8F | GGACAGTGAGAGACTTCAGTATG |
| 101 | PPFIBP1_exon9F | TGGTTTGCAAGATGAAAGGAGAAG |
| 102 | PRKAR1A_7F | CATCGACCGAGACAGCTATAGAAG |
| 103 | PWWP2A_exon1F | TTGTCGTGTCGTTCCGCTT |
| 104 | RANBP2_exon18F | GGGTCACAGACATTTCATGGG |
| 105 | RUNX1_E5_F | ATGACCTCAGGTTTGTCGGTC |
| 106 | RUNX1_E6_F | ACCTACCACAGAGCCATCAAA |
| 107 | RUNX1_E7_F | ACTGCCTTTAACCCTCAGCC |
| 108 | SDC4_exon2F | ATCTGATGACTTTGAGCTGTCTGGC |
| 109 | SDC4_exon4F | GCAGCAACATCTTTGAGAGAACGG |
| 110 | SLC34A2_exon13delF | TGTCAAGGCTCCTGAGACCTTTGAT |
| 111 | SLC34A2_exon4F | TCGTGTGCTCCCTGGATATTCTTAG |
| 112 | SND1_exon10F | GATTCACCTGTCCAGCATCC |
| 113 | SND1_exon11F | CCTTACATGTTTGAGGCCC |
| 114 | SND1_exon14F | AGGATTGCATAGCAAGAAGGAAG |
| 115 | SND1_exon16F | CTTGGTGCAGGAAGGAGAG |
| 116 | SND1_exon9F | GCTCCCACAGCTAATTTGGAC |
| 117 | SQSTM1_exon5F | CGAGTGTGAATTTCCTGAAGAAC |
| 118 | STAT5B_E15_F | GTGACTCAGAAATTGGCGGC |
| 119 | STRN_exon3F | TGAATCAGGGAGATATGAAGCCTCC |
| 120 | TAX1BP1_exon8F | GCAGTTATGTTTGGCTGAAAAGG |
| 121 | TFG_exon3F | GTGCAGTAGGATACTGAAACTGAC |
| 122 | TFG_exon4F | GAGAACCAGGACCTTCCAC |
| 123 | TFG_exon5F_new | ATGTTATGTCAGCGTTTGGCTTAAC |
| 124 | TFG_exon6F_new | CAGCAGCCACCATATACAGG |
| 125 | TMPRSS2_exon1F | TAAGCAGGAGGCGGAGGC |
| 126 | TMPRSS2_exon2F | CAGATACCTATCATTACTCGATGCTG |
| 127 | TMPRSS2_exon3F | TCCTGACGCAGGCTTCCA |
| 128 | TMPRSS2_exon5F | CTCTAACTGGTGTGATGGCGT |
| 129 | TPM3_exon2F | GCAAAAGCTGGAAGAAGCTGA |
| 130 | TPM3_exon8F | AGTTTGCTGAGAGATCGGTAGC |
| 131 | TPM4_exon8F | GGAAAAGACAATTGATGACCTGGA |

-continued

Table of forward primers specific to genes that are capable of undergoing genomic alteration.

| SEQ ID NO | Primer name | Sequence |
|---|---|---|
| 132 | TPR_exon15F | CAAACAACAGGAGTTGCCATTCC |
| 133 | TRIM24_exon3F | GTTCACAAAAGACCACACTGTC |
| 134 | TRIM24_exon8F | TCACTGTGATCCTAGTTTCTGG |
| 135 | TRIM24_exon9F | TCCCAACACAGATCAGCCT |
| 136 | VCL_exon16F | CGATGGTGATGGATGCAAAAG |
| 137 | ZBTB16_E2_F | TGGGGTCGAGCTTCCTGATA |
| 138 | ZBTB16_E3_F | GTTCCTGGATAGTTTGCGGC |
| 139 | ZBTB16_E4_F | TTTCGAAGGAGGATGCCCTG |
| 140 | ZC3HAV1_exon3F | CATCTGCAACAGCAAGCACA |
| 141 | AGBL4_exon5_6F | CCAGAGTGTGCAACAACGAAAG |
| 142 | AR_exon2_F_rdsgn | TGTGGAAGCTGCAAGGTCTTC |
| 143 | AR_exon3_F | CCATCTTGTCGTCTTCGGAAATG |
| 144 | BAG4_exon1_F | ATGGCTACTATCCCTCGGGAG |
| 145 | BAG4_exon2_F | GCTCCTTACCCAAGTACATATCCTG |
| 146 | BAIAP2L1_exon9_F | CGATATGTTTAATAACCCAGCCAC |
| 147 | BCAN_exon13F | AAGAGAACGGTCGTTGGGAG |
| 148 | BCR_exon4_F | TTCTATGATGGGCTCTTCCCCC |
| 149 | BCR_exon7_F | CTCTGCTCTACAAGCCTGTGGAC |
| 150 | BCR_exon9_F | CGTCTTCCTGTTCACCGACCT |
| 151 | BTBD1_exon4F | AAGCACTTTCCTTAATCCGGTTC |
| 152 | HMGN2P46_exon1_F | AGGTGAATCTTTTGGTTGGTGA |
| 153 | HMGN2P46_exon2_F | CATGCTTGTCAAAAATCAGAGGC |
| 154 | C8orf34_exon2_F_rdsgn | GGAACCGTGGACAACTTCAAA |
| 155 | CAPZA2_exon4_F | GCATTTGCACAGTATAACTTGGAC |
| 156 | CD47_exon7F | GGTTTGAGTATCTTAGCTCTAGCAC |
| 157 | CD74_exon8F | GAAAGAGTCACTGGAACTGGAGG |
| 158 | CNTRL_exon15_F | GCCAACCAGCTCAAGGAAGAGTT |
| 159 | CNTRL_exon38_F | GCAGGAAGAGGAGAGGTGG |
| 160 | CNTRL_exon39_F | CCAGCCTGAAGGAAGCACTTAA |
| 161 | CNTRL_exon40_F | AGCTCAACCAGATGCAGTATGAG |
| 162 | CTNNB1_exon1_F | AGGTCGAGGACGGTCGG |
| 163 | CUX1_exon1_F_rdsgn | TCTCAAGATGGCGGCCAATGTG |
| 164 | CUX1_exon7_F | ATGTCCACCACCTCAAAGCTGG |
| 165 | CUX1_exon8_9_F | CAAAGGCCGACGAGATTGAAATGAT |
| 166 | CUX1_exon8_F | AACTCGAACAGAATTATTTGACCTGAA |
| 167 | DDX5_exon2_F | GAGAAGAATTTTTATCAAGAGCACCCTG |
| 168 | EGFR_exon15F | TGCCATCCAAACTGCACCTAC |

-continued

Table of forward primers specific to genes that are capable of undergoing genomic alteration.

| SEQ ID NO | Primer name | Sequence |
|---|---|---|
| 169 | EGFR_exon24F_rdsgn | TCTCCAAAATGGCCCGAGAC |
| 170 | ERBB2_exon14_15_F | TTTGGACCGGAGGCTGACC |
| 171 | ERBB2_exon15F | GAAGTTTCCAGATGAGGAGGG |
| 172 | ERBB2_exon7-8_F | CCTGTCCCTACAACTACCTTTCTAC |
| 173 | ESR1_exon3_F | AACGAGCCCAGCGGCTAC |
| 174 | ESR1_exon4_F | CCATTATGGAGTCTGGTCCTGT |
| 175 | ESR1_exon5_F | GGCTCCGTAAATGCTACGAAGTG |
| 176 | ESR1_exon6_F_rdsgn | CAGACAGGGAGCTGGTTCACA |
| 177 | ESR1_exon7_F | ACCCAGGGAAGCTACTGTTTG |
| 178 | ETV6_exon4F | TGGAAACTCTATACACACACAGCC |
| 179 | ETV6_exon5F | CACATCATGGTCTCTGTCTCCC |
| 180 | ETV6_exon7F | ACATTATCAGGAAGGAGCCAGG |
| 181 | FGFR1_exon1_F | ACAAGCCACGGCGGACTCT |
| 182 | FGFR1_exon17_F | TTCAAGCAGCTGGTGGAAGAC |
| 183 | FGFR1_exon18_F | CACAAATTTCCCCAAAGACTGCG |
| 184 | FGFR1_exon2_F | GTCACAGCCACACTCTGCAC |
| 185 | FGFR1OP_exon5_F | TTAGAAGTGATCAGGCGCTGTC |
| 186 | FGFR1OP_exon6_F | TCCACCAAAGTCACCAGAGG |
| 187 | FGFR1OP_exon7_F | GACAAGGTAAGAAGAAGACAAGCG |
| 188 | FGFR2_exon17F | AGAAGACTTGGATCGAATTCTCAC |
| 189 | FGFR2_exon18F | CGAACCATGCCTTCCTCAGTATCC |
| 190 | FGFR3_exon17F | TCCTTACCGTGACGTCCA |
| 191 | FIP1L1_exon10_F | GTTGGGAAGTGGCAGGATCGA |
| 192 | FIP1L1_exon11_F | CTATAACTATCAGCCGAGTAGAAGGCAG |
| 193 | FIP1L1_exon12_F | TCTTCCACCTCCTCCGACTGT |
| 194 | FIP1L1_exon14_F | TTTTCCTCCTCCACCAGGCG |
| 195 | FIP1L1_exon15_F | GGACATTCCTCTGGTTATGATAGTCG |
| 196 | FIP1L1_exon16_F | GACAGAGAAAGAGAACGCACCA |
| 197 | FIPIL1_exon17_F | ACGACACAGGGAGAAAGAGG |
| 198 | FIP1L1_exon18_F | AGAAGGAAAAGAAGCGGGCA |
| 199 | FIP1L1_exon9_F | TGCCCTTCCATCTACAAAAGC |
| 200 | HERV-K_F | GATTCCCGAGTACGTCTACAGTGA |
| 201 | HERVK17_F | TTTCCACACTCTCATTCCGGA |
| 202 | HNRNPA2B1_exon1_F | TGCGGGAAATCGGGCTGAA |
| 203 | LMNA_exon2F | GAGCTGCATGATCTGCGG |
| 204 | MDK_exon4F | CCCAAGACCAAAGCAAAGG |
| 205 | MET_exon13F | ACAGCACTGTTATTACTACTTGGG |

-continued

Table of forward primers specific to genes that are capable of undergoing genomic alteration.

| SEQ ID NO | Primer name | Sequence |
|---|---|---|
| 206 | MPRIP_exon21F | AGAAGTCCCCTGACAGTGCC |
| 207 | NACC2_exon4F_rdsgn | GACTGGCATCCGCTCGTC |
| 208 | NFASC_exon21F | TCCAGGCTGAAAATGACTTCGGG |
| 209 | PAX8_exon10F | ACATCCCCACCAGCGGAC |
| 210 | PAX8_exon7F | GAGTGCCCATTTGAGCGG |
| 211 | PAX8_exon8F | CTTCCAACACGCCACTGG |
| 212 | PAX8_exon9F | CGCCCTTCAATGCCTTTCC |
| 213 | PCM1_E23_F | CTCCCAAGTCAAAAAGTAAGAAGAGGA |
| 214 | PCM1_E24_F | CAGCAGAAAGAATCATGAGCAACTGGAAA |
| 215 | PCM1_E25_F | CCATGAGCTGCAGCTACTAAAC |
| 216 | PCM1_E26_F | ATAGCATCAAACTCAGAACTTACTCCT |
| 217 | PCM1_E36_F | ACTCCTGAAAGCTCTCTGGCTG |
| 218 | PCM1_E37_F | GATTTTGTAAAAGTTGAAGATTTACCACTG |
| 219 | QKI_exon6F | ACACATTGGCACCAGCTACATC |
| 220 | RBPMS_exon5F | CAAACTCGTAGGGACTCCAAAC |
| 221 | SLC45A3_exon1_F | AACCAGCCTGCACGCGCT |
| 222 | SEC61G_5'UTRF_rdsgn | CTCCAGTGCTACGTGTCCCTG |
| 223 | TCF3_exon16_F | ACCCTCCCTGACCTGTCTC |
| 224 | TPM4_exon6F | CTGAAAAGGAGGACAAATATGAAGAAG |
| 225 | TPR_exon21F | TTGAAACAGCACCTCAGTAATATGG |
| 226 | TPR_exon6F | GGGAATGAGATTCTAGAGCTTAAATG |
| 227 | UBTF_exon2_F | AACGGAGAAGCCGACTGC |
| 228 | ZMYM2_exon16_F | TGTATATCCCAGTTCCTATGCACATG |
| 229 | ZMYM2_exon17_F | AGTTGCTTACAATGACGGATATGATGAGT |
| 230 | AFAP1_exon13_F | AGCAGTCAGCCAAAGAAAGC |
| 231 | AFAP1_exon14_F | GCTCCGCAAGGAAAGAAAAGA |
| 232 | AKAP9_exon18F | CAGCTACAAGAAGAGATTAAGAGACTT |
| 233 | AKAP9_exon7F | GACTTCACAATGCAAATTAGTTTCTTG |
| 234 | AKAP9_exon9F | GAACTTCAGAAAATACACCAGTTAGAACT |
| 235 | AXL_exon20_F | TGCTGATAGGGGCTCCCCA |
| 236 | BCR_exon10_F | TGGACGCTTTGAAGATCAAGATC |
| 237 | BCR_exon11_F | CTGCTTATGTCTCCCAGCATG |
| 238 | BCR_exon12_F | CGTGCAGAGTGGAGGGAGAA |
| 239 | BCR_exon15_F | GCAAAGACGCGCGTCTACAG |
| 240 | BCR_exon16_F | AAGGAGGACGGCGAGAGC |
| 241 | BCR_exon17_F | AGGACAGAGACTGGCAGCG |
| 242 | BCR_exon20_F | TTCACTGACGAGTTCTACCCCAA |

-continued

Table of forward primers specific to genes that are capable of undergoing genomic alteration.

| SEQ ID NO | Primer name | Sequence |
|---|---|---|
| 243 | BCR_exon3_F | CTAGCGAGGAGACTTACCTGAG |
| 244 | BCR_exon5_F | AAATGGCTGAGAAGTGCTGTC |
| 245 | HMGN2P46_exon2_F_rdsgn | GGAACCACACTTCGAGAATCAC |
| 246 | CCDC6_exon3F | GGAGAATGACACCATTTCTAAGCA |
| 247 | CCDC6_exon4F | AGCACTAGTTAATCGCCTCTGGAAA |
| 248 | CCDC6_exon5F | TGAAGTGGAACGGCTGAAGA |
| 249 | CCDC6_exon6F | TCTCCGAGAGTGAGTCCAGC |
| 250 | CCDC6_exon7F | CAGCCCGATCCCTTACACAC |
| 251 | DCBLD1_exon2_F | CCAGACCTGTGCTTCTGACTAT |
| 252 | EGFR_exon1_F | AGTCGGGCTCTGGAGGAAAAG |
| 253 | EML4_exon10F | GGACTTGGCACTTTTGAGCG |
| 254 | EML4_exon11F | GCTTACTGTATGGGACTGGCA |
| 255 | EML4_exon12F | TTTCTTCTGGACCTGGAGCG |
| 256 | EML4_exon19F | CTATGTAGTCTCTGAAAATGGAAGAAAAT A |
| 257 | EML4_exon1F | CGCTTTCCCCGCAAGATGGA |
| 258 | EML4_exon21F | AAGGACATTGATTGGACGACA |
| 259 | EML4_exon22F | CGATGACTTTTGTAAAGTCCATCTGTTTCA |
| 260 | EML4_exon23F | AAAGCCACCCTTCTGGAGGA |
| 261 | EML4_exon3F | GTGCTGTCTCAATTGCAGGAAAAG |
| 262 | EML4_exon4F | CACAGACAAACTCCAGAAAGCA |
| 263 | EML4_exon7F | ATCAGAACGGAACTGCCTCC |
| 264 | EML4_exon8F | GAACTCAGCGACACTACCTGG |
| 265 | EML4_exon9F | GCAACTGGACAGATAGCTGG |
| 266 | ESR1_exon8_F | GGAGAGGAGTTTGTGTGCCT |
| 267 | ESR1_exon9_F | GCCCAGCTCCTCCTCATC |
| 268 | ETV6_exon6F | GATCCCAACGGACTGGCTC |
| 269 | EWSR1_exon8_F | TGGAGGCATGAGCAGAGGT |
| 270 | EZR_exon11F | CTAAGGAGGAGCTGGAGAGACA |
| 271 | EZR_exon12F | GAGGCGCAAGGAGGATGAA |
| 272 | FIP1L1_exon8_F | ATGGAAGTTACACCAGGTGCAGAG |
| 273 | FRMD4A_exon2_F | ATGGGAATCGGAGACCATG |
| 274 | GOPC_exon5F | TGCAGAGGACGTAATGACTTGA |
| 275 | GOPC_exon6F | GGTCCAATTAGAAAAGTTCTCCTCCTTA |
| 276 | GOPC_exon7F | ACCTAAGGGACACAAAGCATA |
| 277 | GOPC_exon8F_rdsgn | AGGTGGTAACCCTGGTGCTAGTT |
| 278 | HIP1_exon29F | AAGCATGACGCTGACACAGA |
| 279 | IRF2BP2_exon1_F | CAGGCAGGTTGTTGGGTTTCG |

-continued

| Table of forward primers specific to genes that are capable of undergoing genomic alteration. | | |
|---|---|---|
| SEQ ID NO | Primer name | Sequence |
| 280 | KIAA1549_exon17F | GATACGAAGACTATGGAATGACTCC |
| 281 | KIF5B_exon18F | CATGAAATGGAAAAGGAGCACTTA |
| 282 | KIF5B_exon19F | AGTTTGAGAGATGAAGTAGAAGCA |
| 283 | KIF5B_exon20F | AGTTGAAAGCCACAGATCAGGA |
| 284 | KIF5B_exon21F | ACGAGAACAAGCAAGACAAGAC |
| 285 | MECOM_exon2_F | AGAGCAGAGGTCAAACCTGA |
| 286 | MET_exon11F | AGCCAGTGATGATCTCAATGGG |
| 287 | MYB_exon10_F | AGTTCAACTCCCAAGCGTTCCC |
| 288 | MYB_exon11_F | AACACCATTTCATAGAGACCAGACTG |
| 289 | MYB_exon12_F | TCAAACATGCACTTGCAGCTCAAG |
| 290 | MYB_exon13_F | TGCTGAGTTTCAAGAAAATGGACC |
| 291 | MYB_exon14_F | AGGGGACAGTCTGAATACCCA |
| 292 | MYB_exon15_F | TGTTCTCAAAGCATTTACAGTACCT |
| 293 | MYB_exon8_F | TTAGAATTGCTCCTAATGTCAACCGAGA |
| 294 | MYB_exon9_F | ACCTCTTAGAATTTGCAGAAACACT |
| 295 | NCOA4_exon9F | CAACCTCAGCCAGTTATCTTCTGG |
| 296 | PAN3_exon1_F | AGGCAGTAGCGGGGGAC |
| 297 | PAX3_exon7_F | TCCAACCCCATGAACCCCAC |
| 298 | PPFIBP1_exon11F | CAAAAAATGAAAAAAGCTGTGGAGTCC |
| 299 | PPFIBP1_exon9F_rdsgn | GGTCAGATGCAGTATGAAAAGCA |
| 300 | SCAF11_exon1_F | CCTGGGAACCTACTGTGGGG |
| 301 | SDC4_exon3F | TGGAAGACTCCATGATCGGC |
| 302 | SND1_exon12F | GCCTTTTCAGAGCGTACCTG |
| 303 | SND1_exon13F | GACCAGAGATCATCACACTACG |
| 304 | SND1_exon15F | GTCTCAAACTCTATTTGCCAAAGGAAACTT |
| 305 | SPTBN1_exon6_F | AGGGACGGCATGGCCTTC |
| 306 | SS18_exon10_F | AACACAGCCTGGACCACCA |
| 307 | SS18_exon9_F | AGTACCCAGGGCAGCAAGG |
| 308 | TMPRSS2_exon4F | ACCTTCCTCGTGGGAGCT |
| 309 | TPM3_exon2F_rdsgn | TTTGAAGGATGCCCAGGAGAAG |
| 310 | TPM3_exon4F | CTAAGCACATTGCAGAAGAGGC |
| 311 | TPM3_exon5F | AGGAGACTTGGAACGCACAG |
| 312 | TPM3_exon6F | GTCACCAACAACCTCAAGTCTC |
| 313 | TPM3_exon7F_rdsgn | GAAGATAAATATGAGGAAGAAATCAAGAT T |
| 314 | TRIM24_exon12_F | CAGAACGGTCCAGTCACCAA |
| 315 | FGFR3_exon17F_new | GAGGCCCACCTTCAAGCAG |

Table of reverse primers specific to genes that are capable of undergoing genomic alteration.

| SEQ ID NO | Primer name | Sequence |
|---|---|---|
| 316 | ABL1_E2a_R | CTTCACTCAGACCCTGAGGC |
| 317 | ABL1_E2b_R | CAACGAAAAGGTTGGGGTCA |
| 318 | ABL1_E3_R | GCTTCACACCATTCCCCATTG |
| 319 | ABL1_E4_R | GATGATGAACCAACTCGGCCA |
| 320 | AFF1_E11_R | ATGTGCTGATGCCACTGGTT |
| 321 | AFF1_E6_R | GGCTCAGCTGTACTAGGCG |
| 322 | AFF1_E9-10_R_rdsgn | GCTTCTCTGGGGTTTGTTCACT |
| 323 | ALK_exon19R | AGAGAGGATCAGCGAGAGTG |
| 324 | ALK_exon20RL | TCAGCTTGTACTCAGGGCTCT |
| 325 | ALK_exon21R | CTTGGGTCGTTGGGCATTC |
| 326 | BRAF_exon10R | CGTTAGTTAGTGAGCCAGGT |
| 327 | BRAF_exon11R | CAGGAATCTCCCAATCATCACTC |
| 328 | BRAF_exon8R | AGGGCTGTGGAATTGGAATG |
| 329 | BRAF_exon9R | CTCCATCACCACGAAATCCTTG |
| 330 | ERG_exon10R | AAGGCGGCTACTTGTTGGTC |
| 331 | ERG_exon11R | GAGGAACTGCCAAAGCTGGAT |
| 332 | ERG_exon2R | CTTTCCTCGGGTCTCCAAAG |
| 333 | ERG_exon3R | CCCATCTACCAGCTGTTCAG |
| 334 | ERG_exon4RS | TGGTCCTCACTCACAACTGATAAGG |
| 335 | ERG_exon5RS | CCACCATCTTCCCGCCTTTG |
| 336 | ERG_exon8R | CAGGAGATCAGCCTGGAC |
| 337 | ERG_exon9R | GGTCTTCAGTTTTGGGCACTG |
| 338 | MECOM_E2_R | TGCATCTGGCATTTCTTCCAAAG |
| 339 | MLLT3_E10_R | ATGTCATTAACCTTCTGTGAAGCTCTAC |
| 340 | MLLT3_E5_R | TGCTGCTGCTGCTGGTATGAATAC |
| 341 | MLLT3_E7_R | TCTGATTCCTCCTCATTGTCATCA |
| 342 | MLLT3_E9_R | TTTGCTTATCTGATTTGCTTTGCTTTATTG |
| 343 | MYH11_E28_R | TCTCTTTCTCCAGCGTCTGC |
| 344 | MYH11_E29_R | CTCGGCCTCGTTAAGCATCC |
| 345 | MYH11_E30_R | GCAGCTTCGTAGACACGTTG |
| 346 | MYH11_E32_R | CCTCTCATCCGCGTATTTGGA |
| 347 | MYH11_E33_R | TCCATCTGGGTCTCCAGGG |
| 348 | MYH11_E34_R | GTTGCTTTCGCTCGTCTTCC |
| 349 | RARA_E3_R | GGCTGGGCACTATCTCTTCA |
| 350 | RET_exon11RS | ATGAAGGAGAAGAGGACAGCGG |
| 351 | RET_exon12RL | TCCTAGAGTTTTTCCAAGAACCAAG |
| 352 | RET_exon7R | GGACGTTGATGCCACTGAAT |
| 353 | RET_exon8R | CTCTTGCTGACTGCACAGGACAG |

-continued

Table of reverse primers specific to genes that are capable of undergoing genomic alteration.

| SEQ ID NO | Primer name | Sequence |
|---|---|---|
| 354 | ROS1_exon34R | GGTCAGTGGGATTGTAACAACCAGA |
| 355 | ROS1_exon35R | CTTCGTTTATAAGCACTGTCACC |
| 356 | ROS1_exon36R | GAGGGAAGGCAGGAAGATT |
| 357 | RUNX1T1_E2_R | GCGTCTTCACATCCACAGGT |
| 358 | ACTR1A_exon3_R | AAGATGTCGCCTTCAAGGGCT |
| 359 | AHCYL1_exon2R | GTTTTGGTGGGGAATTTGGTGAAC |
| 360 | AKAP12_exon4_R | AGTAGCCATCTCTTTATCGGAGTCTC |
| 361 | AR_CE3_R | GGTCTGGTCATTTTGAGATGCTTG |
| 362 | AR_CE5_R | ACAACGTGATCCCAAAAGATGTG |
| 363 | AR_CE4_R | ATGCAGTATGGCTTGGGGTT |
| 364 | BAIAP2L1_exon2_3R | AGGATCATAGCGTTTACAGCTTTCT |
| 365 | BICC1_exon2_3R | TGCGTATTTGTTTCCTCCATGATC |
| 366 | CCDC170_exon2_R | AGTGGTTTAACTGCTCCCGC |
| 367 | CLDN7_exon2_R | GCACCAGGGAGACCACCATT |
| 368 | EGFR_exon14R | GGCACTGTATGCACTCAGAGTT |
| 369 | EGFR_exon15R | CAGGTCTTGACGCAGTGG |
| 370 | EGFR_exon18R | GCTTGGTTGGGAGCTTCTC |
| 371 | ERBB2_exon17R | AAGACCACGACCAGCAGAAT |
| 372 | ERBB2_ex8-int8_R | TGAGTGGGTACCTCACACC |
| 373 | ETV1_exon4_R | CTTCTGCAAGCCATGTTTCCT |
| 374 | ETV1_exon6_R | TGAACATGGACTGTGGGGTTCTTTC |
| 375 | ETV1_exon7_R | GGAGGGCCTCATTCCCACTT |
| 376 | ETV1_exon2_R | TGGTGACCATGTAAGGCACT |
| 377 | ETV1_exon2b_R | AGCATTTAGCTGGAGATTTCCTCA |
| 378 | ETV1_exon5_R | AACTTTCAGCCTGATAGTCTGGTACAA |
| 379 | ETV1_exon3_R | TTTTCTTTTCCTGACATTTGTTGGTTTC |
| 380 | ETV1_exon11_R | AGTTCATAGCTGGCCTGTTTTTCTG |
| 381 | ETV1_exon12_R | AGAAAAGGGCTTCTGGATCACACA |
| 382 | ETV4_exon1_2_R | CGAGACCTGCTCCCAGGA |
| 383 | ETV4_exon3_R | CATGAGCTTCCCCAGCGG |
| 384 | ETV4_exon5_R | CTGAATGGAAATCAGGAACAAACTGC |
| 385 | ETV4_exon4_R | AGCGAGCCACGTCTCCTG |
| 386 | ETV5_exon2_R | CAGCATTGAGTAATTTCTGGGGG |
| 387 | ETV5_exon8_R | AACTCCTGGCTGAGGAGGGAA |
| 388 | FGFR1_exon8_R | AGCACCTCCATCTCTTTGTCG |
| 389 | FGFR1_exon6_R | TGTCAGAGGGCACCACAGAG |
| 390 | FGFR1_exon9_R | AGATGATGATCTCCAGGTACAGG |

-continued

Table of reverse primers specific to genes that are capable of undergoing genomic alteration.

| SEQ ID NO | Primer name | Sequence |
|---|---|---|
| 391 | FGFR1_exon10_R | GAACCAGAAGAACCCCAGAGTTC |
| 392 | JAK2_exon9_R | CCATCAATTAATGACACGAAAGACAAAGC |
| 393 | JAK2_exon10_R | ACAGTCCAGTCTGATTACCTGC |
| 394 | JAK2_exon11_R | TGTCCCACTGAGGTTGTACT |
| 395 | JAK2_exon12_R | TGGTGAGGTTGGTACATCAGAA |
| 396 | JAK2_exon13_R | TGACCGTAGTCTCCTACTTCTCT |
| 397 | JAK2_exon14_R | TTAAAACCAAATGCTTGTGAGAAAGCT |
| 398 | JAK2_exon15_R | TCTTTTTCAGATATGTATCTAGTGATCCAA |
| 399 | JAK2_exon16_R | TCTCTGATAAGCAGAATATTTTTGGCACA |
| 400 | JAK2_exon17_R | GCATTCAGGTGGTACCCATGGTATT |
| 401 | JAK2_exon18_R | CCACTTTGGTGCAGGAAGCTGA |
| 402 | JAK2_exon19_R | AGGGCACCTATCCTCATATTTGGTAAC |
| 403 | MET_exon11R | GGAGTGGTACAACAGATTATCTCTG |
| 404 | MET_exon15R | CTGCACTTGTCGGCATGAAC |
| 405 | NOP2_exon16_R | GGATGACCTGAGGCAAGTCTA |
| 406 | NRG1_exon6R | CTCCGCACATTTTACAAGATGG |
| 407 | NRG1_exon5_6R | GTGGTGGATGTAGATGTAGATGAAGAAG |
| 408 | NRG1_exon2R | AACCTGCAGCCGATTCCTG |
| 409 | NRG1_exon3R | GAATCAGCCAGTGATGCTTTGT |
| 410 | NRG1_exon4R | TGCTCCTTCAGTTGAGGCTG |
| 411 | NTRK1-exon10R_rdsgn | GTGTTTCGTCCTTCTTCTCCACC |
| 412 | NTRK1-exon12R | TGTCATGAAATGCAGGGACATGG |
| 413 | NTRK1-exon9R | ACCAGTGGTGCATCTCCA |
| 414 | NTRK1-exon11R | AGCGTAGAAAGGAAGAGGCAGG |
| 415 | NTRK2_exon13_R_rdsgn | TGGTGTCCCCGATGTCATTC |
| 416 | NTRK2_exon16_R_rdsgn | GCTGGCAGAGTCATCATCATTG |
| 417 | NTRK3_exon14R | GTCCTCCTCACCACTGATGAC |
| 418 | NTRK3_exon15R | CTTCAGCACGATGTCTCTCCTCTTA |
| 419 | NTRK3_exon11_12R | GGACTCACTTCGTCAAACAAGAT |
| 420 | PAWR_exon3_R | TAATTGCATCTTCTCGTTTCCGCT |
| 421 | PBX1_exon3_R | CTGGGGGTCTGTGGGTTC |
| 422 | PCDH11X_exon11_R | CTTGAGTGCAGTTGTCAGAGGC |
| 423 | PDGFRA_exon12_R | TGATTCAATGACCCTCCAGCG |
| 424 | PDGFRB_exon11_R | GGATGATAAGGGAGATGATGGTGAG |
| 425 | PDGFRB_exon9_R | TGTCTGTTCCCCACTGTCAGG |
| 426 | PDGFRB_exon10_R | AGCTGGCTCTCCTCTTCGGA |
| 427 | PDGFRB_exon12_R | AGCTCACAGACTCAATCACCTTC |

-continued

Table of reverse primers specific to genes that are capable of undergoing genomic alteration.

| SEQ ID NO | Primer name | Sequence |
|---|---|---|
| 428 | PLAG1_exon4_R | GCTTTAGGTGGCTTCTCAAGTTTC |
| 429 | PLAG1_exon3_R | GACTCTTCGTGGAAGAGAGTGG |
| 430 | PLAG1_exon2_R | GAATGAAGCATTCTGGGTGCC |
| 431 | POLH_exon2_R | GTCCATGTCCACGAGAGCAA |
| 432 | PPARG_exon2R | AATGGCATCTCTGTGTCAACC |
| 433 | PPARGC1A_exon2R | AGGAAGATCTGGGCAAAGAGG |
| 434 | PPHLN1_exon3R | GTCTAGCAGTGGTGGTTTCTTTG |
| 435 | RAD51_exon4R_rdsg | GGTGGAATTCAGTTGCAGTGG |
| 436 | RUNX1_Exon4_R | CCTCGCTCATCTTGCCTGG |
| 437 | SHC1_exon2R_rdsgn | CCCTTCCACCCGAGTCCT |
| 438 | KIAA1598_exon7_R | TTCTCTGTTCAAGAACTTCTGAATTTAA |
| 439 | KIAA1598_exon8_R | GCTCCAGGTTTACTTGCATCTC |
| 440 | KIAA1598_exon9_R | AGCAGAAGGTGGCTTTGTCT |
| 441 | TACC1_exon7_R | TCCACAGGACACCGACACA |
| 442 | TACC3_exon11R | TTCTTCCCGTGGAGCTCCTC |
| 443 | TACC3_exon10R | GAGCAGGTCCACTATAGGTC |
| 444 | TACC3_exon8R | TCTACCAGGACTGTCCCTCA |
| 445 | TACC3_exon14R_rdsgn2 | GGGTGATCCTTGCCAGGTAAT |
| 446 | TACC3_exon6R | TCACTGCCTGGACAGCTTGTG |
| 447 | YAP1_exon4_R | TCCTGAGTCATGGCTTGTTCC |
| 448 | ABL1_E5_R_rdsgn | GCACCAGGTTAGGGTGTTTGA |
| 449 | AFF1_E4_R_redsgn | CCAGGCGATGAGTGTGAGAC |
| 450 | AFF1_E8_R | CGTTCCTTGCTGAGAATTTGAGT |
| 451 | CCAR2_exon4_R | AGTCATGCAAGCTGGTAACAA |
| 452 | CCDC170_exon10_R | GGATTTGTTTAGATCTTCAATGGCTTTA |
| 453 | CCDC170_exon6_R | TAACTTCCCTTTCAAGAGCTTCTTTTG |
| 454 | CCDC170_exon7_R | CAACTGTTCAACAAGCTCAGAT |
| 455 | CCDC170_exon8_R | GCCATCTGGTCCAACTTCATTTTCT |
| 456 | CCDC170_exon9_R | GGAGGCTCATGTGTAATTCTTTGCTCT |
| 457 | CIT_exon23_R | AGCTGTTACGAAGAGCATCAA |
| 458 | EGFR_exon17a_R | GTGGCGATGGACGGGATCT |
| 459 | EGFR_exon17b_R | GCATGAAGAGGCCGATCCC |
| 460 | EGFR_exon8_R | TCCTCCATCTCATAGCTGTCG |
| 461 | ERBB4_exon18_R | GAGCTTGATTGGGTGCTGTG |
| 462 | ERG_exon6R | TTCTTTCACCGCCCACTCCAG |
| 463 | ERG_exon7R | CCGTGGAGAGTTTTGTAAGGCTT |
| 464 | ETV1_exon10R | ATCCTCGCCGTTGGTATGTGG |

-continued

| Table of reverse primers specific to genes that are capable of undergoing genomic alteration. | | |
|---|---|---|
| SEQ ID NO | Primer name | Sequence |
| 465 | ETV1_exon8R | TCGTCGGCAAAGGAGGAAAG |
| 466 | ETV1_exon9R | GGACAACACAGGTGTCATCAT |
| 467 | FGFR1_exon7R | GCCACTGTTTGTTGGCGG |
| 468 | FLI1_exon3_R | AGCTTGCTGCATTTGCTAAC |
| 469 | FLI1_exon4_R | TTATGGCCCACTCCAGCCATT |
| 470 | FLI1_exon5_R | ATCGTGAGGATTGGTCGGTG |
| 471 | FLI1_exon6_R | GTTATTGCCCCAAGCTCCTCT |
| 472 | FLI1_exon7_R | TATTCTTACTGATCGTTTGTGCCC |
| 473 | FLI1_exon8_R | GTTGGCTAGGCGACTGCT |
| 474 | FLI1_exon9_R | GAGAGCAGCTCCAGGAGGAATTG |
| 475 | FOXO1_exon2_R | TCTGCACACGAATGAACTTGC |
| 476 | GPHN_exon11_R | GACATGCGATGTCTTCTAGCCAC |
| 477 | MBIP_exon4_R | CATTGATTTCAGCTTGCTTTCTTTC |
| 478 | MLLT3_E6_R_redsgn | TGGTCTGGGATGGTGTGAAG |
| 479 | MX1_exon12_R | CCACGATACTGATTTTCAAATTTCTGG |
| 480 | MX1_exon9_R | AAGTTTTTCTGCCAGGCAGGG |
| 481 | MYH11_E31_R_rdsgn | CTCTTCCAGAGCTTCCACGG |
| 482 | NCOA3_exon14_R | CTGCTCGGTTATATGGAGGACGAA |
| 483 | NCOA3_exon15_R | TAAGCCCCAGTCTCCTGAGGAA |
| 484 | NFIB_exon10_R | GGGCTTAGTCCCACATATCG |
| 485 | NFIB_exon11_R | GGGGTATAAATGCCTGCCGT |
| 486 | NFIB_exon12_R | AGATGGGTGTCCTATTTGACACTTGG |
| 487 | NFIB_exon9_R | GCCAGGCACTTTCCCTACTA |
| 488 | NTRK2_exon14R | AAAGGCAAAATCCCACCACAGA |
| 489 | NTRK2_exon15R | CAACACCTTGTCTTGATTTTACTTTCCC |
| 490 | NTRK2_exon17_R | TTCGCCTAGCTCCCTTTTCA |
| 491 | NTRK3_exon13R | AGAACCACCAACAGGACACAG |
| 492 | PDGFRA_exon2_R | ACAGCCTAAGACCAGGAACGC |
| 493 | PPARG_exon7_R | AGGTTGTCTTGAATGTCTTCAATGGGC |
| 494 | RET_exon10_R | GTGCCATAGCCAGCTTTAATCC |
| 495 | RET_exon9_R | CAGGTCTTGGTGCTGGGAG |
| 496 | ROS1_exon32_R_rdsgn | GAATTTTTACTCCCTTCTAGTAATTTGG |
| 497 | ROS1_exon33R | TTCCATGTGCAAACACTACTGC |
| 498 | SEPT14_exon10_R | GCTTCCTTATCTCCTCCTGTTGA |
| 499 | SSX1_exon4_R | CTGGAAGTCTGTGGCCTGTTT |
| 500 | SSX1_exon5_R | GGGATGATTCTGTGGAGCCT |
| 501 | SSX1_exon6_R | TGCTTCTGACACTCCCTTCG |

-continued

Table of reverse primers specific to genes that are capable of undergoing genomic alteration.

| SEQ ID NO | Primer name | Sequence |
|---|---|---|
| 502 | SSX2_exon3_R | TCATCTTTTCCCACTCTTCCTTAGAGA |
| 503 | SSX2_exon4_R | AGTCTTCGGCCCGTTTATTACA |
| 504 | SSX2_exon5_R | CTTCGGGGAGATTCCCTGGAG |
| 505 | SSX2_exon6_R | CTGGCACTTCCTCCGAATCA |
| 506 | TACC3_exon13a_R | CCTTCTGCTTCTGAACTTCCT |
| 507 | TACC3_exon13b_R | TTGGTCTTTTTCTTTTAGAACTTTCTGGAT |
| 508 | TACC3_exon5_R | TGCCAACTGCACCACAGG |
| 509 | TACC3_exon7R | AGGAAGTTCCAAACTGCTCCAGGTA |
| 510 | TACC3_exon9R | AAGAAATCGAACTCCACAAGC |
| 511 | TACC3_midExon4_R | TCTCCGCTTTGCATTCTTCCT |
| 512 | YAP1_exon5_R | GTGGCTGTTTCACTGGAGCA |

Table of forward primers specific to control housekeeping genes.

| SEQ ID NO | Primer name | Sequence |
|---|---|---|
| 513 | TBP_F_rdsgn | CTTTGCAGTGACCCAGCATCACT |
| 514 | ITGB7-F | GCACGCACCTATGTGGAAAC |
| 515 | PSMB2_F_rdsgn | TCTTCGGAGTCGGACCCCATAT |
| 516 | EMC7_A_F | TCGGTTTCCTTAAGACAGATGG |
| 517 | EMC7_B_F_rdsgn | ACTTTCTAATGAACCCAATGGTTAT |
| 518 | GPI_F | GCATCACAAGATCCTCCTGG |
| 519 | REEP5_F | CCAGCCTACATCTCAATTAAAGC |
| 520 | RRP1_F_rdsgn | CGGGCCGCAGGTGGTTTT |
| 521 | CHFR_F | AGTATTGTGATTACAGGGTCTGG |
| 522 | REL_F | GAATCAATCCATTCAATGTCCCTG |
| 523 | NASP_F_rdsgn | CAGGAAGCAGCTAGTCTTTTAGGTAAG |
| 524 | POMK_F_rdsgn_2 | GAAGGAGCTGTAAAGAGAGTCTT |
| 525 | FRMD8_F | GATAGCAGAGAGAAGCATGTCC |
| 526 | SLC4A1AP_A_F_ rdsgn | TCGGCAGGAAGCAGTATCT |
| 527 | SNAP29_F | GATCGACAGCAACCTAGATGAG |
| 528 | TUBGCP2_A_F_ rdsgn | CATCCACGACCCATACAGTGAGTTTATG |
| 529 | SNRPD3_F_rdsgn | GACAACATGAACTGCCAGATGTCCAA |
| 530 | PUM1_F | TCAGACCAGCAGGTAATTAATGAGA |
| 531 | CIAO1_F | CGTTTGGGTCTGGGAAGTTGATGA |
| 532 | SRSF4_F | TGGAACTGAAGTCAATGGGAG |

-continued

Table of forward primers specific to control housekeeping genes.

| SEQ ID NO | Primer name | Sequence |
|---|---|---|
| 533 | VCP_E1-2_F_new | GCTTCTGGAGCCGATTCAAA |
| 534 | RER1_E3_F_new | GGCTAGACAAGTCCACACCC |
| 535 | CHMP2A_E2-3_F | AAGCAAGGCCAGATGGATGC |
| 536 | RAB7A_E1_F | GTTTAGTCTCCTCCTCGGCG |
| 537 | ACTB_F | GAGACCGCGTCCGCC |

Table of reverse primers specific to control housekeeping genes.

| SEQ ID NO | Primer name | Sequence |
|---|---|---|
| 538 | TBP-R | GCATCTCCAGCACACTCTTC |
| 539 | ITGB7-R | AGCCAAACAGGAAACAGACCAG |
| 540 | PSMB2-R | AGGTAGTCCATGTAATACAGCG |
| 541 | EMC7_A-R | ACGGGATCAAATCTGTAAGCTG |
| 542 | EMC7_B-R | GTCTCATGTCAGGATCACTTGT |
| 543 | GPI-R | AAGGTCCTCTGGACTCTTGC |
| 544 | REEP5-R | CCATGACAGGAAGATATCAGAGAAG |
| 545 | RRP1_R | CTGGAGGAGTGGCTTGTC |
| 546 | CHFR-R | CTTTCTGTCTGGGAGAGCTG |
| 547 | REL-R | CATGTTCATCAGGGAGAAAAACTTG |
| 548 | NASP-R | CTTGCCAACTCCAGAAGTGA |

-continued

| Table of reverse primers specific to control housekeeping genes. | | |
|---|---|---|
| SEQ ID NO | Primer name | Sequence |
| 549 | POMK-R | CCTTGGAGAGATTTCAGCATCT |
| 550 | FRMD8-R | GAACTCCAGCCACAAGATG |
| 551 | SLC4A1AP_A-R | TCAGACGCTTCTTCTCAATCAG |
| 552 | SNAP29-R | TGTCATCTTGCTCCTCAATTTCTG |
| 553 | TUBGCP2_A-R | ACTTGTCGTTGTAATCCTCCTG |
| 554 | SNRPD3-R | GATTTTGCTGCCACGGATG |
| 555 | PUM1_R | ACCACGTGATTGCCATTCTG |
| 556 | CIAO1_R | GCCAAACCACATGCTTGACA |
| 557 | SRSF4_R | CTTCGAGAGCGAGACCTTGAAT |
| 558 | VCP_E2_R_new | ACAATTAACCGATTGGGACGG |
| 559 | RER1_E3-4_R_new | GTCACAATGTACCAACCCTGC |
| 560 | CHMP2A_E3_R | TTGAGGGACACAGCCTGGAT |
| 561 | RAB7A_E1-2_R | AGGTCATCCTTCAAACGCGG |
| 562 | ACTB_R | ATCATCCATGGTGAGCTGGC |

| Table of forward primers specific to target genes related to protein expression | | |
|---|---|---|
| SEQ ID NO | Primer name | Sequence |
| 563 | CD274_3UTR_F | CAAAGAAGCAAAGTGATACACATTTG |
| 564 | CD274_EXON4_F | GTGAAAGTCAATGCCCCATACAAC |
| 565 | CD274_EXON3_F | GGCATTTGCTGAACGCATTTACTG |
| 566 | PDCD1-EXON3_4_5_F | CCGCACGAGGGACAATAGGA |
| 567 | CTLA4-EXON1_2_F | CTTCTCTTCATCCCTGTCTTCTG |
| 568 | CTLA4-EXON4_F | GCTGTTTCTTTGAGCAAAATGCTAAAGA |
| 569 | CD47-EXON3_F | GAAGGTGAAACGATCATCGAGC |
| 570 | CD47-EXON9_10_11_F | GAGGAACCCCTTAATGCATTCAAAG |
| 571 | LAG3-EXON8_F | CTTTGGAGAAGACAGTGGCGAC |
| 572 | LAG3_EXON2-F_rdsgn | TTTGGGTGGCTCCAGTGAAG |
| 573 | HAVCR2_EXON3-F_rdsgn | AGTTGGTCATCAAACCAGCCAAG |
| 574 | HAVCR2_EXON7-F_rdsgn | CAAAGAGAAGATACAGAATTTAAGCCTCAT |
| 575 | PDCD1_EXON2-F_rdsgn | GCCAGGATGGTTCTTAGACTCC |
| 576 | CD14_exon1_1F | GAAGACTTATCGACCATGGAGC |
| 577 | CD27_exon1-2_1F | CAGATGTGTGAGCCAGGAAC |
| 578 | CD39_exon1_1F | CTTGAGAAAGGATTGCTGGTCA |
| 579 | CD40_exon6-7_1F | GACTGATGTTGTCTGTGGTCC |
| 580 | CD70_exon1_2F | CTTGGTGATCTGCCTCGTG |
| 581 | CD80_exon1_1F | TCTCAGAAGTGGAGTCTTACCC |
| 582 | FOXP3_exon6-7_1F | AGAGGACTTCCTCAAGCACTG |
| 583 | ICOS_exon3_1F | TGTGCAGCCTTTGTTGTAGT |
| 584 | ICOS_exon1-2_2F | GCATTAAAGTTTTAACAGGAGA |
| 585 | TIGIT_exon3_1F | AGATTCCATTGCTTGGAGCC |
| 586 | TNFRSF18_exon2-3_1F | TACAGTCCCAGGGGAAATTCAG |

-continued

Table of forward primers specific to target genes related to protein expression

| SEQ ID NO | Primer name | Sequence |
|---|---|---|
| 587 | VISTA_exon4-5_1F | TGCGGATGGACAGCAACATT |
| 588 | VISTA_exon2-3_2F | CCTCCCAGGATAGTGAAAACATC |

Table of reverse primers specific to target genes related to protein expression

| SEQ ID NO | Primer name | Sequence |
|---|---|---|
| 589 | CD274_3UTR_R | GAACCCCTAAACCACAGGTTGAG |
| 590 | CD274_EXON4_R | CTCAGCCTGACATGTCAGTTCATG |
| 591 | CD274_EXON3_R | CTACTGGGAATTTGCATTCAATTGTC |
| 592 | PDCD1_EXON2_R | AGAAGCTGCAGGTGAAGGTG |
| 593 | PDCD1-EXON3_4_5_R | GGAAATCCAGCTCCCCATAGTC |
| 594 | CTLA4-EXON1_2_R | GCATACTCACACACAAAGCTGG |
| 595 | CTLA4-EXON4_R | TTGCTTTTCACATTCTGGCTCTG |
| 596 | CD47-EXON3_R | CTGTCCCCAGAACAGGAGTATAG |
| 597 | CD47-EXON9_10_11_R | CCTTTCACGTCTTACTACTCTCCA |
| 598 | LAG3-EXON2_R | CAGAAGGCTGAGATCCTGGAG |
| 599 | LAG3-EXON8_R | GGTTCTTGCTCCAGCTCCTC |
| 600 | HAVCR2-EXON3_R | CCATGTCCCCTGGTGGTAAG |
| 601 | HAVCR2-EXON7_R | GGTATAGATGTTTTCTTCTGAGCGA |
| 602 | CD14_exon2_1R | CGCAGCGGAAATCTTCATCG |
| 603 | CD27_exon2_1R | GTCAGGAGAGAAGGAGACCC |
| 604 | CD39_exon1-2_1R | TCACGTTAGACTCTTGAAACCC |
| 605 | CD40_exon7_1R | GATAAAGACCAGCACCAAGAGG |
| 606 | CD70_exon1-2_2R | AGCTACGTCCCACCCAAG |
| 607 | CD80_exon1-2_1R | GTGGATTTAGTTTCACAGCTTGC |

-continued

Table of reverse primers specific to target genes related to protein expression

| SEQ ID NO | Primer name | Sequence |
|---|---|---|
| 608 | FOXP3_exon7_1R | TCTCTCTCTGGAGGAGACATTG |
| 609 | ICOS_exon3-4_1R | GCACACTGGATGAATACTTCTTT |
| 610 | ICOS_exon2_2R | TTTGTACACCTCCGTTGTGA |
| 611 | TIGIT_exon3-4_1R | GGATTCTGAGGGCTTTCTTCTT |
| 612 | TNFRSF18_exon3-4_1R | CAGCAGTCTGTCCAAGGTTTG |
| 613 | VISTA_exon5_1R | AGGACAGGGGGTGCCTGA |
| 614 | VISTA_exon3_2R | CTGCCTTTGCTTGTAGACCA |

Table of other sequences

| SEQ ID NO | Sequence name | Sequence |
|---|---|---|
| 615 | Barcode_sequence | NNNNNNNNNN |
| 616 | Universal indexed forward primer | AATGATACGGCGACCACCGAG ATCTACACCTAGCGCTACACT CTTTCCCTACACGACGCTCTT CCGATC*T |
| 617 | Universal indexed reverse primer | CAAGCAGAAGACGGCATACGA GATAACCGCGGGTGACTGGAG TTCAGACGTGTGCTCTTCCGA TC*T |

The invention claimed is:

1. A method of detecting genomic alteration and/or detecting gene expression and/or quantifying a level of gene expression using RNA in a biological sample, comprising:

(a) extracting RNA from the biological sample and converting the RNA to complementary DNA (cDNA);

(b) performing a plurality of multiplexed PCR reactions on the converted cDNA using (I) a plurality of forward and reverse primer pairs specific to a plurality of target genes that are capable of undergoing genomic alteration, wherein each forward primer of the plurality of forward and reverse primer pairs specific to the plurality of target genes that are capable of undergoing genomic alteration is complementary to a sequence located about 50 base pairs upstream of an exonic junction of each target gene that is capable of undergoing genomic alteration, wherein each reverse primer of the plurality of forward and reverse primer pairs specific to the plurality of target genes that are capable of undergoing genomic alteration is complementary to a sequence located about 50 base pairs downstream of an exonic junction of each target gene that is capable of undergoing genomic alteration, and/or (II) a plurality of forward and reverse primer pairs specific to a plurality of control housekeeping genes, wherein:

(i) each forward primer of the plurality of forward and reverse primer pairs specific to the plurality of control housekeeping genes is complementary to a sequence spanning an exon-exon junction of each control housekeeping gene, wherein each reverse primer of the plurality of forward and reverse primer pairs specific to the plurality of control housekeeping genes is complementary to a sequence about 100 base pairs downstream of the sequence spanning the exon-exon junction of each control housekeeping gene, (ii) each reverse primer of the plurality of forward and reverse primer pairs specific to the plurality of control housekeeping genes is complementary to a sequence spanning an exon-exon junction of each control housekeeping gene, wherein each forward primer of the plurality of forward and reverse primer pairs specific to the plurality of control housekeeping genes is complementary to a sequence about 100 base pairs downstream of the sequence spanning the exon-exon junction of each control housekeeping gene, or (iii) each forward and each reverse primer of the plurality of forward and reverse primer pairs specific to the plurality of control housekeeping genes is complementary to consecutive sequences spanning an exon-exon junction of each control housekeeping gene, and/or (III) a plurality of primer sets specific to a plurality of target genes related to protein expression, wherein each primer set comprises a plurality of forward and reverse primer pairs specific to each target gene related to protein expression, wherein:

(i) each forward primer of the of the plurality of forward and reverse primer pairs specific to each target gene related to protein expression is complementary to a sequence spanning an exon-exon junction of each target gene related to protein expression, wherein each reverse primer of the of the plurality of forward and reverse primer pairs specific to each target gene related to protein expression is complementary to a sequence about 100 base pairs downstream of the sequence spanning the exon-exon junction of each target gene related to protein expression, (ii) each reverse primer of the plurality of forward and reverse primer pairs specific to the plurality of target genes related to protein expression is complementary to a sequence spanning an exon-exon junction of each target gene related to protein expression, wherein each forward primer of the plurality of forward and reverse primer pairs specific to the plurality of target genes related to protein expression is complementary to a sequence about 100 base pairs downstream of the sequence spanning the exon-exon junction of each target gene related to protein expression, or (iii) each forward and each reverse primer of the plurality of forward and reverse primer pairs specific to the plurality of target genes related to protein expression is complementary to consecutive sequences spanning an exon-exon junction of each target gene related to protein expression, thereby generating a plurality of amplicons;

(c) amplifying the plurality of amplicons from step (b) by using universal indexed adapter primers to generate a sequencing library;

(d) subjecting the sequencing library from step (c) to multiplex sequencing on a next- generation sequencing platform to obtain a plurality of sequencing reads;

(e) performing a sequence alignment of the plurality of sequencing reads obtained from step (d) to a reference genome, (I) if the sequence alignment results in a partial alignment to the reference genome of an exon from a first gene and a partial alignment to the reference genome of an exon from a second gene, then:

(i) determining the sequence alignment as a split read, (ii) counting/enumerating the number of split reads from step (e)(I)(i) that supports a fusion junction, and (iii) if the number of split reads from step (e)(I)(ii) is two or more, then determining the first gene and the second gene as fusion partners, (II) if the sequence alignment results in an alignment to the reference genome of the control housekeeping gene, then:

(i) determining the sequence alignment as a consensus read of the control housekeeping gene, (ii) counting/enumerating consensus read pairs of the control housekeeping gene from step (e) (II) (i), and (iii) determining the level of gene expression of the control housekeeping gene, (III) if the sequence alignment results in an alignment to the reference genome of the target gene related to protein expression, (i) determining the sequence alignment as a consensus read of the target gene related to protein expression, (ii) counting/enumerating consensus read pairs of the target gene related to protein expression from step (e)(III)(i), and (iii) determining the level of gene expression of the target gene related to protein expression; and (f) determining presence or absence of the genomic alteration and/or determining presence or absence of the gene expression and/or quantifying the level of the gene expression based on the sequence alignment from step (e).

2. The method of claim 1, wherein the RNA is selected from the group consisting of cell-free RNA (cfRNA) and RNA encapsulated within tissues and/or cells.

3. The method of claim 1, wherein the biological sample is selected from the group consisting of a liquid sample, a tissue sample, and a cell sample.

4. The method of claim 3, wherein the liquid sample is a bodily fluid, wherein optionally the bodily fluid is selected from the group consisting of blood, bone marrow, cerebral spinal fluid, peritoneal fluid, pleural fluid, lymph fluid, ascites, serous fluid, sputum, lacrimal fluid, stool, urine, saliva, ductal fluid from breast, gastric juice and pancreatic juice, wherein optionally the bodily fluid is blood, and wherein optionally the blood is plasma.

5. The method of claim 3, wherein the tissue sample is a frozen tissue sample or a fixed tissue sample, and wherein optionally the fixed tissue sample is a Formalin-Fixed Paraffin-Embedded (FFPE) tissue sample.

6. The method of claim 1, wherein the biological sample is obtained from a subject having or suspected of having cancer.

7. The method of claim 6, wherein the cancer is selected from the group consisting of leukemia, lung cancer, colorectal cancer, breast cancer, pancreatic cancer, prostate cancer, nasopharyngeal cancer, liver cancer, cholangiocarcinoma, esophageal cancer, urothelial cancer, and gastrointestinal cancer.

8. The method of claim 6, wherein the cancer is selected from the group consisting of metastatic prostate cancer, metastatic lung cancer, metastatic breast cancer, and leukemia.

9. The method of claim 1, wherein the amount of RNA used in step (a) is from 6 ng to 100 ng.

10. The method of claim 1, wherein step (a) is performed using a reverse transcription kit, wherein the reverse transcription kit comprises a buffer for performing reverse transcription, a reverse transcriptase enzyme and a plurality of random primers.

11. The method of claim 1, wherein the plurality of multiplexed PCR reactions performed on the converted cDNA comprises 3 to 15 PCR cycles.

12. The method of claim 1, wherein each forward primer and/or reverse primer of the plurality of forward and reverse primer pairs specific to:

the plurality of target genes that are capable of undergoing genomic alteration;

the plurality of control housekeeping genes; and/or the plurality of target gene genes related to protein expression, comprises a barcode sequence on its 5' end, wherein the barcode sequence of each forward primer and/or reverse primer corresponding to:

each target gene that is capable of undergoing genomic alteration;

each control housekeeping gene; and each target gene related to protein expression is unique.

13. The method of claim 12, wherein the barcode sequence is an oligonucleotide comprising 10 to 16 random nucleotides.

14. The method of claim 1, wherein the target gene that is capable of undergoing genomic alteration comprises an exon from a gene known to undergo fusion fused to an exon from a partner gene of the gene known to undergo fusion.

15. The method of claim 14, wherein the gene known to undergo fusion is selected from the group consisting of ALK receptor tyrosine kinase, RET proto-oncogene, ROS proto-oncogene 1, fibroblast growth factor receptor 1 (FGFR1), fibroblast growth factor receptor 2 (FGFR2), fibroblast growth factor receptor 3 (FGFR3), neurotrophic receptor tyrosine kinase 1 (NTRK1), neurotrophic receptor tyrosine kinase 2 (NTRK2), neurotrophic receptor tyrosine kinase 3 (NTRK3), neuregulin 1 (NRG1), B-Raf proto-oncogene, serine/threonine kinase (BRAF), transmembrane serine protease 2 (TMPRSS2), MET proto-oncogene, receptor tyrosine kinase (MET), epidermal growth factor receptor (EGFR), estrogen receptor 1 (ESR1), platelet derived growth factor receptor alpha (PDGFRA), androgen receptor (AR), BCR activator of RhoGEF and GTPase (BCR), core-binding factor subunit beta (CBFB), lysine methyltransferase 2A (KMT2A), nucleophosmin 1 (NPM1), PML nuclear body scaffold (PML), and RUNX family transcription factor 1 (RUNX1).

16. The method of claim 14, wherein the partner gene of the gene known to undergo fusion is selected from the group consisting of EMAP like 4 (EML4), kinesin family member 5B (KIF5B), coiled-coil domain containing 6 (CCDC6), CD74molecule (CD74), transforming acidic coiled-coil containing protein 3 (TACC3), ezrin EZR), ETS transcription factor ERG (ERG), ArfGAP with GTPase domain, ankyrin repeat and PH domain 3 (AGAP3), A-kinase anchoring protein 9 (AKAP9), KIAA1549,tropomyosin 3 (TPM3), translocated promoter region, nuclear basket protein (TPR), trafficking from ER to golgi regulator (TFG), lamin A/C (LMNA), BicC family RNA binding protein 1 (BICC1), RAD51 recombinase (RAD51), CD47 molecule (CD47), Yes1 associated transcriptional regulator (YAP1), ETS variant transcription factor 1(ETV1), ETS variant transcription factor 4 (ETV4), ETS variant transcription factor 5(ETV5), ETS variant transcription factor 6 (ETV6), factor interacting with PAPOLA and CPSF1 (FIPIL1), centriolin (CNTRL), ABL proto-oncogene 1, non-receptor tyrosine kinase (ABL1), AF4/FMR2 family member 1 (AFF1), MDS1 and EVIL complex locus (MECOM), MLLT3 super elongation complex subunit (MLLT3), myosin heavy chain 11 (MYH11), PBX homeobox 1 (PBX1), retinoic acid receptor alpha (RARA), and RUNX1 partner transcriptional co-repressor 1 (RUNX1T1).

17. The method of claim 1, wherein the number of the plurality of forward and reverse primer pairs specific to the plurality of target genes that are capable of undergoing genomic alteration, the plurality of forward and reverse primer pairs specific to the plurality of control housekeeping genes, and the plurality of primer sets specific to a plurality of target genes related to protein expression is at least 300.

18. The method of claim 1, wherein the length of the plurality of amplicons generated in step (b) is 90 to 110 base pairs.

19. The method of claim 1, further comprising purifying the plurality of amplicons from step (b) and/or purifying the sequencing library obtained from step (c) using a plurality of paramagnetic beads; and wherein optionally the paramagnetic beads are selected from the group consisting of AMPure XP beads, SPRI beads, and dynabeads.

20. The method of claim 12, further comprising a step of deriving a consensus read of each sequence from the plurality of sequencing reads obtained from step (d), wherein the step further comprises:

(I) detecting the presence of the barcode sequence from each sequencing read, ((II) performing cluster reassignment for the plurality of sequencing reads having the same barcode sequence to generate a plurality of barcode clusters, wherein each barcode cluster contains reads from the same amplicon and with the same barcode sequence, and ((III) performing consensus calling for each barcode cluster to obtain the consensus read of each sequence.

21. The method of claim 1, wherein the step of determining presence or absence of the genomic alteration and/or determining presence or absence of the gene expression and/or quantifying the level of the gene expression, further comprises performing variant calling of the sequence alignment from step (e).

22. The method of claim 21, wherein the step of variant calling comprises:

(i) identifying differences between a consensus read and a reference genome based on the sequence alignment from step (e); and (ii) determining the read count of sequence alignments comprising genomic alteration.

23. The method of claim 21, wherein the genomic alteration is selected from the group consisting of insertions, deletions, and single nucleotide variants, wherein optionally the insertion is a duplication.

* * * * *

SEQUENCE LISTING

```
Sequence total quantity: 617
SEQ ID NO: 1            moltype = DNA  length = 19
FEATURE                 Location/Qualifiers
misc_feature            1..19
                        note = Forward Primer AGAP3_exon9F
source                  1..19
                        mol_type = other DNA
                        organism = synthetic construct
SEQUENCE: 1
agaagaaggc tgccgagtg                                              19

SEQ ID NO: 2            moltype = DNA  length = 18
FEATURE                 Location/Qualifiers
misc_feature            1..18
                        note = Forward Primer AGK_exon2F
```

```
source                1..18
                      mol_type = other DNA
                      organism = synthetic construct
SEQUENCE: 2
gctctgcctg ctgacctg                                           18

SEQ ID NO: 3          moltype = DNA  length = 23
FEATURE               Location/Qualifiers
misc_feature          1..23
                      note = Forward Primer AGTRAP_exon5F
source                1..23
                      mol_type = other DNA
                      organism = synthetic construct
SEQUENCE: 3
cagagcacag cattaaagtt tgg                                     23

SEQ ID NO: 4          moltype = DNA  length = 23
FEATURE               Location/Qualifiers
misc_feature          1..23
                      note = Forward Primer AKAP9_exon21F
source                1..23
                      mol_type = other DNA
                      organism = synthetic construct
SEQUENCE: 4
aggcatctgt aaagtcatgt gtc                                     23

SEQ ID NO: 5          moltype = DNA  length = 24
FEATURE               Location/Qualifiers
misc_feature          1..24
                      note = Forward Primer AKAP9_exon8F
source                1..24
                      mol_type = other DNA
                      organism = synthetic construct
SEQUENCE: 5
gagcaactca accaagtgaa aatg                                    24

SEQ ID NO: 6          moltype = DNA  length = 25
FEATURE               Location/Qualifiers
misc_feature          1..25
                      note = Forward Primer ARMC10_exon4F
source                1..25
                      mol_type = other DNA
                      organism = synthetic construct
SEQUENCE: 6
gcactaaata acctgagtgt gaatg                                   25

SEQ ID NO: 7          moltype = DNA  length = 19
FEATURE               Location/Qualifiers
misc_feature          1..19
                      note = Forward Primer ATIC_exon7F
source                1..19
                      mol_type = other DNA
                      organism = synthetic construct
SEQUENCE: 7
gtacacactg cagcccaag                                          19

SEQ ID NO: 8          moltype = DNA  length = 19
FEATURE               Location/Qualifiers
misc_feature          1..19
                      note = Forward Primer BCR_E1_F
source                1..19
                      mol_type = other DNA
                      organism = synthetic construct
SEQUENCE: 8
gcagatctgg cccaacgat                                          19

SEQ ID NO: 9          moltype = DNA  length = 25
FEATURE               Location/Qualifiers
misc_feature          1..25
                      note = Forward Primer BCR_E13_F
source                1..25
                      mol_type = other DNA
                      organism = synthetic construct
SEQUENCE: 9
ctgaccaact cgtgtgtgaa actcc                                   25

SEQ ID NO: 10         moltype = DNA  length = 20
FEATURE               Location/Qualifiers
misc_feature          1..20
```

```
                       note = Forward Primer BCR_E14_F
source                 1..20
                       mol_type = other DNA
                       organism = synthetic construct
SEQUENCE: 10
cggggctcta tgggtttctg                                              20

SEQ ID NO: 11          moltype = DNA  length = 22
FEATURE                Location/Qualifiers
misc_feature           1..22
                       note = Forward Primer BCR_E18_F
source                 1..22
                       mol_type = other DNA
                       organism = synthetic construct
SEQUENCE: 11
gtcttcggag tcaagattgc tg                                           22

SEQ ID NO: 12          moltype = DNA  length = 18
FEATURE                Location/Qualifiers
misc_feature           1..18
                       note = Forward Primer BCR_E19_F
source                 1..18
                       mol_type = other DNA
                       organism = synthetic construct
SEQUENCE: 12
atctaccgcg tgtccggt                                                18

SEQ ID NO: 13          moltype = DNA  length = 20
FEATURE                Location/Qualifiers
misc_feature           1..20
                       note = Forward Primer BCR_E2_F_rdsgn
source                 1..20
                       mol_type = other DNA
                       organism = synthetic construct
SEQUENCE: 13
acattgatga ctcgccctcc                                              20

SEQ ID NO: 14          moltype = DNA  length = 22
FEATURE                Location/Qualifiers
misc_feature           1..22
                       note = Forward Primer BCR_E6_F
source                 1..22
                       mol_type = other DNA
                       organism = synthetic construct
SEQUENCE: 14
aagatgccaa ggatccaacg ac                                           22

SEQ ID NO: 15          moltype = DNA  length = 21
FEATURE                Location/Qualifiers
misc_feature           1..21
                       note = Forward Primer BCR_E8_F
source                 1..21
                       mol_type = other DNA
                       organism = synthetic construct
SEQUENCE: 15
caatgaggag atcacacccc g                                            21

SEQ ID NO: 16          moltype = DNA  length = 18
FEATURE                Location/Qualifiers
misc_feature           1..18
                       note = Forward Primer BRAF_exon1F
source                 1..18
                       mol_type = other DNA
                       organism = synthetic construct
SEQUENCE: 16
tcttcggctg cggaccct                                                18

SEQ ID NO: 17          moltype = DNA  length = 24
FEATURE                Location/Qualifiers
misc_feature           1..24
                       note = Forward Primer BRAF_exon2F
source                 1..24
                       mol_type = other DNA
                       organism = synthetic construct
SEQUENCE: 17
gaacatatag aggccctatt ggac                                         24

SEQ ID NO: 18          moltype = DNA  length = 19
FEATURE                Location/Qualifiers
```

```
misc_feature          1..19
                      note = Forward Primer BRAF_exon3F
source                1..19
                      mol_type = other DNA
                      organism = synthetic construct
SEQUENCE: 18
gagcaacccc aagtcacca                                        19

SEQ ID NO: 19         moltype = DNA  length = 21
FEATURE               Location/Qualifiers
misc_feature          1..21
                      note = Forward Primer BRAF_exon4F
source                1..21
                      mol_type = other DNA
                      organism = synthetic construct
SEQUENCE: 19
tgagaggtct aatcccagag t                                     21

SEQ ID NO: 20         moltype = DNA  length = 25
FEATURE               Location/Qualifiers
misc_feature          1..25
                      note = Forward Primer BTF3L4_exon3F
source                1..25
                      mol_type = other DNA
                      organism = synthetic construct
SEQUENCE: 20
cagagttctc taaaaaaact ggctg                                 25

SEQ ID NO: 21         moltype = DNA  length = 21
FEATURE               Location/Qualifiers
misc_feature          1..21
                      note = Forward Primer CARS_exon17F
source                1..21
                      mol_type = other DNA
                      organism = synthetic construct
SEQUENCE: 21
gagaaggagt gcggaagatt g                                     21

SEQ ID NO: 22         moltype = DNA  length = 20
FEATURE               Location/Qualifiers
misc_feature          1..20
                      note = Forward Primer CBFB_E4_F
source                1..20
                      mol_type = other DNA
                      organism = synthetic construct
SEQUENCE: 22
tggtatgggc tgtctggagt                                       20

SEQ ID NO: 23         moltype = DNA  length = 19
FEATURE               Location/Qualifiers
misc_feature          1..19
                      note = Forward Primer CBFB_E5_F
source                1..19
                      mol_type = other DNA
                      organism = synthetic construct
SEQUENCE: 23
cggagaagga cacgcgaat                                        19

SEQ ID NO: 24         moltype = DNA  length = 22
FEATURE               Location/Qualifiers
misc_feature          1..22
                      note = Forward Primer CCDC6_exon1FS
source                1..22
                      mol_type = other DNA
                      organism = synthetic construct
SEQUENCE: 24
caaggcactg caggaggaga ac                                    22

SEQ ID NO: 25         moltype = DNA  length = 26
FEATURE               Location/Qualifiers
misc_feature          1..26
                      note = Forward Primer CCDC6_exon2F
source                1..26
                      mol_type = other DNA
                      organism = synthetic construct
SEQUENCE: 25
gaattcctca ctaatgagct ctccag                                26

SEQ ID NO: 26         moltype = DNA  length = 19
```

```
FEATURE                Location/Qualifiers
misc_feature           1..19
                       note = Forward Primer CCDC6_exon8F
source                 1..19
                       mol_type = other DNA
                       organism = synthetic construct
SEQUENCE: 26
cttcacgtgc agcacatgg                                               19

SEQ ID NO: 27          moltype = DNA  length = 23
FEATURE                Location/Qualifiers
misc_feature           1..23
                       note = Forward Primer CCDC91_exon11F
source                 1..23
                       mol_type = other DNA
                       organism = synthetic construct
SEQUENCE: 27
ggcagtgaaa agaacaagag atg                                          23

SEQ ID NO: 28          moltype = DNA  length = 22
FEATURE                Location/Qualifiers
misc_feature           1..22
                       note = Forward Primer CD74_exon6FS
source                 1..22
                       mol_type = other DNA
                       organism = synthetic construct
SEQUENCE: 28
tccttggagc aaaagcccac tg                                           22

SEQ ID NO: 29          moltype = DNA  length = 22
FEATURE                Location/Qualifiers
misc_feature           1..22
                       note = Forward Primer CDC27_exon16F
source                 1..22
                       mol_type = other DNA
                       organism = synthetic construct
SEQUENCE: 29
ttgatcccaa gaaccctcta tg                                           22

SEQ ID NO: 30          moltype = DNA  length = 21
FEATURE                Location/Qualifiers
misc_feature           1..21
                       note = Forward Primer CLTC_exon30F
source                 1..21
                       mol_type = other DNA
                       organism = synthetic construct
SEQUENCE: 30
catgccctat ttcatccagg t                                            21

SEQ ID NO: 31          moltype = DNA  length = 25
FEATURE                Location/Qualifiers
misc_feature           1..25
                       note = Forward Primer CLTC_exon31F
source                 1..25
                       mol_type = other DNA
                       organism = synthetic construct
SEQUENCE: 31
gaagaagaac aagctacaga gacac                                        25

SEQ ID NO: 32          moltype = DNA  length = 18
FEATURE                Location/Qualifiers
misc_feature           1..18
                       note = Forward Primer CUX1_exon10F_new
source                 1..18
                       mol_type = other DNA
                       organism = synthetic construct
SEQUENCE: 32
gccaatcact ccctccag                                                18

SEQ ID NO: 33          moltype = DNA  length = 20
FEATURE                Location/Qualifiers
misc_feature           1..20
                       note = Forward Primer DCTN1_exon16F
source                 1..20
                       mol_type = other DNA
                       organism = synthetic construct
SEQUENCE: 33
atgactgcgt tctggtgctg                                              20
```

```
SEQ ID NO: 34          moltype = DNA  length = 21
FEATURE                Location/Qualifiers
misc_feature           1..21
                       note = Forward Primer DCTN1_exon26F
source                 1..21
                       mol_type = other DNA
                       organism = synthetic construct
SEQUENCE: 34
cattgctact ctggtctctg g                                            21

SEQ ID NO: 35          moltype = DNA  length = 21
FEATURE                Location/Qualifiers
misc_feature           1..21
                       note = Forward Primer EML4_exon13F
source                 1..21
                       mol_type = other DNA
                       organism = synthetic construct
SEQUENCE: 35
ctactgtaga gcccacacct g                                            21

SEQ ID NO: 36          moltype = DNA  length = 24
FEATURE                Location/Qualifiers
misc_feature           1..24
                       note = Forward Primer EML4_exon14F
source                 1..24
                       mol_type = other DNA
                       organism = synthetic construct
SEQUENCE: 36
attaactgga ggagggaaag acag                                         24

SEQ ID NO: 37          moltype = DNA  length = 24
FEATURE                Location/Qualifiers
misc_feature           1..24
                       note = Forward Primer EML4_exon15F
source                 1..24
                       mol_type = other DNA
                       organism = synthetic construct
SEQUENCE: 37
cgaggaacat ttaatgatgg cttc                                         24

SEQ ID NO: 38          moltype = DNA  length = 25
FEATURE                Location/Qualifiers
misc_feature           1..25
                       note = Forward Primer EML4_exon16F
source                 1..25
                       mol_type = other DNA
                       organism = synthetic construct
SEQUENCE: 38
tgctcttgac atgtgctcag gacag                                        25

SEQ ID NO: 39          moltype = DNA  length = 25
FEATURE                Location/Qualifiers
misc_feature           1..25
                       note = Forward Primer EML4_exon17F
source                 1..25
                       mol_type = other DNA
                       organism = synthetic construct
SEQUENCE: 39
ctgtgcagat tttcatccaa gtggc                                        25

SEQ ID NO: 40          moltype = DNA  length = 25
FEATURE                Location/Qualifiers
misc_feature           1..25
                       note = Forward Primer EML4_exon18F
source                 1..25
                       mol_type = other DNA
                       organism = synthetic construct
SEQUENCE: 40
tctatccaca cagacgggaa tgaac                                        25

SEQ ID NO: 41          moltype = DNA  length = 25
FEATURE                Location/Qualifiers
misc_feature           1..25
                       note = Forward Primer EML4_exon20FS
source                 1..25
                       mol_type = other DNA
                       organism = synthetic construct
SEQUENCE: 41
ataatgtcta actcgggaga ctatg                                        25
```

```
SEQ ID NO: 42          moltype = DNA  length = 22
FEATURE                Location/Qualifiers
misc_feature           1..22
                       note = Forward Primer EML4_exon2F
source                 1..22
                       mol_type = other DNA
                       organism = synthetic construct
SEQUENCE: 42
gcaatctctg aagatcatgt gg                                           22

SEQ ID NO: 43          moltype = DNA  length = 27
FEATURE                Location/Qualifiers
misc_feature           1..27
                       note = Forward Primer EML4_exon5F
source                 1..27
                       mol_type = other DNA
                       organism = synthetic construct
SEQUENCE: 43
gcagacaagc ataaagatgt catcatc                                      27

SEQ ID NO: 44          moltype = DNA  length = 24
FEATURE                Location/Qualifiers
misc_feature           1..24
                       note = Forward Primer EPS15_exon22F
source                 1..24
                       mol_type = other DNA
                       organism = synthetic construct
SEQUENCE: 44
aatcatttgg aggtggattt gctg                                         24

SEQ ID NO: 45          moltype = DNA  length = 24
FEATURE                Location/Qualifiers
misc_feature           1..24
                       note = Forward Primer ERC1_exon12F
source                 1..24
                       mol_type = other DNA
                       organism = synthetic construct
SEQUENCE: 45
gaggtggaaa atgagaagaa tgac                                         24

SEQ ID NO: 46          moltype = DNA  length = 20
FEATURE                Location/Qualifiers
misc_feature           1..20
                       note = Forward Primer EWSR1_exon7F
source                 1..20
                       mol_type = other DNA
                       organism = synthetic construct
SEQUENCE: 46
ctacagccaa gctccaagtc                                              20

SEQ ID NO: 47          moltype = DNA  length = 20
FEATURE                Location/Qualifiers
misc_feature           1..20
                       note = Forward Primer EWSR1_exon9_10F
source                 1..20
                       mol_type = other DNA
                       organism = synthetic construct
SEQUENCE: 47
gcttcaataa gcctggtgga                                              20

SEQ ID NO: 48          moltype = DNA  length = 18
FEATURE                Location/Qualifiers
misc_feature           1..18
                       note = Forward Primer EZR_exon10F
source                 1..18
                       mol_type = other DNA
                       organism = synthetic construct
SEQUENCE: 48
ggctgcagga ctatgagg                                                18

SEQ ID NO: 49          moltype = DNA  length = 19
FEATURE                Location/Qualifiers
misc_feature           1..19
                       note = Forward Primer FAM131B_exon2F
source                 1..19
                       mol_type = other DNA
                       organism = synthetic construct
SEQUENCE: 49
```

```
catggacagc accagctca                                              19

SEQ ID NO: 50          moltype = DNA  length = 18
FEATURE                Location/Qualifiers
misc_feature           1..18
                       note = Forward Primer FCHSD1_exon13F
source                 1..18
                       mol_type = other DNA
                       organism = synthetic construct
SEQUENCE: 50
gatgaggtgg agcaggag                                               18

SEQ ID NO: 51          moltype = DNA  length = 28
FEATURE                Location/Qualifiers
misc_feature           1..28
                       note = Forward Primer FGFR1OP_exon12FS
source                 1..28
                       mol_type = other DNA
                       organism = synthetic construct
SEQUENCE: 51
gtggaaatag atgacatcaa taccagtg                                    28

SEQ ID NO: 52          moltype = DNA  length = 18
FEATURE                Location/Qualifiers
misc_feature           1..18
                       note = Forward Primer GHR_exon1F
source                 1..18
                       mol_type = other DNA
                       organism = synthetic construct
SEQUENCE: 52
cgaacccgcg ctctctga                                               18

SEQ ID NO: 53          moltype = DNA  length = 20
FEATURE                Location/Qualifiers
misc_feature           1..20
                       note = Forward Primer GOLGA5_exon7F
source                 1..20
                       mol_type = other DNA
                       organism = synthetic construct
SEQUENCE: 53
ggccagatac atcagctcag                                             20

SEQ ID NO: 54          moltype = DNA  length = 23
FEATURE                Location/Qualifiers
misc_feature           1..23
                       note = Forward Primer GOPC_exon4F
source                 1..23
                       mol_type = other DNA
                       organism = synthetic construct
SEQUENCE: 54
tgttctccag gctgaagtat atg                                         23

SEQ ID NO: 55          moltype = DNA  length = 27
FEATURE                Location/Qualifiers
misc_feature           1..27
                       note = Forward Primer GOPC_exon8F
source                 1..27
                       mol_type = other DNA
                       organism = synthetic construct
SEQUENCE: 55
caagtgggga aatcaaagta ttacaag                                     27

SEQ ID NO: 56          moltype = DNA  length = 25
FEATURE                Location/Qualifiers
misc_feature           1..25
                       note = Forward Primer GTF2I_exon4F
source                 1..25
                       mol_type = other DNA
                       organism = synthetic construct
SEQUENCE: 56
cagttgagga ctatttctgc ttttg                                       25

SEQ ID NO: 57          moltype = DNA  length = 18
FEATURE                Location/Qualifiers
misc_feature           1..18
                       note = Forward Primer HIP1_exon21F
source                 1..18
                       mol_type = other DNA
                       organism = synthetic construct
```

```
SEQUENCE: 57
accacctgcc tcagagcc                                          18

SEQ ID NO: 58           moltype = DNA  length = 23
FEATURE                 Location/Qualifiers
misc_feature            1..23
                        note = Forward Primer HIP1_exon28F
source                  1..23
                        mol_type = other DNA
                        organism = synthetic construct
SEQUENCE: 58
ctcaaccatt tccggcaaat cac                                    23

SEQ ID NO: 59           moltype = DNA  length = 19
FEATURE                 Location/Qualifiers
misc_feature            1..19
                        note = Forward Primer HIP1_exon30F
source                  1..19
                        mol_type = other DNA
                        organism = synthetic construct
SEQUENCE: 59
cttgctggtg ttgctgagg                                         19

SEQ ID NO: 60           moltype = DNA  length = 22
FEATURE                 Location/Qualifiers
misc_feature            1..22
                        note = Forward Primer IRF2BP2_E1a_F
source                  1..22
                        mol_type = other DNA
                        organism = synthetic construct
SEQUENCE: 60
gagcaagttt aagaaggagc cg                                     22

SEQ ID NO: 61           moltype = DNA  length = 20
FEATURE                 Location/Qualifiers
misc_feature            1..20
                        note = Forward Primer IRF2BP2_E1b_F
source                  1..20
                        mol_type = other DNA
                        organism = synthetic construct
SEQUENCE: 61
gcaggttgtt gggtttcgag                                        20

SEQ ID NO: 62           moltype = DNA  length = 22
FEATURE                 Location/Qualifiers
misc_feature            1..22
                        note = Forward Primer IRF2BP2_E2_F
source                  1..22
                        mol_type = other DNA
                        organism = synthetic construct
SEQUENCE: 62
ggagaggtct attgtcccag tg                                     22

SEQ ID NO: 63           moltype = DNA  length = 20
FEATURE                 Location/Qualifiers
misc_feature            1..20
                        note = Forward Primer KIAA1468_exon10FS
source                  1..20
                        mol_type = other DNA
                        organism = synthetic construct
SEQUENCE: 63
ctgcctgcca cacattgttc                                        20

SEQ ID NO: 64           moltype = DNA  length = 19
FEATURE                 Location/Qualifiers
misc_feature            1..19
                        note = Forward Primer KIAA1549_exon12F
source                  1..19
                        mol_type = other DNA
                        organism = synthetic construct
SEQUENCE: 64
acgcaggaga taagacgcc                                         19

SEQ ID NO: 65           moltype = DNA  length = 19
FEATURE                 Location/Qualifiers
misc_feature            1..19
                        note = Forward Primer KIAA1549_exon13F
source                  1..19
                        mol_type = other DNA
```

```
                       organism = synthetic construct
SEQUENCE: 65
cttatcgcca tgcagccga                                            19

SEQ ID NO: 66          moltype = DNA  length = 19
FEATURE                Location/Qualifiers
misc_feature           1..19
                       note = Forward Primer KIAA1549_exon14F
source                 1..19
                       mol_type = other DNA
                       organism = synthetic construct
SEQUENCE: 66
acaagatcct ggaccccac                                            19

SEQ ID NO: 67          moltype = DNA  length = 19
FEATURE                Location/Qualifiers
misc_feature           1..19
                       note = Forward Primer KIAA1549_exon15F
source                 1..19
                       mol_type = other DNA
                       organism = synthetic construct
SEQUENCE: 67
agcgatggca cctacagga                                            19

SEQ ID NO: 68          moltype = DNA  length = 18
FEATURE                Location/Qualifiers
misc_feature           1..18
                       note = Forward Primer KIAA1549_exon16F
source                 1..18
                       mol_type = other DNA
                       organism = synthetic construct
SEQUENCE: 68
aagagaggcg agccaccc                                             18

SEQ ID NO: 69          moltype = DNA  length = 18
FEATURE                Location/Qualifiers
misc_feature           1..18
                       note = Forward Primer KIAA1549_exon18F
source                 1..18
                       mol_type = other DNA
                       organism = synthetic construct
SEQUENCE: 69
ggaggagatg ccgtcggt                                             18

SEQ ID NO: 70          moltype = DNA  length = 19
FEATURE                Location/Qualifiers
misc_feature           1..19
                       note = Forward Primer KIAA1549_exon19F
source                 1..19
                       mol_type = other DNA
                       organism = synthetic construct
SEQUENCE: 70
aagcagaggc agccagtat                                            19

SEQ ID NO: 71          moltype = DNA  length = 25
FEATURE                Location/Qualifiers
misc_feature           1..25
                       note = Forward Primer KIF5B_exon15F
source                 1..25
                       mol_type = other DNA
                       organism = synthetic construct
SEQUENCE: 71
cttgcagaaa taggaattgc tgtgg                                     25

SEQ ID NO: 72          moltype = DNA  length = 25
FEATURE                Location/Qualifiers
misc_feature           1..25
                       note = Forward Primer KIF5B_exon16FS
source                 1..25
                       mol_type = other DNA
                       organism = synthetic construct
SEQUENCE: 72
tgaaaaggag ttagcagcat gtcag                                     25

SEQ ID NO: 73          moltype = DNA  length = 24
FEATURE                Location/Qualifiers
misc_feature           1..24
                       note = Forward Primer KIF5B_exon17F
source                 1..24
```

```
                        mol_type = other DNA
                        organism = synthetic construct
SEQUENCE: 73
atgccctcag tgaagaacta gtcc                                            24

SEQ ID NO: 74           moltype = DNA  length = 26
FEATURE                 Location/Qualifiers
misc_feature            1..26
                        note = Forward Primer KIF5B_exon22F
source                  1..26
                        mol_type = other DNA
                        organism = synthetic construct
SEQUENCE: 74
gaacttcaga ctttacacaa cctgcg                                          26

SEQ ID NO: 75           moltype = DNA  length = 24
FEATURE                 Location/Qualifiers
misc_feature            1..24
                        note = Forward Primer KIF5B_exon23FS
source                  1..24
                        mol_type = other DNA
                        organism = synthetic construct
SEQUENCE: 75
atcttgaaca gctcactaaa gtgc                                            24

SEQ ID NO: 76           moltype = DNA  length = 25
FEATURE                 Location/Qualifiers
misc_feature            1..25
                        note = Forward Primer KIF5B_exon24F_new
source                  1..25
                        mol_type = other DNA
                        organism = synthetic construct
SEQUENCE: 76
gaagcagtca ggtcaaagaa tatgg                                           25

SEQ ID NO: 77           moltype = DNA  length = 24
FEATURE                 Location/Qualifiers
misc_feature            1..24
                        note = Forward Primer KLC1_exon9F
source                  1..24
                        mol_type = other DNA
                        organism = synthetic construct
SEQUENCE: 77
tgcacatgaa agggagtttg gttc                                            24

SEQ ID NO: 78           moltype = DNA  length = 21
FEATURE                 Location/Qualifiers
misc_feature            1..21
                        note = Forward Primer KMT2A_E10_F
source                  1..21
                        mol_type = other DNA
                        organism = synthetic construct
SEQUENCE: 78
ccagggtggt ttgctttctc t                                               21

SEQ ID NO: 79           moltype = DNA  length = 20
FEATURE                 Location/Qualifiers
misc_feature            1..20
                        note = Forward Primer KMT2A_E11_F
source                  1..20
                        mol_type = other DNA
                        organism = synthetic construct
SEQUENCE: 79
tctgtcacgt ttgtggaagg                                                 20

SEQ ID NO: 80           moltype = DNA  length = 20
FEATURE                 Location/Qualifiers
misc_feature            1..20
                        note = Forward Primer KMT2A_E5_F
source                  1..20
                        mol_type = other DNA
                        organism = synthetic construct
SEQUENCE: 80
aagcccaagt ttggtggtcg                                                 20

SEQ ID NO: 81           moltype = DNA  length = 21
FEATURE                 Location/Qualifiers
misc_feature            1..21
                        note = Forward Primer KMT2A_E6_F
```

```
source                1..21
                      mol_type = other DNA
                      organism = synthetic construct
SEQUENCE: 81
caatggatgc cttccaaagc c                                                 21

SEQ ID NO: 82         moltype = DNA  length = 20
FEATURE               Location/Qualifiers
misc_feature          1..20
                      note = Forward Primer KMT2A_E7_F
source                1..20
                      mol_type = other DNA
                      organism = synthetic construct
SEQUENCE: 82
aaaccactcc tagtgagccc                                                   20

SEQ ID NO: 83         moltype = DNA  length = 18
FEATURE               Location/Qualifiers
misc_feature          1..18
                      note = Forward Primer KMT2A_E8_F
source                1..18
                      mol_type = other DNA
                      organism = synthetic construct
SEQUENCE: 83
gctccccgcc caagtatc                                                     18

SEQ ID NO: 84         moltype = DNA  length = 20
FEATURE               Location/Qualifiers
misc_feature          1..20
                      note = Forward Primer KMT2A_E9_F
source                1..20
                      mol_type = other DNA
                      organism = synthetic construct
SEQUENCE: 84
gcagatggag tccacaggat                                                   20

SEQ ID NO: 85         moltype = DNA  length = 23
FEATURE               Location/Qualifiers
misc_feature          1..23
                      note = Forward Primer KTN1_exon29F
source                1..23
                      mol_type = other DNA
                      organism = synthetic construct
SEQUENCE: 85
catgctaaaa gagagggaga gtg                                               23

SEQ ID NO: 86         moltype = DNA  length = 25
FEATURE               Location/Qualifiers
misc_feature          1..25
                      note = Forward Primer LRIG3_exon16F
source                1..25
                      mol_type = other DNA
                      organism = synthetic construct
SEQUENCE: 86
ttcttaccac aacatgacag tagtg                                             25

SEQ ID NO: 87         moltype = DNA  length = 21
FEATURE               Location/Qualifiers
misc_feature          1..21
                      note = Forward Primer MKRN1_exon4F
source                1..21
                      mol_type = other DNA
                      organism = synthetic construct
SEQUENCE: 87
atccaatgga tgctgcccag a                                                 21

SEQ ID NO: 88         moltype = DNA  length = 21
FEATURE               Location/Qualifiers
misc_feature          1..21
                      note = Forward Primer MSN_exon11F
source                1..21
                      mol_type = other DNA
                      organism = synthetic construct
SEQUENCE: 88
gacagaagaa ggagagtgag g                                                 21

SEQ ID NO: 89         moltype = DNA  length = 24
FEATURE               Location/Qualifiers
misc_feature          1..24
```

```
                        note = Forward Primer NCOA4_exon6FS
source                  1..24
                        mol_type = other DNA
                        organism = synthetic construct
SEQUENCE: 89
ttgaagctga cacaattact ctgc                                              24

SEQ ID NO: 90           moltype = DNA  length = 22
FEATURE                 Location/Qualifiers
misc_feature            1..22
                        note = Forward Primer NCOA4_exon7F
source                  1..22
                        mol_type = other DNA
                        organism = synthetic construct
SEQUENCE: 90
cctggagaag agaggctgta tc                                                22

SEQ ID NO: 91           moltype = DNA  length = 23
FEATURE                 Location/Qualifiers
misc_feature            1..23
                        note = Forward Primer NCOA4_exon8F_new
source                  1..23
                        mol_type = other DNA
                        organism = synthetic construct
SEQUENCE: 91
aggactggct tacccaaaag cag                                               23

SEQ ID NO: 92           moltype = DNA  length = 20
FEATURE                 Location/Qualifiers
misc_feature            1..20
                        note = Forward Primer NPM1_E4_F
source                  1..20
                        mol_type = other DNA
                        organism = synthetic construct
SEQUENCE: 92
aagtgtggtt cagggccagt                                                   20

SEQ ID NO: 93           moltype = DNA  length = 20
FEATURE                 Location/Qualifiers
misc_feature            1..20
                        note = Forward Primer NPM1_E5_F
source                  1..20
                        mol_type = other DNA
                        organism = synthetic construct
SEQUENCE: 93
tatctggaaa gcggtctgcc                                                   20

SEQ ID NO: 94           moltype = DNA  length = 19
FEATURE                 Location/Qualifiers
misc_feature            1..19
                        note = Forward Primer NUP214_exon21F
source                  1..19
                        mol_type = other DNA
                        organism = synthetic construct
SEQUENCE: 94
aagaccccac cagtgagat                                                    19

SEQ ID NO: 95           moltype = DNA  length = 23
FEATURE                 Location/Qualifiers
misc_feature            1..23
                        note = Forward Primer PAPSS1_exon5F
source                  1..23
                        mol_type = other DNA
                        organism = synthetic construct
SEQUENCE: 95
ctcctgtgat gtaaatgact gtg                                               23

SEQ ID NO: 96           moltype = DNA  length = 18
FEATURE                 Location/Qualifiers
misc_feature            1..18
                        note = Forward Primer PML_E3_F
source                  1..18
                        mol_type = other DNA
                        organism = synthetic construct
SEQUENCE: 96
agttcaaggt gcgcctgc                                                     18

SEQ ID NO: 97           moltype = DNA  length = 19
FEATURE                 Location/Qualifiers
```

```
misc_feature           1..19
                       note = Forward Primer PML_E6a_F
source                 1..19
                       mol_type = other DNA
                       organism = synthetic construct
SEQUENCE: 97
cttcctgccc aacagcaac                                              19

SEQ ID NO: 98          moltype = DNA  length = 21
FEATURE                Location/Qualifiers
misc_feature           1..21
                       note = Forward Primer PML_E6b_F
source                 1..21
                       mol_type = other DNA
                       organism = synthetic construct
SEQUENCE: 98
tgccccagga aggtcatcaa g                                           21

SEQ ID NO: 99          moltype = DNA  length = 21
FEATURE                Location/Qualifiers
misc_feature           1..21
                       note = Forward Primer PPFIBP1_exon12F
source                 1..21
                       mol_type = other DNA
                       organism = synthetic construct
SEQUENCE: 99
atgcaagaca cggtggtact g                                           21

SEQ ID NO: 100         moltype = DNA  length = 23
FEATURE                Location/Qualifiers
misc_feature           1..23
                       note = Forward Primer PPFIBP1_exon8F
source                 1..23
                       mol_type = other DNA
                       organism = synthetic construct
SEQUENCE: 100
ggacagtgag agacttcagt atg                                         23

SEQ ID NO: 101         moltype = DNA  length = 24
FEATURE                Location/Qualifiers
misc_feature           1..24
                       note = Forward Primer PPFIBP1_exon9F
source                 1..24
                       mol_type = other DNA
                       organism = synthetic construct
SEQUENCE: 101
tggtttgcaa gatgaaagga gaag                                        24

SEQ ID NO: 102         moltype = DNA  length = 24
FEATURE                Location/Qualifiers
misc_feature           1..24
                       note = Forward Primer PRKAR1A_7F
source                 1..24
                       mol_type = other DNA
                       organism = synthetic construct
SEQUENCE: 102
catcgaccga gacagctata gaag                                        24

SEQ ID NO: 103         moltype = DNA  length = 19
FEATURE                Location/Qualifiers
misc_feature           1..19
                       note = Forward Primer PWWP2A_exon1F
source                 1..19
                       mol_type = other DNA
                       organism = synthetic construct
SEQUENCE: 103
ttgtcgtgtc gttccgctt                                              19

SEQ ID NO: 104         moltype = DNA  length = 21
FEATURE                Location/Qualifiers
misc_feature           1..21
                       note = Forward Primer RANBP2_exon18F
source                 1..21
                       mol_type = other DNA
                       organism = synthetic construct
SEQUENCE: 104
gggtcacaga catttcatgg g                                           21

SEQ ID NO: 105         moltype = DNA  length = 21
```

```
FEATURE                Location/Qualifiers
misc_feature           1..21
                       note = Forward Primer RUNX1_E5_F
source                 1..21
                       mol_type = other DNA
                       organism = synthetic construct
SEQUENCE: 105
atgacctcag gtttgtcggt c                                            21

SEQ ID NO: 106         moltype = DNA  length = 21
FEATURE                Location/Qualifiers
misc_feature           1..21
                       note = Forward Primer RUNX1_E6_F
source                 1..21
                       mol_type = other DNA
                       organism = synthetic construct
SEQUENCE: 106
acctaccaca gagccatcaa a                                            21

SEQ ID NO: 107         moltype = DNA  length = 20
FEATURE                Location/Qualifiers
misc_feature           1..20
                       note = Forward Primer RUNX1_E7_F
source                 1..20
                       mol_type = other DNA
                       organism = synthetic construct
SEQUENCE: 107
actgccttta accctcagcc                                              20

SEQ ID NO: 108         moltype = DNA  length = 25
FEATURE                Location/Qualifiers
misc_feature           1..25
                       note = Forward Primer SDC4_exon2F
source                 1..25
                       mol_type = other DNA
                       organism = synthetic construct
SEQUENCE: 108
atctgatgac tttgagctgt ctggc                                        25

SEQ ID NO: 109         moltype = DNA  length = 24
FEATURE                Location/Qualifiers
misc_feature           1..24
                       note = Forward Primer SDC4_exon4F
source                 1..24
                       mol_type = other DNA
                       organism = synthetic construct
SEQUENCE: 109
gcagcaacat ctttgagaga acgg                                         24

SEQ ID NO: 110         moltype = DNA  length = 25
FEATURE                Location/Qualifiers
misc_feature           1..25
                       note = Forward Primer SLC34A2_exon13delF
source                 1..25
                       mol_type = other DNA
                       organism = synthetic construct
SEQUENCE: 110
tgtcaaggct cctgagacct ttgat                                        25

SEQ ID NO: 111         moltype = DNA  length = 25
FEATURE                Location/Qualifiers
misc_feature           1..25
                       note = Forward Primer SLC34A2_exon4F
source                 1..25
                       mol_type = other DNA
                       organism = synthetic construct
SEQUENCE: 111
tcgtgtgctc cctggatatt cttag                                        25

SEQ ID NO: 112         moltype = DNA  length = 20
FEATURE                Location/Qualifiers
misc_feature           1..20
                       note = Forward Primer SND1_exon10F
source                 1..20
                       mol_type = other DNA
                       organism = synthetic construct
SEQUENCE: 112
gattcacctg tccagcatcc                                              20
```

```
SEQ ID NO: 113         moltype = DNA  length = 19
FEATURE                Location/Qualifiers
misc_feature           1..19
                       note = Forward Primer SND1_exon11F
source                 1..19
                       mol_type = other DNA
                       organism = synthetic construct
SEQUENCE: 113
ccttacatgt ttgaggccc                                           19

SEQ ID NO: 114         moltype = DNA  length = 23
FEATURE                Location/Qualifiers
misc_feature           1..23
                       note = Forward Primer SND1_exon14F
source                 1..23
                       mol_type = other DNA
                       organism = synthetic construct
SEQUENCE: 114
aggattgcat agcaagaagg aag                                      23

SEQ ID NO: 115         moltype = DNA  length = 19
FEATURE                Location/Qualifiers
misc_feature           1..19
                       note = Forward Primer SND1_exon16F
source                 1..19
                       mol_type = other DNA
                       organism = synthetic construct
SEQUENCE: 115
cttggtgcag gaaggagag                                           19

SEQ ID NO: 116         moltype = DNA  length = 21
FEATURE                Location/Qualifiers
misc_feature           1..21
                       note = Forward Primer SND1_exon9F
source                 1..21
                       mol_type = other DNA
                       organism = synthetic construct
SEQUENCE: 116
gctcccacag ctaatttgga c                                        21

SEQ ID NO: 117         moltype = DNA  length = 23
FEATURE                Location/Qualifiers
misc_feature           1..23
                       note = Forward Primer SQSTM1_exon5F
source                 1..23
                       mol_type = other DNA
                       organism = synthetic construct
SEQUENCE: 117
cgagtgtgaa tttcctgaag aac                                      23

SEQ ID NO: 118         moltype = DNA  length = 20
FEATURE                Location/Qualifiers
misc_feature           1..20
                       note = Forward Primer STAT5B_E15_F
source                 1..20
                       mol_type = other DNA
                       organism = synthetic construct
SEQUENCE: 118
gtgactcaga aattggcggc                                          20

SEQ ID NO: 119         moltype = DNA  length = 25
FEATURE                Location/Qualifiers
misc_feature           1..25
                       note = Forward Primer STRN_exon3F
source                 1..25
                       mol_type = other DNA
                       organism = synthetic construct
SEQUENCE: 119
tgaatcaggg agatatgaag cctcc                                    25

SEQ ID NO: 120         moltype = DNA  length = 23
FEATURE                Location/Qualifiers
misc_feature           1..23
                       note = Forward Primer TAX1BP1_exon8F
source                 1..23
                       mol_type = other DNA
                       organism = synthetic construct
SEQUENCE: 120
gcagttatgt ttggctgaaa agg                                      23
```

```
SEQ ID NO: 121          moltype = DNA  length = 24
FEATURE                 Location/Qualifiers
misc_feature            1..24
                        note = Forward Primer TFG_exon3F
source                  1..24
                        mol_type = other DNA
                        organism = synthetic construct
SEQUENCE: 121
gtgcagtagg atactgaaac tgac                                          24

SEQ ID NO: 122          moltype = DNA  length = 19
FEATURE                 Location/Qualifiers
misc_feature            1..19
                        note = Forward Primer TFG_exon4F
source                  1..19
                        mol_type = other DNA
                        organism = synthetic construct
SEQUENCE: 122
gagaaccagg accttccac                                                19

SEQ ID NO: 123          moltype = DNA  length = 25
FEATURE                 Location/Qualifiers
misc_feature            1..25
                        note = Forward Primer TFG_exon5F_new
source                  1..25
                        mol_type = other DNA
                        organism = synthetic construct
SEQUENCE: 123
atgttatgtc agcgtttggc ttaac                                         25

SEQ ID NO: 124          moltype = DNA  length = 20
FEATURE                 Location/Qualifiers
misc_feature            1..20
                        note = Forward Primer TFG_exon6F_new
source                  1..20
                        mol_type = other DNA
                        organism = synthetic construct
SEQUENCE: 124
cagcagccac catatacagg                                               20

SEQ ID NO: 125          moltype = DNA  length = 18
FEATURE                 Location/Qualifiers
misc_feature            1..18
                        note = Forward Primer TMPRSS2_exon1F
source                  1..18
                        mol_type = other DNA
                        organism = synthetic construct
SEQUENCE: 125
taagcaggag gcggaggc                                                 18

SEQ ID NO: 126          moltype = DNA  length = 26
FEATURE                 Location/Qualifiers
misc_feature            1..26
                        note = Forward Primer TMPRSS2_exon2F
source                  1..26
                        mol_type = other DNA
                        organism = synthetic construct
SEQUENCE: 126
cagataccta tcattactcg atgctg                                        26

SEQ ID NO: 127          moltype = DNA  length = 18
FEATURE                 Location/Qualifiers
misc_feature            1..18
                        note = Forward Primer TMPRSS2_exon3F
source                  1..18
                        mol_type = other DNA
                        organism = synthetic construct
SEQUENCE: 127
tcctgacgca ggcttcca                                                 18

SEQ ID NO: 128          moltype = DNA  length = 21
FEATURE                 Location/Qualifiers
misc_feature            1..21
                        note = Forward Primer TMPRSS2_exon5F
source                  1..21
                        mol_type = other DNA
                        organism = synthetic construct
SEQUENCE: 128
```

```
ctctaactgg tgtgatggcg t                                            21

SEQ ID NO: 129          moltype = DNA  length = 21
FEATURE                 Location/Qualifiers
misc_feature            1..21
                        note = Forward Primer TPM3_exon2F
source                  1..21
                        mol_type = other DNA
                        organism = synthetic construct
SEQUENCE: 129
gcaaaagctg gaagaagctg a                                            21

SEQ ID NO: 130          moltype = DNA  length = 22
FEATURE                 Location/Qualifiers
misc_feature            1..22
                        note = Forward Primer TPM3_exon8F
source                  1..22
                        mol_type = other DNA
                        organism = synthetic construct
SEQUENCE: 130
agtttgctga gagatcggta gc                                           22

SEQ ID NO: 131          moltype = DNA  length = 24
FEATURE                 Location/Qualifiers
misc_feature            1..24
                        note = Forward Primer TPM4_exon8F
source                  1..24
                        mol_type = other DNA
                        organism = synthetic construct
SEQUENCE: 131
ggaaaagaca attgatgacc tgga                                         24

SEQ ID NO: 132          moltype = DNA  length = 23
FEATURE                 Location/Qualifiers
misc_feature            1..23
                        note = Forward Primer TPR_exon15F
source                  1..23
                        mol_type = other DNA
                        organism = synthetic construct
SEQUENCE: 132
caaacaacag gagttgccat tcc                                          23

SEQ ID NO: 133          moltype = DNA  length = 22
FEATURE                 Location/Qualifiers
misc_feature            1..22
                        note = Forward Primer TRIM24_exon3F
source                  1..22
                        mol_type = other DNA
                        organism = synthetic construct
SEQUENCE: 133
gttcacaaaa gaccacactg tc                                           22

SEQ ID NO: 134          moltype = DNA  length = 22
FEATURE                 Location/Qualifiers
misc_feature            1..22
                        note = Forward Primer TRIM24_exon8F
source                  1..22
                        mol_type = other DNA
                        organism = synthetic construct
SEQUENCE: 134
tcactgtgat cctagtttct gg                                           22

SEQ ID NO: 135          moltype = DNA  length = 19
FEATURE                 Location/Qualifiers
misc_feature            1..19
                        note = Forward Primer TRIM24_exon9F
source                  1..19
                        mol_type = other DNA
                        organism = synthetic construct
SEQUENCE: 135
tcccaacaca gatcagcct                                               19

SEQ ID NO: 136          moltype = DNA  length = 21
FEATURE                 Location/Qualifiers
misc_feature            1..21
                        note = Forward Primer VCL_exon16F
source                  1..21
                        mol_type = other DNA
                        organism = synthetic construct
```

```
SEQUENCE: 136
cgatggtgat ggatgcaaaa g                                              21

SEQ ID NO: 137         moltype = DNA  length = 20
FEATURE                Location/Qualifiers
misc_feature           1..20
                       note = Forward Primer ZBTB16_E2_F
source                 1..20
                       mol_type = other DNA
                       organism = synthetic construct
SEQUENCE: 137
tggggtcgag cttcctgata                                                20

SEQ ID NO: 138         moltype = DNA  length = 20
FEATURE                Location/Qualifiers
misc_feature           1..20
                       note = Forward Primer ZBTB16_E3_F
source                 1..20
                       mol_type = other DNA
                       organism = synthetic construct
SEQUENCE: 138
gttcctggat agtttgcggc                                                20

SEQ ID NO: 139         moltype = DNA  length = 20
FEATURE                Location/Qualifiers
misc_feature           1..20
                       note = Forward Primer ZBTB16_E4_F
source                 1..20
                       mol_type = other DNA
                       organism = synthetic construct
SEQUENCE: 139
tttcgaagga ggatgccctg                                                20

SEQ ID NO: 140         moltype = DNA  length = 20
FEATURE                Location/Qualifiers
misc_feature           1..20
                       note = Forward Primer ZC3HAV1_exon3F
source                 1..20
                       mol_type = other DNA
                       organism = synthetic construct
SEQUENCE: 140
catctgcaac agcaagcaca                                                20

SEQ ID NO: 141         moltype = DNA  length = 22
FEATURE                Location/Qualifiers
misc_feature           1..22
                       note = Forward Primer AGBL4_exon5_6F
source                 1..22
                       mol_type = other DNA
                       organism = synthetic construct
SEQUENCE: 141
ccagagtgtg caacaacgaa ag                                             22

SEQ ID NO: 142         moltype = DNA  length = 21
FEATURE                Location/Qualifiers
misc_feature           1..21
                       note = Forward Primer AR_exon2_F_rdsgn
source                 1..21
                       mol_type = other DNA
                       organism = synthetic construct
SEQUENCE: 142
tgtggaagct gcaaggtctt c                                              21

SEQ ID NO: 143         moltype = DNA  length = 23
FEATURE                Location/Qualifiers
misc_feature           1..23
                       note = Forward Primer AR_exon3_F
source                 1..23
                       mol_type = other DNA
                       organism = synthetic construct
SEQUENCE: 143
ccatcttgtc gtcttcggaa atg                                            23

SEQ ID NO: 144         moltype = DNA  length = 21
FEATURE                Location/Qualifiers
misc_feature           1..21
                       note = Forward Primer BAG4_exon1_F
source                 1..21
                       mol_type = other DNA
```

```
                         organism = synthetic construct
SEQUENCE: 144
atggctacta tccctcggga g                                               21

SEQ ID NO: 145           moltype = DNA  length = 25
FEATURE                  Location/Qualifiers
misc_feature             1..25
                         note = Forward Primer BAG4_exon2_F
source                   1..25
                         mol_type = other DNA
                         organism = synthetic construct
SEQUENCE: 145
gctccttacc caagtacata tcctg                                           25

SEQ ID NO: 146           moltype = DNA  length = 24
FEATURE                  Location/Qualifiers
misc_feature             1..24
                         note = Forward Primer BAIAP2L1_exon9_F
source                   1..24
                         mol_type = other DNA
                         organism = synthetic construct
SEQUENCE: 146
cgatatgttt aataacccag ccac                                            24

SEQ ID NO: 147           moltype = DNA  length = 20
FEATURE                  Location/Qualifiers
misc_feature             1..20
                         note = Forward Primer BCAN_exon13F
source                   1..20
                         mol_type = other DNA
                         organism = synthetic construct
SEQUENCE: 147
aagagaacgg tcgttgggag                                                 20

SEQ ID NO: 148           moltype = DNA  length = 22
FEATURE                  Location/Qualifiers
misc_feature             1..22
                         note = Forward Primer BCR_exon4_F
source                   1..22
                         mol_type = other DNA
                         organism = synthetic construct
SEQUENCE: 148
ttctatgatg ggctcttccc cc                                              22

SEQ ID NO: 149           moltype = DNA  length = 23
FEATURE                  Location/Qualifiers
misc_feature             1..23
                         note = Forward Primer BCR_exon7_F
source                   1..23
                         mol_type = other DNA
                         organism = synthetic construct
SEQUENCE: 149
ctctgctcta caagcctgtg gac                                             23

SEQ ID NO: 150           moltype = DNA  length = 21
FEATURE                  Location/Qualifiers
misc_feature             1..21
                         note = Forward Primer BCR_exon9_F
source                   1..21
                         mol_type = other DNA
                         organism = synthetic construct
SEQUENCE: 150
cgtcttcctg ttcaccgacc t                                               21

SEQ ID NO: 151           moltype = DNA  length = 23
FEATURE                  Location/Qualifiers
misc_feature             1..23
                         note = Forward Primer BTBD1_exon4F
source                   1..23
                         mol_type = other DNA
                         organism = synthetic construct
SEQUENCE: 151
aagcactttc cttaatccgg ttc                                             23

SEQ ID NO: 152           moltype = DNA  length = 22
FEATURE                  Location/Qualifiers
misc_feature             1..22
                         note = Forward Primer HMGN2P46_exon1_F
source                   1..22
```

```
                        mol_type = other DNA
                        organism = synthetic construct
SEQUENCE: 152
aggtgaatct tttggttggt ga                                              22

SEQ ID NO: 153          moltype = DNA  length = 23
FEATURE                 Location/Qualifiers
misc_feature            1..23
                        note = Forward Primer HMGN2P46_exon2_F
source                  1..23
                        mol_type = other DNA
                        organism = synthetic construct
SEQUENCE: 153
catgcttgtc aaaaatcaga ggc                                             23

SEQ ID NO: 154          moltype = DNA  length = 21
FEATURE                 Location/Qualifiers
misc_feature            1..21
                        note = Forward Primer C8orf34_exon2_F_rdsgn
source                  1..21
                        mol_type = other DNA
                        organism = synthetic construct
SEQUENCE: 154
ggaaccgtgg acaacttcaa a                                               21

SEQ ID NO: 155          moltype = DNA  length = 24
FEATURE                 Location/Qualifiers
misc_feature            1..24
                        note = Forward Primer CAPZA2_exon4_F
source                  1..24
                        mol_type = other DNA
                        organism = synthetic construct
SEQUENCE: 155
gcatttgcac agtataactt ggac                                            24

SEQ ID NO: 156          moltype = DNA  length = 25
FEATURE                 Location/Qualifiers
misc_feature            1..25
                        note = Forward Primer CD47_exon7F
source                  1..25
                        mol_type = other DNA
                        organism = synthetic construct
SEQUENCE: 156
ggtttgagta tcttagctct agcac                                           25

SEQ ID NO: 157          moltype = DNA  length = 23
FEATURE                 Location/Qualifiers
misc_feature            1..23
                        note = Forward Primer CD74_exon8F
source                  1..23
                        mol_type = other DNA
                        organism = synthetic construct
SEQUENCE: 157
gaaagagtca ctggaactgg agg                                             23

SEQ ID NO: 158          moltype = DNA  length = 23
FEATURE                 Location/Qualifiers
misc_feature            1..23
                        note = Forward Primer CNTRL_exon15_F
source                  1..23
                        mol_type = other DNA
                        organism = synthetic construct
SEQUENCE: 158
gccaaccagc tcaaggaaga gtt                                             23

SEQ ID NO: 159          moltype = DNA  length = 19
FEATURE                 Location/Qualifiers
misc_feature            1..19
                        note = Forward Primer CNTRL_exon38_F
source                  1..19
                        mol_type = other DNA
                        organism = synthetic construct
SEQUENCE: 159
gcaggaagag gagaggtgg                                                  19

SEQ ID NO: 160          moltype = DNA  length = 22
FEATURE                 Location/Qualifiers
misc_feature            1..22
                        note = Forward Primer CNTRL_exon39_F
```

```
source                  1..22
                        mol_type = other DNA
                        organism = synthetic construct
SEQUENCE: 160
ccagcctgaa ggaagcactt aa                                            22

SEQ ID NO: 161          moltype = DNA  length = 23
FEATURE                 Location/Qualifiers
misc_feature            1..23
                        note = Forward Primer CNTRL_exon40_F
source                  1..23
                        mol_type = other DNA
                        organism = synthetic construct
SEQUENCE: 161
agctcaacca gatgcagtat gag                                           23

SEQ ID NO: 162          moltype = DNA  length = 17
FEATURE                 Location/Qualifiers
misc_feature            1..17
                        note = Forward Primer CTNNB1_exon1_F
source                  1..17
                        mol_type = other DNA
                        organism = synthetic construct
SEQUENCE: 162
aggtcgagga cggtcgg                                                  17

SEQ ID NO: 163          moltype = DNA  length = 22
FEATURE                 Location/Qualifiers
misc_feature            1..22
                        note = Forward Primer CUX1_exon1_F_rdsgn
source                  1..22
                        mol_type = other DNA
                        organism = synthetic construct
SEQUENCE: 163
tctcaagatg gcggccaatg tg                                            22

SEQ ID NO: 164          moltype = DNA  length = 22
FEATURE                 Location/Qualifiers
misc_feature            1..22
                        note = Forward Primer CUX1_exon7_F
source                  1..22
                        mol_type = other DNA
                        organism = synthetic construct
SEQUENCE: 164
atgtccacca cctcaaagct gg                                            22

SEQ ID NO: 165          moltype = DNA  length = 25
FEATURE                 Location/Qualifiers
misc_feature            1..25
                        note = Forward Primer CUX1_exon8_9_F
source                  1..25
                        mol_type = other DNA
                        organism = synthetic construct
SEQUENCE: 165
caaaggccga cgagattgaa atgat                                         25

SEQ ID NO: 166          moltype = DNA  length = 27
FEATURE                 Location/Qualifiers
misc_feature            1..27
                        note = Forward Primer CUX1_exon8_F
source                  1..27
                        mol_type = other DNA
                        organism = synthetic construct
SEQUENCE: 166
aactcgaaca gaattatttg acctgaa                                       27

SEQ ID NO: 167          moltype = DNA  length = 28
FEATURE                 Location/Qualifiers
misc_feature            1..28
                        note = Forward Primer DDX5_exon2_F
source                  1..28
                        mol_type = other DNA
                        organism = synthetic construct
SEQUENCE: 167
gagaagaatt tttatcaaga gcaccctg                                      28

SEQ ID NO: 168          moltype = DNA  length = 21
FEATURE                 Location/Qualifiers
misc_feature            1..21
```

```
                        note = Forward Primer EGFR_exon15F
source                  1..21
                        mol_type = other DNA
                        organism = synthetic construct
SEQUENCE: 168
tgccatccaa actgcaccta c                                            21

SEQ ID NO: 169          moltype = DNA  length = 20
FEATURE                 Location/Qualifiers
misc_feature            1..20
                        note = Forward Primer EGFR_exon24F_rdsgn
source                  1..20
                        mol_type = other DNA
                        organism = synthetic construct
SEQUENCE: 169
tctccaaaat ggcccgagac                                              20

SEQ ID NO: 170          moltype = DNA  length = 19
FEATURE                 Location/Qualifiers
misc_feature            1..19
                        note = Forward Primer ERBB2_exon14_15_F
source                  1..19
                        mol_type = other DNA
                        organism = synthetic construct
SEQUENCE: 170
tttggaccgg aggctgacc                                               19

SEQ ID NO: 171          moltype = DNA  length = 21
FEATURE                 Location/Qualifiers
misc_feature            1..21
                        note = Forward Primer ERBB2_exon15F
source                  1..21
                        mol_type = other DNA
                        organism = synthetic construct
SEQUENCE: 171
gaagtttcca gatgaggagg g                                            21

SEQ ID NO: 172          moltype = DNA  length = 25
FEATURE                 Location/Qualifiers
misc_feature            1..25
                        note = Forward Primer ERBB2_exon7-8_F
source                  1..25
                        mol_type = other DNA
                        organism = synthetic construct
SEQUENCE: 172
cctgtcccta caactacctt tctac                                        25

SEQ ID NO: 173          moltype = DNA  length = 18
FEATURE                 Location/Qualifiers
misc_feature            1..18
                        note = Forward Primer ESR1_exon3_F
source                  1..18
                        mol_type = other DNA
                        organism = synthetic construct
SEQUENCE: 173
aacgagccca gcggctac                                                18

SEQ ID NO: 174          moltype = DNA  length = 22
FEATURE                 Location/Qualifiers
misc_feature            1..22
                        note = Forward Primer ESR1_exon4_F
source                  1..22
                        mol_type = other DNA
                        organism = synthetic construct
SEQUENCE: 174
ccattatgga gtctggtcct gt                                           22

SEQ ID NO: 175          moltype = DNA  length = 23
FEATURE                 Location/Qualifiers
misc_feature            1..23
                        note = Forward Primer ESR1_exon5_F
source                  1..23
                        mol_type = other DNA
                        organism = synthetic construct
SEQUENCE: 175
ggctccgtaa atgctacgaa gtg                                          23

SEQ ID NO: 176          moltype = DNA  length = 21
FEATURE                 Location/Qualifiers
```

```
misc_feature           1..21
                       note = Forward Primer ESR1_exon6_F_rdsgn
source                 1..21
                       mol_type = other DNA
                       organism = synthetic construct
SEQUENCE: 176
cagacaggga gctggttcac a                                            21

SEQ ID NO: 177         moltype = DNA  length = 21
FEATURE                Location/Qualifiers
misc_feature           1..21
                       note = Forward Primer ESR1_exon7_F
source                 1..21
                       mol_type = other DNA
                       organism = synthetic construct
SEQUENCE: 177
acccagggaa gctactgttt g                                            21

SEQ ID NO: 178         moltype = DNA  length = 24
FEATURE                Location/Qualifiers
misc_feature           1..24
                       note = Forward Primer ETV6_exon4F
source                 1..24
                       mol_type = other DNA
                       organism = synthetic construct
SEQUENCE: 178
tggaaactct atacacacac agcc                                         24

SEQ ID NO: 179         moltype = DNA  length = 22
FEATURE                Location/Qualifiers
misc_feature           1..22
                       note = Forward Primer ETV6_exon5F
source                 1..22
                       mol_type = other DNA
                       organism = synthetic construct
SEQUENCE: 179
cacatcatgg tctctgtctc cc                                           22

SEQ ID NO: 180         moltype = DNA  length = 22
FEATURE                Location/Qualifiers
misc_feature           1..22
                       note = Forward Primer ETV6_exon7F
source                 1..22
                       mol_type = other DNA
                       organism = synthetic construct
SEQUENCE: 180
acattatcag gaaggagcca gg                                           22

SEQ ID NO: 181         moltype = DNA  length = 19
FEATURE                Location/Qualifiers
misc_feature           1..19
                       note = Forward Primer FGFR1_exon1_F
source                 1..19
                       mol_type = other DNA
                       organism = synthetic construct
SEQUENCE: 181
acaagccacg gcggactct                                               19

SEQ ID NO: 182         moltype = DNA  length = 21
FEATURE                Location/Qualifiers
misc_feature           1..21
                       note = Forward Primer FGFR1_exon17_F
source                 1..21
                       mol_type = other DNA
                       organism = synthetic construct
SEQUENCE: 182
ttcaagcagc tggtggaaga c                                            21

SEQ ID NO: 183         moltype = DNA  length = 23
FEATURE                Location/Qualifiers
misc_feature           1..23
                       note = Forward Primer FGFR1_exon18_F
source                 1..23
                       mol_type = other DNA
                       organism = synthetic construct
SEQUENCE: 183
cacaaatttc cccaaagact gcg                                          23

SEQ ID NO: 184         moltype = DNA  length = 20
```

```
FEATURE                 Location/Qualifiers
misc_feature            1..20
                        note = Forward Primer FGFR1_exon2_F
source                  1..20
                        mol_type = other DNA
                        organism = synthetic construct
SEQUENCE: 184
gtcacagcca cactctgcac                                              20

SEQ ID NO: 185          moltype = DNA  length = 22
FEATURE                 Location/Qualifiers
misc_feature            1..22
                        note = Forward Primer FGFR1OP_exon5_F
source                  1..22
                        mol_type = other DNA
                        organism = synthetic construct
SEQUENCE: 185
ttagaagtga tcaggcgctg tc                                           22

SEQ ID NO: 186          moltype = DNA  length = 20
FEATURE                 Location/Qualifiers
misc_feature            1..20
                        note = Forward Primer FGFR1OP_exon6_F
source                  1..20
                        mol_type = other DNA
                        organism = synthetic construct
SEQUENCE: 186
tccaccaaag tcaccagagg                                              20

SEQ ID NO: 187          moltype = DNA  length = 24
FEATURE                 Location/Qualifiers
misc_feature            1..24
                        note = Forward Primer FGFR1OP_exon7_F
source                  1..24
                        mol_type = other DNA
                        organism = synthetic construct
SEQUENCE: 187
gacaaggtaa gaagaagaca agcg                                         24

SEQ ID NO: 188          moltype = DNA  length = 24
FEATURE                 Location/Qualifiers
misc_feature            1..24
                        note = Forward Primer FGFR2_exon17F
source                  1..24
                        mol_type = other DNA
                        organism = synthetic construct
SEQUENCE: 188
agaagacttg gatcgaattc tcac                                         24

SEQ ID NO: 189          moltype = DNA  length = 24
FEATURE                 Location/Qualifiers
misc_feature            1..24
                        note = Forward Primer FGFR2_exon18F
source                  1..24
                        mol_type = other DNA
                        organism = synthetic construct
SEQUENCE: 189
cgaaccatgc cttcctcagt atcc                                         24

SEQ ID NO: 190          moltype = DNA  length = 18
FEATURE                 Location/Qualifiers
misc_feature            1..18
                        note = Forward Primer FGFR3_exon17F
source                  1..18
                        mol_type = other DNA
                        organism = synthetic construct
SEQUENCE: 190
tccttaccgt gacgtcca                                                18

SEQ ID NO: 191          moltype = DNA  length = 21
FEATURE                 Location/Qualifiers
misc_feature            1..21
                        note = Forward Primer FIP1L1_exon10_F
source                  1..21
                        mol_type = other DNA
                        organism = synthetic construct
SEQUENCE: 191
gttgggaagt ggcaggatcg a                                            21
```

```
SEQ ID NO: 192          moltype = DNA  length = 28
FEATURE                 Location/Qualifiers
misc_feature            1..28
                        note = Forward Primer FIP1L1_exon11_F
source                  1..28
                        mol_type = other DNA
                        organism = synthetic construct
SEQUENCE: 192
ctataactat cagccgagta gaaggcag                                      28

SEQ ID NO: 193          moltype = DNA  length = 21
FEATURE                 Location/Qualifiers
misc_feature            1..21
                        note = Forward Primer FIP1L1_exon12_F
source                  1..21
                        mol_type = other DNA
                        organism = synthetic construct
SEQUENCE: 193
tcttccacct cctccgactg t                                             21

SEQ ID NO: 194          moltype = DNA  length = 20
FEATURE                 Location/Qualifiers
misc_feature            1..20
                        note = Forward Primer FIP1L1_exon14_F
source                  1..20
                        mol_type = other DNA
                        organism = synthetic construct
SEQUENCE: 194
ttttcctcct ccaccaggcg                                               20

SEQ ID NO: 195          moltype = DNA  length = 26
FEATURE                 Location/Qualifiers
misc_feature            1..26
                        note = Forward Primer FIP1L1_exon15_F
source                  1..26
                        mol_type = other DNA
                        organism = synthetic construct
SEQUENCE: 195
ggacattcct ctggttatga tagtcg                                        26

SEQ ID NO: 196          moltype = DNA  length = 22
FEATURE                 Location/Qualifiers
misc_feature            1..22
                        note = Forward Primer FIP1L1_exon16_F
source                  1..22
                        mol_type = other DNA
                        organism = synthetic construct
SEQUENCE: 196
gacagagaaa gagaacgcac ca                                            22

SEQ ID NO: 197          moltype = DNA  length = 20
FEATURE                 Location/Qualifiers
misc_feature            1..20
                        note = Forward Primer FIP1L1_exon17_F
source                  1..20
                        mol_type = other DNA
                        organism = synthetic construct
SEQUENCE: 197
acgacacagg gagaaagagg                                               20

SEQ ID NO: 198          moltype = DNA  length = 20
FEATURE                 Location/Qualifiers
misc_feature            1..20
                        note = Forward Primer FIP1L1_exon18_F
source                  1..20
                        mol_type = other DNA
                        organism = synthetic construct
SEQUENCE: 198
agaaggaaaa gaagcgggca                                               20

SEQ ID NO: 199          moltype = DNA  length = 21
FEATURE                 Location/Qualifiers
misc_feature            1..21
                        note = Forward Primer FIP1L1_exon9_F
source                  1..21
                        mol_type = other DNA
                        organism = synthetic construct
SEQUENCE: 199
tgcccttcca tctacaaaag c                                             21
```

```
SEQ ID NO: 200         moltype = DNA  length = 24
FEATURE                Location/Qualifiers
misc_feature           1..24
                       note = Forward Primer HERV-K_F
source                 1..24
                       mol_type = other DNA
                       organism = synthetic construct
SEQUENCE: 200
gattcccgag tacgtctaca gtga                                        24

SEQ ID NO: 201         moltype = DNA  length = 21
FEATURE                Location/Qualifiers
misc_feature           1..21
                       note = Forward Primer HERVK17_F
source                 1..21
                       mol_type = other DNA
                       organism = synthetic construct
SEQUENCE: 201
tttccacact ctcattccgg a                                           21

SEQ ID NO: 202         moltype = DNA  length = 19
FEATURE                Location/Qualifiers
misc_feature           1..19
                       note = Forward Primer HNRNPA2B1_exon1_F
source                 1..19
                       mol_type = other DNA
                       organism = synthetic construct
SEQUENCE: 202
tgcgggaaat cgggctgaa                                              19

SEQ ID NO: 203         moltype = DNA  length = 18
FEATURE                Location/Qualifiers
misc_feature           1..18
                       note = Forward Primer LMNA_exon2F
source                 1..18
                       mol_type = other DNA
                       organism = synthetic construct
SEQUENCE: 203
gagctgcatg atctgcgg                                               18

SEQ ID NO: 204         moltype = DNA  length = 19
FEATURE                Location/Qualifiers
misc_feature           1..19
                       note = Forward Primer MDK_exon4F
source                 1..19
                       mol_type = other DNA
                       organism = synthetic construct
SEQUENCE: 204
cccaagacca aagcaaagg                                              19

SEQ ID NO: 205         moltype = DNA  length = 24
FEATURE                Location/Qualifiers
misc_feature           1..24
                       note = Forward Primer MET_exon13F
source                 1..24
                       mol_type = other DNA
                       organism = synthetic construct
SEQUENCE: 205
acagcactgt tattactact tggg                                        24

SEQ ID NO: 206         moltype = DNA  length = 20
FEATURE                Location/Qualifiers
misc_feature           1..20
                       note = Forward Primer MPRIP_exon21F
source                 1..20
                       mol_type = other DNA
                       organism = synthetic construct
SEQUENCE: 206
agaagtcccc tgacagtgcc                                             20

SEQ ID NO: 207         moltype = DNA  length = 18
FEATURE                Location/Qualifiers
misc_feature           1..18
                       note = Forward Primer NACC2_exon4F_rdsgn
source                 1..18
                       mol_type = other DNA
                       organism = synthetic construct
SEQUENCE: 207
```

```
gactggcatc cgctcgtc                                                18

SEQ ID NO: 208          moltype = DNA  length = 23
FEATURE                 Location/Qualifiers
misc_feature            1..23
                        note = Forward Primer NFASC_exon21F
source                  1..23
                        mol_type = other DNA
                        organism = synthetic construct
SEQUENCE: 208
tccaggctga aaatgacttc ggg                                          23

SEQ ID NO: 209          moltype = DNA  length = 18
FEATURE                 Location/Qualifiers
misc_feature            1..18
                        note = Forward Primer PAX8_exon10F
source                  1..18
                        mol_type = other DNA
                        organism = synthetic construct
SEQUENCE: 209
acatccccac cagcggac                                                18

SEQ ID NO: 210          moltype = DNA  length = 18
FEATURE                 Location/Qualifiers
misc_feature            1..18
                        note = Forward Primer PAX8_exon7F
source                  1..18
                        mol_type = other DNA
                        organism = synthetic construct
SEQUENCE: 210
gagtgcccat ttgagcgg                                                18

SEQ ID NO: 211          moltype = DNA  length = 18
FEATURE                 Location/Qualifiers
misc_feature            1..18
                        note = Forward Primer PAX8_exon8F
source                  1..18
                        mol_type = other DNA
                        organism = synthetic construct
SEQUENCE: 211
cttccaacac gccactgg                                                18

SEQ ID NO: 212          moltype = DNA  length = 19
FEATURE                 Location/Qualifiers
misc_feature            1..19
                        note = Forward Primer PAX8_exon9F
source                  1..19
                        mol_type = other DNA
                        organism = synthetic construct
SEQUENCE: 212
cgcccttcaa tgcctttcc                                               19

SEQ ID NO: 213          moltype = DNA  length = 27
FEATURE                 Location/Qualifiers
misc_feature            1..27
                        note = Forward Primer PCM1_E23_F
source                  1..27
                        mol_type = other DNA
                        organism = synthetic construct
SEQUENCE: 213
ctcccaagtc aaaaagtaag aagagga                                      27

SEQ ID NO: 214          moltype = DNA  length = 29
FEATURE                 Location/Qualifiers
misc_feature            1..29
                        note = Forward Primer PCM1_E24_F
source                  1..29
                        mol_type = other DNA
                        organism = synthetic construct
SEQUENCE: 214
cagcagaaag aatcatgagc aactggaaa                                    29

SEQ ID NO: 215          moltype = DNA  length = 22
FEATURE                 Location/Qualifiers
misc_feature            1..22
                        note = Forward Primer PCM1_E25_F
source                  1..22
                        mol_type = other DNA
                        organism = synthetic construct
```

```
SEQUENCE: 215
ccatgagctg cagctactaa ac                                          22

SEQ ID NO: 216          moltype = DNA  length = 27
FEATURE                 Location/Qualifiers
misc_feature            1..27
                        note = Forward Primer PCM1_E26_F
source                  1..27
                        mol_type = other DNA
                        organism = synthetic construct
SEQUENCE: 216
atagcatcaa actcagaact tactcct                                     27

SEQ ID NO: 217          moltype = DNA  length = 22
FEATURE                 Location/Qualifiers
misc_feature            1..22
                        note = Forward Primer PCM1_E36_F
source                  1..22
                        mol_type = other DNA
                        organism = synthetic construct
SEQUENCE: 217
actcctgaaa gctctctggc tg                                          22

SEQ ID NO: 218          moltype = DNA  length = 30
FEATURE                 Location/Qualifiers
misc_feature            1..30
                        note = Forward Primer PCM1_E37_F
source                  1..30
                        mol_type = other DNA
                        organism = synthetic construct
SEQUENCE: 218
gattttgtaa aagttgaaga tttaccactg                                  30

SEQ ID NO: 219          moltype = DNA  length = 22
FEATURE                 Location/Qualifiers
misc_feature            1..22
                        note = Forward Primer QKI_exon6F
source                  1..22
                        mol_type = other DNA
                        organism = synthetic construct
SEQUENCE: 219
acacattggc accagctaca tc                                          22

SEQ ID NO: 220          moltype = DNA  length = 22
FEATURE                 Location/Qualifiers
misc_feature            1..22
                        note = Forward Primer RBPMS_exon5F
source                  1..22
                        mol_type = other DNA
                        organism = synthetic construct
SEQUENCE: 220
caaactcgta gggactccaa ac                                          22

SEQ ID NO: 221          moltype = DNA  length = 18
FEATURE                 Location/Qualifiers
misc_feature            1..18
                        note = Forward Primer SLC45A3_exon1_F
source                  1..18
                        mol_type = other DNA
                        organism = synthetic construct
SEQUENCE: 221
aaccagcctg cacgcgct                                               18

SEQ ID NO: 222          moltype = DNA  length = 21
FEATURE                 Location/Qualifiers
misc_feature            1..21
                        note = Forward Primer SEC61G_5'UTRF_rdsgn
source                  1..21
                        mol_type = other DNA
                        organism = synthetic construct
SEQUENCE: 222
ctccagtgct acgtgtccct g                                           21

SEQ ID NO: 223          moltype = DNA  length = 19
FEATURE                 Location/Qualifiers
misc_feature            1..19
                        note = Forward Primer TCF3_exon16_F
source                  1..19
                        mol_type = other DNA
```

```
                        organism = synthetic construct
SEQUENCE: 223
accctccctg acctgtctc                                            19

SEQ ID NO: 224          moltype = DNA  length = 27
FEATURE                 Location/Qualifiers
misc_feature            1..27
                        note = Forward Primer TPM4_exon6F
source                  1..27
                        mol_type = other DNA
                        organism = synthetic construct
SEQUENCE: 224
ctgaaaagga ggacaaatat gaagaag                                   27

SEQ ID NO: 225          moltype = DNA  length = 25
FEATURE                 Location/Qualifiers
misc_feature            1..25
                        note = Forward Primer TPR_exon21F
source                  1..25
                        mol_type = other DNA
                        organism = synthetic construct
SEQUENCE: 225
ttgaaacagc acctcagtaa tatgg                                     25

SEQ ID NO: 226          moltype = DNA  length = 26
FEATURE                 Location/Qualifiers
misc_feature            1..26
                        note = Forward Primer TPR_exon6F
source                  1..26
                        mol_type = other DNA
                        organism = synthetic construct
SEQUENCE: 226
gggaatgaga ttctagagct taaatg                                    26

SEQ ID NO: 227          moltype = DNA  length = 18
FEATURE                 Location/Qualifiers
misc_feature            1..18
                        note = Forward Primer UBTF_exon2_F
source                  1..18
                        mol_type = other DNA
                        organism = synthetic construct
SEQUENCE: 227
aacggagaag ccgactgc                                             18

SEQ ID NO: 228          moltype = DNA  length = 26
FEATURE                 Location/Qualifiers
misc_feature            1..26
                        note = Forward Primer ZMYM2_exon16_F
source                  1..26
                        mol_type = other DNA
                        organism = synthetic construct
SEQUENCE: 228
tgtatatccc agttcctatg cacatg                                    26

SEQ ID NO: 229          moltype = DNA  length = 29
FEATURE                 Location/Qualifiers
misc_feature            1..29
                        note = Forward Primer ZMYM2_exon17_F
source                  1..29
                        mol_type = other DNA
                        organism = synthetic construct
SEQUENCE: 229
agttgcttac aatgacggat atgatgagt                                 29

SEQ ID NO: 230          moltype = DNA  length = 20
FEATURE                 Location/Qualifiers
misc_feature            1..20
                        note = Forward Primer AFAP1_exon13_F
source                  1..20
                        mol_type = other DNA
                        organism = synthetic construct
SEQUENCE: 230
agcagtcagc caaagaaagc                                           20

SEQ ID NO: 231          moltype = DNA  length = 21
FEATURE                 Location/Qualifiers
misc_feature            1..21
                        note = Forward Primer AFAP1_exon14_F
source                  1..21
```

```
                         mol_type = other DNA
                         organism = synthetic construct
SEQUENCE: 231
gctccgcaag gaaagaaaag a                                          21

SEQ ID NO: 232           moltype = DNA  length = 27
FEATURE                  Location/Qualifiers
misc_feature             1..27
                         note = Forward Primer AKAP9_exon18F
source                   1..27
                         mol_type = other DNA
                         organism = synthetic construct
SEQUENCE: 232
cagctacaag aagagattaa gagactt                                    27

SEQ ID NO: 233           moltype = DNA  length = 27
FEATURE                  Location/Qualifiers
misc_feature             1..27
                         note = Forward Primer AKAP9_exon7F
source                   1..27
                         mol_type = other DNA
                         organism = synthetic construct
SEQUENCE: 233
gacttcacaa tgcaaattag tttcttg                                    27

SEQ ID NO: 234           moltype = DNA  length = 29
FEATURE                  Location/Qualifiers
misc_feature             1..29
                         note = Forward Primer AKAP9_exon9F
source                   1..29
                         mol_type = other DNA
                         organism = synthetic construct
SEQUENCE: 234
gaacttcaga aaatacacca gttagaact                                  29

SEQ ID NO: 235           moltype = DNA  length = 19
FEATURE                  Location/Qualifiers
misc_feature             1..19
                         note = Forward Primer AXL_exon20_F
source                   1..19
                         mol_type = other DNA
                         organism = synthetic construct
SEQUENCE: 235
tgctgatagg ggctcccca                                             19

SEQ ID NO: 236           moltype = DNA  length = 23
FEATURE                  Location/Qualifiers
misc_feature             1..23
                         note = Forward Primer BCR_exon10_F
source                   1..23
                         mol_type = other DNA
                         organism = synthetic construct
SEQUENCE: 236
tggacgcttt gaagatcaag atc                                        23

SEQ ID NO: 237           moltype = DNA  length = 21
FEATURE                  Location/Qualifiers
misc_feature             1..21
                         note = Forward Primer BCR_exon11_F
source                   1..21
                         mol_type = other DNA
                         organism = synthetic construct
SEQUENCE: 237
ctgcttatgt ctcccagcat g                                          21

SEQ ID NO: 238           moltype = DNA  length = 20
FEATURE                  Location/Qualifiers
misc_feature             1..20
                         note = Forward Primer BCR_exon12_F
source                   1..20
                         mol_type = other DNA
                         organism = synthetic construct
SEQUENCE: 238
cgtgcagagt ggagggagaa                                            20

SEQ ID NO: 239           moltype = DNA  length = 20
FEATURE                  Location/Qualifiers
misc_feature             1..20
                         note = Forward Primer BCR_exon15_F
```

```
source                  1..20
                        mol_type = other DNA
                        organism = synthetic construct
SEQUENCE: 239
gcaaagacgc gcgtctacag                                              20

SEQ ID NO: 240          moltype = DNA  length = 18
FEATURE                 Location/Qualifiers
misc_feature            1..18
                        note = Forward Primer BCR_exon16_F
source                  1..18
                        mol_type = other DNA
                        organism = synthetic construct
SEQUENCE: 240
aaggaggacg gcgagagc                                                18

SEQ ID NO: 241          moltype = DNA  length = 19
FEATURE                 Location/Qualifiers
misc_feature            1..19
                        note = Forward Primer BCR_exon17_F
source                  1..19
                        mol_type = other DNA
                        organism = synthetic construct
SEQUENCE: 241
aggacagaga ctggcagcg                                               19

SEQ ID NO: 242          moltype = DNA  length = 23
FEATURE                 Location/Qualifiers
misc_feature            1..23
                        note = Forward Primer BCR_exon20_F
source                  1..23
                        mol_type = other DNA
                        organism = synthetic construct
SEQUENCE: 242
ttcactgacg agttctaccc caa                                          23

SEQ ID NO: 243          moltype = DNA  length = 22
FEATURE                 Location/Qualifiers
misc_feature            1..22
                        note = Forward Primer BCR_exon3_F
source                  1..22
                        mol_type = other DNA
                        organism = synthetic construct
SEQUENCE: 243
ctagcgagga gacttacctg ag                                           22

SEQ ID NO: 244          moltype = DNA  length = 21
FEATURE                 Location/Qualifiers
misc_feature            1..21
                        note = Forward Primer BCR_exon5_F
source                  1..21
                        mol_type = other DNA
                        organism = synthetic construct
SEQUENCE: 244
aaatggctga gaagtgctgt c                                            21

SEQ ID NO: 245          moltype = DNA  length = 22
FEATURE                 Location/Qualifiers
misc_feature            1..22
                        note = Forward Primer HMGN2P46_exon2_F_rdsgn
source                  1..22
                        mol_type = other DNA
                        organism = synthetic construct
SEQUENCE: 245
ggaaccacac ttcgagaatc ac                                           22

SEQ ID NO: 246          moltype = DNA  length = 24
FEATURE                 Location/Qualifiers
misc_feature            1..24
                        note = Forward Primer CCDC6_exon3F
source                  1..24
                        mol_type = other DNA
                        organism = synthetic construct
SEQUENCE: 246
ggagaatgac accatttcta agca                                         24

SEQ ID NO: 247          moltype = DNA  length = 25
FEATURE                 Location/Qualifiers
misc_feature            1..25
```

```
                        note = Forward Primer CCDC6_exon4F
source                  1..25
                        mol_type = other DNA
                        organism = synthetic construct
SEQUENCE: 247
agcactagtt aatcgcctct ggaaa                                    25

SEQ ID NO: 248          moltype = DNA  length = 20
FEATURE                 Location/Qualifiers
misc_feature            1..20
                        note = Forward Primer CCDC6_exon5F
source                  1..20
                        mol_type = other DNA
                        organism = synthetic construct
SEQUENCE: 248
tgaagtggaa cggctgaaga                                          20

SEQ ID NO: 249          moltype = DNA  length = 20
FEATURE                 Location/Qualifiers
misc_feature            1..20
                        note = Forward Primer CCDC6_exon6F
source                  1..20
                        mol_type = other DNA
                        organism = synthetic construct
SEQUENCE: 249
tctccgagag tgagtccagc                                          20

SEQ ID NO: 250          moltype = DNA  length = 20
FEATURE                 Location/Qualifiers
misc_feature            1..20
                        note = Forward Primer CCDC6_exon7F
source                  1..20
                        mol_type = other DNA
                        organism = synthetic construct
SEQUENCE: 250
cagcccgatc ccttacacac                                          20

SEQ ID NO: 251          moltype = DNA  length = 22
FEATURE                 Location/Qualifiers
misc_feature            1..22
                        note = Forward Primer DCBLD1_exon2_F
source                  1..22
                        mol_type = other DNA
                        organism = synthetic construct
SEQUENCE: 251
ccagacctgt gcttctgact at                                       22

SEQ ID NO: 252          moltype = DNA  length = 21
FEATURE                 Location/Qualifiers
misc_feature            1..21
                        note = Forward Primer EGFR_exon1_F
source                  1..21
                        mol_type = other DNA
                        organism = synthetic construct
SEQUENCE: 252
agtcgggctc tggaggaaaa g                                        21

SEQ ID NO: 253          moltype = DNA  length = 20
FEATURE                 Location/Qualifiers
misc_feature            1..20
                        note = Forward Primer EML4_exon10F
source                  1..20
                        mol_type = other DNA
                        organism = synthetic construct
SEQUENCE: 253
ggacttggca cttttgagcg                                          20

SEQ ID NO: 254          moltype = DNA  length = 21
FEATURE                 Location/Qualifiers
misc_feature            1..21
                        note = Forward Primer EML4_exon11F
source                  1..21
                        mol_type = other DNA
                        organism = synthetic construct
SEQUENCE: 254
gcttactgta tgggactggc a                                        21

SEQ ID NO: 255          moltype = DNA  length = 20
FEATURE                 Location/Qualifiers
```

```
misc_feature          1..20
                      note = Forward Primer EML4_exon12F
source                1..20
                      mol_type = other DNA
                      organism = synthetic construct
SEQUENCE: 255
tttcttctgg acctggagcg                                             20

SEQ ID NO: 256        moltype = DNA  length = 30
FEATURE               Location/Qualifiers
misc_feature          1..30
                      note = Forward Primer EML4_exon19F
source                1..30
                      mol_type = other DNA
                      organism = synthetic construct
SEQUENCE: 256
ctatgtagtc tctgaaaatg gaagaaaata                                  30

SEQ ID NO: 257        moltype = DNA  length = 20
FEATURE               Location/Qualifiers
misc_feature          1..20
                      note = Forward Primer EML4_exon1F
source                1..20
                      mol_type = other DNA
                      organism = synthetic construct
SEQUENCE: 257
cgctttcccc gcaagatgga                                             20

SEQ ID NO: 258        moltype = DNA  length = 21
FEATURE               Location/Qualifiers
misc_feature          1..21
                      note = Forward Primer EML4_exon21F
source                1..21
                      mol_type = other DNA
                      organism = synthetic construct
SEQUENCE: 258
aaggacattg attggacgac a                                           21

SEQ ID NO: 259        moltype = DNA  length = 30
FEATURE               Location/Qualifiers
misc_feature          1..30
                      note = Forward Primer EML4_exon22F
source                1..30
                      mol_type = other DNA
                      organism = synthetic construct
SEQUENCE: 259
cgatgacttt tgtaaagtcc atctgtttca                                  30

SEQ ID NO: 260        moltype = DNA  length = 20
FEATURE               Location/Qualifiers
misc_feature          1..20
                      note = Forward Primer EML4_exon23F
source                1..20
                      mol_type = other DNA
                      organism = synthetic construct
SEQUENCE: 260
aaagccaccc ttctggagga                                             20

SEQ ID NO: 261        moltype = DNA  length = 24
FEATURE               Location/Qualifiers
misc_feature          1..24
                      note = Forward Primer EML4_exon3F
source                1..24
                      mol_type = other DNA
                      organism = synthetic construct
SEQUENCE: 261
gtgctgtctc aattgcagga aaag                                        24

SEQ ID NO: 262        moltype = DNA  length = 22
FEATURE               Location/Qualifiers
misc_feature          1..22
                      note = Forward Primer EML4_exon4F
source                1..22
                      mol_type = other DNA
                      organism = synthetic construct
SEQUENCE: 262
cacagacaaa ctccagaaag ca                                          22

SEQ ID NO: 263        moltype = DNA  length = 20
```

```
FEATURE                Location/Qualifiers
misc_feature           1..20
                       note = Forward Primer EML4_exon7F
source                 1..20
                       mol_type = other DNA
                       organism = synthetic construct
SEQUENCE: 263
atcagaacgg aactgcctcc                                              20

SEQ ID NO: 264         moltype = DNA  length = 21
FEATURE                Location/Qualifiers
misc_feature           1..21
                       note = Forward Primer EML4_exon8F
source                 1..21
                       mol_type = other DNA
                       organism = synthetic construct
SEQUENCE: 264
gaactcagcg acactacctg g                                            21

SEQ ID NO: 265         moltype = DNA  length = 20
FEATURE                Location/Qualifiers
misc_feature           1..20
                       note = Forward Primer EML4_exon9F
source                 1..20
                       mol_type = other DNA
                       organism = synthetic construct
SEQUENCE: 265
gcaactggac agatagctgg                                              20

SEQ ID NO: 266         moltype = DNA  length = 20
FEATURE                Location/Qualifiers
misc_feature           1..20
                       note = Forward Primer ESR1_exon8_F
source                 1..20
                       mol_type = other DNA
                       organism = synthetic construct
SEQUENCE: 266
ggagaggagt ttgtgtgcct                                              20

SEQ ID NO: 267         moltype = DNA  length = 18
FEATURE                Location/Qualifiers
misc_feature           1..18
                       note = Forward Primer ESR1_exon9_F
source                 1..18
                       mol_type = other DNA
                       organism = synthetic construct
SEQUENCE: 267
gcccagctcc tcctcatc                                                18

SEQ ID NO: 268         moltype = DNA  length = 19
FEATURE                Location/Qualifiers
misc_feature           1..19
                       note = Forward Primer ETV6_exon6F
source                 1..19
                       mol_type = other DNA
                       organism = synthetic construct
SEQUENCE: 268
gatcccaacg gactggctc                                               19

SEQ ID NO: 269         moltype = DNA  length = 19
FEATURE                Location/Qualifiers
misc_feature           1..19
                       note = Forward Primer EWSR1_exon8_F
source                 1..19
                       mol_type = other DNA
                       organism = synthetic construct
SEQUENCE: 269
tggaggcatg agcagaggt                                               19

SEQ ID NO: 270         moltype = DNA  length = 22
FEATURE                Location/Qualifiers
misc_feature           1..22
                       note = Forward Primer EZR_exon11F
source                 1..22
                       mol_type = other DNA
                       organism = synthetic construct
SEQUENCE: 270
ctaaggagga gctggagaga ca                                           22
```

```
SEQ ID NO: 271          moltype = DNA  length = 19
FEATURE                 Location/Qualifiers
misc_feature            1..19
                        note = Forward Primer EZR_exon12F
source                  1..19
                        mol_type = other DNA
                        organism = synthetic construct
SEQUENCE: 271
gaggcgcaag gaggatgaa                                              19

SEQ ID NO: 272          moltype = DNA  length = 24
FEATURE                 Location/Qualifiers
misc_feature            1..24
                        note = Forward Primer FIP1L1_exon8_F
source                  1..24
                        mol_type = other DNA
                        organism = synthetic construct
SEQUENCE: 272
atggaagtta caccaggtgc agag                                        24

SEQ ID NO: 273          moltype = DNA  length = 19
FEATURE                 Location/Qualifiers
misc_feature            1..19
                        note = Forward Primer FRMD4A_exon2_F
source                  1..19
                        mol_type = other DNA
                        organism = synthetic construct
SEQUENCE: 273
atgggaatcg gagaccatg                                              19

SEQ ID NO: 274          moltype = DNA  length = 22
FEATURE                 Location/Qualifiers
misc_feature            1..22
                        note = Forward Primer GOPC_exon5F
source                  1..22
                        mol_type = other DNA
                        organism = synthetic construct
SEQUENCE: 274
tgcagaggac gtaatgactt ga                                          22

SEQ ID NO: 275          moltype = DNA  length = 28
FEATURE                 Location/Qualifiers
misc_feature            1..28
                        note = Forward Primer GOPC_exon6F
source                  1..28
                        mol_type = other DNA
                        organism = synthetic construct
SEQUENCE: 275
ggtccaatta gaaaagttct cctcctta                                    28

SEQ ID NO: 276          moltype = DNA  length = 21
FEATURE                 Location/Qualifiers
misc_feature            1..21
                        note = Forward Primer GOPC_exon7F
source                  1..21
                        mol_type = other DNA
                        organism = synthetic construct
SEQUENCE: 276
acctaaggga cacaaagcat a                                           21

SEQ ID NO: 277          moltype = DNA  length = 23
FEATURE                 Location/Qualifiers
misc_feature            1..23
                        note = Forward Primer GOPC_exon8F_rdsgn
source                  1..23
                        mol_type = other DNA
                        organism = synthetic construct
SEQUENCE: 277
aggtggtaac cctggtgcta gtt                                         23

SEQ ID NO: 278          moltype = DNA  length = 20
FEATURE                 Location/Qualifiers
misc_feature            1..20
                        note = Forward Primer HIP1_exon29F
source                  1..20
                        mol_type = other DNA
                        organism = synthetic construct
SEQUENCE: 278
aagcatgacg ctgacacaga                                             20
```

```
SEQ ID NO: 279          moltype = DNA  length = 21
FEATURE                 Location/Qualifiers
misc_feature            1..21
                        note = Forward Primer IRF2BP2_exon1_F
source                  1..21
                        mol_type = other DNA
                        organism = synthetic construct
SEQUENCE: 279
caggcaggtt gttgggtttc g                                            21

SEQ ID NO: 280          moltype = DNA  length = 25
FEATURE                 Location/Qualifiers
misc_feature            1..25
                        note = Forward Primer KIAA1549_exon17F
source                  1..25
                        mol_type = other DNA
                        organism = synthetic construct
SEQUENCE: 280
gatacgaaga ctatggaatg actcc                                        25

SEQ ID NO: 281          moltype = DNA  length = 24
FEATURE                 Location/Qualifiers
misc_feature            1..24
                        note = Forward Primer KIF5B_exon18F
source                  1..24
                        mol_type = other DNA
                        organism = synthetic construct
SEQUENCE: 281
catgaaatgg aaaaggagca ctta                                         24

SEQ ID NO: 282          moltype = DNA  length = 24
FEATURE                 Location/Qualifiers
misc_feature            1..24
                        note = Forward Primer KIF5B_exon19F
source                  1..24
                        mol_type = other DNA
                        organism = synthetic construct
SEQUENCE: 282
agtttgagag atgaagtaga agca                                         24

SEQ ID NO: 283          moltype = DNA  length = 22
FEATURE                 Location/Qualifiers
misc_feature            1..22
                        note = Forward Primer KIF5B_exon20F
source                  1..22
                        mol_type = other DNA
                        organism = synthetic construct
SEQUENCE: 283
agttgaaagc cacagatcag ga                                           22

SEQ ID NO: 284          moltype = DNA  length = 22
FEATURE                 Location/Qualifiers
misc_feature            1..22
                        note = Forward Primer KIF5B_exon21F
source                  1..22
                        mol_type = other DNA
                        organism = synthetic construct
SEQUENCE: 284
acgagaacaa gcaagacaag ac                                           22

SEQ ID NO: 285          moltype = DNA  length = 20
FEATURE                 Location/Qualifiers
misc_feature            1..20
                        note = Forward Primer MECOM_exon2_F
source                  1..20
                        mol_type = other DNA
                        organism = synthetic construct
SEQUENCE: 285
agagcagagg tcaaacctga                                              20

SEQ ID NO: 286          moltype = DNA  length = 22
FEATURE                 Location/Qualifiers
misc_feature            1..22
                        note = Forward Primer MET_exon11F
source                  1..22
                        mol_type = other DNA
                        organism = synthetic construct
SEQUENCE: 286
```

```
agccagtgat gatctcaatg gg                                            22

SEQ ID NO: 287         moltype = DNA  length = 22
FEATURE                Location/Qualifiers
misc_feature           1..22
                       note = Forward Primer MYB_exon10_F
source                 1..22
                       mol_type = other DNA
                       organism = synthetic construct
SEQUENCE: 287
agttcaactc ccaagcgttc cc                                            22

SEQ ID NO: 288         moltype = DNA  length = 26
FEATURE                Location/Qualifiers
misc_feature           1..26
                       note = Forward Primer MYB_exon11_F
source                 1..26
                       mol_type = other DNA
                       organism = synthetic construct
SEQUENCE: 288
aacaccattt catagagacc agactg                                        26

SEQ ID NO: 289         moltype = DNA  length = 24
FEATURE                Location/Qualifiers
misc_feature           1..24
                       note = Forward Primer MYB_exon12_F
source                 1..24
                       mol_type = other DNA
                       organism = synthetic construct
SEQUENCE: 289
tcaaacatgc acttgcagct caag                                          24

SEQ ID NO: 290         moltype = DNA  length = 24
FEATURE                Location/Qualifiers
misc_feature           1..24
                       note = Forward Primer MYB_exon13_F
source                 1..24
                       mol_type = other DNA
                       organism = synthetic construct
SEQUENCE: 290
tgctgagttt caagaaaatg gacc                                          24

SEQ ID NO: 291         moltype = DNA  length = 21
FEATURE                Location/Qualifiers
misc_feature           1..21
                       note = Forward Primer MYB_exon14_F
source                 1..21
                       mol_type = other DNA
                       organism = synthetic construct
SEQUENCE: 291
aggggacagt ctgaataccc a                                             21

SEQ ID NO: 292         moltype = DNA  length = 25
FEATURE                Location/Qualifiers
misc_feature           1..25
                       note = Forward Primer MYB_exon15_F
source                 1..25
                       mol_type = other DNA
                       organism = synthetic construct
SEQUENCE: 292
tgttctcaaa gcatttacag tacct                                         25

SEQ ID NO: 293         moltype = DNA  length = 28
FEATURE                Location/Qualifiers
misc_feature           1..28
                       note = Forward Primer MYB_exon8_F
source                 1..28
                       mol_type = other DNA
                       organism = synthetic construct
SEQUENCE: 293
ttagaattgc tcctaatgtc aaccgaga                                      28

SEQ ID NO: 294         moltype = DNA  length = 25
FEATURE                Location/Qualifiers
misc_feature           1..25
                       note = Forward Primer MYB_exon9_F
source                 1..25
                       mol_type = other DNA
                       organism = synthetic construct
```

```
SEQUENCE: 294
acctcttaga atttgcagaa acact                                        25

SEQ ID NO: 295         moltype = DNA  length = 24
FEATURE                Location/Qualifiers
misc_feature           1..24
                       note = Forward Primer NCOA4_exon9F
source                 1..24
                       mol_type = other DNA
                       organism = synthetic construct
SEQUENCE: 295
caacctcagc cagttatctt ctgg                                         24

SEQ ID NO: 296         moltype = DNA  length = 17
FEATURE                Location/Qualifiers
misc_feature           1..17
                       note = Forward Primer PAN3_exon1_F
source                 1..17
                       mol_type = other DNA
                       organism = synthetic construct
SEQUENCE: 296
aggcagtagc gggggac                                                 17

SEQ ID NO: 297         moltype = DNA  length = 20
FEATURE                Location/Qualifiers
misc_feature           1..20
                       note = Forward Primer PAX3_exon7_F
source                 1..20
                       mol_type = other DNA
                       organism = synthetic construct
SEQUENCE: 297
tccaacccca tgaaccccac                                              20

SEQ ID NO: 298         moltype = DNA  length = 27
FEATURE                Location/Qualifiers
misc_feature           1..27
                       note = Forward Primer PPFIBP1_exon11F
source                 1..27
                       mol_type = other DNA
                       organism = synthetic construct
SEQUENCE: 298
caaaaaatga aaaaagctgt ggagtcc                                      27

SEQ ID NO: 299         moltype = DNA  length = 23
FEATURE                Location/Qualifiers
misc_feature           1..23
                       note = Forward Primer PPFIBP1_exon9F_rdsgn
source                 1..23
                       mol_type = other DNA
                       organism = synthetic construct
SEQUENCE: 299
ggtcagatgc agtatgaaaa gca                                          23

SEQ ID NO: 300         moltype = DNA  length = 20
FEATURE                Location/Qualifiers
misc_feature           1..20
                       note = Forward Primer SCAF11_exon1_F
source                 1..20
                       mol_type = other DNA
                       organism = synthetic construct
SEQUENCE: 300
cctgggaacc tactgtgggg                                              20

SEQ ID NO: 301         moltype = DNA  length = 20
FEATURE                Location/Qualifiers
misc_feature           1..20
                       note = Forward Primer SDC4_exon3F
source                 1..20
                       mol_type = other DNA
                       organism = synthetic construct
SEQUENCE: 301
tggaagactc catgatcggc                                              20

SEQ ID NO: 302         moltype = DNA  length = 20
FEATURE                Location/Qualifiers
misc_feature           1..20
                       note = Forward Primer SND1_exon12F
source                 1..20
                       mol_type = other DNA
```

```
                        organism = synthetic construct
SEQUENCE: 302
gccttttcag agcgtacctg                                                20

SEQ ID NO: 303          moltype = DNA  length = 22
FEATURE                 Location/Qualifiers
misc_feature            1..22
                        note = Forward Primer SND1_exon13F
source                  1..22
                        mol_type = other DNA
                        organism = synthetic construct
SEQUENCE: 303
gaccagagat catcacacta cg                                             22

SEQ ID NO: 304          moltype = DNA  length = 30
FEATURE                 Location/Qualifiers
misc_feature            1..30
                        note = Forward Primer SND1_exon15F
source                  1..30
                        mol_type = other DNA
                        organism = synthetic construct
SEQUENCE: 304
gtctcaaact ctatttgcca aaggaaactt                                     30

SEQ ID NO: 305          moltype = DNA  length = 18
FEATURE                 Location/Qualifiers
misc_feature            1..18
                        note = Forward Primer SPTBN1_exon6_F
source                  1..18
                        mol_type = other DNA
                        organism = synthetic construct
SEQUENCE: 305
agggacggca tggccttc                                                  18

SEQ ID NO: 306          moltype = DNA  length = 19
FEATURE                 Location/Qualifiers
misc_feature            1..19
                        note = Forward Primer SS18_exon10_F
source                  1..19
                        mol_type = other DNA
                        organism = synthetic construct
SEQUENCE: 306
aacacagcct ggaccacca                                                 19

SEQ ID NO: 307          moltype = DNA  length = 19
FEATURE                 Location/Qualifiers
misc_feature            1..19
                        note = Forward Primer SS18_exon9_F
source                  1..19
                        mol_type = other DNA
                        organism = synthetic construct
SEQUENCE: 307
agtacccagg gcagcaagg                                                 19

SEQ ID NO: 308          moltype = DNA  length = 18
FEATURE                 Location/Qualifiers
misc_feature            1..18
                        note = Forward Primer TMPRSS2_exon4F
source                  1..18
                        mol_type = other DNA
                        organism = synthetic construct
SEQUENCE: 308
accttcctcg tgggagct                                                  18

SEQ ID NO: 309          moltype = DNA  length = 22
FEATURE                 Location/Qualifiers
misc_feature            1..22
                        note = Forward Primer TPM3_exon2F_rdsgn
source                  1..22
                        mol_type = other DNA
                        organism = synthetic construct
SEQUENCE: 309
tttgaaggat gcccaggaga ag                                             22

SEQ ID NO: 310          moltype = DNA  length = 22
FEATURE                 Location/Qualifiers
misc_feature            1..22
                        note = Forward Primer TPM3_exon4F
source                  1..22
```

```
                        mol_type = other DNA
                        organism = synthetic construct
SEQUENCE: 310
ctaagcacat tgcagaagag gc                                              22

SEQ ID NO: 311          moltype = DNA  length = 20
FEATURE                 Location/Qualifiers
misc_feature            1..20
                        note = Forward Primer TPM3_exon5F
source                  1..20
                        mol_type = other DNA
                        organism = synthetic construct
SEQUENCE: 311
aggagacttg gaacgcacag                                                 20

SEQ ID NO: 312          moltype = DNA  length = 22
FEATURE                 Location/Qualifiers
misc_feature            1..22
                        note = Forward Primer TPM3_exon6F
source                  1..22
                        mol_type = other DNA
                        organism = synthetic construct
SEQUENCE: 312
gtcaccaaca acctcaagtc tc                                              22

SEQ ID NO: 313          moltype = DNA  length = 30
FEATURE                 Location/Qualifiers
misc_feature            1..30
                        note = Forward Primer TPM3_exon7F_rdsgn
source                  1..30
                        mol_type = other DNA
                        organism = synthetic construct
SEQUENCE: 313
gaagataaat atgaggaaga aatcaagatt                                      30

SEQ ID NO: 314          moltype = DNA  length = 20
FEATURE                 Location/Qualifiers
misc_feature            1..20
                        note = Forward Primer TRIM24_exon12_F
source                  1..20
                        mol_type = other DNA
                        organism = synthetic construct
SEQUENCE: 314
cagaacggtc cagtcaccaa                                                 20

SEQ ID NO: 315          moltype = DNA  length = 19
FEATURE                 Location/Qualifiers
misc_feature            1..19
                        note = Forward Primer FGFR3_exon17F_new
source                  1..19
                        mol_type = other DNA
                        organism = synthetic construct
SEQUENCE: 315
gaggcccacc ttcaagcag                                                  19

SEQ ID NO: 316          moltype = DNA  length = 20
FEATURE                 Location/Qualifiers
misc_feature            1..20
                        note = Reverse Primer ABL1_E2a_R
source                  1..20
                        mol_type = other DNA
                        organism = synthetic construct
SEQUENCE: 316
cttcactcag accctgaggc                                                 20

SEQ ID NO: 317          moltype = DNA  length = 20
FEATURE                 Location/Qualifiers
misc_feature            1..20
                        note = Reverse Primer ABL1_E2b_R
source                  1..20
                        mol_type = other DNA
                        organism = synthetic construct
SEQUENCE: 317
caacgaaaag gttggggtca                                                 20

SEQ ID NO: 318          moltype = DNA  length = 21
FEATURE                 Location/Qualifiers
misc_feature            1..21
                        note = Reverse Primer ABL1_E3_R
```

```
source                1..21
                      mol_type = other DNA
                      organism = synthetic construct
SEQUENCE: 318
gcttcacacc attccccatt g                                            21

SEQ ID NO: 319        moltype = DNA  length = 21
FEATURE               Location/Qualifiers
misc_feature          1..21
                      note = Reverse Primer ABL1_E4_R
source                1..21
                      mol_type = other DNA
                      organism = synthetic construct
SEQUENCE: 319
gatgatgaac caactcggcc a                                            21

SEQ ID NO: 320        moltype = DNA  length = 20
FEATURE               Location/Qualifiers
misc_feature          1..20
                      note = Reverse Primer AFF1_E11_R
source                1..20
                      mol_type = other DNA
                      organism = synthetic construct
SEQUENCE: 320
atgtgctgat gccactggtt                                              20

SEQ ID NO: 321        moltype = DNA  length = 19
FEATURE               Location/Qualifiers
misc_feature          1..19
                      note = Reverse Primer AFF1_E6_R
source                1..19
                      mol_type = other DNA
                      organism = synthetic construct
SEQUENCE: 321
ggctcagctg tactaggcg                                               19

SEQ ID NO: 322        moltype = DNA  length = 22
FEATURE               Location/Qualifiers
misc_feature          1..22
                      note = Reverse Primer AFF1_E9-10_R_rdsgn
source                1..22
                      mol_type = other DNA
                      organism = synthetic construct
SEQUENCE: 322
gcttctctgg ggtttgttca ct                                           22

SEQ ID NO: 323        moltype = DNA  length = 20
FEATURE               Location/Qualifiers
misc_feature          1..20
                      note = Reverse Primer ALK_exon19R
source                1..20
                      mol_type = other DNA
                      organism = synthetic construct
SEQUENCE: 323
agagaggatc agcgagagtg                                              20

SEQ ID NO: 324        moltype = DNA  length = 21
FEATURE               Location/Qualifiers
misc_feature          1..21
                      note = Reverse Primer ALK_exon20RL
source                1..21
                      mol_type = other DNA
                      organism = synthetic construct
SEQUENCE: 324
tcagcttgta ctcagggctc t                                            21

SEQ ID NO: 325        moltype = DNA  length = 19
FEATURE               Location/Qualifiers
misc_feature          1..19
                      note = Reverse Primer ALK_exon21R
source                1..19
                      mol_type = other DNA
                      organism = synthetic construct
SEQUENCE: 325
cttgggtcgt tgggcattc                                               19

SEQ ID NO: 326        moltype = DNA  length = 20
FEATURE               Location/Qualifiers
misc_feature          1..20
```

```
                        note = Reverse Primer BRAF_exon10R
source                  1..20
                        mol_type = other DNA
                        organism = synthetic construct
SEQUENCE: 326
cgttagttag tgagccaggt                                             20

SEQ ID NO: 327          moltype = DNA  length = 23
FEATURE                 Location/Qualifiers
misc_feature            1..23
                        note = Reverse Primer BRAF_exon11R
source                  1..23
                        mol_type = other DNA
                        organism = synthetic construct
SEQUENCE: 327
caggaatctc ccaatcatca ctc                                         23

SEQ ID NO: 328          moltype = DNA  length = 20
FEATURE                 Location/Qualifiers
misc_feature            1..20
                        note = Reverse Primer BRAF_exon8R
source                  1..20
                        mol_type = other DNA
                        organism = synthetic construct
SEQUENCE: 328
agggctgtgg aattggaatg                                             20

SEQ ID NO: 329          moltype = DNA  length = 22
FEATURE                 Location/Qualifiers
misc_feature            1..22
                        note = Reverse Primer BRAF_exon9R
source                  1..22
                        mol_type = other DNA
                        organism = synthetic construct
SEQUENCE: 329
ctccatcacc acgaaatcct tg                                          22

SEQ ID NO: 330          moltype = DNA  length = 20
FEATURE                 Location/Qualifiers
misc_feature            1..20
                        note = Reverse Primer ERG_exon10R
source                  1..20
                        mol_type = other DNA
                        organism = synthetic construct
SEQUENCE: 330
aaggcggcta cttgttggtc                                             20

SEQ ID NO: 331          moltype = DNA  length = 21
FEATURE                 Location/Qualifiers
misc_feature            1..21
                        note = Reverse Primer ERG_exon11R
source                  1..21
                        mol_type = other DNA
                        organism = synthetic construct
SEQUENCE: 331
gaggaactgc caaagctgga t                                           21

SEQ ID NO: 332          moltype = DNA  length = 20
FEATURE                 Location/Qualifiers
misc_feature            1..20
                        note = Reverse Primer ERG_exon2R
source                  1..20
                        mol_type = other DNA
                        organism = synthetic construct
SEQUENCE: 332
ctttcctcgg gtctccaaag                                             20

SEQ ID NO: 333          moltype = DNA  length = 20
FEATURE                 Location/Qualifiers
misc_feature            1..20
                        note = Reverse Primer ERG_exon3R
source                  1..20
                        mol_type = other DNA
                        organism = synthetic construct
SEQUENCE: 333
cccatctacc agctgttcag                                             20

SEQ ID NO: 334          moltype = DNA  length = 25
FEATURE                 Location/Qualifiers
```

```
misc_feature          1..25
                      note = Reverse Primer ERG_exon4RS
source                1..25
                      mol_type = other DNA
                      organism = synthetic construct
SEQUENCE: 334
tggtcctcac tcacaactga taagg                                    25

SEQ ID NO: 335        moltype = DNA  length = 20
FEATURE               Location/Qualifiers
misc_feature          1..20
                      note = Reverse Primer ERG_exon5RS
source                1..20
                      mol_type = other DNA
                      organism = synthetic construct
SEQUENCE: 335
ccaccatctt cccgcctttg                                          20

SEQ ID NO: 336        moltype = DNA  length = 18
FEATURE               Location/Qualifiers
misc_feature          1..18
                      note = Reverse Primer ERG_exon8R
source                1..18
                      mol_type = other DNA
                      organism = synthetic construct
SEQUENCE: 336
caggagatca gcctggac                                            18

SEQ ID NO: 337        moltype = DNA  length = 21
FEATURE               Location/Qualifiers
misc_feature          1..21
                      note = Reverse Primer ERG_exon9R
source                1..21
                      mol_type = other DNA
                      organism = synthetic construct
SEQUENCE: 337
ggtcttcagt tttgggcact g                                        21

SEQ ID NO: 338        moltype = DNA  length = 23
FEATURE               Location/Qualifiers
misc_feature          1..23
                      note = Reverse Primer MECOM_E2_R
source                1..23
                      mol_type = other DNA
                      organism = synthetic construct
SEQUENCE: 338
tgcatctggc atttcttcca aag                                      23

SEQ ID NO: 339        moltype = DNA  length = 28
FEATURE               Location/Qualifiers
misc_feature          1..28
                      note = Reverse Primer MLLT3_E10_R
source                1..28
                      mol_type = other DNA
                      organism = synthetic construct
SEQUENCE: 339
atgtcattaa ccttctgtga agctctac                                 28

SEQ ID NO: 340        moltype = DNA  length = 24
FEATURE               Location/Qualifiers
misc_feature          1..24
                      note = Reverse Primer MLLT3_E5_R
source                1..24
                      mol_type = other DNA
                      organism = synthetic construct
SEQUENCE: 340
tgctgctgct gctggtatga atac                                     24

SEQ ID NO: 341        moltype = DNA  length = 24
FEATURE               Location/Qualifiers
misc_feature          1..24
                      note = Reverse Primer MLLT3_E7_R
source                1..24
                      mol_type = other DNA
                      organism = synthetic construct
SEQUENCE: 341
tctgattcct cctcattgtc atca                                     24

SEQ ID NO: 342        moltype = DNA  length = 30
```

```
FEATURE                Location/Qualifiers
misc_feature           1..30
                       note = Reverse Primer MLLT3_E9_R
source                 1..30
                       mol_type = other DNA
                       organism = synthetic construct
SEQUENCE: 342
tttgcttatc tgatttgctt tgctttattg                                  30

SEQ ID NO: 343         moltype = DNA  length = 20
FEATURE                Location/Qualifiers
misc_feature           1..20
                       note = Reverse Primer MYH11_E28_R
source                 1..20
                       mol_type = other DNA
                       organism = synthetic construct
SEQUENCE: 343
tctctttctc cagcgtctgc                                             20

SEQ ID NO: 344         moltype = DNA  length = 20
FEATURE                Location/Qualifiers
misc_feature           1..20
                       note = Reverse Primer MYH11_E29_R
source                 1..20
                       mol_type = other DNA
                       organism = synthetic construct
SEQUENCE: 344
ctcggcctcg ttaagcatcc                                             20

SEQ ID NO: 345         moltype = DNA  length = 20
FEATURE                Location/Qualifiers
misc_feature           1..20
                       note = Reverse Primer MYH11_E30_R
source                 1..20
                       mol_type = other DNA
                       organism = synthetic construct
SEQUENCE: 345
gcagcttcgt agacacgttg                                             20

SEQ ID NO: 346         moltype = DNA  length = 21
FEATURE                Location/Qualifiers
misc_feature           1..21
                       note = Reverse Primer MYH11_E32_R
source                 1..21
                       mol_type = other DNA
                       organism = synthetic construct
SEQUENCE: 346
cctctcatcc gcgtatttgg a                                           21

SEQ ID NO: 347         moltype = DNA  length = 19
FEATURE                Location/Qualifiers
misc_feature           1..19
                       note = Reverse Primer MYH11_E33_R
source                 1..19
                       mol_type = other DNA
                       organism = synthetic construct
SEQUENCE: 347
tccatctggg tctccaggg                                              19

SEQ ID NO: 348         moltype = DNA  length = 20
FEATURE                Location/Qualifiers
misc_feature           1..20
                       note = Reverse Primer MYH11_E34_R
source                 1..20
                       mol_type = other DNA
                       organism = synthetic construct
SEQUENCE: 348
gttgctttcg ctcgtcttcc                                             20

SEQ ID NO: 349         moltype = DNA  length = 20
FEATURE                Location/Qualifiers
misc_feature           1..20
                       note = Reverse Primer RARA_E3_R
source                 1..20
                       mol_type = other DNA
                       organism = synthetic construct
SEQUENCE: 349
ggctgggcac tatctcttca                                             20
```

```
SEQ ID NO: 350          moltype = DNA  length = 22
FEATURE                 Location/Qualifiers
misc_feature            1..22
                        note = Reverse Primer RET_exon11RS
source                  1..22
                        mol_type = other DNA
                        organism = synthetic construct
SEQUENCE: 350
atgaaggaga agaggacagc gg                                          22

SEQ ID NO: 351          moltype = DNA  length = 25
FEATURE                 Location/Qualifiers
misc_feature            1..25
                        note = Reverse Primer RET_exon12RL
source                  1..25
                        mol_type = other DNA
                        organism = synthetic construct
SEQUENCE: 351
tcctagagtt tttccaagaa ccaag                                       25

SEQ ID NO: 352          moltype = DNA  length = 20
FEATURE                 Location/Qualifiers
misc_feature            1..20
                        note = Reverse Primer RET_exon7R
source                  1..20
                        mol_type = other DNA
                        organism = synthetic construct
SEQUENCE: 352
ggacgttgat gccactgaat                                             20

SEQ ID NO: 353          moltype = DNA  length = 23
FEATURE                 Location/Qualifiers
misc_feature            1..23
                        note = Reverse Primer RET_exon8R
source                  1..23
                        mol_type = other DNA
                        organism = synthetic construct
SEQUENCE: 353
ctcttgctga ctgcacagga cag                                         23

SEQ ID NO: 354          moltype = DNA  length = 25
FEATURE                 Location/Qualifiers
misc_feature            1..25
                        note = Reverse Primer ROS1_exon34R
source                  1..25
                        mol_type = other DNA
                        organism = synthetic construct
SEQUENCE: 354
ggtcagtggg attgtaacaa ccaga                                       25

SEQ ID NO: 355          moltype = DNA  length = 23
FEATURE                 Location/Qualifiers
misc_feature            1..23
                        note = Reverse Primer ROS1_exon35R
source                  1..23
                        mol_type = other DNA
                        organism = synthetic construct
SEQUENCE: 355
cttcgtttat aagcactgtc acc                                         23

SEQ ID NO: 356          moltype = DNA  length = 19
FEATURE                 Location/Qualifiers
misc_feature            1..19
                        note = Reverse Primer ROS1_exon36R
source                  1..19
                        mol_type = other DNA
                        organism = synthetic construct
SEQUENCE: 356
gagggaaggc aggaagatt                                              19

SEQ ID NO: 357          moltype = DNA  length = 20
FEATURE                 Location/Qualifiers
misc_feature            1..20
                        note = Reverse Primer RUNX1T1_E2_R
source                  1..20
                        mol_type = other DNA
                        organism = synthetic construct
SEQUENCE: 357
gcgtcttcac atccacaggt                                             20
```

```
SEQ ID NO: 358          moltype = DNA  length = 21
FEATURE                 Location/Qualifiers
misc_feature            1..21
                        note = Reverse Primer ACTR1A_exon3_R
source                  1..21
                        mol_type = other DNA
                        organism = synthetic construct
SEQUENCE: 358
aagatgtcgc cttcaagggc t                                             21

SEQ ID NO: 359          moltype = DNA  length = 24
FEATURE                 Location/Qualifiers
misc_feature            1..24
                        note = Reverse Primer AHCYL1_exon2R
source                  1..24
                        mol_type = other DNA
                        organism = synthetic construct
SEQUENCE: 359
gttttggtgg ggaatttggt gaac                                          24

SEQ ID NO: 360          moltype = DNA  length = 26
FEATURE                 Location/Qualifiers
misc_feature            1..26
                        note = Reverse Primer AKAP12_exon4_R
source                  1..26
                        mol_type = other DNA
                        organism = synthetic construct
SEQUENCE: 360
agtagccatc tctttatcgg agtctc                                        26

SEQ ID NO: 361          moltype = DNA  length = 24
FEATURE                 Location/Qualifiers
misc_feature            1..24
                        note = Reverse Primer AR_CE3_R
source                  1..24
                        mol_type = other DNA
                        organism = synthetic construct
SEQUENCE: 361
ggtctggtca ttttgagatg cttg                                          24

SEQ ID NO: 362          moltype = DNA  length = 23
FEATURE                 Location/Qualifiers
misc_feature            1..23
                        note = Reverse Primer AR_CE5_R
source                  1..23
                        mol_type = other DNA
                        organism = synthetic construct
SEQUENCE: 362
acaacgtgat cccaaaagat gtg                                           23

SEQ ID NO: 363          moltype = DNA  length = 20
FEATURE                 Location/Qualifiers
misc_feature            1..20
                        note = Reverse Primer AR_CE4_R
source                  1..20
                        mol_type = other DNA
                        organism = synthetic construct
SEQUENCE: 363
atgcagtatg gcttggggtt                                               20

SEQ ID NO: 364          moltype = DNA  length = 25
FEATURE                 Location/Qualifiers
misc_feature            1..25
                        note = Reverse Primer BAIAP2L1_exon2_3R
source                  1..25
                        mol_type = other DNA
                        organism = synthetic construct
SEQUENCE: 364
aggatcatag cgtttacagc tttct                                         25

SEQ ID NO: 365          moltype = DNA  length = 24
FEATURE                 Location/Qualifiers
misc_feature            1..24
                        note = Reverse Primer BICC1_exon2_3R
source                  1..24
                        mol_type = other DNA
                        organism = synthetic construct
SEQUENCE: 365
```

```
tgcgtatttg tttcctccat gatc                                              24

SEQ ID NO: 366          moltype = DNA  length = 20
FEATURE                 Location/Qualifiers
misc_feature            1..20
                        note = Reverse Primer CCDC170_exon2_R
source                  1..20
                        mol_type = other DNA
                        organism = synthetic construct
SEQUENCE: 366
agtggtttaa ctgctcccgc                                                   20

SEQ ID NO: 367          moltype = DNA  length = 20
FEATURE                 Location/Qualifiers
misc_feature            1..20
                        note = Reverse Primer CLDN7_exon2_R
source                  1..20
                        mol_type = other DNA
                        organism = synthetic construct
SEQUENCE: 367
gcaccaggga gaccaccatt                                                   20

SEQ ID NO: 368          moltype = DNA  length = 22
FEATURE                 Location/Qualifiers
misc_feature            1..22
                        note = Reverse Primer EGFR_exon14R
source                  1..22
                        mol_type = other DNA
                        organism = synthetic construct
SEQUENCE: 368
ggcactgtat gcactcagag tt                                                22

SEQ ID NO: 369          moltype = DNA  length = 18
FEATURE                 Location/Qualifiers
misc_feature            1..18
                        note = Reverse Primer EGFR_exon15R
source                  1..18
                        mol_type = other DNA
                        organism = synthetic construct
SEQUENCE: 369
caggtcttga cgcagtgg                                                     18

SEQ ID NO: 370          moltype = DNA  length = 19
FEATURE                 Location/Qualifiers
misc_feature            1..19
                        note = Reverse Primer EGFR_exon18R
source                  1..19
                        mol_type = other DNA
                        organism = synthetic construct
SEQUENCE: 370
gcttggttgg gagcttctc                                                    19

SEQ ID NO: 371          moltype = DNA  length = 20
FEATURE                 Location/Qualifiers
misc_feature            1..20
                        note = Reverse Primer ERBB2_exon17R
source                  1..20
                        mol_type = other DNA
                        organism = synthetic construct
SEQUENCE: 371
aagaccacga ccagcagaat                                                   20

SEQ ID NO: 372          moltype = DNA  length = 19
FEATURE                 Location/Qualifiers
misc_feature            1..19
                        note = Reverse Primer ERBB2_ex8-int8_R
source                  1..19
                        mol_type = other DNA
                        organism = synthetic construct
SEQUENCE: 372
tgagtgggta cctcacacc                                                    19

SEQ ID NO: 373          moltype = DNA  length = 21
FEATURE                 Location/Qualifiers
misc_feature            1..21
                        note = Reverse Primer ETV1_exon4_R
source                  1..21
                        mol_type = other DNA
                        organism = synthetic construct
```

```
SEQUENCE: 373
cttctgcaag ccatgtttcc t                                          21

SEQ ID NO: 374          moltype = DNA  length = 25
FEATURE                 Location/Qualifiers
misc_feature            1..25
                        note = Reverse Primer ETV1_exon6_R
source                  1..25
                        mol_type = other DNA
                        organism = synthetic construct
SEQUENCE: 374
tgaacatgga ctgtggggtt ctttc                                      25

SEQ ID NO: 375          moltype = DNA  length = 20
FEATURE                 Location/Qualifiers
misc_feature            1..20
                        note = Reverse Primer ETV1_exon7_R
source                  1..20
                        mol_type = other DNA
                        organism = synthetic construct
SEQUENCE: 375
ggagggcctc attcccactt                                            20

SEQ ID NO: 376          moltype = DNA  length = 20
FEATURE                 Location/Qualifiers
misc_feature            1..20
                        note = Reverse Primer ETV1_exon2_R
source                  1..20
                        mol_type = other DNA
                        organism = synthetic construct
SEQUENCE: 376
tggtgaccat gtaaggcact                                            20

SEQ ID NO: 377          moltype = DNA  length = 24
FEATURE                 Location/Qualifiers
misc_feature            1..24
                        note = Reverse Primer ETV1_exon2b_R
source                  1..24
                        mol_type = other DNA
                        organism = synthetic construct
SEQUENCE: 377
agcatttagc tggagatttc ctca                                       24

SEQ ID NO: 378          moltype = DNA  length = 27
FEATURE                 Location/Qualifiers
misc_feature            1..27
                        note = Reverse Primer ETV1_exon5_R
source                  1..27
                        mol_type = other DNA
                        organism = synthetic construct
SEQUENCE: 378
aactttcagc ctgatagtct ggtacaa                                    27

SEQ ID NO: 379          moltype = DNA  length = 28
FEATURE                 Location/Qualifiers
misc_feature            1..28
                        note = Reverse Primer ETV1_exon3_R
source                  1..28
                        mol_type = other DNA
                        organism = synthetic construct
SEQUENCE: 379
ttttcttttc ctgacatttg ttggtttc                                   28

SEQ ID NO: 380          moltype = DNA  length = 25
FEATURE                 Location/Qualifiers
misc_feature            1..25
                        note = Reverse Primer ETV1_exon11_R
source                  1..25
                        mol_type = other DNA
                        organism = synthetic construct
SEQUENCE: 380
agttcatagc tggcctgttt ttctg                                      25

SEQ ID NO: 381          moltype = DNA  length = 24
FEATURE                 Location/Qualifiers
misc_feature            1..24
                        note = Reverse Primer ETV1_exon12_R
source                  1..24
                        mol_type = other DNA
```

```
                         organism = synthetic construct
SEQUENCE: 381
agaaaagggc ttctggatca caca                                  24

SEQ ID NO: 382           moltype = DNA  length = 18
FEATURE                  Location/Qualifiers
misc_feature             1..18
                         note = Reverse Primer ETV4_exon1_2_R
source                   1..18
                         mol_type = other DNA
                         organism = synthetic construct
SEQUENCE: 382
cgagacctgc tcccagga                                         18

SEQ ID NO: 383           moltype = DNA  length = 18
FEATURE                  Location/Qualifiers
misc_feature             1..18
                         note = Reverse Primer ETV4_exon3_R
source                   1..18
                         mol_type = other DNA
                         organism = synthetic construct
SEQUENCE: 383
catgagcttc cccagcgg                                         18

SEQ ID NO: 384           moltype = DNA  length = 26
FEATURE                  Location/Qualifiers
misc_feature             1..26
                         note = Reverse Primer ETV4_exon5_R
source                   1..26
                         mol_type = other DNA
                         organism = synthetic construct
SEQUENCE: 384
ctgaatggaa atcaggaaca aactgc                                26

SEQ ID NO: 385           moltype = DNA  length = 18
FEATURE                  Location/Qualifiers
misc_feature             1..18
                         note = Reverse Primer ETV4_exon4_R
source                   1..18
                         mol_type = other DNA
                         organism = synthetic construct
SEQUENCE: 385
agcgagccac gtctcctg                                         18

SEQ ID NO: 386           moltype = DNA  length = 23
FEATURE                  Location/Qualifiers
misc_feature             1..23
                         note = Reverse Primer ETV5_exon2_R
source                   1..23
                         mol_type = other DNA
                         organism = synthetic construct
SEQUENCE: 386
cagcattgag taatttctgg ggg                                   23

SEQ ID NO: 387           moltype = DNA  length = 21
FEATURE                  Location/Qualifiers
misc_feature             1..21
                         note = Reverse Primer ETV5_exon8_R
source                   1..21
                         mol_type = other DNA
                         organism = synthetic construct
SEQUENCE: 387
aactcctggc tgaggaggga a                                     21

SEQ ID NO: 388           moltype = DNA  length = 21
FEATURE                  Location/Qualifiers
misc_feature             1..21
                         note = Reverse Primer FGFR1_exon8_R
source                   1..21
                         mol_type = other DNA
                         organism = synthetic construct
SEQUENCE: 388
agcacctcca tctctttgtc g                                     21

SEQ ID NO: 389           moltype = DNA  length = 20
FEATURE                  Location/Qualifiers
misc_feature             1..20
                         note = Reverse Primer FGFR1_exon6_R
source                   1..20
```

```
                        mol_type = other DNA
                        organism = synthetic construct
SEQUENCE: 389
tgtcagaggg caccacagag                                             20

SEQ ID NO: 390          moltype = DNA  length = 23
FEATURE                 Location/Qualifiers
misc_feature            1..23
                        note = Reverse Primer FGFR1_exon9_R
source                  1..23
                        mol_type = other DNA
                        organism = synthetic construct
SEQUENCE: 390
agatgatgat ctccaggtac agg                                         23

SEQ ID NO: 391          moltype = DNA  length = 23
FEATURE                 Location/Qualifiers
misc_feature            1..23
                        note = Reverse Primer FGFR1_exon10_R
source                  1..23
                        mol_type = other DNA
                        organism = synthetic construct
SEQUENCE: 391
gaaccagaag aaccccagag ttc                                         23

SEQ ID NO: 392          moltype = DNA  length = 29
FEATURE                 Location/Qualifiers
misc_feature            1..29
                        note = Reverse Primer JAK2_exon9_R
source                  1..29
                        mol_type = other DNA
                        organism = synthetic construct
SEQUENCE: 392
ccatcaatta atgacacgaa agacaaagc                                   29

SEQ ID NO: 393          moltype = DNA  length = 22
FEATURE                 Location/Qualifiers
misc_feature            1..22
                        note = Reverse Primer JAK2_exon10_R
source                  1..22
                        mol_type = other DNA
                        organism = synthetic construct
SEQUENCE: 393
acagtccagt ctgattacct gc                                          22

SEQ ID NO: 394          moltype = DNA  length = 20
FEATURE                 Location/Qualifiers
misc_feature            1..20
                        note = Reverse Primer JAK2_exon11_R
source                  1..20
                        mol_type = other DNA
                        organism = synthetic construct
SEQUENCE: 394
tgtcccactg aggttgtact                                             20

SEQ ID NO: 395          moltype = DNA  length = 22
FEATURE                 Location/Qualifiers
misc_feature            1..22
                        note = Reverse Primer JAK2_exon12_R
source                  1..22
                        mol_type = other DNA
                        organism = synthetic construct
SEQUENCE: 395
tggtgaggtt ggtacatcag aa                                          22

SEQ ID NO: 396          moltype = DNA  length = 23
FEATURE                 Location/Qualifiers
misc_feature            1..23
                        note = Reverse Primer JAK2_exon13_R
source                  1..23
                        mol_type = other DNA
                        organism = synthetic construct
SEQUENCE: 396
tgaccgtagt ctcctacttc tct                                         23

SEQ ID NO: 397          moltype = DNA  length = 27
FEATURE                 Location/Qualifiers
misc_feature            1..27
                        note = Reverse Primer JAK2_exon14_R
```

```
source                  1..27
                        mol_type = other DNA
                        organism = synthetic construct
SEQUENCE: 397
ttaaaaccaa atgcttgtga gaaagct                                          27

SEQ ID NO: 398          moltype = DNA  length = 30
FEATURE                 Location/Qualifiers
misc_feature            1..30
                        note = Reverse Primer JAK2_exon15_R
source                  1..30
                        mol_type = other DNA
                        organism = synthetic construct
SEQUENCE: 398
tctttttcag atatgtatct agtgatccaa                                       30

SEQ ID NO: 399          moltype = DNA  length = 29
FEATURE                 Location/Qualifiers
misc_feature            1..29
                        note = Reverse Primer JAK2_exon16_R
source                  1..29
                        mol_type = other DNA
                        organism = synthetic construct
SEQUENCE: 399
tctctgataa gcagaatatt tttggcaca                                        29

SEQ ID NO: 400          moltype = DNA  length = 25
FEATURE                 Location/Qualifiers
misc_feature            1..25
                        note = Reverse Primer JAK2_exon17_R
source                  1..25
                        mol_type = other DNA
                        organism = synthetic construct
SEQUENCE: 400
gcattcaggt ggtacccatg gtatt                                            25

SEQ ID NO: 401          moltype = DNA  length = 22
FEATURE                 Location/Qualifiers
misc_feature            1..22
                        note = Reverse Primer JAK2_exon18_R
source                  1..22
                        mol_type = other DNA
                        organism = synthetic construct
SEQUENCE: 401
ccactttggt gcaggaagct ga                                               22

SEQ ID NO: 402          moltype = DNA  length = 27
FEATURE                 Location/Qualifiers
misc_feature            1..27
                        note = Reverse Primer JAK2_exon19_R
source                  1..27
                        mol_type = other DNA
                        organism = synthetic construct
SEQUENCE: 402
agggcaccta tcctcatatt tggtaac                                          27

SEQ ID NO: 403          moltype = DNA  length = 25
FEATURE                 Location/Qualifiers
misc_feature            1..25
                        note = Reverse Primer MET_exon11R
source                  1..25
                        mol_type = other DNA
                        organism = synthetic construct
SEQUENCE: 403
ggagtggtac aacagattat ctctg                                            25

SEQ ID NO: 404          moltype = DNA  length = 20
FEATURE                 Location/Qualifiers
misc_feature            1..20
                        note = Reverse Primer MET_exon15R
source                  1..20
                        mol_type = other DNA
                        organism = synthetic construct
SEQUENCE: 404
ctgcacttgt cggcatgaac                                                  20

SEQ ID NO: 405          moltype = DNA  length = 21
FEATURE                 Location/Qualifiers
misc_feature            1..21
```

```
                        note = Reverse Primer NOP2_exon16_R
source                  1..21
                        mol_type = other DNA
                        organism = synthetic construct
SEQUENCE: 405
ggatgacctg aggcaagtct a                                              21

SEQ ID NO: 406          moltype = DNA  length = 22
FEATURE                 Location/Qualifiers
misc_feature            1..22
                        note = Reverse Primer NRG1_exon6R
source                  1..22
                        mol_type = other DNA
                        organism = synthetic construct
SEQUENCE: 406
ctccgcacat tttacaagat gg                                             22

SEQ ID NO: 407          moltype = DNA  length = 28
FEATURE                 Location/Qualifiers
misc_feature            1..28
                        note = Reverse Primer NRG1_exon5_6R
source                  1..28
                        mol_type = other DNA
                        organism = synthetic construct
SEQUENCE: 407
gtggtggatg tagatgtaga tgaagaag                                       28

SEQ ID NO: 408          moltype = DNA  length = 19
FEATURE                 Location/Qualifiers
misc_feature            1..19
                        note = Reverse Primer NRG1_exon2R
source                  1..19
                        mol_type = other DNA
                        organism = synthetic construct
SEQUENCE: 408
aacctgcagc cgattcctg                                                 19

SEQ ID NO: 409          moltype = DNA  length = 22
FEATURE                 Location/Qualifiers
misc_feature            1..22
                        note = Reverse Primer NRG1_exon3R
source                  1..22
                        mol_type = other DNA
                        organism = synthetic construct
SEQUENCE: 409
gaatcagcca gtgatgcttt gt                                             22

SEQ ID NO: 410          moltype = DNA  length = 20
FEATURE                 Location/Qualifiers
misc_feature            1..20
                        note = Reverse Primer NRG1_exon4R
source                  1..20
                        mol_type = other DNA
                        organism = synthetic construct
SEQUENCE: 410
tgctccttca gttgaggctg                                                20

SEQ ID NO: 411          moltype = DNA  length = 23
FEATURE                 Location/Qualifiers
misc_feature            1..23
                        note = Reverse Primer NTRK1-exon10R_rdsgn
source                  1..23
                        mol_type = other DNA
                        organism = synthetic construct
SEQUENCE: 411
gtgtttcgtc cttcttctcc acc                                            23

SEQ ID NO: 412          moltype = DNA  length = 23
FEATURE                 Location/Qualifiers
misc_feature            1..23
                        note = Reverse Primer NTRK1-exon12R
source                  1..23
                        mol_type = other DNA
                        organism = synthetic construct
SEQUENCE: 412
tgtcatgaaa tgcagggaca tgg                                            23

SEQ ID NO: 413          moltype = DNA  length = 18
FEATURE                 Location/Qualifiers
```

```
misc_feature           1..18
                       note = Reverse Primer NTRK1-exon9R
source                 1..18
                       mol_type = other DNA
                       organism = synthetic construct
SEQUENCE: 413
accagtggtg catctcca                                            18

SEQ ID NO: 414         moltype = DNA  length = 22
FEATURE                Location/Qualifiers
misc_feature           1..22
                       note = Reverse Primer NTRK1-exon11R
source                 1..22
                       mol_type = other DNA
                       organism = synthetic construct
SEQUENCE: 414
agcgtagaaa ggaagaggca gg                                       22

SEQ ID NO: 415         moltype = DNA  length = 20
FEATURE                Location/Qualifiers
misc_feature           1..20
                       note = Reverse Primer NTRK2_exon13_R_rdsgn
source                 1..20
                       mol_type = other DNA
                       organism = synthetic construct
SEQUENCE: 415
tggtgtcccc gatgtcattc                                          20

SEQ ID NO: 416         moltype = DNA  length = 22
FEATURE                Location/Qualifiers
misc_feature           1..22
                       note = Reverse Primer NTRK2_exon16_R_rdsgn
source                 1..22
                       mol_type = other DNA
                       organism = synthetic construct
SEQUENCE: 416
gctggcagag tcatcatcat tg                                       22

SEQ ID NO: 417         moltype = DNA  length = 21
FEATURE                Location/Qualifiers
misc_feature           1..21
                       note = Reverse Primer NTRK3_exon14R
source                 1..21
                       mol_type = other DNA
                       organism = synthetic construct
SEQUENCE: 417
gtcctcctca ccactgatga c                                        21

SEQ ID NO: 418         moltype = DNA  length = 25
FEATURE                Location/Qualifiers
misc_feature           1..25
                       note = Reverse Primer NTRK3_exon15R
source                 1..25
                       mol_type = other DNA
                       organism = synthetic construct
SEQUENCE: 418
cttcagcacg atgtctctcc tctta                                    25

SEQ ID NO: 419         moltype = DNA  length = 23
FEATURE                Location/Qualifiers
misc_feature           1..23
                       note = Reverse Primer NTRK3_exon11_12R
source                 1..23
                       mol_type = other DNA
                       organism = synthetic construct
SEQUENCE: 419
ggactcactt cgtcaaacaa gat                                      23

SEQ ID NO: 420         moltype = DNA  length = 24
FEATURE                Location/Qualifiers
misc_feature           1..24
                       note = Reverse Primer PAWR_exon3_R
source                 1..24
                       mol_type = other DNA
                       organism = synthetic construct
SEQUENCE: 420
taattgcatc ttctcgtttc cgct                                     24

SEQ ID NO: 421         moltype = DNA  length = 18
```

```
FEATURE                 Location/Qualifiers
misc_feature            1..18
                        note = Reverse Primer PBX1_exon3_R
source                  1..18
                        mol_type = other DNA
                        organism = synthetic construct
SEQUENCE: 421
ctgggggtct gtgggttc                                          18

SEQ ID NO: 422          moltype = DNA  length = 22
FEATURE                 Location/Qualifiers
misc_feature            1..22
                        note = Reverse Primer PCDH11X_exon11_R
source                  1..22
                        mol_type = other DNA
                        organism = synthetic construct
SEQUENCE: 422
cttgagtgca gttgtcagag gc                                     22

SEQ ID NO: 423          moltype = DNA  length = 21
FEATURE                 Location/Qualifiers
misc_feature            1..21
                        note = Reverse Primer PDGFRA_exon12_R
source                  1..21
                        mol_type = other DNA
                        organism = synthetic construct
SEQUENCE: 423
tgattcaatg accctccagc g                                      21

SEQ ID NO: 424          moltype = DNA  length = 25
FEATURE                 Location/Qualifiers
misc_feature            1..25
                        note = Reverse Primer PDGFRB_exon11_R
source                  1..25
                        mol_type = other DNA
                        organism = synthetic construct
SEQUENCE: 424
ggatgataag ggagatgatg gtgag                                  25

SEQ ID NO: 425          moltype = DNA  length = 21
FEATURE                 Location/Qualifiers
misc_feature            1..21
                        note = Reverse Primer PDGFRB_exon9_R
source                  1..21
                        mol_type = other DNA
                        organism = synthetic construct
SEQUENCE: 425
tgtctgttcc ccactgtcag g                                      21

SEQ ID NO: 426          moltype = DNA  length = 20
FEATURE                 Location/Qualifiers
misc_feature            1..20
                        note = Reverse Primer PDGFRB_exon10_R
source                  1..20
                        mol_type = other DNA
                        organism = synthetic construct
SEQUENCE: 426
agctggctct cctcttcgga                                        20

SEQ ID NO: 427          moltype = DNA  length = 23
FEATURE                 Location/Qualifiers
misc_feature            1..23
                        note = Reverse Primer PDGFRB_exon12_R
source                  1..23
                        mol_type = other DNA
                        organism = synthetic construct
SEQUENCE: 427
agctcacaga ctcaatcacc ttc                                    23

SEQ ID NO: 428          moltype = DNA  length = 24
FEATURE                 Location/Qualifiers
misc_feature            1..24
                        note = Reverse Primer PLAG1_exon4_R
source                  1..24
                        mol_type = other DNA
                        organism = synthetic construct
SEQUENCE: 428
gctttaggtg gcttctcaag tttc                                   24
```

```
SEQ ID NO: 429          moltype = DNA  length = 22
FEATURE                 Location/Qualifiers
misc_feature            1..22
                        note = Reverse Primer PLAG1_exon3_R
source                  1..22
                        mol_type = other DNA
                        organism = synthetic construct
SEQUENCE: 429
gactcttcgt ggaagagagt gg                                            22

SEQ ID NO: 430          moltype = DNA  length = 21
FEATURE                 Location/Qualifiers
misc_feature            1..21
                        note = Reverse Primer PLAG1_exon2_R
source                  1..21
                        mol_type = other DNA
                        organism = synthetic construct
SEQUENCE: 430
gaatgaagca ttctgggtgc c                                             21

SEQ ID NO: 431          moltype = DNA  length = 20
FEATURE                 Location/Qualifiers
misc_feature            1..20
                        note = Reverse Primer POLH_exon2_R
source                  1..20
                        mol_type = other DNA
                        organism = synthetic construct
SEQUENCE: 431
gtccatgtcc acgagagcaa                                               20

SEQ ID NO: 432          moltype = DNA  length = 21
FEATURE                 Location/Qualifiers
misc_feature            1..21
                        note = Reverse Primer PPARG_exon2R
source                  1..21
                        mol_type = other DNA
                        organism = synthetic construct
SEQUENCE: 432
aatggcatct ctgtgtcaac c                                             21

SEQ ID NO: 433          moltype = DNA  length = 21
FEATURE                 Location/Qualifiers
misc_feature            1..21
                        note = Reverse Primer PPARGC1A_exon2R
source                  1..21
                        mol_type = other DNA
                        organism = synthetic construct
SEQUENCE: 433
aggaagatct gggcaaagag g                                             21

SEQ ID NO: 434          moltype = DNA  length = 23
FEATURE                 Location/Qualifiers
misc_feature            1..23
                        note = Reverse Primer PPHLN1_exon3R
source                  1..23
                        mol_type = other DNA
                        organism = synthetic construct
SEQUENCE: 434
gtctagcagt ggtggtttct ttg                                           23

SEQ ID NO: 435          moltype = DNA  length = 21
FEATURE                 Location/Qualifiers
misc_feature            1..21
                        note = Reverse Primer RAD51_exon4R_rdsg
source                  1..21
                        mol_type = other DNA
                        organism = synthetic construct
SEQUENCE: 435
ggtggaattc agttgcagtg g                                             21

SEQ ID NO: 436          moltype = DNA  length = 19
FEATURE                 Location/Qualifiers
misc_feature            1..19
                        note = Reverse Primer RUNX1_Exon4_R
source                  1..19
                        mol_type = other DNA
                        organism = synthetic construct
SEQUENCE: 436
cctcgctcat cttgcctgg                                                19
```

```
SEQ ID NO: 437          moltype = DNA  length = 18
FEATURE                 Location/Qualifiers
misc_feature            1..18
                        note = Reverse Primer SHC1_exon2R_rdsgn
source                  1..18
                        mol_type = other DNA
                        organism = synthetic construct
SEQUENCE: 437
cccttccacc cgagtcct                                                18

SEQ ID NO: 438          moltype = DNA  length = 28
FEATURE                 Location/Qualifiers
misc_feature            1..28
                        note = Reverse Primer KIAA1598_exon7_R
source                  1..28
                        mol_type = other DNA
                        organism = synthetic construct
SEQUENCE: 438
ttctctgttc aagaacttct gaatttaa                                     28

SEQ ID NO: 439          moltype = DNA  length = 22
FEATURE                 Location/Qualifiers
misc_feature            1..22
                        note = Reverse Primer KIAA1598_exon8_R
source                  1..22
                        mol_type = other DNA
                        organism = synthetic construct
SEQUENCE: 439
gctccaggtt tacttgcatc tc                                           22

SEQ ID NO: 440          moltype = DNA  length = 20
FEATURE                 Location/Qualifiers
misc_feature            1..20
                        note = Reverse Primer KIAA1598_exon9_R
source                  1..20
                        mol_type = other DNA
                        organism = synthetic construct
SEQUENCE: 440
agcagaaggt ggctttgtct                                              20

SEQ ID NO: 441          moltype = DNA  length = 19
FEATURE                 Location/Qualifiers
misc_feature            1..19
                        note = Reverse Primer TACC1_exon7_R
source                  1..19
                        mol_type = other DNA
                        organism = synthetic construct
SEQUENCE: 441
tccacaggac accgacaca                                               19

SEQ ID NO: 442          moltype = DNA  length = 20
FEATURE                 Location/Qualifiers
misc_feature            1..20
                        note = Reverse Primer TACC3_exon11R
source                  1..20
                        mol_type = other DNA
                        organism = synthetic construct
SEQUENCE: 442
ttcttcccgt ggagctcctc                                              20

SEQ ID NO: 443          moltype = DNA  length = 20
FEATURE                 Location/Qualifiers
misc_feature            1..20
                        note = Reverse Primer TACC3_exon10R
source                  1..20
                        mol_type = other DNA
                        organism = synthetic construct
SEQUENCE: 443
gagcaggtcc actataggtc                                              20

SEQ ID NO: 444          moltype = DNA  length = 20
FEATURE                 Location/Qualifiers
misc_feature            1..20
                        note = Reverse Primer TACC3_exon8R
source                  1..20
                        mol_type = other DNA
                        organism = synthetic construct
SEQUENCE: 444
```

```
tctaccagga ctgtccctca                                              20

SEQ ID NO: 445         moltype = DNA  length = 21
FEATURE                Location/Qualifiers
misc_feature           1..21
                       note = Reverse Primer TACC3_exon14R_rdsgn2
source                 1..21
                       mol_type = other DNA
                       organism = synthetic construct
SEQUENCE: 445
gggtgatcct tgccaggtaa t                                            21

SEQ ID NO: 446         moltype = DNA  length = 21
FEATURE                Location/Qualifiers
misc_feature           1..21
                       note = Reverse Primer TACC3_exon6R
source                 1..21
                       mol_type = other DNA
                       organism = synthetic construct
SEQUENCE: 446
tcactgcctg gacagcttgt g                                            21

SEQ ID NO: 447         moltype = DNA  length = 21
FEATURE                Location/Qualifiers
misc_feature           1..21
                       note = Reverse Primer YAP1_exon4_R
source                 1..21
                       mol_type = other DNA
                       organism = synthetic construct
SEQUENCE: 447
tcctgagtca tggcttgttc c                                            21

SEQ ID NO: 448         moltype = DNA  length = 21
FEATURE                Location/Qualifiers
misc_feature           1..21
                       note = Reverse Primer ABL1_E5_R_rdsgn
source                 1..21
                       mol_type = other DNA
                       organism = synthetic construct
SEQUENCE: 448
gcaccaggtt agggtgtttg a                                            21

SEQ ID NO: 449         moltype = DNA  length = 20
FEATURE                Location/Qualifiers
misc_feature           1..20
                       note = Reverse Primer AFF1_E4_R_redsgn
source                 1..20
                       mol_type = other DNA
                       organism = synthetic construct
SEQUENCE: 449
ccaggcgatg agtgtgagac                                              20

SEQ ID NO: 450         moltype = DNA  length = 23
FEATURE                Location/Qualifiers
misc_feature           1..23
                       note = Reverse Primer AFF1_E8_R
source                 1..23
                       mol_type = other DNA
                       organism = synthetic construct
SEQUENCE: 450
cgttccttgc tgagaatttg agt                                          23

SEQ ID NO: 451         moltype = DNA  length = 21
FEATURE                Location/Qualifiers
misc_feature           1..21
                       note = Reverse Primer CCAR2_exon4_R
source                 1..21
                       mol_type = other DNA
                       organism = synthetic construct
SEQUENCE: 451
agtcatgcaa gctggtaaca a                                            21

SEQ ID NO: 452         moltype = DNA  length = 28
FEATURE                Location/Qualifiers
misc_feature           1..28
                       note = Reverse Primer CCDC170_exon10_R
source                 1..28
                       mol_type = other DNA
                       organism = synthetic construct
```

```
SEQUENCE: 452
ggatttgttt agatcttcaa tggcttta                                   28

SEQ ID NO: 453         moltype = DNA  length = 27
FEATURE                Location/Qualifiers
misc_feature           1..27
                       note = Reverse Primer CCDC170_exon6_R
source                 1..27
                       mol_type = other DNA
                       organism = synthetic construct
SEQUENCE: 453
taacttccct ttcaagagct tcttttg                                    27

SEQ ID NO: 454         moltype = DNA  length = 22
FEATURE                Location/Qualifiers
misc_feature           1..22
                       note = Reverse Primer CCDC170_exon7_R
source                 1..22
                       mol_type = other DNA
                       organism = synthetic construct
SEQUENCE: 454
caactgttca acaagctcag at                                         22

SEQ ID NO: 455         moltype = DNA  length = 25
FEATURE                Location/Qualifiers
misc_feature           1..25
                       note = Reverse Primer CCDC170_exon8_R
source                 1..25
                       mol_type = other DNA
                       organism = synthetic construct
SEQUENCE: 455
gccatctggt ccaacttcat tttct                                      25

SEQ ID NO: 456         moltype = DNA  length = 27
FEATURE                Location/Qualifiers
misc_feature           1..27
                       note = Reverse Primer CCDC170_exon9_R
source                 1..27
                       mol_type = other DNA
                       organism = synthetic construct
SEQUENCE: 456
ggaggctcat gtgtaattct ttgctct                                    27

SEQ ID NO: 457         moltype = DNA  length = 21
FEATURE                Location/Qualifiers
misc_feature           1..21
                       note = Reverse Primer CIT_exon23_R
source                 1..21
                       mol_type = other DNA
                       organism = synthetic construct
SEQUENCE: 457
agctgttacg aagagcatca a                                          21

SEQ ID NO: 458         moltype = DNA  length = 19
FEATURE                Location/Qualifiers
misc_feature           1..19
                       note = Reverse Primer EGFR_exon17a_R
source                 1..19
                       mol_type = other DNA
                       organism = synthetic construct
SEQUENCE: 458
gtggcgatgg acgggatct                                             19

SEQ ID NO: 459         moltype = DNA  length = 19
FEATURE                Location/Qualifiers
misc_feature           1..19
                       note = Reverse Primer EGFR_exon17b_R
source                 1..19
                       mol_type = other DNA
                       organism = synthetic construct
SEQUENCE: 459
gcatgaagag gccgatccc                                             19

SEQ ID NO: 460         moltype = DNA  length = 21
FEATURE                Location/Qualifiers
misc_feature           1..21
                       note = Reverse Primer EGFR_exon8_R
source                 1..21
                       mol_type = other DNA
```

```
                        organism = synthetic construct
SEQUENCE: 460
tcctccatct catagctgtc g                                              21

SEQ ID NO: 461          moltype = DNA  length = 20
FEATURE                 Location/Qualifiers
misc_feature            1..20
                        note = Reverse Primer ERBB4_exon18_R
source                  1..20
                        mol_type = other DNA
                        organism = synthetic construct
SEQUENCE: 461
gagcttgatt gggtgctgtg                                                20

SEQ ID NO: 462          moltype = DNA  length = 21
FEATURE                 Location/Qualifiers
misc_feature            1..21
                        note = Reverse Primer ERG_exon6R
source                  1..21
                        mol_type = other DNA
                        organism = synthetic construct
SEQUENCE: 462
ttctttcacc gcccactcca g                                              21

SEQ ID NO: 463          moltype = DNA  length = 23
FEATURE                 Location/Qualifiers
misc_feature            1..23
                        note = Reverse Primer ERG_exon7R
source                  1..23
                        mol_type = other DNA
                        organism = synthetic construct
SEQUENCE: 463
ccgtggagag ttttgtaagg ctt                                            23

SEQ ID NO: 464          moltype = DNA  length = 21
FEATURE                 Location/Qualifiers
misc_feature            1..21
                        note = Reverse Primer ETV1_exon10R
source                  1..21
                        mol_type = other DNA
                        organism = synthetic construct
SEQUENCE: 464
atcctcgccg ttggtatgtg g                                              21

SEQ ID NO: 465          moltype = DNA  length = 20
FEATURE                 Location/Qualifiers
misc_feature            1..20
                        note = Reverse Primer ETV1_exon8R
source                  1..20
                        mol_type = other DNA
                        organism = synthetic construct
SEQUENCE: 465
tcgtcggcaa aggaggaaag                                                20

SEQ ID NO: 466          moltype = DNA  length = 21
FEATURE                 Location/Qualifiers
misc_feature            1..21
                        note = Reverse Primer ETV1_exon9R
source                  1..21
                        mol_type = other DNA
                        organism = synthetic construct
SEQUENCE: 466
ggacaacaca ggtgtcatca t                                              21

SEQ ID NO: 467          moltype = DNA  length = 19
FEATURE                 Location/Qualifiers
misc_feature            1..19
                        note = Reverse Primer FGFR1_exon7R
source                  1..19
                        mol_type = other DNA
                        organism = synthetic construct
SEQUENCE: 467
gccactgttt tgttggcgg                                                 19

SEQ ID NO: 468          moltype = DNA  length = 20
FEATURE                 Location/Qualifiers
misc_feature            1..20
                        note = Reverse Primer FLI1_exon3_R
source                  1..20
```

```
                        mol_type = other DNA
                        organism = synthetic construct
SEQUENCE: 468
agcttgctgc atttgctaac                                                20

SEQ ID NO: 469          moltype = DNA  length = 21
FEATURE                 Location/Qualifiers
misc_feature            1..21
                        note = Reverse Primer FLI1_exon4_R
source                  1..21
                        mol_type = other DNA
                        organism = synthetic construct
SEQUENCE: 469
ttatggccca ctccagccat t                                              21

SEQ ID NO: 470          moltype = DNA  length = 20
FEATURE                 Location/Qualifiers
misc_feature            1..20
                        note = Reverse Primer FLI1_exon5_R
source                  1..20
                        mol_type = other DNA
                        organism = synthetic construct
SEQUENCE: 470
atcgtgagga ttggtcggtg                                                20

SEQ ID NO: 471          moltype = DNA  length = 21
FEATURE                 Location/Qualifiers
misc_feature            1..21
                        note = Reverse Primer FLI1_exon6_R
source                  1..21
                        mol_type = other DNA
                        organism = synthetic construct
SEQUENCE: 471
gttattgccc caagctcctc t                                              21

SEQ ID NO: 472          moltype = DNA  length = 24
FEATURE                 Location/Qualifiers
misc_feature            1..24
                        note = Reverse Primer FLI1_exon7_R
source                  1..24
                        mol_type = other DNA
                        organism = synthetic construct
SEQUENCE: 472
tattcttact gatcgtttgt gccc                                           24

SEQ ID NO: 473          moltype = DNA  length = 18
FEATURE                 Location/Qualifiers
misc_feature            1..18
                        note = Reverse Primer FLI1_exon8_R
source                  1..18
                        mol_type = other DNA
                        organism = synthetic construct
SEQUENCE: 473
gttggctagg cgactgct                                                  18

SEQ ID NO: 474          moltype = DNA  length = 23
FEATURE                 Location/Qualifiers
misc_feature            1..23
                        note = Reverse Primer FLI1_exon9_R
source                  1..23
                        mol_type = other DNA
                        organism = synthetic construct
SEQUENCE: 474
gagagcagct ccaggaggaa ttg                                            23

SEQ ID NO: 475          moltype = DNA  length = 21
FEATURE                 Location/Qualifiers
misc_feature            1..21
                        note = Reverse Primer FOXO1_exon2_R
source                  1..21
                        mol_type = other DNA
                        organism = synthetic construct
SEQUENCE: 475
tctgcacacg aatgaacttg c                                              21

SEQ ID NO: 476          moltype = DNA  length = 23
FEATURE                 Location/Qualifiers
misc_feature            1..23
                        note = Reverse Primer GPHN_exon11_R
```

```
source                  1..23
                        mol_type = other DNA
                        organism = synthetic construct
SEQUENCE: 476
gacatgcgat gtcttctagc cac                                            23

SEQ ID NO: 477          moltype = DNA  length = 25
FEATURE                 Location/Qualifiers
misc_feature            1..25
                        note = Reverse Primer MBIP_exon4_R
source                  1..25
                        mol_type = other DNA
                        organism = synthetic construct
SEQUENCE: 477
cattgatttc agcttgcttt ctttc                                          25

SEQ ID NO: 478          moltype = DNA  length = 20
FEATURE                 Location/Qualifiers
misc_feature            1..20
                        note = Reverse Primer MLLT3_E6_R_redsgn
source                  1..20
                        mol_type = other DNA
                        organism = synthetic construct
SEQUENCE: 478
tggtctggga tggtgtgaag                                                20

SEQ ID NO: 479          moltype = DNA  length = 27
FEATURE                 Location/Qualifiers
misc_feature            1..27
                        note = Reverse Primer MX1_exon12_R
source                  1..27
                        mol_type = other DNA
                        organism = synthetic construct
SEQUENCE: 479
ccacgatact gattttcaaa tttctgg                                        27

SEQ ID NO: 480          moltype = DNA  length = 21
FEATURE                 Location/Qualifiers
misc_feature            1..21
                        note = Reverse Primer MX1_exon9_R
source                  1..21
                        mol_type = other DNA
                        organism = synthetic construct
SEQUENCE: 480
aagtttttct gccaggcagg g                                              21

SEQ ID NO: 481          moltype = DNA  length = 20
FEATURE                 Location/Qualifiers
misc_feature            1..20
                        note = Reverse Primer MYH11_E31_R_rdsgn
source                  1..20
                        mol_type = other DNA
                        organism = synthetic construct
SEQUENCE: 481
ctcttccaga gcttccacgg                                                20

SEQ ID NO: 482          moltype = DNA  length = 24
FEATURE                 Location/Qualifiers
misc_feature            1..24
                        note = Reverse Primer NCOA3_exon14_R
source                  1..24
                        mol_type = other DNA
                        organism = synthetic construct
SEQUENCE: 482
ctgctcggtt atatggagga cgaa                                           24

SEQ ID NO: 483          moltype = DNA  length = 22
FEATURE                 Location/Qualifiers
misc_feature            1..22
                        note = Reverse Primer NCOA3_exon15_R
source                  1..22
                        mol_type = other DNA
                        organism = synthetic construct
SEQUENCE: 483
taagccccag tctcctgagg aa                                             22

SEQ ID NO: 484          moltype = DNA  length = 20
FEATURE                 Location/Qualifiers
misc_feature            1..20
```

```
                        note = Reverse Primer NFIB_exon10_R
source                  1..20
                        mol_type = other DNA
                        organism = synthetic construct
SEQUENCE: 484
gggcttagtc ccacatatcg                                              20

SEQ ID NO: 485          moltype = DNA  length = 20
FEATURE                 Location/Qualifiers
misc_feature            1..20
                        note = Reverse Primer NFIB_exon11_R
source                  1..20
                        mol_type = other DNA
                        organism = synthetic construct
SEQUENCE: 485
ggggtataaa tgcctgccgt                                              20

SEQ ID NO: 486          moltype = DNA  length = 26
FEATURE                 Location/Qualifiers
misc_feature            1..26
                        note = Reverse Primer NFIB_exon12_R
source                  1..26
                        mol_type = other DNA
                        organism = synthetic construct
SEQUENCE: 486
agatgggtgt cctatttgac acttgg                                       26

SEQ ID NO: 487          moltype = DNA  length = 20
FEATURE                 Location/Qualifiers
misc_feature            1..20
                        note = Reverse Primer NFIB_exon9_R
source                  1..20
                        mol_type = other DNA
                        organism = synthetic construct
SEQUENCE: 487
gccaggcact ttccctacta                                              20

SEQ ID NO: 488          moltype = DNA  length = 22
FEATURE                 Location/Qualifiers
misc_feature            1..22
                        note = Reverse Primer NTRK2_exon14R
source                  1..22
                        mol_type = other DNA
                        organism = synthetic construct
SEQUENCE: 488
aaaggcaaaa tcccaccaca ga                                           22

SEQ ID NO: 489          moltype = DNA  length = 28
FEATURE                 Location/Qualifiers
misc_feature            1..28
                        note = Reverse Primer NTRK2_exon15R
source                  1..28
                        mol_type = other DNA
                        organism = synthetic construct
SEQUENCE: 489
caacaccttg tcttgatttt actttccc                                     28

SEQ ID NO: 490          moltype = DNA  length = 20
FEATURE                 Location/Qualifiers
misc_feature            1..20
                        note = Reverse Primer NTRK2_exon17_R
source                  1..20
                        mol_type = other DNA
                        organism = synthetic construct
SEQUENCE: 490
ttcgcctagc tccctttca                                               20

SEQ ID NO: 491          moltype = DNA  length = 21
FEATURE                 Location/Qualifiers
misc_feature            1..21
                        note = Reverse Primer NTRK3_exon13R
source                  1..21
                        mol_type = other DNA
                        organism = synthetic construct
SEQUENCE: 491
agaaccacca acaggacaca g                                            21

SEQ ID NO: 492          moltype = DNA  length = 21
FEATURE                 Location/Qualifiers
```

```
misc_feature         1..21
                     note = Reverse Primer PDGFRA_exon2_R
source               1..21
                     mol_type = other DNA
                     organism = synthetic construct
SEQUENCE: 492
acagcctaag accaggaacg c                                         21

SEQ ID NO: 493       moltype = DNA  length = 27
FEATURE              Location/Qualifiers
misc_feature         1..27
                     note = Reverse Primer PPARG_exon7_R
source               1..27
                     mol_type = other DNA
                     organism = synthetic construct
SEQUENCE: 493
aggttgtctt gaatgtcttc aatgggc                                   27

SEQ ID NO: 494       moltype = DNA  length = 22
FEATURE              Location/Qualifiers
misc_feature         1..22
                     note = Reverse Primer RET_exon10_R
source               1..22
                     mol_type = other DNA
                     organism = synthetic construct
SEQUENCE: 494
gtgccatagc cagctttaat cc                                        22

SEQ ID NO: 495       moltype = DNA  length = 19
FEATURE              Location/Qualifiers
misc_feature         1..19
                     note = Reverse Primer RET_exon9_R
source               1..19
                     mol_type = other DNA
                     organism = synthetic construct
SEQUENCE: 495
caggtcttgg tgctgggag                                            19

SEQ ID NO: 496       moltype = DNA  length = 28
FEATURE              Location/Qualifiers
misc_feature         1..28
                     note = Reverse Primer ROS1_exon32_R_rdsgn
source               1..28
                     mol_type = other DNA
                     organism = synthetic construct
SEQUENCE: 496
gaatttttac tcccttctag taatttgg                                  28

SEQ ID NO: 497       moltype = DNA  length = 22
FEATURE              Location/Qualifiers
misc_feature         1..22
                     note = Reverse Primer ROS1_exon33R
source               1..22
                     mol_type = other DNA
                     organism = synthetic construct
SEQUENCE: 497
ttccatgtgc aaacactact gc                                        22

SEQ ID NO: 498       moltype = DNA  length = 23
FEATURE              Location/Qualifiers
misc_feature         1..23
                     note = Reverse Primer SEPT14_exon10_R
source               1..23
                     mol_type = other DNA
                     organism = synthetic construct
SEQUENCE: 498
gcttccttat ctcctcctgt tga                                       23

SEQ ID NO: 499       moltype = DNA  length = 21
FEATURE              Location/Qualifiers
misc_feature         1..21
                     note = Reverse Primer SSX1_exon4_R
source               1..21
                     mol_type = other DNA
                     organism = synthetic construct
SEQUENCE: 499
ctggaagtct gtggcctgtt t                                         21

SEQ ID NO: 500       moltype = DNA  length = 20
```

```
FEATURE                 Location/Qualifiers
misc_feature            1..20
                        note = Reverse Primer SSX1_exon5_R
source                  1..20
                        mol_type = other DNA
                        organism = synthetic construct
SEQUENCE: 500
gggatgattc tgtggagcct                                              20

SEQ ID NO: 501          moltype = DNA  length = 20
FEATURE                 Location/Qualifiers
misc_feature            1..20
                        note = Reverse Primer SSX1_exon6_R
source                  1..20
                        mol_type = other DNA
                        organism = synthetic construct
SEQUENCE: 501
tgcttctgac actcccttcg                                              20

SEQ ID NO: 502          moltype = DNA  length = 27
FEATURE                 Location/Qualifiers
misc_feature            1..27
                        note = Reverse Primer SSX2_exon3_R
source                  1..27
                        mol_type = other DNA
                        organism = synthetic construct
SEQUENCE: 502
tcatcttttc ccactcttcc ttagaga                                      27

SEQ ID NO: 503          moltype = DNA  length = 22
FEATURE                 Location/Qualifiers
misc_feature            1..22
                        note = Reverse Primer SSX2_exon4_R
source                  1..22
                        mol_type = other DNA
                        organism = synthetic construct
SEQUENCE: 503
agtcttcggc ccgtttatta ca                                           22

SEQ ID NO: 504          moltype = DNA  length = 21
FEATURE                 Location/Qualifiers
misc_feature            1..21
                        note = Reverse Primer SSX2_exon5_R
source                  1..21
                        mol_type = other DNA
                        organism = synthetic construct
SEQUENCE: 504
cttcggggag attccctgga g                                            21

SEQ ID NO: 505          moltype = DNA  length = 20
FEATURE                 Location/Qualifiers
misc_feature            1..20
                        note = Reverse Primer SSX2_exon6_R
source                  1..20
                        mol_type = other DNA
                        organism = synthetic construct
SEQUENCE: 505
ctggcacttc ctccgaatca                                              20

SEQ ID NO: 506          moltype = DNA  length = 21
FEATURE                 Location/Qualifiers
misc_feature            1..21
                        note = Reverse Primer TACC3_exon13a_R
source                  1..21
                        mol_type = other DNA
                        organism = synthetic construct
SEQUENCE: 506
ccttctgctt ctgaacttcc t                                            21

SEQ ID NO: 507          moltype = DNA  length = 30
FEATURE                 Location/Qualifiers
misc_feature            1..30
                        note = Reverse Primer TACC3_exon13b_R
source                  1..30
                        mol_type = other DNA
                        organism = synthetic construct
SEQUENCE: 507
ttggtctttt tcttttagaa ctttctggat                                   30
```

```
SEQ ID NO: 508          moltype = DNA  length = 18
FEATURE                 Location/Qualifiers
misc_feature            1..18
                        note = Reverse Primer TACC3_exon5_R
source                  1..18
                        mol_type = other DNA
                        organism = synthetic construct
SEQUENCE: 508
tgccaactgc accacagg                                                18

SEQ ID NO: 509          moltype = DNA  length = 25
FEATURE                 Location/Qualifiers
misc_feature            1..25
                        note = Reverse Primer TACC3_exon7R
source                  1..25
                        mol_type = other DNA
                        organism = synthetic construct
SEQUENCE: 509
aggaagttcc aaactgctcc aggta                                        25

SEQ ID NO: 510          moltype = DNA  length = 21
FEATURE                 Location/Qualifiers
misc_feature            1..21
                        note = Reverse Primer TACC3_exon9R
source                  1..21
                        mol_type = other DNA
                        organism = synthetic construct
SEQUENCE: 510
aagaaatcga actccacaag c                                            21

SEQ ID NO: 511          moltype = DNA  length = 21
FEATURE                 Location/Qualifiers
misc_feature            1..21
                        note = Reverse Primer TACC3_midExon4_R
source                  1..21
                        mol_type = other DNA
                        organism = synthetic construct
SEQUENCE: 511
tctccgcttt gcattcttcc t                                            21

SEQ ID NO: 512          moltype = DNA  length = 20
FEATURE                 Location/Qualifiers
misc_feature            1..20
                        note = Reverse Primer YAP1_exon5_R
source                  1..20
                        mol_type = other DNA
                        organism = synthetic construct
SEQUENCE: 512
gtggctgttt cactggagca                                              20

SEQ ID NO: 513          moltype = DNA  length = 23
FEATURE                 Location/Qualifiers
misc_feature            1..23
                        note = Forward Primer TBP_F_rdsgn
source                  1..23
                        mol_type = other DNA
                        organism = synthetic construct
SEQUENCE: 513
ctttgcagtg acccagcatc act                                          23

SEQ ID NO: 514          moltype = DNA  length = 20
FEATURE                 Location/Qualifiers
misc_feature            1..20
                        note = Forward Primer ITGB7-F
source                  1..20
                        mol_type = other DNA
                        organism = synthetic construct
SEQUENCE: 514
gcacgcacct atgtggaaac                                              20

SEQ ID NO: 515          moltype = DNA  length = 22
FEATURE                 Location/Qualifiers
misc_feature            1..22
                        note = Forward Primer PSMB2_F_rdsgn
source                  1..22
                        mol_type = other DNA
                        organism = synthetic construct
SEQUENCE: 515
tcttcggagt cggaccccat at                                           22
```

```
SEQ ID NO: 516          moltype = DNA  length = 22
FEATURE                 Location/Qualifiers
misc_feature            1..22
                        note = Forward Primer EMC7_A_F
source                  1..22
                        mol_type = other DNA
                        organism = synthetic construct
SEQUENCE: 516
tcggtttcct taagacagat gg                                          22

SEQ ID NO: 517          moltype = DNA  length = 25
FEATURE                 Location/Qualifiers
misc_feature            1..25
                        note = Forward Primer EMC7_B_F_rdsgn
source                  1..25
                        mol_type = other DNA
                        organism = synthetic construct
SEQUENCE: 517
actttctaat gaacccaatg gttat                                       25

SEQ ID NO: 518          moltype = DNA  length = 20
FEATURE                 Location/Qualifiers
misc_feature            1..20
                        note = Forward Primer GPI_F
source                  1..20
                        mol_type = other DNA
                        organism = synthetic construct
SEQUENCE: 518
gcatcacaag atcctcctgg                                             20

SEQ ID NO: 519          moltype = DNA  length = 23
FEATURE                 Location/Qualifiers
misc_feature            1..23
                        note = Forward Primer REEP5_F
source                  1..23
                        mol_type = other DNA
                        organism = synthetic construct
SEQUENCE: 519
ccagcctaca tctcaattaa agc                                         23

SEQ ID NO: 520          moltype = DNA  length = 18
FEATURE                 Location/Qualifiers
misc_feature            1..18
                        note = Forward Primer RRP1_F_rdsgn
source                  1..18
                        mol_type = other DNA
                        organism = synthetic construct
SEQUENCE: 520
cgggccgcag gtggtttt                                               18

SEQ ID NO: 521          moltype = DNA  length = 23
FEATURE                 Location/Qualifiers
misc_feature            1..23
                        note = Forward Primer CHFR_F
source                  1..23
                        mol_type = other DNA
                        organism = synthetic construct
SEQUENCE: 521
agtattgtga ttacagggtc tgg                                         23

SEQ ID NO: 522          moltype = DNA  length = 24
FEATURE                 Location/Qualifiers
misc_feature            1..24
                        note = Forward Primer REL_F
source                  1..24
                        mol_type = other DNA
                        organism = synthetic construct
SEQUENCE: 522
gaatcaatcc attcaatgtc cctg                                        24

SEQ ID NO: 523          moltype = DNA  length = 27
FEATURE                 Location/Qualifiers
misc_feature            1..27
                        note = Forward Primer NASP_F_rdsgn
source                  1..27
                        mol_type = other DNA
                        organism = synthetic construct
SEQUENCE: 523
```

```
caggaagcag ctagtctttt aggtaag                                         27

SEQ ID NO: 524          moltype = DNA  length = 23
FEATURE                 Location/Qualifiers
misc_feature            1..23
                        note = Forward Primer POMK_F_rdsgn_2
source                  1..23
                        mol_type = other DNA
                        organism = synthetic construct
SEQUENCE: 524
gaaggagctg taaagagagt ctt                                             23

SEQ ID NO: 525          moltype = DNA  length = 22
FEATURE                 Location/Qualifiers
misc_feature            1..22
                        note = Forward Primer FRMD8_F
source                  1..22
                        mol_type = other DNA
                        organism = synthetic construct
SEQUENCE: 525
gatagcagag agaagcatgt cc                                              22

SEQ ID NO: 526          moltype = DNA  length = 19
FEATURE                 Location/Qualifiers
misc_feature            1..19
                        note = Forward Primer SLC4A1AP_A_F_rdsgn
source                  1..19
                        mol_type = other DNA
                        organism = synthetic construct
SEQUENCE: 526
tcggcaggaa gcagtatct                                                  19

SEQ ID NO: 527          moltype = DNA  length = 22
FEATURE                 Location/Qualifiers
misc_feature            1..22
                        note = Forward Primer SNAP29_F
source                  1..22
                        mol_type = other DNA
                        organism = synthetic construct
SEQUENCE: 527
gatcgacagc aacctagatg ag                                              22

SEQ ID NO: 528          moltype = DNA  length = 28
FEATURE                 Location/Qualifiers
misc_feature            1..28
                        note = Forward Primer TUBGCP2_A_F_rdsgn
source                  1..28
                        mol_type = other DNA
                        organism = synthetic construct
SEQUENCE: 528
catccacgac ccatacagtg agtttatg                                        28

SEQ ID NO: 529          moltype = DNA  length = 26
FEATURE                 Location/Qualifiers
misc_feature            1..26
                        note = Forward Primer SNRPD3_F_rdsgn
source                  1..26
                        mol_type = other DNA
                        organism = synthetic construct
SEQUENCE: 529
gacaacatga actgccagat gtccaa                                          26

SEQ ID NO: 530          moltype = DNA  length = 25
FEATURE                 Location/Qualifiers
misc_feature            1..25
                        note = Forward Primer PUM1_F
source                  1..25
                        mol_type = other DNA
                        organism = synthetic construct
SEQUENCE: 530
tcagaccagc aggtaattaa tgaga                                           25

SEQ ID NO: 531          moltype = DNA  length = 24
FEATURE                 Location/Qualifiers
misc_feature            1..24
                        note = Forward Primer CIAO1_F
source                  1..24
                        mol_type = other DNA
                        organism = synthetic construct
```

```
SEQUENCE: 531
cgtttgggtc tgggaagttg atga                                    24

SEQ ID NO: 532          moltype = DNA  length = 21
FEATURE                 Location/Qualifiers
misc_feature            1..21
                        note = Forward Primer SRSF4_F
source                  1..21
                        mol_type = other DNA
                        organism = synthetic construct
SEQUENCE: 532
tggaactgaa gtcaatggga g                                       21

SEQ ID NO: 533          moltype = DNA  length = 20
FEATURE                 Location/Qualifiers
misc_feature            1..20
                        note = Forward Primer VCP_E1-2_F_new
source                  1..20
                        mol_type = other DNA
                        organism = synthetic construct
SEQUENCE: 533
gcttctggag ccgattcaaa                                         20

SEQ ID NO: 534          moltype = DNA  length = 20
FEATURE                 Location/Qualifiers
misc_feature            1..20
                        note = Forward Primer RER1_E3_F_new
source                  1..20
                        mol_type = other DNA
                        organism = synthetic construct
SEQUENCE: 534
ggctagacaa gtccacaccc                                         20

SEQ ID NO: 535          moltype = DNA  length = 20
FEATURE                 Location/Qualifiers
misc_feature            1..20
                        note = Forward Primer CHMP2A_E2-3_F
source                  1..20
                        mol_type = other DNA
                        organism = synthetic construct
SEQUENCE: 535
aagcaaggcc agatggatgc                                         20

SEQ ID NO: 536          moltype = DNA  length = 20
FEATURE                 Location/Qualifiers
misc_feature            1..20
                        note = Forward Primer RAB7A_E1_F
source                  1..20
                        mol_type = other DNA
                        organism = synthetic construct
SEQUENCE: 536
gtttagtctc ctcctcggcg                                         20

SEQ ID NO: 537          moltype = DNA  length = 15
FEATURE                 Location/Qualifiers
misc_feature            1..15
                        note = Forward Primer ACTB_F
source                  1..15
                        mol_type = other DNA
                        organism = synthetic construct
SEQUENCE: 537
gagaccgcgt ccgcc                                              15

SEQ ID NO: 538          moltype = DNA  length = 20
FEATURE                 Location/Qualifiers
misc_feature            1..20
                        note = Reverse Primer TBP-R
source                  1..20
                        mol_type = other DNA
                        organism = synthetic construct
SEQUENCE: 538
gcatctccag cacactcttc                                         20

SEQ ID NO: 539          moltype = DNA  length = 22
FEATURE                 Location/Qualifiers
misc_feature            1..22
                        note = Reverse Primer ITGB7-R
source                  1..22
                        mol_type = other DNA
```

```
                        organism = synthetic construct
SEQUENCE: 539
agccaaacag gaaacagacc ag                                    22

SEQ ID NO: 540          moltype = DNA  length = 22
FEATURE                 Location/Qualifiers
misc_feature            1..22
                        note = Reverse Primer PSMB2-R
source                  1..22
                        mol_type = other DNA
                        organism = synthetic construct
SEQUENCE: 540
aggtagtcca tgtaatacag cg                                    22

SEQ ID NO: 541          moltype = DNA  length = 22
FEATURE                 Location/Qualifiers
misc_feature            1..22
                        note = Reverse Primer EMC7_A-R
source                  1..22
                        mol_type = other DNA
                        organism = synthetic construct
SEQUENCE: 541
acgggatcaa atctgtaagc tg                                    22

SEQ ID NO: 542          moltype = DNA  length = 22
FEATURE                 Location/Qualifiers
misc_feature            1..22
                        note = Reverse Primer EMC7_B-R
source                  1..22
                        mol_type = other DNA
                        organism = synthetic construct
SEQUENCE: 542
gtctcatgtc aggatcactt gt                                    22

SEQ ID NO: 543          moltype = DNA  length = 20
FEATURE                 Location/Qualifiers
misc_feature            1..20
                        note = Reverse Primer GPI-R
source                  1..20
                        mol_type = other DNA
                        organism = synthetic construct
SEQUENCE: 543
aaggtcctct ggactcttgc                                       20

SEQ ID NO: 544          moltype = DNA  length = 25
FEATURE                 Location/Qualifiers
misc_feature            1..25
                        note = Reverse Primer REEP5-R
source                  1..25
                        mol_type = other DNA
                        organism = synthetic construct
SEQUENCE: 544
ccatgacagg aagatatcag agaag                                 25

SEQ ID NO: 545          moltype = DNA  length = 18
FEATURE                 Location/Qualifiers
misc_feature            1..18
                        note = Reverse Primer RRP1_R
source                  1..18
                        mol_type = other DNA
                        organism = synthetic construct
SEQUENCE: 545
ctggaggagt ggcttgtc                                         18

SEQ ID NO: 546          moltype = DNA  length = 20
FEATURE                 Location/Qualifiers
misc_feature            1..20
                        note = Reverse Primer CHFR-R
source                  1..20
                        mol_type = other DNA
                        organism = synthetic construct
SEQUENCE: 546
ctttctgtct gggagagctg                                       20

SEQ ID NO: 547          moltype = DNA  length = 25
FEATURE                 Location/Qualifiers
misc_feature            1..25
                        note = Reverse Primer REL-R
source                  1..25
```

```
                         mol_type = other DNA
                         organism = synthetic construct
SEQUENCE: 547
catgttcatc agggagaaaa acttg                                            25

SEQ ID NO: 548           moltype = DNA  length = 20
FEATURE                  Location/Qualifiers
misc_feature             1..20
                         note = Reverse Primer NASP-R
source                   1..20
                         mol_type = other DNA
                         organism = synthetic construct
SEQUENCE: 548
cttgccaact ccagaagtga                                                  20

SEQ ID NO: 549           moltype = DNA  length = 22
FEATURE                  Location/Qualifiers
misc_feature             1..22
                         note = Reverse Primer POMK-R
source                   1..22
                         mol_type = other DNA
                         organism = synthetic construct
SEQUENCE: 549
ccttggagag atttcagcat ct                                               22

SEQ ID NO: 550           moltype = DNA  length = 19
FEATURE                  Location/Qualifiers
misc_feature             1..19
                         note = Reverse Primer FRMD8-R
source                   1..19
                         mol_type = other DNA
                         organism = synthetic construct
SEQUENCE: 550
gaactccagc cacaagatg                                                   19

SEQ ID NO: 551           moltype = DNA  length = 22
FEATURE                  Location/Qualifiers
misc_feature             1..22
                         note = Reverse Primer SLC4A1AP_A-R
source                   1..22
                         mol_type = other DNA
                         organism = synthetic construct
SEQUENCE: 551
tcagacgctt cttctcaatc ag                                               22

SEQ ID NO: 552           moltype = DNA  length = 24
FEATURE                  Location/Qualifiers
misc_feature             1..24
                         note = Reverse Primer SNAP29-R
source                   1..24
                         mol_type = other DNA
                         organism = synthetic construct
SEQUENCE: 552
tgtcatcttg ctcctcaatt tctg                                             24

SEQ ID NO: 553           moltype = DNA  length = 22
FEATURE                  Location/Qualifiers
misc_feature             1..22
                         note = Reverse Primer TUBGCP2_A-R
source                   1..22
                         mol_type = other DNA
                         organism = synthetic construct
SEQUENCE: 553
acttgtcgtt gtaatcctcc tg                                               22

SEQ ID NO: 554           moltype = DNA  length = 19
FEATURE                  Location/Qualifiers
misc_feature             1..19
                         note = Reverse Primer SNRPD3-R
source                   1..19
                         mol_type = other DNA
                         organism = synthetic construct
SEQUENCE: 554
gattttgctg ccacggatg                                                   19

SEQ ID NO: 555           moltype = DNA  length = 20
FEATURE                  Location/Qualifiers
misc_feature             1..20
                         note = Reverse Primer PUM1_R
```

```
source                  1..20
                        mol_type = other DNA
                        organism = synthetic construct
SEQUENCE: 555
accacgtgat tgccattctg                                              20

SEQ ID NO: 556          moltype = DNA  length = 20
FEATURE                 Location/Qualifiers
misc_feature            1..20
                        note = Reverse Primer CIAO1_R
source                  1..20
                        mol_type = other DNA
                        organism = synthetic construct
SEQUENCE: 556
gccaaaccac atgcttgaca                                              20

SEQ ID NO: 557          moltype = DNA  length = 22
FEATURE                 Location/Qualifiers
misc_feature            1..22
                        note = Reverse Primer SRSF4_R
source                  1..22
                        mol_type = other DNA
                        organism = synthetic construct
SEQUENCE: 557
cttcgagagc gagaccttga at                                           22

SEQ ID NO: 558          moltype = DNA  length = 21
FEATURE                 Location/Qualifiers
misc_feature            1..21
                        note = Reverse Primer VCP_E2_R_new
source                  1..21
                        mol_type = other DNA
                        organism = synthetic construct
SEQUENCE: 558
acaattaacc gattgggacg g                                            21

SEQ ID NO: 559          moltype = DNA  length = 21
FEATURE                 Location/Qualifiers
misc_feature            1..21
                        note = Reverse Primer RER1_E3-4_R_new
source                  1..21
                        mol_type = other DNA
                        organism = synthetic construct
SEQUENCE: 559
gtcacaatgt accaaccctg c                                            21

SEQ ID NO: 560          moltype = DNA  length = 20
FEATURE                 Location/Qualifiers
misc_feature            1..20
                        note = Reverse Primer CHMP2A_E3_R
source                  1..20
                        mol_type = other DNA
                        organism = synthetic construct
SEQUENCE: 560
ttgagggaca cagcctggat                                              20

SEQ ID NO: 561          moltype = DNA  length = 20
FEATURE                 Location/Qualifiers
misc_feature            1..20
                        note = Reverse Primer RAB7A_E1-2_R
source                  1..20
                        mol_type = other DNA
                        organism = synthetic construct
SEQUENCE: 561
aggtcatcct tcaaacgcgg                                              20

SEQ ID NO: 562          moltype = DNA  length = 20
FEATURE                 Location/Qualifiers
misc_feature            1..20
                        note = Reverse Primer ACTB_R
source                  1..20
                        mol_type = other DNA
                        organism = synthetic construct
SEQUENCE: 562
atcatccatg gtgagctggc                                              20

SEQ ID NO: 563          moltype = DNA  length = 26
FEATURE                 Location/Qualifiers
misc_feature            1..26
```

```
                        note = Forward Primer CD274_3UTR_F
source                  1..26
                        mol_type = other DNA
                        organism = synthetic construct
SEQUENCE: 563
caaagaagca aagtgataca catttg                                        26

SEQ ID NO: 564          moltype = DNA  length = 24
FEATURE                 Location/Qualifiers
misc_feature            1..24
                        note = Forward Primer CD274_EXON4_F
source                  1..24
                        mol_type = other DNA
                        organism = synthetic construct
SEQUENCE: 564
gtgaaagtca atgccccata caac                                          24

SEQ ID NO: 565          moltype = DNA  length = 24
FEATURE                 Location/Qualifiers
misc_feature            1..24
                        note = Forward Primer CD274_EXON3_F
source                  1..24
                        mol_type = other DNA
                        organism = synthetic construct
SEQUENCE: 565
ggcatttgct gaacgcattt actg                                          24

SEQ ID NO: 566          moltype = DNA  length = 20
FEATURE                 Location/Qualifiers
misc_feature            1..20
                        note = Forward Primer PDCD1-EXON3_4_5_F
source                  1..20
                        mol_type = other DNA
                        organism = synthetic construct
SEQUENCE: 566
ccgcacgagg gacaatagga                                               20

SEQ ID NO: 567          moltype = DNA  length = 23
FEATURE                 Location/Qualifiers
misc_feature            1..23
                        note = Forward Primer CTLA4-EXON1_2_F
source                  1..23
                        mol_type = other DNA
                        organism = synthetic construct
SEQUENCE: 567
cttctcttca tccctgtctt ctg                                           23

SEQ ID NO: 568          moltype = DNA  length = 28
FEATURE                 Location/Qualifiers
misc_feature            1..28
                        note = Forward Primer CTLA4-EXON4_F
source                  1..28
                        mol_type = other DNA
                        organism = synthetic construct
SEQUENCE: 568
gctgtttctt tgagcaaaat gctaaaga                                      28

SEQ ID NO: 569          moltype = DNA  length = 22
FEATURE                 Location/Qualifiers
misc_feature            1..22
                        note = Forward Primer CD47-EXON3_F
source                  1..22
                        mol_type = other DNA
                        organism = synthetic construct
SEQUENCE: 569
gaaggtgaaa cgatcatcga gc                                            22

SEQ ID NO: 570          moltype = DNA  length = 25
FEATURE                 Location/Qualifiers
misc_feature            1..25
                        note = Forward Primer CD47-EXON9_10_11_F
source                  1..25
                        mol_type = other DNA
                        organism = synthetic construct
SEQUENCE: 570
gaggaacccc ttaatgcatt caaag                                         25

SEQ ID NO: 571          moltype = DNA  length = 22
FEATURE                 Location/Qualifiers
```

```
misc_feature           1..22
                       note = Forward Primer LAG3-EXON8_F
source                 1..22
                       mol_type = other DNA
                       organism = synthetic construct
SEQUENCE: 571
ctttggagaa gacagtggcg ac                                          22

SEQ ID NO: 572         moltype = DNA  length = 20
FEATURE                Location/Qualifiers
misc_feature           1..20
                       note = Forward Primer LAG3_EXON2-F_rdsgn
source                 1..20
                       mol_type = other DNA
                       organism = synthetic construct
SEQUENCE: 572
tttgggtggc tccagtgaag                                             20

SEQ ID NO: 573         moltype = DNA  length = 23
FEATURE                Location/Qualifiers
misc_feature           1..23
                       note = Forward Primer HAVCR2_EXON3-F_rdsgn
source                 1..23
                       mol_type = other DNA
                       organism = synthetic construct
SEQUENCE: 573
agttggtcat caaaccagcc aag                                         23

SEQ ID NO: 574         moltype = DNA  length = 30
FEATURE                Location/Qualifiers
misc_feature           1..30
                       note = Forward Primer HAVCR2_EXON7-F_rdsgn
source                 1..30
                       mol_type = other DNA
                       organism = synthetic construct
SEQUENCE: 574
caaagagaag atacagaatt taagcctcat                                  30

SEQ ID NO: 575         moltype = DNA  length = 22
FEATURE                Location/Qualifiers
misc_feature           1..22
                       note = Forward Primer PDCD1_EXON2-F_rdsgn
source                 1..22
                       mol_type = other DNA
                       organism = synthetic construct
SEQUENCE: 575
gccaggatgg ttcttagact cc                                          22

SEQ ID NO: 576         moltype = DNA  length = 22
FEATURE                Location/Qualifiers
misc_feature           1..22
                       note = Forward Primer CD14_exon1_1F
source                 1..22
                       mol_type = other DNA
                       organism = synthetic construct
SEQUENCE: 576
gaagacttat cgaccatgga gc                                          22

SEQ ID NO: 577         moltype = DNA  length = 20
FEATURE                Location/Qualifiers
misc_feature           1..20
                       note = Forward Primer CD27_exon1-2_1F
source                 1..20
                       mol_type = other DNA
                       organism = synthetic construct
SEQUENCE: 577
cagatgtgtg agccaggaac                                             20

SEQ ID NO: 578         moltype = DNA  length = 22
FEATURE                Location/Qualifiers
misc_feature           1..22
                       note = Forward Primer CD39_exon1_1F
source                 1..22
                       mol_type = other DNA
                       organism = synthetic construct
SEQUENCE: 578
cttgagaaag gattgctggt ca                                          22

SEQ ID NO: 579         moltype = DNA  length = 21
```

```
FEATURE                 Location/Qualifiers
misc_feature            1..21
                        note = Forward Primer CD40_exon6-7_1F
source                  1..21
                        mol_type = other DNA
                        organism = synthetic construct
SEQUENCE: 579
gactgatgtt gtctgtggtc c                                             21

SEQ ID NO: 580          moltype = DNA  length = 19
FEATURE                 Location/Qualifiers
misc_feature            1..19
                        note = Forward Primer CD70_exon1_2F
source                  1..19
                        mol_type = other DNA
                        organism = synthetic construct
SEQUENCE: 580
cttggtgatc tgcctcgtg                                                19

SEQ ID NO: 581          moltype = DNA  length = 22
FEATURE                 Location/Qualifiers
misc_feature            1..22
                        note = Forward Primer CD80_exon1_1F
source                  1..22
                        mol_type = other DNA
                        organism = synthetic construct
SEQUENCE: 581
tctcagaagt ggagtcttac cc                                            22

SEQ ID NO: 582          moltype = DNA  length = 21
FEATURE                 Location/Qualifiers
misc_feature            1..21
                        note = Forward Primer FOXP3_exon6-7_1F
source                  1..21
                        mol_type = other DNA
                        organism = synthetic construct
SEQUENCE: 582
agaggacttc ctcaagcact g                                             21

SEQ ID NO: 583          moltype = DNA  length = 20
FEATURE                 Location/Qualifiers
misc_feature            1..20
                        note = Forward Primer ICOS_exon3_1F
source                  1..20
                        mol_type = other DNA
                        organism = synthetic construct
SEQUENCE: 583
tgtgcagcct ttgttgtagt                                               20

SEQ ID NO: 584          moltype = DNA  length = 22
FEATURE                 Location/Qualifiers
misc_feature            1..22
                        note = Forward Primer ICOS_exon1-2_2F
source                  1..22
                        mol_type = other DNA
                        organism = synthetic construct
SEQUENCE: 584
gcattaaagt tttaacagga ga                                            22

SEQ ID NO: 585          moltype = DNA  length = 20
FEATURE                 Location/Qualifiers
misc_feature            1..20
                        note = Forward Primer TIGIT_exon3_1F
source                  1..20
                        mol_type = other DNA
                        organism = synthetic construct
SEQUENCE: 585
agattccatt gcttggagcc                                               20

SEQ ID NO: 586          moltype = DNA  length = 22
FEATURE                 Location/Qualifiers
misc_feature            1..22
                        note = Forward Primer TNFRSF18_exon2-3_1F
source                  1..22
                        mol_type = other DNA
                        organism = synthetic construct
SEQUENCE: 586
tacagtccca ggggaaattc ag                                            22
```

```
SEQ ID NO: 587          moltype = DNA  length = 20
FEATURE                 Location/Qualifiers
misc_feature            1..20
                        note = Forward Primer VISTA_exon4-5_1F
source                  1..20
                        mol_type = other DNA
                        organism = synthetic construct
SEQUENCE: 587
tgcggatgga cagcaacatt                                              20

SEQ ID NO: 588          moltype = DNA  length = 23
FEATURE                 Location/Qualifiers
misc_feature            1..23
                        note = Forward Primer VISTA_exon2-3_2F
source                  1..23
                        mol_type = other DNA
                        organism = synthetic construct
SEQUENCE: 588
cctcccagga tagtgaaaac atc                                          23

SEQ ID NO: 589          moltype = DNA  length = 23
FEATURE                 Location/Qualifiers
misc_feature            1..23
                        note = Reverse Primer CD274_3UTR_R
source                  1..23
                        mol_type = other DNA
                        organism = synthetic construct
SEQUENCE: 589
gaacccctaa accacaggtt gag                                          23

SEQ ID NO: 590          moltype = DNA  length = 24
FEATURE                 Location/Qualifiers
misc_feature            1..24
                        note = Reverse Primer CD274_EXON4_R
source                  1..24
                        mol_type = other DNA
                        organism = synthetic construct
SEQUENCE: 590
ctcagcctga catgtcagtt catg                                         24

SEQ ID NO: 591          moltype = DNA  length = 26
FEATURE                 Location/Qualifiers
misc_feature            1..26
                        note = Reverse Primer CD274_EXON3_R
source                  1..26
                        mol_type = other DNA
                        organism = synthetic construct
SEQUENCE: 591
ctactgggaa tttgcattca attgtc                                       26

SEQ ID NO: 592          moltype = DNA  length = 20
FEATURE                 Location/Qualifiers
misc_feature            1..20
                        note = Reverse Primer PDCD1_EXON2_R
source                  1..20
                        mol_type = other DNA
                        organism = synthetic construct
SEQUENCE: 592
agaagctgca ggtgaaggtg                                              20

SEQ ID NO: 593          moltype = DNA  length = 22
FEATURE                 Location/Qualifiers
misc_feature            1..22
                        note = Reverse Primer PDCD1-EXON3_4_5_R
source                  1..22
                        mol_type = other DNA
                        organism = synthetic construct
SEQUENCE: 593
ggaaatccag ctccccatag tc                                           22

SEQ ID NO: 594          moltype = DNA  length = 22
FEATURE                 Location/Qualifiers
misc_feature            1..22
                        note = Reverse Primer CTLA4-EXON1_2_R
source                  1..22
                        mol_type = other DNA
                        organism = synthetic construct
SEQUENCE: 594
gcatactcac acacaaagct gg                                           22
```

```
SEQ ID NO: 595         moltype = DNA  length = 23
FEATURE                Location/Qualifiers
misc_feature           1..23
                       note = Reverse Primer CTLA4-EXON4_R
source                 1..23
                       mol_type = other DNA
                       organism = synthetic construct
SEQUENCE: 595
ttgcttttca cattctggct ctg                                          23

SEQ ID NO: 596         moltype = DNA  length = 23
FEATURE                Location/Qualifiers
misc_feature           1..23
                       note = Reverse Primer CD47-EXON3_R
source                 1..23
                       mol_type = other DNA
                       organism = synthetic construct
SEQUENCE: 596
ctgtccccag aacaggagta tag                                          23

SEQ ID NO: 597         moltype = DNA  length = 24
FEATURE                Location/Qualifiers
misc_feature           1..24
                       note = Reverse Primer CD47-EXON9_10_11_R
source                 1..24
                       mol_type = other DNA
                       organism = synthetic construct
SEQUENCE: 597
cctttcacgt cttactactc tcca                                         24

SEQ ID NO: 598         moltype = DNA  length = 21
FEATURE                Location/Qualifiers
misc_feature           1..21
                       note = Reverse Primer LAG3-EXON2_R
source                 1..21
                       mol_type = other DNA
                       organism = synthetic construct
SEQUENCE: 598
cagaaggctg agatcctgga g                                            21

SEQ ID NO: 599         moltype = DNA  length = 20
FEATURE                Location/Qualifiers
misc_feature           1..20
                       note = Reverse Primer LAG3-EXON8_R
source                 1..20
                       mol_type = other DNA
                       organism = synthetic construct
SEQUENCE: 599
ggttcttgct ccagctcctc                                              20

SEQ ID NO: 600         moltype = DNA  length = 20
FEATURE                Location/Qualifiers
misc_feature           1..20
                       note = Reverse Primer HAVCR2-EXON3_R
source                 1..20
                       mol_type = other DNA
                       organism = synthetic construct
SEQUENCE: 600
ccatgtcccc tggtggtaag                                              20

SEQ ID NO: 601         moltype = DNA  length = 25
FEATURE                Location/Qualifiers
misc_feature           1..25
                       note = Reverse Primer HAVCR2-EXON7_R
source                 1..25
                       mol_type = other DNA
                       organism = synthetic construct
SEQUENCE: 601
ggtatagatg ttttcttctg agcga                                        25

SEQ ID NO: 602         moltype = DNA  length = 20
FEATURE                Location/Qualifiers
misc_feature           1..20
                       note = Reverse Primer CD14_exon2_1R
source                 1..20
                       mol_type = other DNA
                       organism = synthetic construct
SEQUENCE: 602
```

```
cgcagcggaa atcttcatcg                                              20

SEQ ID NO: 603         moltype = DNA  length = 20
FEATURE                Location/Qualifiers
misc_feature           1..20
                       note = Reverse Primer CD27_exon2_1R
source                 1..20
                       mol_type = other DNA
                       organism = synthetic construct
SEQUENCE: 603
gtcaggagag aaggagaccc                                              20

SEQ ID NO: 604         moltype = DNA  length = 22
FEATURE                Location/Qualifiers
misc_feature           1..22
                       note = Reverse Primer CD39_exon1-2_1R
source                 1..22
                       mol_type = other DNA
                       organism = synthetic construct
SEQUENCE: 604
tcacgttaga ctcttgaaac cc                                           22

SEQ ID NO: 605         moltype = DNA  length = 22
FEATURE                Location/Qualifiers
misc_feature           1..22
                       note = Reverse Primer CD40_exon7_1R
source                 1..22
                       mol_type = other DNA
                       organism = synthetic construct
SEQUENCE: 605
gataaagacc agcaccaaga gg                                           22

SEQ ID NO: 606         moltype = DNA  length = 18
FEATURE                Location/Qualifiers
misc_feature           1..18
                       note = Reverse Primer CD70_exon1-2_2R
source                 1..18
                       mol_type = other DNA
                       organism = synthetic construct
SEQUENCE: 606
agctacgtcc cacccaag                                                18

SEQ ID NO: 607         moltype = DNA  length = 23
FEATURE                Location/Qualifiers
misc_feature           1..23
                       note = Reverse Primer CD80_exon1-2_1R
source                 1..23
                       mol_type = other DNA
                       organism = synthetic construct
SEQUENCE: 607
gtggatttag tttcacagct tgc                                          23

SEQ ID NO: 608         moltype = DNA  length = 22
FEATURE                Location/Qualifiers
misc_feature           1..22
                       note = Reverse Primer FOXP3_exon7_1R
source                 1..22
                       mol_type = other DNA
                       organism = synthetic construct
SEQUENCE: 608
tctctctctg gaggagacat tg                                           22

SEQ ID NO: 609         moltype = DNA  length = 23
FEATURE                Location/Qualifiers
misc_feature           1..23
                       note = Reverse Primer ICOS_exon3-4_1R
source                 1..23
                       mol_type = other DNA
                       organism = synthetic construct
SEQUENCE: 609
gcacactgga tgaatacttc ttt                                          23

SEQ ID NO: 610         moltype = DNA  length = 20
FEATURE                Location/Qualifiers
misc_feature           1..20
                       note = Reverse Primer ICOS_exon2_2R
source                 1..20
                       mol_type = other DNA
                       organism = synthetic construct
```

```
SEQUENCE: 610
tttgtacacc tccgttgtga                                            20

SEQ ID NO: 611         moltype = DNA  length = 22
FEATURE                Location/Qualifiers
misc_feature           1..22
                       note = Reverse Primer TIGIT_exon3-4_1R
source                 1..22
                       mol_type = other DNA
                       organism = synthetic construct
SEQUENCE: 611
ggattctgag ggctttcttc tt                                         22

SEQ ID NO: 612         moltype = DNA  length = 21
FEATURE                Location/Qualifiers
misc_feature           1..21
                       note = Reverse Primer TNFRSF18_exon3-4_1R
source                 1..21
                       mol_type = other DNA
                       organism = synthetic construct
SEQUENCE: 612
cagcagtctg tccaaggttt g                                          21

SEQ ID NO: 613         moltype = DNA  length = 18
FEATURE                Location/Qualifiers
misc_feature           1..18
                       note = Reverse Primer VISTA_exon5_1R
source                 1..18
                       mol_type = other DNA
                       organism = synthetic construct
SEQUENCE: 613
aggacagggg gtgcctga                                              18

SEQ ID NO: 614         moltype = DNA  length = 20
FEATURE                Location/Qualifiers
misc_feature           1..20
                       note = Reverse Primer VISTA_exon3_2R
source                 1..20
                       mol_type = other DNA
                       organism = synthetic construct
SEQUENCE: 614
ctgcctttgc ttgtagacca                                            20

SEQ ID NO: 615         moltype =   length =
SEQUENCE: 615
000

SEQ ID NO: 616         moltype = DNA  length = 70
FEATURE                Location/Qualifiers
misc_feature           1..70
                       note = Universal indexed forward primer
source                 1..70
                       mol_type = other DNA
                       organism = synthetic construct
SEQUENCE: 616
aatgatacgg cgaccaccga gatctacacc tagcgctaca ctctttccct acacgacgct  60
cttccgatct                                                       70

SEQ ID NO: 617         moltype = DNA  length = 66
FEATURE                Location/Qualifiers
misc_feature           1..66
                       note = Universal indexed reverse primer
source                 1..66
                       mol_type = other DNA
                       organism = synthetic construct
SEQUENCE: 617
caagcagaag acggcatacg agataaccgc gggtgactgg agttcagacg tgtgctcttc  60
cgatct                                                           66
```